US012635974B2

(12) United States Patent
Dayton et al.

(10) Patent No.: US 12,635,974 B2
(45) Date of Patent: May 26, 2026

(54) METHODS AND SYSTEMS FOR USING PHASE CHANGE NANODROPLETS TO ENHANCE SONOTHROMBOLYSIS

(71) Applicants: The University of North Carolina at Chapel Hill, Chapel Hill, NC (US); The Regents of the University of Michigan, Ann Arbor, MI (US); North Carolina State University, Raleigh, NC (US)

(72) Inventors: Paul Alexander Dayton, Carrboro, NC (US); Jinwook Kim, Chapel Hill, NC (US); Xiaoning Jiang, Cary, NC (US); Zhen Xu, Ann Arbor, MI (US)

(73) Assignees: The Regents of the University of Michigan, Ann Arbor, MI (US); North Carolina State University, Raleigh, NC (US); The University of North Carolina at Chapel Hill, Chapel Hill, NC (US)

( * ) Notice: Subject to any disclaimer, the term of this patent is extended or adjusted under 35 U.S.C. 154(b) by 380 days.

(21) Appl. No.: 17/016,304

(22) Filed: Sep. 9, 2020

(65) Prior Publication Data

US 2020/0405258 A1     Dec. 31, 2020

Related U.S. Application Data

(63) Continuation-in-part of application No. 16/317,983, filed as application No. PCT/US2017/042372 on Jul. 17, 2017, now abandoned.

(Continued)

(51) Int. Cl.
*A61B 8/08*          (2006.01)
*A61B 8/00*          (2006.01)
(Continued)

(52) U.S. Cl.
CPC ............ *A61B 8/0891* (2013.01); *A61B 8/085* (2013.01); *A61B 8/481* (2013.01); *A61B 8/5246* (2013.01);
(Continued)

(58) Field of Classification Search
CPC ....... A61B 8/0891; A61B 8/085; A61B 8/481; A61B 8/5246; A61B 17/22004;
(Continued)

(56) References Cited

U.S. PATENT DOCUMENTS

| | | | |
|---|---|---|---|
| 4,375,818 A | 3/1983 | Suwaki et al. | |
| 4,423,153 A | 12/1983 | Ranney et al. | |
| (Continued) | | | |

FOREIGN PATENT DOCUMENTS

| | | |
|---|---|---|
| CA | 2 773 181 | 2/2018 |
| EP | 1 073 716 B1 | 4/2004 |
| (Continued) | | |

OTHER PUBLICATIONS

Non-Final Office Action for U.S. Appl. No. 15/990,171 (Sep. 16, 2021).

(Continued)

*Primary Examiner* — Jonathan Cwern
(74) *Attorney, Agent, or Firm* — Jenkins, Taylor & Hunt, P.A.

(57) ABSTRACT

A method for using metastable perfluorocarbon nanodroplets for ultrasonic lysis of blood clots includes administering metastable perfluorocarbon nanodroplets into a blood vessel that includes or that leads to a blood vessel that includes a blood clot, the metastable perfluorocarbon nanodroplets (Continued)

each have a liquid core comprising a perfluorocarbon material that has a boiling point below 25° C. at atmospheric pressure and that remains stable in liquid form at 25° C. at atmospheric pressure. The method further includes applying ultrasound energy to the perfluorocarbon nanodroplets within or surrounding the blood clot, causing the perfluorocarbon nanodroplets to vaporize and convert to bubbles, which cavitate and lyse the blood clot.

39 Claims, 50 Drawing Sheets

Related U.S. Application Data

(60) Provisional application No. 62/897,759, filed on Sep. 9, 2019, provisional application No. 62/362,687, filed on Jul. 15, 2016.

(51) Int. Cl.
| | | |
|---|---|---|
| *A61B 17/22* | (2006.01) | |
| *A61M 5/142* | (2006.01) | |
| *A61N 7/00* | (2006.01) | |
| *A61N 7/02* | (2006.01) | |

(52) U.S. Cl.
CPC ....... *A61B 17/22004* (2013.01); *A61M 5/142* (2013.01); *A61N 7/02* (2013.01); *A61B 2017/22008* (2013.01); *A61B 2017/22014* (2013.01); *A61B 2017/22088* (2013.01); *A61B 2017/22089* (2013.01); *A61N 2007/0039* (2013.01)

(58) Field of Classification Search
CPC ........... A61B 2017/22008; A61B 2017/22014; A61B 2017/22088; A61B 2017/22089; A61B 2017/00154; A61B 8/06; A61B 18/28; A61B 2018/0041; A61B 2018/266; A61B 2090/365; A61B 18/26; A61B 2017/22024; A61B 2017/22084; A61B 2090/378; A61B 17/2202; A61B 17/22012; A61M 5/142; A61N 7/02; A61N 2007/0039; A61N 2007/0004; A61N 2007/0043; A61N 2007/0065
See application file for complete search history.

(56) References Cited

U.S. PATENT DOCUMENTS

| | | | |
|---|---|---|---|
| 4,870,953 | A | 10/1989 | DonMicheal et al. |
| 4,951,677 | A | 8/1990 | Crowley et al. |
| 4,957,656 | A | 9/1990 | Cerny et al. |
| 5,254,112 | A | 10/1993 | Sinofsky et al. |
| 5,380,411 | A | 1/1995 | Schlief |
| 5,413,550 | A * | 5/1995 | Castel ................ A61H 23/0245 |
| | | | 601/3 |
| 5,454,373 | A | 10/1995 | Koger et al. |
| 5,469,854 | A | 11/1995 | Unger |
| 5,558,853 | A | 9/1996 | Quay |
| 5,585,112 | A | 12/1996 | Unger et al. |
| 5,662,124 | A | 9/1997 | Wilk |
| 5,716,597 | A | 2/1998 | Lohrmann et al. |
| 5,730,955 | A | 3/1998 | Lohrmann |
| 5,735,811 | A * | 4/1998 | Brisken ............ A61B 17/22012 |
| | | | 606/169 |
| 5,740,596 | A | 4/1998 | Corl et al. |
| 5,840,276 | A | 11/1998 | Apfel |
| 5,879,303 | A | 3/1999 | Averkiou et al. |
| 5,906,580 | A | 5/1999 | Kline-Schoder et al. |
| 5,931,805 | A | 8/1999 | Brisken |
| 6,024,703 | A | 2/2000 | Zanelli et al. |
| 6,024,718 | A | 2/2000 | Chen et al. |
| 6,033,645 | A | 3/2000 | Unger et al. |
| 6,071,495 | A | 6/2000 | Unger et al. |
| 6,312,383 | B1 | 11/2001 | Lizzi et al. |
| 6,371,917 | B1 | 4/2002 | Ferrara et al. |
| 6,398,792 | B1 | 6/2002 | O'Connor |
| 6,409,667 | B1 | 6/2002 | Hossack |
| 6,484,052 | B1 | 11/2002 | Visuri et al. |
| 6,491,685 | B2 | 12/2002 | Visuri et al. |
| 6,551,576 | B1 | 4/2003 | Unger |
| 6,656,124 | B2 | 12/2003 | Flesch et al. |
| 6,740,039 | B1 | 5/2004 | Rafter et al. |
| 7,358,226 | B2 | 4/2008 | Dayton et al. |
| 9,427,410 | B2 | 8/2016 | Dayton et al. |
| 9,532,769 | B2 | 1/2017 | Dayton et al. |
| 9,982,290 | B2 | 5/2018 | Janzen et al. |
| 10,493,038 | B2 | 12/2019 | Dayton et al. |
| 11,123,302 | B2 | 9/2021 | Dayton et al. |
| 11,485,994 | B2 | 11/2022 | Janzen et al. |
| 11,883,679 | B2 | 1/2024 | Jiang et al. |
| 2001/0019710 | A1 | 9/2001 | Berg et al. |
| 2001/0028893 | A1 | 10/2001 | Spears |
| 2002/0009391 | A1 | 1/2002 | Marquiss et al. |
| 2002/0043896 | A1 | 4/2002 | Hashimoto |
| 2002/0045890 | A1 | 4/2002 | Celliers et al. |
| 2002/0099290 | A1 | 7/2002 | Haddad |
| 2002/0133099 | A1 | 9/2002 | Ein-Gal |
| 2003/0078227 | A1 | 4/2003 | Greenleaf et al. |
| 2003/0092667 | A1 | 5/2003 | Tachibana et al. |
| 2003/0165431 | A1 | 9/2003 | Pines et al. |
| 2004/0015084 | A1 | 1/2004 | Flesch et al. |
| 2004/0251784 | A1 | 12/2004 | Kuniyasu |
| 2005/0014203 | A1 | 1/2005 | Darfler et al. |
| 2005/0038423 | A1 | 2/2005 | Makin et al. |
| 2005/0084538 | A1 | 4/2005 | Dayton et al. |
| 2006/0078501 | A1 | 4/2006 | Goertz et al. |
| 2007/0035204 | A1 | 2/2007 | Angelsen et al. |
| 2007/0178047 | A1 | 8/2007 | Kawabata |
| 2007/0292495 | A1 | 12/2007 | Ludwig et al. |
| 2008/0182237 | A1 | 7/2008 | Bentwich et al. |
| 2008/0200845 | A1 * | 8/2008 | Sokka ................ A61K 41/0033 |
| | | | 601/3 |
| 2008/0208044 | A1 | 8/2008 | Lecoq et al. |
| 2008/0311046 | A1 | 12/2008 | Kawabata et al. |
| 2008/0312535 | A1 | 12/2008 | Kawabata |
| 2009/0023597 | A1 | 1/2009 | Wong et al. |
| 2009/0076394 | A1 | 3/2009 | Wong et al. |
| 2009/0108710 | A1 * | 4/2009 | Brown ...................... A61B 1/06 |
| | | | 310/367 |
| 2009/0117177 | A1 | 5/2009 | Rapoport et al. |
| 2009/0182237 | A1 | 7/2009 | Bjorn et al. |
| 2009/0317884 | A1 | 12/2009 | Laugharn, Jr. |
| 2010/0009424 | A1 | 1/2010 | Forde et al. |
| 2010/0089133 | A1 | 4/2010 | Yamasaki et al. |
| 2010/0160779 | A1 * | 6/2010 | Browning .......... A61B 5/02007 |
| | | | 600/454 |
| 2010/0224782 | A1 | 9/2010 | Pan et al. |
| 2010/0331686 | A1 | 12/2010 | Hossack et al. |
| 2011/0044903 | A1 | 2/2011 | Borrelli |
| 2012/0172720 | A1 | 7/2012 | Asami et al. |
| 2012/0203103 | A1 | 8/2012 | Wang et al. |
| 2012/0209116 | A1 * | 8/2012 | Hossack ............... A61M 25/00 |
| | | | 604/23 |
| 2012/0220869 | A1 | 8/2012 | Dayton et al. |
| 2012/0270177 | A1 | 10/2012 | Nakashima et al. |
| 2013/0023897 | A1 | 1/2013 | Wallace |
| 2013/0053691 | A1 | 2/2013 | Kawabata et al. |
| 2013/0150725 | A1 | 6/2013 | Choi |
| 2013/0336891 | A1 | 12/2013 | Dayton et al. |
| 2014/0039358 | A1 * | 2/2014 | Zhou ................... A61B 17/2202 |
| | | | 601/3 |
| 2014/0180128 | A1 | 6/2014 | Corl |
| 2014/0242584 | A1 | 8/2014 | Ji |
| 2015/0252355 | A1 | 9/2015 | Janzen et al. |
| 2016/0262727 | A1 * | 9/2016 | Dayton ............... A61B 8/4477 |
| 2018/0221515 | A1 | 8/2018 | Dayton et al. |
| 2018/0274008 | A1 | 9/2018 | Janzen et al. |
| 2021/0007759 | A1 | 1/2021 | Jiang et al. |
| 2021/0267614 | A1 | 9/2021 | Jiang et al. |

(56) References Cited

U.S. PATENT DOCUMENTS

| | | | |
|---|---|---|---|
| 2022/0000790 A1 | 1/2022 | Dayton et al. | |
| 2023/0111075 A1 | 4/2023 | Janzen et al. | |
| 2025/0064469 A1 | 2/2025 | Jiang et al. | |
| 2025/0228576 A1 | 7/2025 | Jiang et al. | |
| 2025/0288307 A1 | 9/2025 | Jiang et al. | |

FOREIGN PATENT DOCUMENTS

| | | | |
|---|---|---|---|
| WO | WO 2011/029094 A2 | 3/2011 | |
| WO | WO 2011/149985 A1 | 12/2011 | |
| WO | WO 2012/048335 A2 | 4/2012 | |
| WO | WO 2014/055832 A1 | 4/2014 | |
| WO | WO 2015/070186 A1 | 5/2015 | |
| WO | WO 2016/118947 A1 | 7/2016 | |

OTHER PUBLICATIONS

Notice of Allowance and Fee(s) Due for U.S. Appl. No. 15/247,840 (May 17, 2021).

Commonly-assigned, co-pending U.S. Appl. No. 17/198,926 for "Multi-Pillar Piezoelectric Stack Ultrasound Transducer and Methods for Using Same," (Unpublished, filed Mar. 11, 2021).

Notification of Transmittal of the International Search Report and the Written Opinion of the International Searching Authority, or the Declaration of International Application No. PCT/US17/42372 (Nov. 24, 2017).

Heidt et al., "Molecular Imaging of Activated Platelets Allows the Detection of Pulmonary Emoblism with Magnetic Resonance Imaging," Sci. Rep., vol. 6, pp. 25044 (2016).

Dilektasli et al., "Catheter-Directed Therapy in Acute Pulmonary Embolism with Right Ventricular Dysfunction: A Promising Modality to Provide Early Hemodynamic Recovery," Med. Sci. Monit., vol. 22, pp. 1265-1273 (2016).

Fan et al., "Tissue Plasminogen Activator Neurotoxicity is Neutralized by Recombinant ADAMTS 13," Sci. Rep., vol. 6, pp. 25971 (2016).

Porter et al., "Diagnostic ultrasound high mechanical index impulses restore microvascular flow in peripheral arterial thromboembolism," Ultrasound Med. Biol., vol. 42, pp. 1531-1540 (2016).

Roberts et al., "Quantitative assessment of placental perfusion by contrast-enhanced ultrasound in macaques and human subjects," Am. J. Obstet. Gynecol, vol. 214, pp. 369.e1-369e8 (2016).

Shelton et al., "Molecular Acoustic Angiography: A New Technique for High-resolution Superharmonic Ultrasound Molecular Imaging," Ultrasound Med. Biol. vol. 42, pp. 769-781 (2016).

Porter et al., "Ultrasound, microbubbles, and thrombolysis," Prog. Cardiovasc. Dis., vol. 44, pp. 101-110 (2001).

Belcik et al., "Augmentation of limb perfusion and reversal of tissue ischemia produced by ultrasound-mediated microbubble cavitation," Circ. Cardiovasc. Imaging, vol. 8, pp. e002979 (2015).

Bader et al., "Shaken and Stirred: Mechanisms of Ultrasound-Enhanced Thrombolysis," Ultrasound Med. Biol., vol. 41, pp. 187-196 (2015).

Hsieh et al., "A laser ultrasound transducer using carbon nanofibers-polydimethylsiloxane compsite thin film," Applied Physics Letters, vol. 106, No. 2, pp. 021902 (2015).

Kuo et al., "Pulmonary embolism response to fragmentation, embolectomy, and catheter thrombolysis (PERFECT): Initial results from a prospective multicenter registry," Chest, vol. 148, pp. 667*673 (2015).

Pacella et al., "Treatment of microvascular micro-embolization using microbubbles and long-tone-burst ultrasound: An invivo study," Ultrasound Med. Biol., vol. 41, pp. 456-464 (2015).

Sista et al., "Catheter-Directed Thrombolysis for Pulmonary Embolism," JACC Cardiovasc. Interv., vol. 8, pp. 1393-1395 (2015).

Wolberg et al., "Venous thrombosis," Nat. Rev. Dis. Prim, vol. 1, pp. 15006 (2015).

Chatterjee et al., "Thrombolysis for pulmonary embolism and risk of all-cause mortality, major bleeding, and intracranial hemorrhage: a meta-analysis," JAMA, vol. 311, pp. 2414-2421 (2014).

Kucher et al., "Randomized, controlled trial of ultrasound-assistaed catheter-directed thrombolysis for acute intermediate-risk pulmonary embolism," Circulation, vol. 129, pp. 479-486 (2014).

Fanikos et al., "Hospital costs of acute pulmonary embolism," Am. J. Med., vol. 126, pp. 127-132 (2013).

Xu et al., "Energy harvesting using a PZT ceramic multilayer stack," Smart Mater. Struct., vol. 22, pp. 65015 (2013).

Bolognese et al., "Real-Time Ultrasound Perfusion Imaging in Acute Stroke: Assessment of Cerebral Perfusion Deficits Related to Arterial Recanalization," resoundund Med. Biol., vol. 39, pp. 745-752 (2013).

Bader et al., "Gauging the likelihood of stable cavitation from ultrasound contrast agents," Phys. Med. Biol., vol. 58, pp. 127-144 (2013).

Weiss et al., "Mechanical clot damage from cavitation during sonothrombolysis," J. Acoust. Soc. Am., vol. 133, pp. 3159-3175 (2013).

Kearon et al., "Antithrombotic therapy for VTE disease: Antithrombotic therapy and prevention of thrombosis, 9th ed: American College of Chest Physicians evidence-based clinical practice guidelines," Chest, vol. 141, pp. e419s-e496s (2012).

Kutty et al., "Microbubble Mediated Thrombus Dissolution with Diagnostic Ultrasound for the Treatment of Chronic Venous Thrombi," PLoS One 7, pp. e51453 (2012).

Goldhaber et al., "Pulmonary embolism and deep vein thrombosis," Lancet, vol. 379, pp. 1835-1846 (2012).

Slikkerveer et al., "Ultrasound enhanced prehospital thrombolysis using microbubbles infusion in pateitns with acute st elevation myocardial infarction: Pilot of the sonolysis study," Ultrasound Med. Biol., vol. 38, pp. 247-252 (2012).

Popovic et al., Massive pulmonary embolism: Percutaneous emergency treatment using an aspirex thrombectomy catheter, Cardiovasc. Intervent. Radiol., vol. 33, pp. 1052-1055 (2010).

MacDougall et al., "Economic burden of deep-vein thrombosis, pulmonary embolism, and postthrombotic syndrome," Am. J. Heal. Pharm., vol. 63, pp. S5-S15 (2006).

Cesarman-Maus et al., "Molecular mechanisms of fibrinolysis," Br. J. Haematol., vol. 129, pp. 307-321 (2005).

Schafer et al., "Influence of ultrasound operating parameters on ultrasound-induced thrombolysis in vitro," Ultrasound Med. Biol., vol. 31, pp. 841-847 (2005).

Dijkmans et al., "Microbubbles and ultrasound: From diagnosis to therapy," Eur. J. Echocardiogr., vol. 5, pp. 245-256 (2004).

Postema et al., "Ultrasound-induced microbubble coalescence," Ultrasound Med. Biol, vol. 30, pp. 1337-1344 (2004).

Mahon et al., "North American clinical experience with the EKOS MicroLysUS infusion catheter for the treatment of embolic stroke," Am. J. Neuroradiol., vol. 24, pp. 534-538 (2003).

Hill et al., "Physical principles of medical ultrasonics," John Wiley & Sons, Chapter 2, pp. 41-59 (2004).

Blinc et al., "Characterization of Ultrasound-Potentiated Fibrinolysis," In Vitro, vol. 8, pp. 2636-2643 (1993).

Gersh et al., "The spatial dynamics of fibrin clot dissolution catalyzed by erythrocyte-bound vs. free fibrinolytics," J. Thromb. Haemost., vol. 8, pp. 1066-1074 (2010).

Goldhaber et al., "Pulmonary embolism and deep vein thrombosis," Circulation, vol. 106, pp. 1436-1438 (2002).

Francis, "Ultrasound-enhanced thrombolysis," Echocardiography, vol. 18, pp. 239-246 (2001).

Atar et al., "Ultrasonic Thrombolysis: Catheter-delivered and transcutaneous applications," Euro. J. Ultrasound, vol. 9, pp. 39-54 (1999).

Final Office Action for U.S. Appl. No. 15/035,211 (May 1, 2020).

Non-Final Office Action for U.S. Appl. No. 15/990,171 (Mar. 19, 2020).

Final Office Action for U.S. Appl. No. 15/247,840 (Feb. 21, 2020).

Applicant-Initiated Interview Summary for U.S. Appl. No. 15/247,840 (Oct. 25, 2019).

Non-Final Office Action for U.S. Appl. No. 15/035,211 (Sep. 26, 2019).

(56) References Cited

OTHER PUBLICATIONS

Notice of Allowance and Fee(s) Due for U.S. Appl. No. 15/880,481 (Aug. 8, 2019).

Guo et al., "Reduced clot debris size in sonothrombolysis assisted with phase-change nanodroplets," Ultrasonics—Sonochemistry, vol. 54, pp. 1-9 (2019).

Non-Final Office Action for U.S. Appl. No. 15/247,840 (Jun. 13, 2019).

Non-Final Office Action for U.S. Appl. No. 15/880,481 (Apr. 5, 2019).

Advisory Action, Examiner-Initiated Interview Summary and AFCP 2.0 Decision for U.S. Appl. No. 15/035,211 (Mar. 7, 2019).

Non-Final Office Action for U.S. Appl. No. 15/247,840 (Oct. 5, 2018).

Final Office Action for U.S. Appl. No. 15/035,211 (Sep. 26, 2018).

Non-Final Office Action for U.S. Appl. No. 15/035,211 (Feb. 9, 2018).

Notice of Allowance and Fee(s) Due and Examiner Initiated Interview Summary for U.S. Appl. No. 14/432,747 (Jan. 10, 2018).

Applicant Initiated Interview Summary for U.S. Appl. No. 14/432,747 (Jul. 24, 2017).

Notice of Allowance for Canadian Patent Application No. 2,773,181 (Jul. 10, 2017).

Final Office Action for U.S. Appl. No. 14/432,747 (May 19, 2017).

Applicant-Initiated Interview Summary for U.S. Appl. No. 14/432,747 (Feb. 22, 2017).

Non-Final Office Action for U.S. Appl. No. 14/432,747 (Oct. 12, 2016).

Office Action for Canadian Patent Application No. 2,773,181 (Sep. 12, 2016).

Notice of Allowance and Fee(s) Due for U.S. Appl. No. 13/393,500 (Aug. 22, 2016).

Notification of Transmittal of the International Search Report and the Written Opinion of the International Searching Authority, or the Declaration for International Application No. PCT/US2016/014685 (Jun. 30, 2016).

Applicant-Initiated Interview Summary for U.S. Appl. No. 13/393,500 (Jun. 21, 2016).

Restriction/Election Requirement for U.S. Appl. No. 14/432,747 (Jun. 3, 2016).

Notice of Allowance, Examiner-Initiated Interview Summary, and AFCP 2.0 Decision for U.S. Appl. No. 13/876,165 (Apr. 28, 2016).

Applicant-Initiated Interview Summary for U.S. Appl. No. 13/876,165 (Mar. 28, 2016).

Final Office Action for U.S. Appl. No. 13/393,500 (Feb. 24, 2016).

Final Office Action for U.S. Appl. No. 13/876,165 (Dec. 31, 2015).

Applicant-Initiated Interview Summary for U.S. Appl. No. 13/393,500 (Nov. 16, 2015).

Non-Final Office Action for U.S. Appl. No. 13/393,500 (Jul. 9, 2015).

Non-Final Office Action for U.S. Appl. No. 13/876,165 (Jun. 10, 2015).

Moyer et al., "High-intensity focused ultrasound ablation enhancement in vivo via phase-shift nanodroplets compared to microbubbles," Journal of Therapeutic Ultrasound, vol. 3, No. 7, pp. 1-9 (2015).

Li et al., "Quantifying Activation of Perfluorocarbon-Based Phase-Change Contrast Agents Using Simultaneous Acoustic and Optical Observation," Ultrasound Med Biol., vol. 41, No. 5, pp. 1-20 (May 2015).

Notification of Transmittal of the International Search Report and the Written Opinion of the International Searching Authority, or the Declaration for PCT International Application No. PCT/US2014/064889 (Apr. 9, 2015).

Restriction and/or Election Requirement for U.S. Appl. No. 13/393,500 (Jan. 27, 2015).

Restriction and/or Election Requirement for U.S. Appl. No. 13/876,165 (Dec. 1, 2014).

Notification of Transmittal of the International Search Report and the Written Opinion of the International Searching Authority, or the Declaration for PCT International Application No. PCT/US2013/063397 (Jan. 16, 2014).

Pajek et al., "High-Intensity Focused Ultrasound Sonothrombolysis: The Use of Perfluorocarbon Droplets to Achieve Clot Lysis at Reduced Acoustic Power," Ultrasound in Med. & Biol., vol. 40, No. 9, pp. 1-11 (2014).

Zhao et al., "Potential and problems in ultrasound-responsive drug delivery systems," International Journal of Nanomedicine, pp. 1-14 (Apr. 2013).

Notification of Transmittal of the International Search Report and the Written Opinion of the International Searching Authority, or the Declaration for International Application No. PCT/US2011/055713 (May 18, 2012).

Notification of Transmittal of the International Search Report and the Written Opinion of the International Searching Authority, or the Declaration for International Patent Application No. PCT/US2010/047988 (Mar. 31, 2011).

Ainslie et al., "Review of scattering and extinction cross-sections, damping factors, and resonance frequencies of a spherical gas bubble," The Journal of the Acoustical Society of America, vol. 130, pp. 3184-3208 (2011).

Seo et al., "Microfluidic consecutive flow-focusing droplet generators," Soft Matter, vol. 3, pp. 986-992 (2007).

Alexandridis et al., "Surface Activity of Poly(ethylene oxide)-block-Poly(propylene oxide)-block-Poly(ethylene oxide) Copolymers," Langmuir, vol. 10, pp. 2604-2612 (1994).

Allen et al., "Effect of Coupled Oscillations on Microbubble Behavior," The Journal of the Acoustical Society of America, vol. 14, No. 3, pp. 1678-1690 (Sep. 2003).

Allen, "Liposomes—Opportunities in Drug Delivery," Drugs, vol. 54, Suppl. 4, pp. 8-14 (1997).

Anderson et al., "Ultrasound Molecular Imaging of Tumor Angiogenesis with an Integrin Targeted Microbubble Contrast Agent," Invest Radiol, vol. 46, No. 4, pp. 1-21 (Apr. 2011).

Anderson, "Shotgun DNA Sequencing Using Cloned DNase I-generated Fragments," Nucleic Acids Research, vol. 9, No. 13, pp. 3015-3027 (Jul. 1981).

Aparicio et al., "Chromatin Immunoprecipitation for Determining the Association of Proteins with Specific Genomic Sequences in Vivo," Current Protocols in Cell Biology, Chapter 17, Unit 17.7, pp. 17.7.1-17.7.23 (2004).

Apfel, "Activatable infusable dispersions containing drops of a superheated liquid for methods of therapy and diagnosis," (1998).

Asami et al., "Acoustic Signal Characterization of Phase Change Nanadroplets in Tissue-Mimicking Phantom Gels," Jpn. J. Appl. Phys., vol. 49 (2010).

Asami et al., "Repeatable vaporization of optically vaporizable perfluorocarbon droplets for photoacoustic contrast enhanced imaging," 2012 IEEE International Ultrasonics Symposium (IUS), pp. 1200-1203 (2012).

Auton et al., "The Force Exerted on a Body in an Inviscid Unsteady Non-Uniform Rotational Flow," J. Fluid Mech., vol. 197, pp. 241-257 (1988).

Joneja et al., "A device for automated hydrodynamic shearing of genomic DNA," Biotechniques, vol. 46, pp. 1-7 (2009).

Behm et al., "Cellular and Molecular Imaging with Targeted Contrast Ultrasound," Ultrasound Quarterly, vol. 22, No. 1, pp. 67-72 (Mar. 2006).

Bekeredjian et al., "Therapeutic Use of Ultrasound Targeted Microbubble Destruction: A Review of Non-Cardiac Applications," Ultraschall in Med, vol. 27, pp. 134-140 (2006).

Bekeredjian et al., "Ultrasound-targeted Microbubble Destruction Can Repeatedly Direct Highly Specific Plasmid Expression to the Heart," Circulation—Journal of the American Heart Association, vol. 108, pp. 1022-1026 (2003).

Bernasconi et al., "A Chemogenomic Analysis of the Human Proteome: Application to Enzyme Families," Journal of Biomolecular Screening, vol. 12, No. 7, pp. 972-982 (2007).

Bloch et al., "Targeted Imaging Using Ultrasound Contrast Agents," IEEE Engineering in Medicine and Biology, vol. 23, No. 5, pp. 18-29 (Sep./Oct. 2004).

(56)                    References Cited

OTHER PUBLICATIONS

Böhmer et al., "Preparation of Monodisperse Polymer Particles and Capsules By Ink-Jet Printing," Colloids and Surfaces A: Physicochem. Eng. Aspects, vol. 289, pp. 96-104 (2006).

Borden et al., "A Stimulus-Responsive Contrast Agent for Ultrasound Molecular Imaging," Biomaterials, vol. 29, No. 5, pp. 1-19 (Feb. 2008).

Borden et al., "Ultrasound Radiation Force Modulates Ligand Availability on Targeted Contrast Agents," Molecular Imaging, vol. 5, No. 3, pp. 139-147 (Jul. 2006).

Borden et al., "Influence of Lipid Shell Physicochemical Properties on Ultrasound-Induced Microbubble Destruction," IEEE Transactions on Ultrasonics, Ferroelectrics, and Frequency Control, vol. 52, No. 11, pp. 1992-2002 (Nov. 2005).

Borden et al., "Surface Phase Behavior and Microstructure of Lipid/PEG-Emulsifier Monolayer-Coated Microbubbles," Colloids and Surfaces B: Biointerfaces, vol. 35, pp. 209-223 (Mar. 2004).

Borden et al., "Dissolution Behavior of Lipid Monolayer-Coated, Air-Filled Microbubbles: Effect of Lipid Hydrophobic Chain Length," Langmuir, vol. 18, pp. 9225-9233 (2002).

Bouakaz et al., "Contrast Superharmonic Imaging: A Feasability Study," Ultrasound in Med. & Biol., vol. 29, No. 4, pp. 547-553 (2003).

Bouakaz et al., "Super Harmonic Imaging: A New Imaging Technique for Improved Contrast Detection," Ultrasound in Med.& Biol., vol. 28, No. 1, pp. 59-68 (2002).

Brennen, "Cavitation and Bubble Dynamics," Oxford University Press (1995).

Burger et al., "Sequencing Complete Mitochondrial and Plastid Genomes," Nature Protocols, vol. 2, No. 3, pp. 603-614 (Mar. 22, 2007).

Burns et al., "Microbubble Contrast for Radiological Imaging: 1. Principles," Ultrasound Quarterly, vol. 22, No. 1, pp. 5-13 (Mar. 2006).

Calderon et al., "A boundary element model of the ransport of a semi-infinite bubble through a microvessel birfurcation," Physics of Fluids, vol. 22, p. 11 (2010).

Campbell, "Tumor Physiology and Delivery of Nanopharmaceuticals," Anti-Cancer Agents in Medicinal Chemistry, vol. 6, No. 6, pp. 503-512 (2006).

Carson et al., "Acoustic Droplet Vaporization," http://www.ultrasound.med.umich.edu/Projects/ADV.html, pp. 1-4 (Downloaded from the Internet Mar. 17, 2015).

Caskey et al., "Direct Observations of Ultrasound Microbubble Contrast Agent Interaction with the Microvessel Wall," The Journal of the Acoustical Society of America, vol. 122, No. 2, pp. 1191-1200 (Aug. 2007).

Chatterjee et al., "A Newtonian Rheological Model for the Interface of Microbubble Contrast Agents," Ultrasound in Med. & Biol.,vol. 29, No. 12, pp. 1749-1757 (Jul. 2003).

Chen et al., "Efficient Gene Delivery to Pancreatic Islets with Ultrasonic Microbubble Destruction Technology," PNAS, vol. 103, No. 22, pp. 8469-8474 (May 30, 2006).

Chen et al., "Multiple Acoustical Matching Layer Design of Ultrasonic Transducer for Medical Application," Jpn. J. Appl. Phys., vol. 41, pp. 6098-6107 (Oct. 2002).

Choi et al., "Spatio-Temporal Analysis of Molecular Delivery Through the Blood-Brain Barrier Using Focused Ultrasound," Physics in Medicine and Biology, vol. 52, pp. 5509-5530 (2007).

Choi et al., "Spatiotemporal evolution of cavitation dynamics exhibited by flowing microbubbles during ultrasound exposure," The Journal of te Acoustical Society of America, vol. 132, pp. 3538-3549 (2012).

Choi et al., "Noninvasive, Transcranial and Localized Opening of the Blood-Brain Barrier Using Focused Ultrasound in Mice," Ultrasound in Medicine and Biology, vol. 33, No. 1, pp. 95-104 (2007).

Chomas et al., "Threshold of Fragmentation for Ultrasonic Contrast Agents," Journal of Biomedical Optics, vol. 6, No. 2, pp. 141-150 (Apr. 2001).

Chomas et al., "Mechanisms of Contrast Agent Destruction," IEEE Transactions Ultrasonics, Ferroelectrics, and Frequency Control, vol. 48, No. 1, pp. 232-248 (Jan. 2001).

Chomas et al., "Optical Observation of Contrast Agent Destruction," Applied Physics Letters, vol. 77, No. 7, pp. 1056-1058 (Aug. 14, 2000).

Chopra et al., "Multifrequency Ultrasound Transducers for Conformal Interstitial Thermal Therapy," IEEE Transactions on Ultrasonics, Ferroelectrics, and Frequency Control, vol. 50, No. 7, pp. 881-889 (Jul. 2003).

Clarke et al., "Production of harmonics in vitro by high-intensity focused ulrasound," Ultrasound in Medicine Biology, vol. 25, pp. 1417-1424 (1999).

Coakley et al., "Ultrasonic Manipulation of Particles and Cells," Bioseparation, vol. 4, pp. 73-83 (1994).

Coussios et al., "Applications of acoustics and cavitation to non-invasive therapy and drug delivery," Annual Review of Fluid Mechanics, vol. 40, pp. 395-420 (2008).

Couture et al., "Ultrasound inernal tattooing," Medical Physics, vol. 38, pp. 1116-1123 (2011).

Couture et al., "A Model for Reflectivity Enhancement Due to Surface Bound Submicrometer Particles," Ultrasound in Medicine & Biology, vol. 32, No. 8, pp. 1247-1255 (May 2006).

Couture et al., "Investigating Perfluorohexane Particles with High-frequency Ultrasound," Ultrasound in Medicine & Biology, vol. 32, No. 1, pp. 73-82 (Sep. 2005).

Cronin et al., "Comprehensive Next-Generation Cancer Genome Sequencing in the Era of Targeted Therapy and Personalized Oncology," Biomarkers Med.; 5(3), pp. 293-305 (2011).

Crowder et al., "Sonic Activation of Molecularly-Targeted Nanoparticles Accelerates Transmembrane Lipid Delivery to Cancer Cells Through Contact-mediated Mechanisms: Implications for Enhanced Local Drug Delivery," Ultrasound in Medicine & Biology, vol. 31, No. 12, pp. 1693-1700 (2005).

Crum, Lawrence A., "Bjerknes Forces on Bubbles in a Stationary Sound Field," The Journal of the Acoustical Society of America, vol. 57, No. 6, Part 1, pp. 1363-1370 (1975).

Crum et al., "The Motion of Bubbles in a Stationary Sound Field," The Journal of the Acoustical Society of America, p. 1411 (1969).

Culp et al., "Successful Microbubble Sonothrombolysis Without Tissue Plasminogen Activator in a Rabbit Model of Acute Ischemic Stroke," Stroke, vol. 42, No. 8, pp. 1-15 (Aug. 2011).

D'Astous et al., "Frequency dependence of ultrasound attenuation and backscatter in breast tissue," Ultrasound in Medicine Biology, vol. 12, pp. 795-808 (1986).

Dayton et al., "Molecular ultrasound imaging using microbubble contrast agents," Frontiers in Bioscience, vol. 12, pp. 5124-5142 (Sep. 1, 2007).

Dayton et al., "Application of Ultrasound to Selectively Localize Nanodroplets for Targeted Imaging and Therapy," Molecular Imaging, vol. 5, No. 3, pp. 1-32 (Jul. 2006).

Dayton et al., "Application of Ultrasound to Selectively Localize Nanodroplets for Targeted Imaging and Therapy," Molecular Imaging, vol. 5, No. 3, pp. 1-32 (2006).

Dayton et al., "Ultrasound-Mediated Therapies Using Oil and Perfluorocarbon-Filled Nanodroplets," Drug Development Research, vol. 67, pp. 42-46 (2006).

Dayton et al., "Ultrasonic Analysis of Peptide- and Antibody-Targeted Microbubble Contrast Agents for Molecular Imaging of $av\beta3$-expressing Cells," Molecular Imaging, vol. 3, No. 2, pp. 1-18 (Apr. 2004).

Dayton et al., "Targeted Imaging Using Ultrasound," Journal of Magnetic Resonance Imaging, vol. 16, pp. 362-377 (2002).

Dayton et al., "The Magnitude of Radiation Force on Ultrasound Contrast Agents," The Journal of the Acoustical Society of America, vol. 112, No. 5, Part 1, pp. 2183-2192 (2002).

Dayton et al., "Optical and Acoustical Dynamics of Microbubble Contrast Agents Inside Neutrophils," Biophysical Journal, vol. 80, pp. 1547-1556 (Mar. 2001).

Dayton et al., "Acoustic Radiation Force in Vivo: A Mechanism to Assist Targeting of Microbubbles," Ultrasound in Med. and Biol. vol. 25, No. 8, pp. 1195-1201 (1999).

(56) References Cited

OTHER PUBLICATIONS

Dayton et al., "Optical and Acoustical Observations of the Effects of Ultrasound on Contrast Agents," IEEE Transactions on Ultrasonics, Ferroelectrics, and Frequency Control,vol. 46, No. 1, pp. 220-232 (Jan. 1999).

Dayton et al., "A Preliminary Evaluation of the Effects of Primary and Secondary Radiation Forces on Acoustic Contrast Agents," IEEE Transactions on Ultrasonics, Ferroelectrics, and Frequency Control, vol. 44, No. 6, pp. 1264-1277 (Nov. 1997).

Dayton et al., "Action of Microbubbles When Insonified: Experimental Evidence," IEEE Ultrasonics Symposium, vol. 2, pp. 1131-1134 (1996).

Deininger, "Random Subcloning of Sonicated DNA: Application to Shotgun DNA Sequence Analysis," Analytical Biochemistry, vol. 129(1), pp. 216-223 (1983).

Deng et al., "Ultrasound-Induced Cell Membrane Porosity," Ultrasound in Medicine & Biology, vol. 30, No. 4, pp. 519-526 (2004).

Desilets et al., "Design of Efficient Broad-Band Piezoelectric Transducers," IEEE Transactions on Sonics and Ultrasonics, vol. SU-25, No. 3, pp. 115-125 (May 1978).

Doinikov et al., "Review of shell models for contrast agent microbubbles," IEEE Trans. Ultrason. Ferroelectr. Freq. Control, vol. 58, pp. 981-993 (2011).

Doinikov et al., "Modeling of Nonlinear Viscous Stress in Encapsulating Shells of Lipid-Coated Contrast Agent Microbubbles," Ultrasonics, vol. 49, No. 2, pp. 1-17 (Feb. 2009).

Doinikov et al., "Resonance Frequencies of Lipid-Shelled Microbubbles in the Regime of Nonlinear Oscillations," Ultrasonics, vol. 49, No. 2, pp. 1-16 (Feb. 2009).

Doinikov et al., "Modeling of the Acoustic Response From Contrast Agent Microbubbles Near a Rigid Wall," Ultrasonics, vol. 49, No. 2, pp. 1-17 (Feb. 2009).

Doinikov et al., "Maxwell Rheological Model for Lipid-Shelled Ultrasound Microbubble Contrast Agents," The Journal of the Acoustical Society of America, vol. 121, No. 6, pp. 1-26 (Jun. 2007).

Doinikov et al., "Spatio-temporal Dynamics of an Encapsulated Gas Bubble in an Ultrasound Field," The Journal of the Acoustical Society of America, vol. 120, No. 2, pp. 1-25 (Aug. 2006).

Dromi et al., "Pulsed-High Intensity Focused Ultrasound and Low Temperature Sensitive Liposomes for Enhanced Targeted Drug Delivery and Antitumor Effect," Clinical Cancer Research, vol. 13, pp. 2722-2727 (2007).

Ellegala et al., "Imaging Tumor Angiogenesis with Contrast Ultrasound and Microbubbles Targeted to $\alpha v \beta 3$," Circulation, Journal of the American Heart Association, vol. 108 pp. 336-341 (2003).

Eshpuniyani et al., "A boundary element model of microbubble sticking and sliding in the microcirculation," International Journal of Heat and Mass Transfer, vol. 51, pp. 5700-5711 (2008).

Evans et al., "Physical Properties of Phase-Change Emulsions," Langmuir, vol. 22, pp. 9538-9545 (Sep. 2006).

Fabiilli et al., "Delivery of Chlorambucil Using an AcousticallyTriggered Perfluoropentane Emulsion," Ultrasound in Medicine and Biology, vol. 36, No. 8, pp. 1-25 (Aug. 2010).

Fabiilli et al., "Delivery of Water-Soluble Drugs Using Acoustically Triggered Perfluorocarbon Double Emulsions," Pharm. Res., vol. 27, No. 12, pp. 1-25 (Dec. 2010).

Fabiilli et al., "The Role of Inertial Cavitation in Acoustic Droplet Vaporization," IEEE Transactions on Ultrasonics, Ferroelectrics, and Frequency Control, vol. 56, No. 5, pp. 1-24 (May 2009).

Fang et al., "Acoustically active perfluorocarbon nanoemulsions as drug delivery carriers for camptothecin: Drug release and cytotoxicity against cancer cells," Ultrasonics, vol. 49, pp. 39-46 (2009).

Farook et al., "Controlling Size and Size Distribution of Electrohydrodynamically Prepared Microbubbles," Bubble Science, Engineering and Technology, vol. 1, No. 1/2, pp. 53-57 (2009).

Farook et al., "Preparation of Suspensions of Phospholipid-coated Microbubbles by Coaxial Electrohydrodynamic Atomization," The Journal of the Royal Society Interface, vol. 6, (32), pp. 271-277 (Jul. 2008).

Ferrara, "Driving Delivery Vehicles with Ultrasound," Advanced Drug Delivery Reviews, vol. 60, No. 10, pp. 1-9 (Jun. 30, 2008).

Ferrara et al., "Ultrasound Microbubble Contrast Agents: Fundamentals and Application to Gene and Drug Delivery," The Annual Review of Biomedical Engineering, vol. 9, pp. 415-447 (2007).

Ferretti et al., "Tumor Interstitial Fluid Pressure as an Early-Response Marker for Anticancer Therapeutics," Neoplasia, vol. 11, No. 9, pp. 874-881 (Sep. 2009).

Feshitan et al., "Microbubble Size Isolation by Differential Centrifugation," Journal of Colloid and Interface Science, 329, pp. 316-324 (2009).

Forsberg et al., "Subharmonic imaging of contrast agents," Ultrasonics, vol. 38, pp. 93-98 (2000).

Ganan-Calvo et al., "Perfectly Monodisperse Microbubbling by Capillary Flow Focusing," Physical Review Letters, vol. 87, No. 27, p. 274501-1-274501-4 (2001).

Gao et al., "Drug-Loaded Nano/Microbubbles for Combining Ultrasonography and Targeted Chemotherapy," Ultrasonics, vol. 48, No. 4, pp. 1-24 (Aug. 2008).

Garstecki et al., "Formation of Bubbles and Droplets in Microfluidic Systems," Bulletin of the Polish Academy of Sciences, vol. 53, No. 4, pp. 361-372 (2005).

Gessner et al., "High-Resolution, High-Contrast Ultrasound Imaging Using a Prototype Dual-Frequency Transducer: In Vitro and In Vivo Studies," IEEE Transactions on Ultrasonics, Ferroelectrics, and Frequency Control, vol. 57, No. 8, pp. 1772-1781 (Aug. 2010).

Gessner et al., "Advances in Molecular Imaging with Ultrasound," Mol Imaging , vol. 9, No. 3, pp. 1-21 (Jun. 2010).

Gessner et al., "Radiation Force-Enhanced Targeted Imaging and Near Real-time Molecular Imaging Using a Dual-Frequency High-Resolution Transducer: In-vitro and In-vivo Results," Proceedings of the 2009 IEEE Ultrasonics Symposium, In Press, pp. 1-4, (2009).

Gessner et al., "Radiation Force-Enhanced Targeted Imaging Using a Dual-Frequency High Resolution Transducer," Abstract Submitted for Peer Review (Publication Date Unknown).

Gessner et al., "High-Resolution In-Vivo Ultraharmonic Contrast Imaging using a Dual-Frequency Transducer," Abstract Submitter for Peer Review (Publication Date Unknown).

Giesecke et al., "Ultrasound-Mediated Cavitation Thresholds of Liquid Perfluorocarbon Droplets in Vitro," Ultrasound in Medicine & Biology, vol. 29, No. 9, pp. 1359-1365 (2003).

Gingrich et al., "Partial CviJI Digestion as an Alternative Approach to Generate Cosmid Sublibraries for Large-Scale Sequencing Projects," Biotechniques, vol. 21 (1), pp. 99-104 (1996).

Giresi et al., "Isolation of Active Regulatory Elements from Eukaryotic Chromatin Using FAIRE (Formaldehyde Assisted Isolation of Regulatory Elements)," Methods, vol. 48, No. 3, pp. 1-13 (Jul. 2009).

Goll, "Design of Broad-Band Fluid-Loaded Ultrasonic Transducers," IEEE Transactions on Sonics and Ultrasonics, vol. SU-26, No. 6, pp. 385-393 (Nov. 1979).

Gramiak et al., "Echocardiography of the aortic root," Invest. Radiol., vol. 3, pp. 356-366 (1968).

Groschl, "Ultrasonic Separation of Suspended Particles—Part I: Fundamentals," Acustica, vol. 84, pp. 432-447 (1998).

Haworth et al., "Towards Aberration Correction of Transcranial Ultrasound Using Acoustic Droplet Vaporization," Ultrasound Med Biol, vol. 34, No. 3, pp. 1-24 (Mar. 2008).

Hengen, "Shearing DNA for Genomic Library Construction," Trends in Biochemical Sciences, vol. 22, pp. 273-274 (1997).

Hettiarachchi et al., "Controllable Microfluidic Synthesis of Multiphase Drug-Carrying Liposomes for Site-Targeted Therapy," Biotechnology Progress, vol. 25, No. 4, pp. 1-17 (2009).

Hettiarachchi et al., "On-chip Generation of Microbubbles as a Practical Technology for Manufacturing Contrast Agents for Ultrasonic Imaging," Lab Chip., vol. 7, No. 4, pp. 1-14 (Apr. 2007).

Hitchcock et al., "Ultrasound-Assisted Thrombolysis for Stroke Therapy: Better Thrombus Break-up with Bubbles," Stroke, vol. 41, pp. 1-8 (Oct. 2010).

(56)　　　　　References Cited

OTHER PUBLICATIONS

Hobbs et al., "Regulation of Transport Pathways in Tumor Vessels: Role of Tumor Type and Microenvironment," Proceedings of the National Academy of Sciences, vol. 95, No. 8, pp. 4607-4612 (Apr. 1998).

Hoff et al., "Oscillations of Polymeric Microbubbles: Effect of the Encapsulating Shell," The Journal of the Acoustical Society of America, vol. 107, No. 4, pp. 2272-2280 (2000).

Hoffman et al., "Genome-Wide Identification of DNA-Protein Interactions Using Chromatin Immunoprecipitation Coupled with Flow Cell Sequencing," Journal of Endocrinology, vol. 201(1), pp. 1-13 (2009).

Hoheisel et al., "Control of Partial Digestion Combining the Enzymes dam Methylase and Mbol," Nucleic Acids Research, vol. 17, No. 23, pp. 9571-9582 (1989).

Hopp et al., "Factory Physics, Foundations of Manufacturing Management," Second Edition, Chapter 7, pp. 213-227 (2008).

Huh et al., "A Gravity-Driven Microfluidic Particle Sorting Device with Hydrodynamic Separation Amplification," Analytical Chemistry, vol. 79, pp. 1-14 (Feb. 2007).

Hurrell, "Voltage to pressure conversion: are you getting 'phased' by the problem?," Journal of Physics: Conference Series, vol. 1, p. 57 (2004).

Hynynen et al., "Local and Reversible Blood-Brain Barrier Disruption by Noninvasive Focused Ultrasound at Frequencies Suitable for Trans-skull Sonications," NeuroImage, vol. 24, pp. 12-20 (2005).

Iyer et al., "Exploiting the Enhanced Permeability and Retention Effect for Tumor Targeting," Drug Discovery Today, vol. 11, No. 17/18, pp. 812-818 (2006).

Janzen et al., "Epigenetics: Tools and Technologies," Drug Discov Today Technol., vol. 7, No. 1, pp. 1-13 (2010).

Janzen et al., "Advances in improving the quality and flexibility of compound management," Journal of Biomolecular Screening, vol. 14, No. 5, pp. 444-451 (2009).

Janzen et al., "High Throughput Screening. Methods and Protocols, Second Edition," (2009).

Janzen et al., "Review: Advances in Improving the Quality and Flexibility of Compound Management," Journal of Biomolecular Screening, vol. 14, No. 5, pp. 444-451 (2009).

Janzen et al., "A Chemogenonic Approach to Discovering Target Selective Drugs," Chemical Biology and Drug Design, vol. 67, Issue 1, pp. 85-86 (2006).

Janzen, "High Throughput Screening: Methods and Protocols," (2002).

Jayaweera et al., "In Vivo Myocardial Kinetics of Air-Filled Albumin Microbubbles During Myocardial Contrast Echocardiography. Comparison with Radiolabeled Red Blood Cells," Circulation Research—The Journal of the American Heart Association, vol. 74, No. 6, pp. 1157-1165 (1994).

Jones et al., "Prospective Thermal Dosimetry: The Key to Hyperthermia's Future," International Journal of Hyperthermia, vol. 22, No. 3, pp. 247-253 (May 2006).

Ten Kate et al., "Molecular imaging of inflammation and intraplaque vasa vasorum: a step forward to identification of vulnerable plaques?," J. Nucl. Cardiol., vol. 17, pp. 897-912 (2010).

Kawabata et al., "Nanoparticles with Multiple Perfluorocarbons for Controllable Ultrasonically Induced Phase Shifting," Japanese Journal of Applied Physics, vol. 44, No. 6B, pp. 4548-4552 (2005).

Kaya et al., "Acoustic Responses of Monodisperse Lipid Encapsulated Microbubble Contrast Agents Produced by Flow Focusing," Bubble Science, Engineering and Technolology, vol. 2, No. 2, pp. 33-40 (Dec. 2010).

Kaya et al., "Changes in Lipid-Encapsulated Microbubble Population During Continuous Infusion and Methods to Maintain Consistency," Ultrasound in Medicine & Biology, vol. 35, No. 10, pp. 1-16 (Oct. 2009).

King et al., "Comparision between maximum radial expansion of ultrasound contrast agents and experimental postexcitation signal results," J. Acoust. Soc. Am., vol. 129, pp. 114-121 (2011).

King et al., "Determination of postexcitation thresholds for single ultrasound contrast agent microbubbles using double passive cavitation detection," J. Acoust. Soc. Am., vol. 127, pp. 3449-3455 (2010).

Klibanov, "Microbubble Contrast Agents—Targeted Ultrasound Imaging and Ultrasound-Assisted Drug-Delivery Applications," Investigative Radiology, vol. 41, No. 3, pp. 354-362 (2006).

Klibanov et al., "Targeting and Ultrasound Imaging of Microbubble-based Contrast Agents," Magnetic Resonance Materials in Physics, Biology, and Medicine, vol. 8, pp. 177-184 (1999).

Klibanov et al., "Targeting of Ultrasound Contrast Material. An in vitro Feasibility Study," Acta Radiologica, Supplement 412, pp. 113-120 (1997).

Knierim et al., "Systematic Comparison of Three Methods for Fragmentation of Long-range PCR Products for Next Generation Sequencing," PLoS One, vol. 6, Issue 11, e28240, pp. 1-6 (Nov. 2011).

Kogan et al., "Microbubbles in Imaging: Applications Beyond Ultrasound," In Bubble Science, Engineering, and Technology, vol. 2, No. 1, pp. 1-11 (Jun. 2010).

Kripfgans et al., "Acoustic Droplet Vaporization for Temporal and Spatial Control of Tissue Occlusion: A Kidney Study," IEEE Transactions on Ultrasonics, Ferroelectrics, and Frequency Control, vol. 52, No. 7, pp. 1101-1110 (2005).

Kripfgans et al., "On the Acoustic Vaporization of Micrometer-Sized Droplets," The Journal of the Acoustical Society of America, vol. 116, No. 1, pp. 272-281 (2004).

Kripfgans et al., "In Vivo Droplet Vaporization for Occlusion Therapy and Phase Aberration Correction," IEEE Transactions on Ultrasonics, Ferroelectrics, and Frequency Control, vol. 49, pp. 726-738 (2002).

Kripfgans et al., "Acoustic Droplet Vaporization for Therapeutic and Diagnostic Applications," Ultrasound in Med. & Biol., vol. 26, No. 7, pp. 1177-1189 (2000).

Krishnan et al., "Inertial lift on a Moving Sphere in Contact with a Plane Wall in a Shear Flow," Phys. Fluids, vol. 7, No. 11, pp. 2538-2545 (1995).

Kruse et al., "Spatial and Temporal-Controlled Tissue Heating on a Modified Clinical Ultrasound Scanner for Generating Mild Hyperthermia in Tumors," IEEE Transactions on Biomedical Engineering, vol. 57, No. 1, pp. 155-166 (Jan. 2010).

Kruse et al., "A New Imaging Strategy Using Wideband Transient Response of Ultrasound Contrast Agents," IEEE Transactions on Ultrasonics, Ferroelectrics and Frequency Control, vol. 52, No. 8, pp. 1-22 (Aug. 2005).

Kwan et al., "Microbubble Dissolution in a Multigas Environment," Langmuir, vol. 26, No. 9,, pp. 6542-6548 (2010).

Lamberti et al., "A New Approach for the Design of Ultrasono-Therapy Transducers," IEEE Transactions on Ultrasonics, Ferroelectrics, and Frequency Control, vol. 44, No. 1, pp. 77-84 (Jan. 1997).

Landmark et al., "Pharmacokinetics of Perfluorobutane Following Intravenous Bolus Injection and Continuous Infusion of Sonazoid™ in Healthy Volunteers and in Patients with Reduced Pulmonary Diffusing Capacity," Ultrasound in Med. & Biol., vol. 34, No. 3, pp. 494-501 (2008).

"DEFINITY®," Lantheus Medical Imaging. WayBack Machine https://web.archive.org/web/20101123011336/http://www.definityimaging.com/main.html? (Nov. 23, 2010).

Lanza et al., "Targeted Ultrasonic Contrast Agents for Molecular Imaging and Therapy," Current Problems in Cardiology, pp. 625-653 (Dec. 2003).

Lanza et al., "High-Frequency Ultrasonic Detection of Thrombi with a Targeted Contrast System," Ultrasound in Med. & Biol., vol. 23, No. 6, pp. 863-870 (1997).

Lanza et al., "A Novel Site—Targeted Ultrasonic Contrast Agent with Broad Biomedical Application," Circulation, vol. 94. pp. 1-9 (1996).

Lediju et al., "Short-lag spatial coherence imaging," 2010 IEEE International Ultrasonics Symposium, pp. 987-990 (2010).

Lee et al., "Oscillatory Vaporization and Acoustic Response of Droplet at High Pressure," International Communications in Heat and Mass Transfer, vol. 35, No. 10, pp. 1302-1306 (2008).

(56)　　　　　　References Cited

OTHER PUBLICATIONS

Leong-Poi et al., "Noninvasive Assessment of Angiogenesis by Ultrasound and Microbubbles Targeted to αv-Integrins," Circulation—Journal of the American Heart Association, vol. 107, pp. 455-460 (2003).

Lindner, "Contrast Ultrasound Molecular Imaging of Inflammation in Cardiovascular Disease," Cardiovascular Research, vol. 84, pp. 182-189 (2009).

Lindner, "Microbubbles in Medical Imaging: Current Applications and Future Directions," Nature Reviews—Drug Discovery, vol. 3, pp. 527-532 (Jun. 2004).

Lindner, "Evolving Applications for Contrast Ultrasound," The American Journal of Cardiology, vol. 90, No. 10A, pp. 72J-80J (2002).

Lindner et al., "Delivery of Drugs with Ultrasound," Echocardiography, vol. 18, No. 4, pp. 329-337 (May 2001).

Lindner et al., "Assessment of Resting Perfusion with Myocardial Contrast Echocardiography: Theoretical and Practical Considerations," The American Heart Journal, vol. 139, No. 2, Part 1, pp. 231-240 (2000).

Lindner et al., "Noninvasive Ultrasound Imaging of Inflammation Using Microbubbles Targeted to Activated Leukocytes," Circulation—Journal of the American Heart Association, vol. 102, No. 22, pp. 2745-2750 (2000).

Linker et al., "In Vivo Molecular Imaging of Adhesion Molecules in Experimental Autoimmune Encephalomyelitis (EAE)," Journal of Autoimmunity, vol. 25, pp. 199-205 (2005).

Lipinski, "Lead- and Drug-like compounds: the rule-of-five revolution," Drug Discovery Today, vol. 1, pp. 337-341 (2004).

Liu et al., "Protein Lysine Methyltransferase G9a Inhibitors: Design, Synthesis, and Structure Activity Relationships of 2,4-Diamino-7-aminoalkoxy-quinazolines," J. Med. Chem., vol. 53, PMCID: PMC2920043, NIHMSID: NIHMS220759, pp. 5844-5857 (2011).

Lo et al., "Acoustic Droplet Vaporization Threshold: Effects of Pulse Duration and Contrast Agent," IEEE Transactions on Ultrasonics, Ferroelectrics, and Frequency Control, vol. 54, No. 5, pp. 933-946 (2007).

Lo et al., "Spatial Control of Gas Bubbles and Their Effects on Acoustic Fields," Ultrasound Med Biol., vol. 32, No. 1, pp. 95-106 (2006).

Lockwood et al., "Modeling and Optimization of High-Frequency Ultrasound Transducers," IEEE Transactions on Ultrasonics, Ferroelectrics, and Frequency Control, vol. 41, No. 2, pp. 225-230 (Mar. 1994).

Lum et al., "Ultrasound Radiation Force Enables Targeted Deposition of Model Drug Carriers Loaded on Microbubbles," Journal of Controlled Release, vol. 111, No. 1-2, pp. 1-15 (Mar. 2006).

Macarron et al., "Impact of high-throughput screening in biomedical research," Nature Reviews Drug Discovery, vol. 10, pp. 188-195 (2011).

Macedo et al., "Acoustic Effects on Gas Bubbles in the Flows of Viscous Fluids and Whole Blood," The Journal of the Acoustical Society of America, vol. 53, No. 5, pp. 1327-1335 (1973).

Marmottant et al., "A Model for Large Amplitude Oscillations of Coated Bubbles Accounting for Buckling and Rupture," The Journal of the Acoustical Society of America, vol. 118, No. 6, pp. 3499-3505 (2005).

Marsh et al., "Molecular Imaging with Targeted Perfluorocarbon Nanoparticles: Quantification of the Concentration Dependence of Contrast Enhancement for Binding to Sparse Cellular Epitopes," Ultrasound Med Biol., vol. 33, No. 6, pp. 1-16 (Jun. 2007).

Martin et al., "Current status and prospects for microbubbles in ultrasound theranostics," Wiley Interdisciplinary Reviews: Nanomedicine and Nanobiotechnology, vol. 5. pp. 329-345 (2013).

Martz et al., "Precision Manufacture of Phase-Change Perflurocarbon Droplets Using Microfluidics," Ultrasound Med Biol., vol. 37, No. 11, pp. 1-13 (Nov. 2011).

Marvel et al., "The Development and Validation of a LIPUS System with Preliminary Observations of Ultrasonic Effects on Human Adult Stem Cells," IEEE Transactions on Ultrasonics, Ferroelectrics, and Frequency Control, vol. 57, No. 9, pp. 1977-1984 (Sep. 2010).

Marvel et al., "Applications of Low Intensity Pulsed Ultrasound for Functional Bone Tissue Engineering using Adult Stem Cells," IEEE International Ultrasonics Symposium Proceedings, pp. 357-360 (2009).

Matsuura et al., "Nanoparticle-Loaded Perfluorocarbon Droplets for Imaging and Therapy," IEEE International Ultrasonics Symposium (IUS), pp. 5-8 (2009).

Mattrey, "The Potential Role of Perfluorochemicals (PFCS) in Diagnostic Imaging," Artificial Cells, Blood Substitutes, and Immobilization Biotechnology, vol. 22, No. 2, pp. 295-313 (1994).

Mckeighen, "Design Guidelines for Medical Ultrasonic Arrays," SPIE, vol. 3341, pp. 1-18 (1998).

Meairs et al., "Microbubbles for Thrombolysis of Acute Ischemic Stroke," Cerebrovascular Diseases, vol. 27, pp. 55-65 (Apr. 16, 2009).

Meyer et al., "Freestream Nuclei and Traveling-Bubble Cavitation," Transactions of the ASME, vol. 114, pp. 672-679 (Dec. 1992).

Meyerson et al., "Advances in Understanding Cancer Genomes Through Second-Generation Sequencing," Nature Reviews, Genetics, vol. 11, pp. 685-696 (Oct. 2010).

Miller et al., "Bioeffects Considerations for Diagnostic Ultrasound Contrast Agents," J Ultrasound Med, vol. 27, pp. 611-632 (2008).

Miller et al., "Lysis and Sonoporation of Epidermoid and Phagocytic Monolayer Cells by Diagnostic Ultrasound Activation of Contrast Agent Gas Bodies," Ultrasound in Medicine and Biology, vol. 27, No. 8, pp. 1107-1113 (2001).

Miller et al., "Sonoporation of Monolayer Cells by Diagnostic Ultrasound Activation of Contrast-Agent Gas Bodies," Ultrasound in Medicine and Biology, vol. 26, No. 4, pp. 661-667 (2000).

Miller et al., "Cavitation Nucleation Agents for Nonthermal Ultrasound Therapy," Journal of the Acoustical Society of America, vol. 107, No. 6, pp. 3480-3486 (Jun. 2000).

Miller et al., "Sonoporation of Cultured Cells in the Rotating Tube Exposure System," Ultrasound in Medicine and Biology, vol. 25, No. 1, pp. 143-449 (1999).

Minnaert, "On musical air-bubbles and the sounds of running water," Philosophical Magazine, vol. 16, pp. 235-248 (1933).

Misaridis et al., "Use of modulated excitation signals in medical ultrasound. Part 1: Basic concepts and expected benefits," IEEE Transactions on Ultrasonics Ferroelectronics and Frequency Control, vol. 52, pp. 177-191 (2005).

Mitragotri, "Healing Sound: The Use of Ultrasound in Drug Delivery and Other Theraputic Applications," Nature Reviews, Drug Discovery, vol. 4, pp. 255-260 (Mar. 2005).

Morgan, "Experimental and Theoretical Evaluation of Ultrasonic Contrast Agent Behavior," Dissertation, University of Virginia, (Jan. 2001).

Morgan et al., "Experimental and Theoretical Evaluation of Microbubble Behavior: Effect of Transmitted Phase and Bubble Size," IEEE Transactions on Ultrasonics, Ferroelectrics, and Frequency Control, vol. 47, No. 6, pp. 1494-1509 (Nov. 2000).

Morgan et al., "Experimental and Theoretical Analysis of Individual Contrast Agent Behavior," IEEE Ultrasonics Symposium, vol. 2, pp. 1685-1688 (1999).

Morgan et al., "Changes in the Echoes from Ultrasonic Contrast Agents with Imaging Parameters," IEEE Transactions on Ultrasonics, Ferroelectrics, and Frequency Control, vol. 45, No. 6, pp. 1537-1548 (Nov. 1998).

Mullin et al., "Effect of Anesthesia Carrier Gas on In-Vivo Circulation Times of Ultrasound Microbubble Contrast Agents in Rats," Contrast Media Mol Imaging, vol. 6, No. 3, pp. 1-14 (2011).

Mulvagh et al., "Contrast Echocardiography: Current and Future Applications," Journal of the American Society of Echocardiography, vol. 13, No. 4, pp. 331-342 (Apr. 2000).

Needles et al., "Nonlinear contrast imaging with an array-based micro-ultrasound system," Ultrasound in Medicine & Biology, vol. 36, pp. 2097-2106 (2010).

Nyborg, "Solutions of the Bio-Heat Transfer Equation," Physics in Medicine and Biology, vol. 33, No. 7, pp. 785-792 (1988).

(56) References Cited

OTHER PUBLICATIONS

Oakley, "Calculation of Ultrasonic Transducer Signal-to-Noise Rations Using the KLM Model," IEEE Transactions on Ultrasonics, Ferroelectrics, and Frequency Control, vol. 44, No. 5, pp. 1018-1026 (Sep. 1997).

Oefner et al., "Efficient Random Subcloning of DNA Sheared in a Recirculating Point-Sink Flow System," Nucleic Acids Research, vol. 24, No. 20, pp. 3879-3886 (1996).

Okpodu et al., "Rapid Isolation of Nuclei From Carrot Suspension Culture Cells Using a BioNebulizer," BioTechniques, vol. 16, No. 1, pp. 154-158 (1994).

Osoegawa et al., "A Bacterial Artificial Chromosome Library for Sequencing the Complete Human Genome," Genome Research, vol. 11, No. 3, pp. 483-496 (2001).

Pan et al., "Study of Sonoporation Dynamics Affected by Ultrasound Duty Cycle," Ultrasound in Medicine and Biology, vol. 31, No. 6, pp. 849-856 (2005).

Pan et al., "Sonoporation of Cells for Drug and Gene Delivery," Conf Proc IEEE Eng Med Biol Soc, vol. 5, pp. 3531-3534 (2004).

Pancholi et al., "Novel Methods for Preparing Phospholipid Coated Microbubbles," Eur. Blophys. J., vol. 37, pp. 515-520 (2008).

Pancholi et al., "Generation of Microbubbles for Diagnostic and Therapeutic Applications Using a Novel Device," Journal of Drug Targeting, vol. 16, No. 6, pp. 494-501 (Jul. 2008).

Park et al., "Unsteady Forces on Spherical Bubbles," Experimnets in Fluids, vol. 19, pp. 167-172 (1995).

Patil et al., "Particle Diameter Influences Adhesion Under Flow," Biophysical Journal, vol. 80, pp. 1733-1743 (Apr. 2001).

Pitt et al., "Phase Transitions of Perfluorocarbon Nanoemulsion Induced with Ultrasound: A Mathematical Model," Ultrasonics Sonochemistry, vol. 21, pp. 879-891 (2014).

Pitt et al., "Ultrasonic Drug Delivery—A General Review," Expert Opinion on Drug Delivery, vol. 1, pp. 1-32 (Nov. 2004).

Plesset et al., "Bubble Dynamics and Cavitation," Annu. Rev. Fluid Mech., vol. 9, pp. 145-185 (1977).

Popa-Burke et al., "Streamlined System for Purifying and Quantifying a Diverse Library of Compounds and the Effect of Compound Concentration Measurements on the Accurate Interpretation of Biological Assay Results," Analytical Chemistry, vol. 76, No. 24, pp. 7278-7287 (Dec. 15, 2004).

Price et al., "Delivery of Colloidal Particles and Red Blood Cells to Tissue Through Microvessel Ruptures Created by Targeted Microbubble Destruction with Ultrasound," Journal of the American Heart Association, vol. 98, pp. 1264-1267 (Sep. 29, 1998).

Prosperetti, "Bubble Phenomena in Sound Fields: Part Two," Ultrasonics, vol. 22, pp. 115-124 (May 1984).

Qamar et al., "Dynamics of Acoustic Droplet Vaporization in Gas Embolotherapy," Applied Physics Letters, vol. 96, pp. 143702-1-143702-3 (2010).

Qamar et al., "Evolution of acoustically vaporized microdroplets in gas embolotherapy," Journal of Biomechanical Engineering, vol. 134, p. 031010-1-031010-13 (2012).

Rapoport, "Phase-shift, stimuli-responsive perfluorocarbon nanodroplets for drug delivery to cancer," Wiley Interdisciplinary Reviews: Nanomedicine and Nanobiotechnology, vol. 4, pp. 492-510 (2012).

Rapoport et al., "Ultrasound-mediated tumor imaging and nanotherapy using drug loaded, block copolymer stabilized perfluorocarbon nanoemulsions," Journal of Controlled Release, vol. 153, pp. 4-15 (2011).

Rapoport et al., "Cavitation Properties of Block Copolymer Stabilized Phase-Shift Nanoemulsions Used as Drug Carriers," Ultrasound Med Biol, vol. 36, No. 3, pp. 1-21 (Mar. 2010).

Rapoport et al., "Controlled and Targeted Tumor Chemotherapy by Ultrasound-activated Nanoemulsions/Microbubbles," J Control Release, vol. 138, No. 3, pp. 1-25 (Sep. 15, 2009).

Rapoport et al., "Microbubble Generation in Phase-Shift Nanoemulsions Used as Anticancer Drug Carriers," Bubble Sci Eng Technol, vol. 1, pp. 1-21 (2009).

Rapoport et al., "Multifunctional Nanoparticles for Combining Ultrasonic Tumor Imaging and Targeted Chemotherapy," J Natl Cancer Inst, vol. 99, pp. 1095-1106 (2007).

Reddy et al., "Coupled Dynamics of Translation and Collapse of Acoustically Driven Microbubbles," J. Acoust. Soc. Am., vol. 112, No. 4, pp. 1346-1352 (Oct. 2002).

Reinhardt et al., "Ultrasound Derived Imaging and Quantification of Cell Adhesion Molecules in Experimental Autoimmune Encephalomyelitis (EAE) by Sensitive Particle Acoustic Quantification (SPAQ)," NeuroImage, vol. 27, pp. 267-278 (2005).

Reznik et al., "The efficiency and stability of bubble formation by acoustic vaporization of submicron perfluorocarbon droplets," Ultrasonics, vol. 53, pp. 1368-1376 (2013).

Reznik et al., "Investigation of Vaporized Submicron Perfluorocarbon Droplets as an Ultrasound Contrast Agent," Ultrasound in Medicine & Biology, vol. 37, pp. 1271-1279 (2011).

Roe, "Shotgun Library Construction for DNA Sequencing," Methods in Molecular Biology, vol. 255, pp. 171-187 (2004).

Rychak et al., "Enhanced Targeting of Ultrasound Contrast Agents Using Acoustic Radiation Force," Ultrasound in Medicine and Biology, vol. 33, No. 7, pp. 1132-1139 (Jul. 2007).

Rychak et al., "Acoustic Radiation Force Enhances Targeted Delivery of Ultrasound Contrast Microbubbles: In Vitro Verification," IEEE Transactions on Ultrasonics, Ferroelectrices, and Frequency Control, vol. 52, No. 3, pp. 421-433 (Mar. 2005).

Rychak et al., "Deformable Gas-Filled Microbubbles Targeted to P-Selectin," Journal of Controlled Release, vol. 114, pp. 288-299 (2006).

Salgaonkar et al., "Passive cavitation imaging with ultrasound arrays," The Journal of the Acoustical Society of America, vol. 126, pp. 3071-3083 (2009).

Sassaroli et al., "Cavitation threshold of microbubbles in gel tunnels by focused ultrasound," Ultrasound in Medicine Biology, vol. 33, pp. 1651-1660 (2007).

Sboros et al., "The Assessment of Microvascular Flow and Tissue Perfusion Using Ultrasound Imaging," Proceedings of the Institution of Mechanical Engineers, Part H: Journal of Engineerying in Medicince, vol. 224, pp. 273-290 (2010).

Sboros, "Response of Contrast Agents to Ultrasound," Advanced Drug Delivery Reviews, No. 60, pp. 1117-1136 (Mar. 2008).

Schad et al., "In Vitro Characterization of Perfluorocarbon Droplets for Focused Ultrasound Therapy," Physics in Medicine and Biology, vol. 55, pp. 4933-4947 (2010).

Schoppee et al., "Chromatin Immunoprecipitation (ChiP): Revisiting the Efficacy of Sample Preparation, Sonication, Quantification of Sheared DNA, and Analysis via PCR," PLoS One, vol. 6, Issue 10, e26015, pp. 1-10 (Oct. 2011).

Schroeder et al., "Ultrasound Triggered Release of Cisplatin from Liposomes in Murine Tumors," Journal of Controlled Release, vol. 137, pp. 63-68 (2009).

Schumann et al., "Targeted-Microbubble Binding Selectively to GPIIb IIIa Receptors of Platelet Thrombi," Investigative Radiology, vol. 37, No. 11, pp. 587-593 (Nov. 2002).

Seed et al., "Representation of DNA Sequences in Recombinant DNA Libraries Prepared by Restriction Enzyme Partial Digestion," Gene, vol. 19, pp. 201-209 (Jun. 1982).

Selfridge et al., "KLM Transducer Model Implementation Using Transfer Matrices," IEEE Ultrasonics Symposium, pp. 875-877 (1985).

Sheeran et al., "Vaporization phenomena for ultrasound phase-change contrast agents assessed via high-speed optical microscopy," 2013 IEEE International Ultrasonics Symposium (IUS), pp. 1841-1844 (Jul. 21-25, 2013).

Sheeran et al., "Toward ultrasound molecular imaging with phase-change contrast agents: an in vitro proof of principle," Ultrasound Med. Biol., vol. 39, No. 5, pp. 893-902 (May 2013).

Sheeran et al., "Phase-transition thresholds and vaporization phenomena for ultrasound phase-change nanoemulsions assessed via high-speed optical microscopy," Physics in Medicine and Biology, vol. 58, p. 4513 (2013).

Sheeran et al., "Phase-change contrast agents for imaging and therapy," Curr. Pharm. Des., vol. 18, pp. 2152-2165 (2012).

(56) References Cited

OTHER PUBLICATIONS

Sheeran et al., "Design of Ultrasonically-Activatable Nanoparticles using Low Boiling Point Perfluorocarbons," Biomaterials, vol. 33, No. 11, pp. 1-21 (Apr. 2012).

Sheeran et al., "Formulation and Acoustic Studies of a New Phase-Shift Agent for Diagnostic and Therapeutic Ultrasound," Langmuir, vol. 27, No. 17, pp. 1-23 (Sep. 6, 2011).

Sheeran et al., "Decafluorobutane as a Phase-Change Contrast Agent for Low-Energy Extravascular Ultrasonic Imaging," Ultrasound in Medicine and Biology, vol. 37, No. 9, pp. 1518-1530 (2011).

Sheeran et al., "Perflourobutane as a Phase-Change Contrast Agent for Low-Energy Extravascular Ultrasound Imaging," pp. 1-8 (Publication Date Unknown).

Shortencarier et al., "A Method for Radiation-Force Localized Drug Delivery Using Gas-Filled Liposphores", IEEE Transactions on Ultrasonics, Ferroelectrics and Frequency Control, vol. 51, No. 7, pp. 822-831 (Jul. 2004).

Shpak et al., "Ultrafast dynamics of the acoustic vaporization of phase-change microdroplets," Journal of the Acoustical Society of America, vol. 134, pp. 1610-1621 (2013a).

Shpak et al., "The role of gas in ultrasonically driven bapor bubble growth," Physics in Medicine and Biology, vol. 58, pp. 2523-2535 (2013b).

Sirsi et al., "Microbubble Compositions, Properties and Biomedial Applications," Bubble Sci. Eng. Technol., vol. 1, pp. 1-28 (Nov. 2009).

Sittampalam et al., "Design of Signal Windows in High Throughput Screening Assays for Drug Discovery," Journal of Biomolecular Screening, vol. 2, No. 3, pp. 159-169 (1997).

Sittampalam et al., "High-Throughput Screening: Advances in Assay Technologies," Current Opinion in Chemical Biology, vol. 1(3), pp. 384-391 (1997).

Staub et al., "Contrast-Enhanced Ultrasound Imaging of the Vasa Vasorum: From Early Atherosclerosis to the Identification of Unstable Plaques," J. Am. Coll. Cardiol. Img., vol. 3, No. 7, pp. 761-771 (Jul. 2010).

Stephens et al., "Efficient Array Design for Sonotherapy," Phys Med Biol., vol. 53, No. 14, pp. 1-42 (Jul. 21, 2008).

Stephens et al., "Multi-frequency Array Development for Drug Delivery Therapies: Characterization and First Use of a Triple Row Ultrasound Probe," IEEE Ultrasonics Symposium, pp. 66-69 (2006).

Stieger et al., "Imaging of Angiogenesis Using Cadence Contrast Pulse Sequencing and Targeted Contrast Agents," Contrast Media & Molecular Imaging, vol. 3(1), pp. 9-18 (2008).

Stieger et al., "Enhancement of Vasular Permeability with Low-Frequency Contrast-Enhanced Ultrasound in the Chorioallantoic Membrane Model," Radiology, vol. 243, No. 1, pp. 112-121 (Apr. 2007).

Streeter et al., "Improving Sensitivity in Ultrasound Molecular Imaging by Tailoring Contrast Agent Size Distribution: In Vivo Studies," Molecular Imaging, vol. 9, No. 2, pp. 1-18 (Apr. 2010).

Stride et al., "Cavitation and Contrast: The Use of Bubbles in Ultrasound Imaging and Therapy," Proceedings of the Institution of Mechanical Engineers, Part H: Journal of Engineering in Medicine, vol. 224, pp. 171-191 (2010).

Strohm et al., "Vaporization of perfluorocarbon droplets using optical irradiation," Biomed. Opt. Express, vol. 2, pp. 1432-1442 (2011).

Takeuchi et al., "Enhanced Visualization of Intravascular and Left Atrial Appendage Thrombus with the Use of a Thrombus-Targeting Ultrasonographic Contrast Agent (MRX-408A1): In Vivo Experimental Echocardioraphic Studies," Journal of the American Society of Echocardiography, vol. 12, No. 12, pp. 1015-1021 (Dec. 1999).

Talu et al., "Needle Size and Injection Rate Impact Microbubble Contrast Agent Population," Ultrasound in Medicine & Biology, vol. 34, No. 7, pp. 1-8 (Jul. 2008).

Talu et al., "Maintaining Monodispersity in a Microbubble Population Formed by Flow-Focusing," Langmuir, vol. 24, No. 5, pp. 1-14 (Mar. 2008).

Talu et al., "Tailoring the Size Distribution of Ultrasound Contrast Agents: Possible Method for Improving Sensitivity in Molecular Imaging," Molecular Imaging, vol. 6, No. 6, pp. 1-19 (2007).

Talu et al., "Long-Term Stability by Lipid Coating Monodisperse Microbubbles Formed by a Flow-Focusing Device," Langmuir, vol. 22, No. 23, pp. 1-10 (Nov. 7, 2006).

Tan et al., "Microfluidic Separation of Satellite Droplets as the Basis of a Monodispersed Micron and Submicron Emulsification System," Lab Chip, vol. 5, pp. 1178-1183 (2005).

Tan et al., "Design of Microfludic Channel Geometries for the Control of Droplet Volume, Chemical Concentration, and Sorting," Lab Chip, vol. 4, pp. 292-298 (2004).

Tartis et al., "Therapeutic Effects of Paclitaxel-Containing Ultrasound Contrast Agents," Ultrasound in Medicine and Biology, vol. 32, No. 11, pp. 1771-1780 (2006).

Teh et al., "Droplet Microfluidics," Lab Chip, vol. 8, pp. 198-220 (2008).

Ten Kate et al., "Molecular Imaging of Inflammation and Intraplaque Vasa Vasorum: A Step Forward to Identification of Vulnerable Plaques?," Journal of Nuclear Cardiology, vol. 17, pp. 897-912 (2010).

Teytelman et al., "Impact of Chromatin Structures on DNA Processing for Genomic Analyses," PLoS One, vol. 4, Issue 8, e6700, pp. 1-11 (Aug. 2009).

Thorstenson et al., "An Automated Hydrodynamic Process for Controlled, Unbiased DNA Shearing," Genome Research, vol. 8, pp. 848-855 (Aug. 1998).

Tinkov et al., "Microbubbles as Ultrasound Triggered Drug Carriers," Journal of Pharmaceutical Sciences, vol. 98, No. 6, pp. 1935-1961 (2009).

Torchilin, "Passive and Active Drug Targeting: Drug Delivery to Tumors as an Example," Handbook of Experimental Pharmacology, pp. 3-53 (2010).

Tortoli et al., "Unexpected Doppler Effects from Microbubbles Moving Through an Ultrasound Beam," IEEE Ultrasonics Symposium, vol. 2, pp. 1729-1732 (1999).

Ueda et al., "Acoustic Cavitation as an Enhancing Mechanism of Low-Frequency Sonophoresis for Transdermal Drug Delivery," Biol. Pharm. Bull., vol. 32, No. 5, pp. 916-920 (2009).

Unger et al., "Therapeutic Applications of Lipid-Coated Microbubbles," Advanced Drug Delivery Reviews, vol. 56, pp. 1291-1314 (2004).

Unger et al., "Therapeutic Applications of Microbubbles," European Journal of Radiology, vol. 42, pp. 160-688 (2002).

Unger et al., "Local Drug and Gene Delivery Through Microbubbles," Progress in Cardiovascular Diseases, vol. 44, No. 1, pp. 45-54 (Jul./Aug. 2001).

Unger et al., "In Vitro Studies of a New Thrombus-Specific Ultrasound Contrast Agent," Am J Cardiol, vol. 81, No. 12A, pp. 58G-61G (1998).

van Wamel et al., "Vibrating Microbubbles Poking Individual Cells: Drug Transfer Into Cells Via Sonoporation," Journal of Controlled Release, vol. 112, pp. 149-155 (2006).

Vedadi et al., "A chemical probe selectively inhibits G9a and GLP methyltransferase activity in cells," Nature Chemical Biology, vol. 7, No. 8, pp. 1-21 (Jul. 10, 2011).

Villanueva, "Molecular Imaging of Cardiovascular Disease Using Ultrasound," J. Nucl. Cardiol., vol. 15, No. 4, pp. 1-18 (2008).

Villanueva et al., "Microbubbles Targeted to Intracellular Adhesion Molecule-1 Bind to Activated Coronary Artery Endothelial Cells," Circulation, vol. 98, pp. 1-6 (1998).

Vorkurka, "Comparison of Rayleigh's, Herring's, and Gilmore Models of Gas Bubbles," Acustica, vol. 59, pp. 214-219 (1986).

Walters et al., "Prediction of 'drug-likeness'", Advanced Drug Delivery Reviews, vol. 54, pp. 255-271 (2002).

Wang et al., "Controllable Microfludic Production of Multicomponent Multiple Emulsions," Lab Chip, vol. 11, pp. 1587-1592 (Mar. 9, 2011).

Ward et al., "Experimental Study of the Effects of Optison Concentration on Sonoporation In Vitro," Ultrasound in Medicine & Biology, vol. 26, No. 7, pp. 1169-1175 (May 2, 2000).

Watanabe et al., "Translational and Radical Motions of a Bubble in an Acoustic Standing Wave Field," Phys. Fluids A, vol. 5, No. 11, pp. 2682-2688 (Nov. 1993).

(56) References Cited

OTHER PUBLICATIONS

Wei et al., "Recent Advances in Myocardial Contrast Echoardiography," Curr. Opin. Cardiol., vol. 12, pp. 539-546 (1997).

Whittingham, "Contrast-specific imaging techniques: technical perspective," Contrast Media in Ultrasonography: Basic Principles and Clinical Applications, pp. 43-70 (2005).

Whitworth, "Discussion of One-D Piezoelectric Transducer Models With Loss," IEEE Transactions on Ultrasonics, Ferroelectrics and Frequency Control, vol. 48, No. 3, pp. 844-846 (May 2001).

Wigle et al., "Accessing Protein Methyltransferase and Demethylase Enzymology Using Microfluidic Capillary Electrophoresis," Chem Biol., vol. 17, No. 7, pp. 1-19 (2010).

Wigle et al., "Screening for Inhibitors of Low-Affinity Epigenetic Peptide-Protein Interactions: An AlphaScreen™-Based Assay for Antagonists of Methyl-Lysine Binding Proteins," Journal of Biomolecular Screening, vol. 15, No. 1, pp. 62-71 (2010).

Wilson et al., "Biomedical photoacoustics beyond thermal expansion using triggered nanodroplet vaporization for contrast-enhanced imaging," Nature Communications, vol. 3, p. 618 (2012).

Wilson et al., "Microbubble-Enhanced US in Body Imaging: What Role?," Radiology, vol. 257, No. 1, pp. 24-39 (Oct. 2010).

Wong et al., "Bubble Evolution in Acoustic Droplet Vaporization at Physiological Temperature via Ultra-high Speed Imaging," Soft Matter, vol. 7, pp. 4009-4016 (Jan. 2011).

Wong et al., "A Novel Method for Producing Partial Restriction Digestion of DNA Fragments by PCR with 5-methyl-CTP," Nucleic Acids Research, vol. 25, No. 20, pp. 4169-4171 (1997).

Wright et al., "Evaluation of New Thrombus-Specific Ultrasound Contrast Agent," Acad Radiol, vol. 5 (supp 1), pp. S240-S242 (1998).

Wu, "Sonograpic Demonstration of Duodenobiliary Reflux with Soda Enhancement," Journal of Clinical Ultrasound, vol. 32, No. 5, pp. 249-252 (Nov. 10, 2003).

Wu et al., "PSPICE Approach for Designing the Ultrasonic Piezoelectric Transducer for Medical Diagnostic Applications," Sensors and Actuators, vol. 75, pp. 186-198 (1999).

Xu et al., "Controllable Preparation of Monodisperse O/W and W/O Emulsions in the Same Microfluidic Device," Langmuir, vol. 22, No. 19, pp. 7943-7946 (Sep. 12, 2006).

Xu et al., "Generation of Monodisperse Particles by Using Microfluidics: Control Over Size, Shape, and Composition," Angew. Chem. Int. Ed., vol. 44, pp. 724-728 (2005).

Yasuda et al., "Using Acoustic Radiation Force as a Concentration Method for Erythrocytes," J. Acoust. Soc. Am., vol. 102, No. 1, pp. 642-645 (Jul. 1997).

Ye et al., "Microbubble Expansion in a Flexible Tube," Transactions of the ASME, vol. 128, pp. 554-563 (Aug. 2006).

Ye et al., "Direct Numerical Simulations of Micro-Bubble Expansion in Gas Embolotherapy," Journal of Biomedical Engineering, vol. 126, pp. 745-759 (Dec. 2004).

Zhang et al., "Acoustic Droplet Vaporization for Enhancement of Thermal Ablation by High Intensity Focused Ultrasound," Acad Radiol., vol. 18, No. 9, pp. 1-20 (Sep. 2011).

Zhang et al., "Initial Investigation of Acoustic Droplet Vaporization for Occulsion in Canine Kidney," Ultrasound Med Biol., vol. 36, No. 10, pp. 1-33 (Oct. 2010).

Zhang et al., "An in Vitro Study of a Phase-Shift Nanoemulsion: A Potential Nucleation Agent for Bubble-Enhanced HIFU Tumor Ablation," Ultrasound in Med. & Biol., vol. 36, No. 11, pp. 1856-1866 (2010).

Zhao et al., "Selective Imaging of Adherent Targeted Ultrasound Contrast Agents," Physics in Medicine and Biology, vol. 52, pp. 2055-2072 (2007).

Zhao et al., "Acoustic response from adherent targeted contrast agents," Journal of the Acoustical Society of America, vol. 120, No. 6, pp. 1-11 (2006).

Zhao et al., "Radiation-Force Assisted Targeting Facilitates Ultrasonic Molecular Imaging," Molecular Imaging, vol. 3, No. 3, pp. 135-148 (Jul. 2004).

Zheng et al., "A Novel Sensitive Targeted Imaging Technique for Ultrasonic Molecular Imaging," IEEE 2007 Ultrasonics Symposium, pp. 957-960 (2007).

Zheng et al., "Ultrasound-Driven Microbubble Oscillation and Translation Within Small Phantom Vessels," Ultrasound in Med. & Biol., vol. 33, No. 12, pp. 1978-1987 (2007).

Zhou et al., "The Size of Sonoporation Pores on the Cell Membrane," Ultrasound in Medicine & Biology, vol. 35, No. 10, pp. 1-10 (Oct. 2009).

Zipparo, "Mid- to High-Power Ultrasound Imaging Arrays—from ARFI to HIFU," IEEE 2003 Ultrasonics Symposium; Honolulu, Hawaii, pp. 684-688 (2003).

Fuciarelli et al., "Induction of Base Damage in DNA Solutions by Ultrasonic Cavitation," Free Radical Biology & Medicine, vol. 18, No. 2, pp. 231-238 (1995).

Goel et al., "Advances in Sonothrombolysis Techniques Using Piezoelectric Transducers," Sensors, vol. 20, pp. 1-17 (2020).

Goel et al., "Examining the Influence of Low-Dose Tissue Plasminogen Activator on Microbubble-Mediated Forward-Viewing Intravascular Sonothrombolysis," Ultrasound in Med. & Biol., vol. 46, No. 7, pp. 1-9 (2020).

Kim et al., "A Comparison of Sonothrombolysis in Aged Clots Between Low-Boiling-Point Phase-Change Nanodroplets and Microbubbles of the Same Composition," Ultrasound in Med. & Biol., vol. 46, No. 11, pp. 1-10 (2020).

Kim et al., "Miniaturized Intracavitary Forward-Looking Ultrasound Transducer for Tissue Ablation," IEEE Transactions on Biomedical Engineering, vol. 67, No. 7, pp. 1-10 (Jul. 2020).

Liu et al., "High-resolution intravascular MRI-guided perivascular ultrasound ablation," Magn Reson Med., vol. 83, pp. 1-14 (2020).

Ma et al., "Deep Penetration of Targeted Nanobubbles Enhanced Cavitation Effect on Thrombolytic Capacity," Bioconjugate Chem, vol. 31, pp. 1-6 (2020).

Non-Final Office Action for U.S. Appl. No. 15/247,840 (Oct. 6, 2020).

Final Office Action for U.S. Appl. No. 15/990,171 (Oct. 2, 2020).

Szablowski et al., "Achieving Spatial and Molecular Specificity with Ultrasound-Targeted Biomolecular Nanotherapeutics," Acc Chem Res., vol. 52, No. 9, pp. 1-17 (Sep. 17, 2019).

Zhang et al., "Sonothrombolysis with Magnetic Microbubbles Under a Rotational Magnetic Field," Ultrasonics, vol. 98, pp. 1-26 (Sep. 2019).

Li et al., "Spontaneous Nucleation of Stable Perfluorocarbon Emulsions for Ultrasound Contrast Agents," Nano Lett., vol. 19, pp. 1-9 (2019).

Rojas et al., "Vaporization Detection Imaging: A Technique for Imaging Low-Boiling-Point Phase-Change Contrast Agents with a High Depth of Penetration and Contrast-to-Tissue Ratio," Ultrasound in Med. & Biol., vol. 45, No. 1, pp. 1-16 (2019).

Engelberger et al., "Enhanced Thrombolysis by Ultrasound-Assisted Catheter-Directed Thrombolysis and Microbubbles in an In Vitro Model of Iliofemoral Deep Vein Thrombosis," Thrombosis and Haemostasis, vol. 119, No. 7/2019, pp. 1094-1101 (Jun. 5, 2019).

Vanhille et al., "Numerical Simulations of the Nonlinear Interaction of a Bubble Cloud and High Intensity Focused Ultrasound Field," Acoustics, vol. 1, pp. 1-12 (2019).

Wu et al., "Focused Ultrasound-Facilitated Brain Drug Delivery Using Optimized Nanodroplets: Vaporization Efficiency Dictates Large Molecular Delivery," Phys Med Biol., vol. 63, No. 3, pp. 1-24 (2019).

Suo et al., "Dynamic assessment of dual-frequency microbubble-mediated sonothrombolysis in vitro," Journal of Applied Physics, vol. 125, pp. 1-11 (Feb. 26, 2019).

Zhong et al., "Low-Intensity Focused Ultrasound-Responsive Phase-Transitional Nanoparticles for Thrombolysis without Vascular Damage: A Synergistic Nonpharmaceutical Strategy," ACS Nano, vol. 13, pp. 1-17 (2019).

Shi et al., "Integrated histotripsy and bubble coalescence transducer for thrombolysis," Ultrasound Med Biol., vol. 44, No. 12, pp. 1-27 (Dec. 2018).

(56) References Cited

OTHER PUBLICATIONS

Brubler et al., "Nanoscaled ultrasound contrast agents for enhanced sonothrombolysis," Colloids and Surfaces B: Biointerfaces, vol. 172, pp. 1-6 (2018).

Mazzolai et al., "Diagnosis and management of acute deep vein thrombosis: a joint consensus document from the European Society of Cardiology working groups of aorta and peripheral vascular diseases and pulmonary circulation and right ventricular function," European Heart Journal, vol. 39, pp. 1-14 (2018).

Goudot et al., "Pulsed cavitational therapy using high-frequency ultrasound for the treatment of deep vein thrombosis in an in vitro model of human blood clot," Physics in Medicine and Biology, vol. 62, No. 24, pp. 1-26 (2017).

Zhang et al., "Noninvasive Thrombolysis using Microtripsy in a Porcine Deep Vein Thrombosis Model," Ultrasound Med Biol., vol. 43, No. 7, pp. 1-27 (Jul. 2017).

Kim et al., "Intravascular forward-looking ultrasound transducers for microbubble-mediated sonothrombolysis," Scientific Reports, vol. 7, No. 3454, pp. 1-10 (Jun. 14, 2017).

Suo et al., "Microbubble mediated dual-frequency high intensity focused ultrasound thrombolysis: An In vitro study," Appl. Phys. Lett., vol. 110, pp. 1-5 (Jan. 10, 2017).

Fix et al., "An evaluation of the sonoporation potential of low-boiling point phase-change ultrasound contrast agents in vitro," Journal of Therapeutic Ultrasound, vol. 5, No. 7, pp. 1-11 (2017).

Yang et al., "Effect of pulse repetition frequency of high-intensity focused ultrasound on in vitro thrombolysis," Ultrasonics Sonochemistry, vol. 35, pp. 1-9 (2017).

Escoffre et al., "Therapeutic Ultrasound," Advances in Experimental Medicine and Biology, vol. 880, pp. 1-15 (2016).

Song et al., "Ultrasound Triggered Tumor Oxygenation with Oxygen-Shuttle Nanoperfluorocarbon to Overcome Hypoxia-Associated Resistance in Cancer Therapies," Nano Lett., vol. 16, pp. 1-9 (2016).

Chu et al., "Focused Ultrasound-Induced Blood-Brain Barrier Opening: Association with Mechanical Index and Cavitation Index Analyzed by Dynamic Contrast-Enhanced Magnetic-Resonance Imaging," Nature, Scientific Reports, vol. 6, No. 33264, pp. 1-13 (Sep. 15, 2016).

Zhang et al., "Histotripsy Thrombolysis on Retracted Clots," Ultrasound Med Biol., vol. 42, No. 8, pp. 1-35 (Aug. 2016).

Bader et al., "Efficacy of histotripsy combined with rt-PA in vitro," Phys Med Biol., vol. 61, No. 14, pp. 1-35 (Jul. 21, 2016).

DiNisio et al., "Deep vein thrombosis and pulmonary embolism," Lancet, vol. 388, pp. 1-14 (Jun. 30, 2016).

Luke et al., "Super-Resolution Ultrasound Imaging in Vivo with Transient Laser-Activated Nanodroplets," Nano Lett., vol. 16, No. 4, pp. 1-9 (Apr. 13, 2016).

Zhang et al., "Histotripsy Thrombolysis on Retracted Clots," Ultrasound in Med. & Biol., vol. 42, No. 8, pp. 1-16 (2016).

Streiff et al., "Guidance for the treatment of deep vein thrombosis and pulmonary embolism," J Thromb Thrombolysis, vol. 41, pp. 1-36 (2016).

Watson et al., "Thrombolysis for accurate deep vein thrombosis," Cochrane Database of Systematic Reviews, vol. 11, pp. 1-62 (2016).

Zhang et al., "Non-invasive Thrombolysis using Microtripsy: A Parameter Study," IEEE Trans Ultrason Ferroelectr Freq Control., vol. 62, No. 12, pp. 1-34 (Dec. 2015).

Dixon et al., "Microbubble-Mediated Intravascular Ultrasound Imaging and Drug Delivery," IEEE Transactions on Ultrasonics, Ferroelectrics, and Frequency Control, vol. 62, No. 9, pp. 1-12 (Sep. 2015).

Heit, "Epidemiology of venous thromboembolism," Nat Rev Cardiol., vol. 12, No. 8, pp. 1-27 (Aug. 2015).

Sen et al., "Mechanical Index," Anatol J Cardiol, vol. 15, pp. 334-336 (2015).

Zhang et al., "Non-invasive Thrombolysis using Histotripsy beyond the "Intrinsic" Threshold (Microtripsy)," IEEE Trans Ultrason Ferroelectr Feq Control., vol. 62, No. 7, pp. 1-35 (Jul. 2015).

Acconcia et al., "The Effect of Short Duration Ultrasound Pulses on the Interaction Between Individual Microbubbles and Fibrin Clots," Ultrasound in Med. & Biol., vol. 41, No. 10, pp. 1-9 (2015).

Engelberger et al., Ultrasound-Assisted Versus Conventional Catheter-Directed Thrombolysis for Acute Iliofemoral Deep Vein Thrombosis, Circ Cardiovasc Interv, pp. 1-9 (2015).

Kim et al., "Phantom evaluation of stacked-type dual-frequency 1-3 composite transducers: A feasibility study on intracavitary acoustic angiography," Ultrasonics, vol. 63, pp. 1-9 (2015).

Lindsey et al., "On the relationship between microbubble fragmentation, deflation, and broadband superharmonic signal production," Ultrasound Med Biol., vol. 41, No. 6, pp. 1-30 (Jun. 2015).

Suo et al., "Thrombolysis using multi-frequency high intensity focused ultrasound at MHz range: an in vitro study," Phys. Med. Biol., vol. 60, pp. 1-17 (2015).

Xu et al., "Dependence of pulsed focused ultrasound induced thrombolysis on duty cycle and cavitation bubble size distribution," Ultrasonics Sonochemistry, vol. 22, pp. 1-7 2015).

Johnston et al., "Mechanical characterization of bulk Sylgard 184 for microfluidics and microengineering," J. Micromech. Microeng., vol. 24, pp. 1-9 (2014).

Pajek et al., "High intensity focused ultrasound sonothrombolysis: the use of perfluorocarbon droplets to achieve clot lysis at reduced acoustic powers," Ultrasound Med Biol., vol. 40, No. 9, pp. 1-22 (Sep. 2014).

Acconcia et al., "Interactions Between Individual Ultrasound-Stimulated Microbubbles and Fibrin Clots," Ultrasound in Med. & Biol., vol. 40, No. 9, pp. 1-17 (2014).

Owings, "FDA Clears EKOS EkoSonic Endovascular System," FDA News, www.fdanews.com/articles/164759-fda-clears-ekos-ekosonic-endovascular-system, pp. 1-2 (May 27, 2014).

Kim et al., "Homogenization of PMN-PT/epoxy 1-3 piezocomposites by resonator measurements and finite element analysis ," Sensors and Actuators A, vol. 206, pp. 1-10 (2014).

Shaw et al., "Pathophysiological mechanisms of high-intensity focused ultrasound-mediated vascular occlusion and relevance to non-invasive fetal surgery," J. R. Soc. Interface, vol. 11, pp. 1-17 (2014).

Dixon et al., "Enhanced Intracellular Delivery of a Model Drug Using Microbubbles Produced by a Microfluidic Device," Ultrasound in Med. & Biol., vol. 39, No. 7, pp. 1-10 (2013).

Holscher et al., "Effects of varying duty cycle and pulse width on high-intensity focused ultrasound (HIFU)-induced transcranial thrombolysis," Journal of Therapeutic Ultrasound, vol. 1, No. 18, pp. 1-5 (2013).

Ma et al., "Design, Fabrication, and Characterization of a Single-Aperture 1.5-MHz/3-MHz Dual-Frequency HIFU Transducer," IEEE Transactions of Ultrasonics, Ferroelectrics, and Frequency Control, vol. 60, No. 7, pp. 1-12 (Jul. 2013).

Sutton et al. "Clot retraction affects the extent of ultrasound-enhanced thrombolysis in an ex vivo porcine thrombosis model," Ultrasound Med Biol., vol. 39, No. 5, pp. 1-23 (May 2013).

Galanaud et al., "The history and historical treatments of deep vein thrombosis,"Journal of Thrombosis and Haemostasis, vol. 11, pp. 1-10 (2013).

Sommer et al., "Applicators for MR-Guided Ultrasonic Ablation of BPH," Invest Radiol., vol. 48, No. 6, pp. 1-18 (Jun. 2013).

Li et al., "Development of Piezoelectric Ultrasonic Thrombolysis Device for Blood Clot Emulsification," International Scholarly Research Network, vol. 2012, pp. 1-7 (2012).

Ballehaninna et al., "Acute superior mesenteric artery embolism: reperfusion with AngioJet hydrodynamic suction thrombectomy and pharmacologic thrombolysis with the EKOS catheter," Vascular, vol. 20, No. 3, pp. 166-170 (2012).

Burgess et al., "High-Intensity Focused Ultrasound (HIFU) for Dissolution of Clots in a Rabbit Model of Embolic Stroke," PLoS One, vol. 7, No. 8, pp. 1-7 (Aug. 2012).

Jin et al., "Ultrasound-triggered thrombolysis using urokinase-loaded nanogels," International Journal of Pharmaceutics, vol. 434, pp. 1-7 (2012).

Wright et al., "In Vitro and In Vivo High Intensity Focused Ultrasound Thrombolysis," Invest Radiol., vol. 47, No. 4, pp. 1-25 (Apr. 2012).

(56)                  References Cited

OTHER PUBLICATIONS

Holscher et al., "Noninvasive Transcranial Clot Lysis Using High Intensity Focused Ultrasound," J Neurol Neurophysiol, pp. 1-7 (2011).
Maxwell et al., "Cavitation clouds created by shock scattering from bubbles during histotripsy," J. Acoust. Soc. Am., vol. 130, No. 4, pp. 1888-1898 (Oct. 2011).
Previtali et al., "Risk factors for venous and arterial thrombosis," Blood Transfus., vol. 9, pp. 1-19 (2011).
Galiuto et al., "The EAE Textbook of Echocardiography," European Society of Cardiology, 2 ed., pp. 1-37 (May 2011).
Karthikesalingam et al., "A Systematic Review of Percutaneous Mechanical Thrombectomy in the Treatment of Deep Venous Thrombosis," Eur J Vasc Endovasc Surg, vol. 41, pp. 1-12 (2011).
Mast et al., "Treatment of Rabbit Liver Cancer In Vivo Using Miniaturized Image-Ablate Ultrasound Arrays," Ultrasound in Med. & Biol., vol. 37, No. 10, pp. 1-13 (2011).
Beckman et al., "Venous Thromboembolism A Public Health Concern," Am J Prev Med, vol. 38, No. 4S, pp. 1-7 (2010).
Kuo et al., "Catheter-directed Therapy for the Treatment of Massive Pulmonary Embolism: Systematic Review and Meta-analysis of Modern Techniques," J Vasc Interv Radiol, vol. 20, pp. 1-10 (2009).
Robert-Ebadi et al., "Use of anticoagulants in elderly patients: practical recommendations," Clinical Interventions in Aging, vol. 4, pp. 165-178 (2009).
"Safety and Effectiveness of a New Generation of Mechanical Devices for Clot Removal in Intracranial Large Vessel Occlusive Disease," The Penumbra Pivotal Stroke Trial, pp. 1-8 (2009).
Datta et al., "Ultrasound-enhanced thrombolysis using Definity as a cavitation nucleation agent," Ultrasound Med Biol., vol. 34, No. 9, pp. 1-24 (Sep. 2008).
Chopra et al., "MRI-compatible transurethral ultrasound system for the treatment of localized prostate cancer using rotational control," Med. Phys., vol. 35, No. 4, pp. 1-13 (Apr. 2008).
Owens, "Ultrasound-Enhanced Thrombolysis: EKOS EndoWave Infusion Catheter System," Seminars in Interventional Radiology, vol. 25, No. 1, pp. 1-5 (2008).
Prokop et al., "Cavitational Mechanisms in Ultrasound-Accelerated Fibrinolysis," Ultrasound in Med. & Biol., vol. 33, No. 6, pp. 1-10 (2007).
Van Ha, "Complications of Inferior Vena Caval Filters," Seminars in Interventional Radiology, vol. 23, No. 2, pp. 1-6 (2006).
Melodelima et al., "Transoesophageal Ultrasound Applicator for Sector-Based Thermal Ablation: First In Vivo Experiments," Ultrasound in Med. & Biol., vol. 29, No. 2, pp. 1-7 (2003).
Greenfield et al., "Recurrent thromboembolism in patients with vena cava filters," Journal of Vascular Surgery, vol. 33, No. 3, pp. 510-514 (2001).
Goodman, "Toward Evidence-Based Medical Statistics. 1: The P Value Fallacy," Ann Intern Med., pp. 995-1004 (1999).
Ward et al., "Ultrasound-induced cell lysis and sonoporation enhanced by contrast agents," The Journal of the Acoustical Society of America, vol. 105, pp. 1-8 (1999).
Tachibana et al., "Albumin Microbubble Echo-Contrast Material as an Enhancer for Ultrasound Accelerated Thrombolysis," Circulation, vol. 92, No. 5, pp. 1-7 (1995).
Mills et al., "Multi-Layered PZT/Polymer Composites to Increase Signal-to-Noise Ratio and Resolution for Medical Ultrasound Transducers Part II: Thick Film Technology," IEEE Transactions on Ultrasonics, Ferroelectrics, and Frequency Control, vol. 49, No. 7, pp. 1005-1014 (Jul. 2002).
Fan et al., "Nonlinear Constitutive Behavior of Soft and Hard PZT: Experiments and Modeling," Acta mater., vol. 47, No. 17, pp. 4415-4425 (1999).
Kahn, "The Clinical Diagnosis of Deep Venous Thrombosis," Arch Intern Med., vol. 158, pp. 1-9 (Nov. 23, 1998).
Anderson et al., "A Population-Based Perspective of the Hospital Incidence and Case-Fatality Rates of Deep Vein Thrombosis and Pulmonary Embolism," Arch Intern Med, vol. 151, pp. 1-6 (May 1991).

Sponer, "Theoretical estimation of the cavitation threshold for very short pulses of ultrasound," Ultrasonics, vol. 29, pp. 376-380 (Sep. 1991).
Stone et al., "Pulsed-high intensity focused ultrasound enhanced tPA mediated thrombolysis in a novel in vivo clot model, a pilot study," Thromb Res., vol. 121, No. 2, pp. 1-15 (2007).
Datta et al., "Correlation of Cavitation with Ultrasound Enhancement of Thrombolysis," Ultrasound Med Biol., vol. 32, No. 8, pp. 1-20 (Aug. 2006).
Mitragotri, "Healing sound: the use of ultrasound in drug delivery and other therapeutic applications," Drug Discovery, vol. 4, pp. 1-6 (Mar. 2005).
Restriction Requirement for U.S. Appl. No. 17/479,395 (Mar. 3, 2023).
Issue Notification for U.S. Appl. No. 15/990,171 (Oct. 13, 2022).
Notice of Allowance Fee(s) Due, Examiner-Initiated Interview Summary and AFCP 2.0 Decision for U.S. Appl. No. 15/990,171 (Jun. 22, 2022).
Final Office Action for U.S. Appl. No. 15/990,171 (Apr. 7, 2022).
Final Office Action for U.S. Appl. No. 16/317,983 (Mar. 8, 2023).
Non-Final Office Action for U.S. Appl. No. 16/317,983 (Jul. 21, 2022).
Restriction Requirement for U.S. Appl. No. 16/317,983 (Feb. 22, 2022).
Non-Final Office Action for U.S. Appl. No. 16/317,983 (Aug. 7, 2023).
Non-Final Office Action for U.S. Appl. No. 17/479,395 (Jun. 23, 2023).
Non-Final Office Action for U.S. Appl. No. 17/198,926 (May 8, 2024).
Final Office Action for U.S. Appl. No. 17/479,395 (Mar. 27, 2024).
Final Office Action for U.S. Appl. No. 16/317,983 (Mar. 4, 2024).
Restriction Requirement for U.S. Appl. No. 17/198,926 (Feb. 16, 2024).
Advisory Action for U.S. Appl. No. 17/479,395 (Aug. 6, 2024).
Kukizaki, et al., "Effect of surfactant type on microbubble formation behavior using Shirasu porous glass (SPG) membranes", Colloids and Surfaces A: Physiochemical and Engineering Aspects 326, p. 129-137. (Year:2008).
Non-Final Office Action for U.S. Appl. No. 17/961,538 (Aug. 4, 2025).
Non-Final Office Action for U.S. Appl. No. 17/198,926 (Jul. 18, 2025).
Applicant-Initiated Interview Summary for U.S. Appl. No. 17/198,926 (Jun. 11, 2025).
Advisory Action for U.S. Appl. No. 17/198,926 (Jun. 4, 2025).
Ma, et al., "Deep Penetration of Targeted Nanobubbles Enhanced Cavitation Effect on Thrombolytic Capacity", Bioconjugate Chemistry, 2020, 31, 369-374.
Matsunaga, Terry O., et al. "Phase-change nanoparticles using highly volatile perfluorocarbons: toward a platform for extravascular ultrasound imaging." *Theranostics* 2.12 (2012): 1185.
Final Office Action for U.S. Appl. No. 17/198,926 (Jan. 23, 2025).
T. Truelsen, S. Begg, C. Mathers, The global burden of cerebrovascular disease, Glob. Burd. Dis. 1-67, (2005).
J.H. Rha, J.L. Saver, The impact of recanalization on ischemic stroke outcome: A meta-analysis, Stroke. 38, 967-973 (2007).
W. Hacke, M. Kaste, et al, Thrombolysis with Alteplase 3 to 4.5 Hours after Acute Ischemic Stroke, N. Engl. J. Med. 359, 1317-1329; (2008).
T.N.I. of N.D. and S. rt-P.S.S. Group, Tissue Plasminogen Activator for Acute Ischemic Stroke, N. Engl. J. Med. 333, 1581-1588, (1995).
J. Edlow, Clinical Policy: Use of Intravenous tPA for the Management of Acute Ischemic Stroke in the Emergency Department., Ann. Emerg. Med. 61, 225-43, (2013).
B.C.V. Campbell, et al, Endovascular Therapy for Ischemic Stroke with Perfusion-Imaging Selection, N. Engl. J. Med. 372, 1009-1018, (2015).
S. Ricci, et al, Sonothrombolysis for acute ischaemic stroke, Cochrane Database Syst. Rev. (2012).

(56)  References Cited

OTHER PUBLICATIONS

Berkhemer, Olvert A., et al. "A randomized trial of intraarterial treatment for acute ischemic stroke." New England Journal of Medicine 372.1: 11-20, (2015).

L. Auboire, C.A. Sennoga, J.M. Hyvelin, F. Ossant, J.M. Escoffre, F. Tranquart, A. Bouakaz, Microbubbles combined with ultrasound therapy in ischemic stroke: A systematic review of in-vivo preclinical studies, PLoS One. 13 (2018).

T.R. Porter, R.F. LeVeen, R. Fox, A. Kricsfeld, F. Xie, Thrombolytic enhancement with perfluorocarbon-exposed sonicated dextrose albumin microbubbles, Am. Heart J. 132 (1996).

A. Angelika, et al, Molecular Imaging of Human Thrombus With Novel Abciximab Immunobubbles and Ultrasound, Stroke. 38, 1508-1514, (2007).

F. Xie, et al, Diagnostic ultrasound combined with glycoprotein lib/lila-targeted microbubbles improves microvascular recovery after acute coronary thrombotic occlusions, Circulation. 119, 1378-1385, (2009).

M.J. Martin, E.M.L. Chung, et al, Enhanced detection of thromboemboli with the use of targeted microbubbles, Stroke. 38, 2726-2732, (2007).

X. Wang, et al, Novel single-chain antibody-targeted microbubbles for molecular ultrasound imaging of thrombosis: Validation of a unique noninvasive method for rapid and sensitive detection of thrombi and monitoring of success or failure of thrombolysis in mice, Circulation. 125, 3117-3126, (2012).

B. Chertok, R. Langer, Circulating magnetic microbubbles for localized real-time control of drug delivery by ultrasonography-guided magnetic targeting and ultrasound, Theranostics. 8, 341-357, (2018).

M. De Saint Victor, D. Carugo, L.C. Barnsley, J. Owen, C.C. Coussios, E. Stride, Magnetic targeting to enhance microbubble delivery in an occluded microarterial bifurcation, Phys. Med. Bioi. 62, 7451-7470, (2017).

A.S. Drozdov, V. V. Vinogradov, I.P. Dudanov, V. V. Vinogradov, Leach-proof magnetic thrombolytic nanoparticles and coatings of enhanced activity, Sci. Rep. 6 28119, (2016).

Y. Gao, C.U. Chan,et al., Controlled nanoparticle release from stable magnetic microbubble oscillations, NPG Asia Mater. 8, e260-10, (2016).

H. Mannell, et al., Site directed vascular gene delivery in vivo by ultrasonic destruction of magnetic nanoparticle coated microbubbles, Nanomedicine Nanotechnology, Bioi. Med. 8, 1309-1318, (2012).

M.D. Torno, et al, Improvement of in vitro thrombolysis employing magnetically-guided microspheres, Thromb. Res. 121, 799-811, (2008).

F. Bi, J. Zhang, Y. Su, Y.C. Tang, J.N. Liu, Chemical conjugation of urokinase to magnetic nanoparticles for targeted thrombolysis, Biomaterials. 30, 5125-5130, (2009).

J. Owen, et al, Magnetic targeting of microbubbles against physiologically relevant flow conditions, Interface Focus. 5, 1-12, (2015).

M. Arruebo, R. Fernandez-Pacheco, M.R. Ibarra, J. Santamaria, Magnetic nanoparticles for drug delivery, Nano Today. 2, 22-32, (2007).

H.L. Karlsson, J. Gustafsson, P. Cronholm, L. Moiler, Size-dependent toxicity of metal oxide particles—A comparison between nano- and micrometer size, Toxicol. Lett. 188 (2009).

A.K. Gupta, A.S.G. Curtis, Surface modified superparamagnetic nanoparticles for drug delivery: Interaction studies with human fibroblasts in culture, J. Mater. Sci. Mater. Med. 15, 493-496, (2004).

H. Otsuka, Y. Nagasaki, K. Kataoka, PEGylated nanoparticles for biological and pharmaceutical applications, Adv. Drug Deliv. Rev. 55, 403-419, (2003).

A. Chilkoti, M.R. Dreher, D.E. Meyer, Design of thermally responsive, recombinant polypeptide carriers for targeted drug delivery, Adv. Drug Deliv. Rev. 54, 1093-1111, (2002).

F. Yang, Y. Li, Z. Chen, Y. Zhang, J. Wu, N. Gu, Superparamagnetic iron oxide nanoparticle-embedded encapsulated microbubbles as dual contrast agents of magnetic resonance and ultrasound imaging, Biomaterials. 30, 3882-3890, (2009).

D. Vlaskou, et al., Magnetic and acoustically active lipospheres for magnetically targeted nucleic acid delivery, Adv. Funct. Mater. 20, 3881-3894, (2010).

C.C. Chen, M.A. Borden, The role of poly(ethylene glycol) brush architecture in complement activation on targeted microbubble surfaces, Biomaterials. 32, 6579-6587, (2011).

A. Barrefelt, et al., Biodistribution, kinetics, and biological fate of SPION microbubbles in the rat, Int. J. Nanomedicine. 8, 3241-3254, (2013).

H.L. Karlsson, P. Cronholm, J. Gustafsson, L. Moiler, Copper Oxide Nanoparticles Are Highly Toxic: A Comparison between Metal Oxide Nanoparticles and Carbon Nanotubes, Chem. Res. Toxicol. 21, 1726-1732, (2008).

B. Ankamwar, et al., Biocompatibility of Fe304nanoparticles evaluated by in vitro cytotoxicity assays using normal, glia and breast cancer cells, Nanotechnology. 21, 75102, (2010).

Y. Anzai, et al., Evaluation of neck and body metastases to nodes with ferumoxtran 10-enhanced MR imaging: phase III safety and efficacy study., Radiology. 228, 777-788, (2003).

R. Weissleder, et al., Superparamagnetic iron oxide: pharmacokinetics and toxicity., AJR. Am. J. Roentgenol. 152, 167-73, (1989).

N. Kucher, et al., Randomized, Controlled Trial of Ultrasound-Assisted Catheter-Directed Thrombolysis for Acute Intermediate-Risk Pulmonary Embolism, Circulation. 129, 479-486, (2014).

Datta, Saurabh, et al. "Ultrasound-enhanced thrombolysis using Definity® as a cavitation nucleation agent." Ultrasound in medicine & biology 34.9: 1421-1433, (2008).

Benjamin, Emelia J., et al. "Heart disease and stroke statistics—2018 update: a report from the American Heart Association." Circulation 137.12: e67-e492, (2018).

Virani, Salim S., et al. "Heart disease and stroke statistics—2020 update: a report from the American Heart Association." Circulation 141.9: e139-e596, (2020).

Nordström, M., et al. "A prospective study of the incidence of deep-vein thrombosis within a defined urban population." Journal of internal medicine 232.2: 155-160, (1992).

Bulger, Christopher M., Chad Jacobs, and Nilesh H. Patel. "Epidemiology of acute deep vein thrombosis." Techniques in vascular and interventional radiology 7.2: 50-54, (2004).

Longstaff, Colin, and K. Kolev. "Basic mechanisms and regulation of fibrinolysis." Journal of Thrombosis and Haemostasis 13: S98-S105, (2015).

Miller, Daniel J., Jennifer R. Simpson, and Brian Silver. "Safety of thrombolysis in acute ischemic stroke: a review of complications, risk factors, and newer technologies." The Neurohospitalist 1.3: 138-147, (2011).

DeVries, James T., et al. "Catheter-based therapy for acute ischemic stroke: A national unmet need." Catheterization and Cardiovascular Interventions 72.5: 705-709, (2008).

Molina, Carlos A., et al. "Transcranial ultrasound in clinical sonothrombolysis (Tucson) trial." Annals of Neurology: Official Journal of the American Neurological Association and the Child Neurology Society 66.1: 28-38, (2009).

Goel, Leela, and Xiaoning Jiang. "Advances in sonothrombolysis techniques using piezoelectric transducers." Sensors 20.5: 1288, (2020).

Martz, Thomas D., et al. "Microfluidic generation of acoustically active nanodroplets." Small 8.12: 1876-1879, (2012).

Paproski, Robert J., et al. "Porphyrin nanodroplets: Sub-micrometer ultrasound and photoacoustic contrast imaging agents." Small 12.3: 371-380, (2016).

Xu, Yurui, et al. "Nanosized phase-changeable "Sonocyte" for promoting ultrasound assessment." Small 16.34: 2002950, (2020).

Kang, Shih-Tsung, Yi-Chen Lin, and Chih-Kuang Yeh. "Mechanical bioeffects of acoustic droplet vaporization in vessel-mimicking phantoms." Ultrasonics sonochemistry 21.5: 1866-1874, (2014).

Duan, Lei, et al. "A multi-gradient targeting drug delivery system based on RGD-I-TRAIL-labeled magnetic microbubbles for cancer

(56)         References Cited

OTHER PUBLICATIONS theranostics." Advanced Functional Materials 26.45: 8313-8324, (2016).

Wang, Siyu, et al. "Targeting and deep-penetrating delivery strategy for stented coronary artery by magnetic guidance and ultrasound stimulation." Ultrasonics Sonochemistry 67: 105188, (2020).

Zhang, Bo, et al. "Ultrasound monitoring of magnet-guided delivery of mesenchymal stem cells labeled with magnetic lipid-polymer hybrid nanobubbles." Biomaterials Science 8.13: 3628-3639, (2020).

Liu, Zhe, et al. "Iron oxide nanoparticle-containing microbubble composites as contrast agents for MR and ultrasound dual-modality imaging." Biomaterials 32.26: 6155-6163, (2011).

Wu, Juefei, et al. "Efficacy of contrast-enhanced US and magnetic microbubbles targeted to vascular cell adhesion molecule-1 for molecular imaging of atherosclerosis." Radiology 260.2: 463-471, (2011).

Cai, Xiaowei, Fang Yang, and Ning Gu. "Applications of magnetic microbubbles for theranostics." Theranostics 2.1: 103, (2012).

Barnsley, Lester C., et al. "A Combined Magnetic-Acoustic Device for Simultaneous, Coaligned Application of Magnetic and Ultrasonic Fields." Advanced materials technologies 3.7: 1800081, (2018).

de Saint Victor, Marie, et al. "Sonothrombolysis with magnetically targeted microbubbles." Ultrasound in medicine & biology 45.5: 1151-1163, (2019).

Chen, Xiaoqiang, et al. "Magnetic targeting improves the therapeutic efficacy of microbubble-mediated obstructive thrombus sonothrombolysis." Thrombosis and haemostasis 119.11: 1752-1766, (2019).

Wang, Siyu, et al. "Accelerating thrombolysis using a precision and clot-penetrating drug delivery strategy by nanoparticle-shelled microbubbles." Science advances 6.31: eaaz8204, (2020).

Zhang, Bohua, Xiaoning Jiang, and Huaiyu Wu. "Ultrasound thrombolysis with magnetic microbubbles under a rotational magnetic field." 2018 IEEE 13th Nanotechnology Materials and Devices Conference (NMDC). IEEE, (2018).

Non-Final Office Action for U.S. Appl. No. 17/479,395 (Dec. 30, 2025).

Final Office Action for U.S. Appl. No. 17/961,538 (Nov. 14, 2025).

* cited by examiner

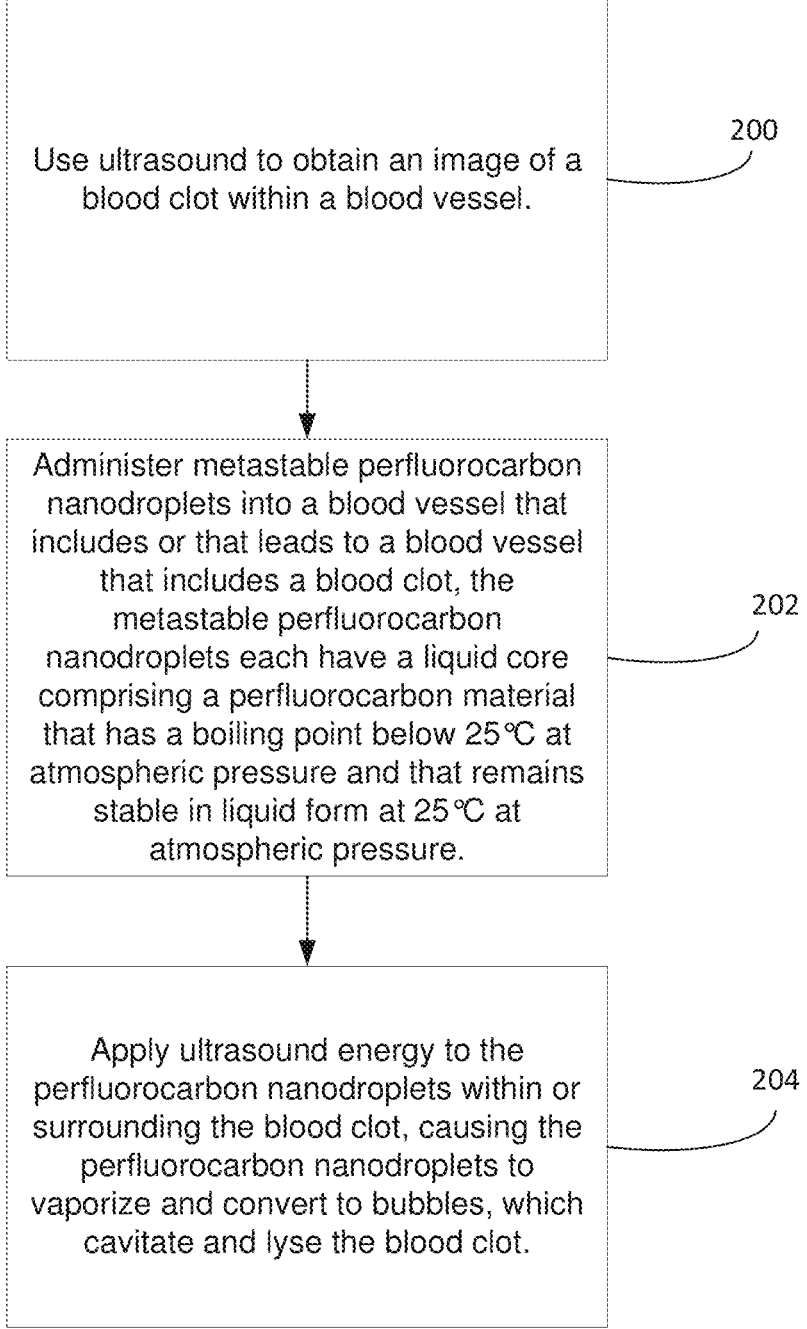

Use ultrasound to obtain an image of a blood clot within a blood vessel.

200

Administer metastable perfluorocarbon nanodroplets into a blood vessel that includes or that leads to a blood vessel that includes a blood clot, the metastable perfluorocarbon nanodroplets each have a liquid core comprising a perfluorocarbon material that has a boiling point below 25°C at atmospheric pressure and that remains stable in liquid form at 25°C at atmospheric pressure.

202

Apply ultrasound energy to the perfluorocarbon nanodroplets within or surrounding the blood clot, causing the perfluorocarbon nanodroplets to vaporize and convert to bubbles, which cavitate and lyse the blood clot.

RETRACTED CLOT LYSIS

MASS DECREASE

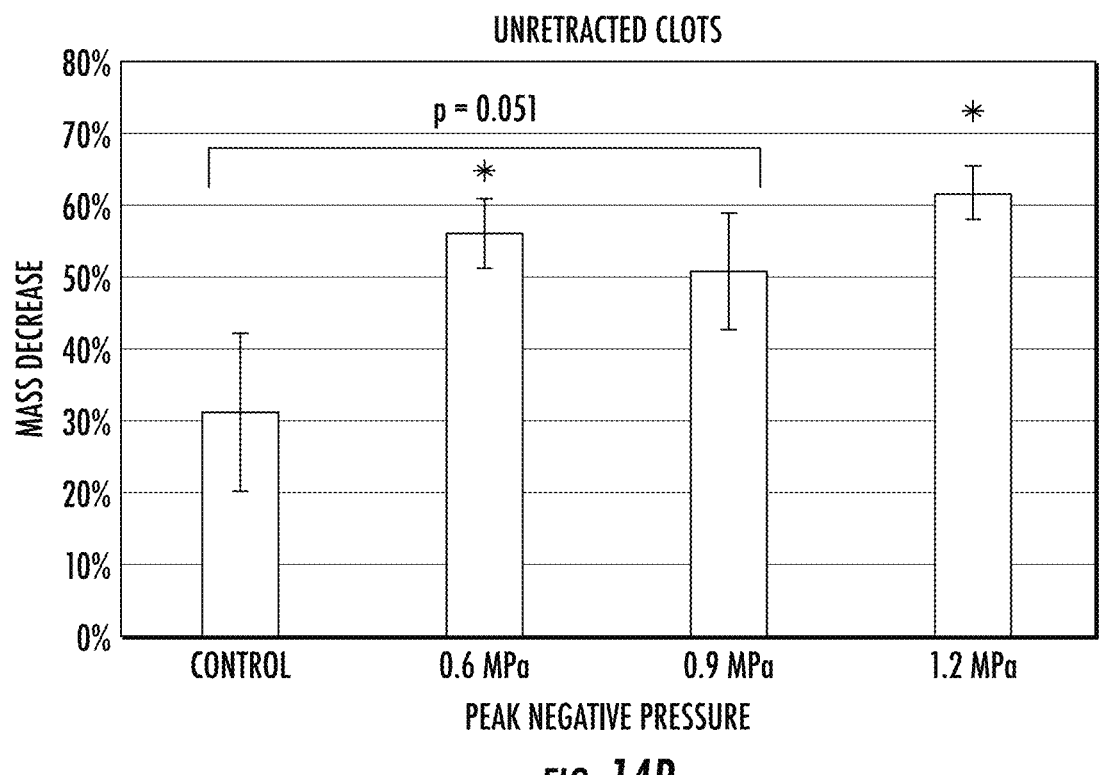
FIG. *14B*
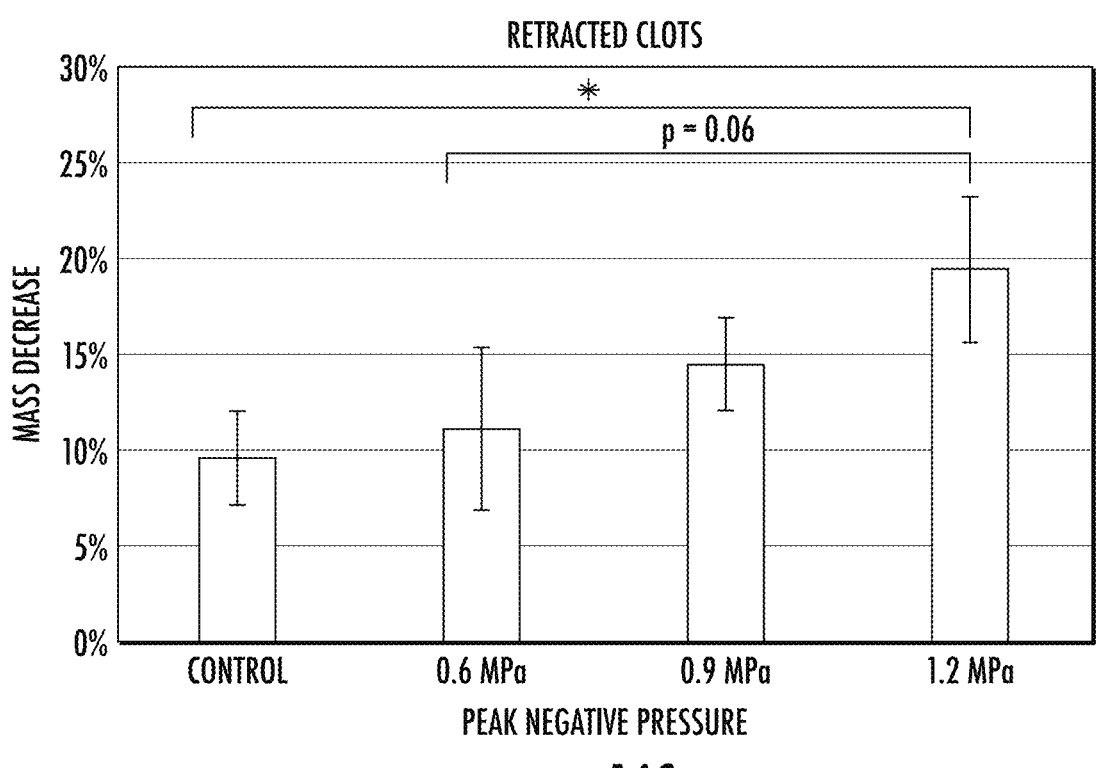
FIG. *14C*

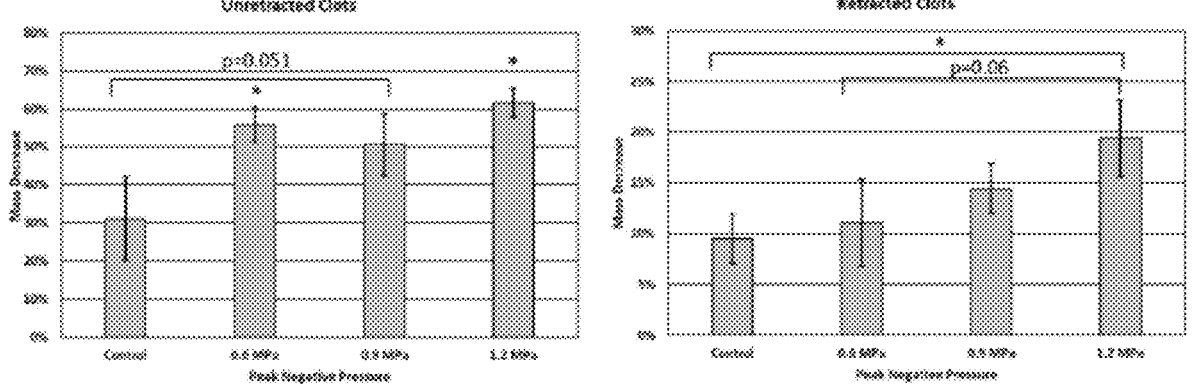
FIG. S1A                                    FIG. S1B

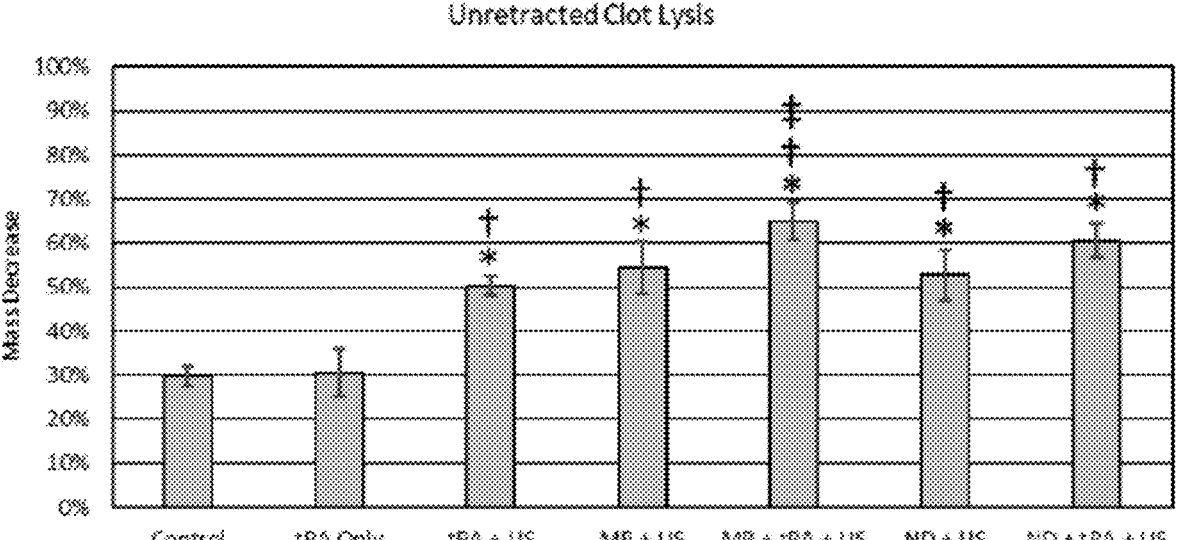
*FIG. S2*

*FIG. S3A*        *FIG. S3B*
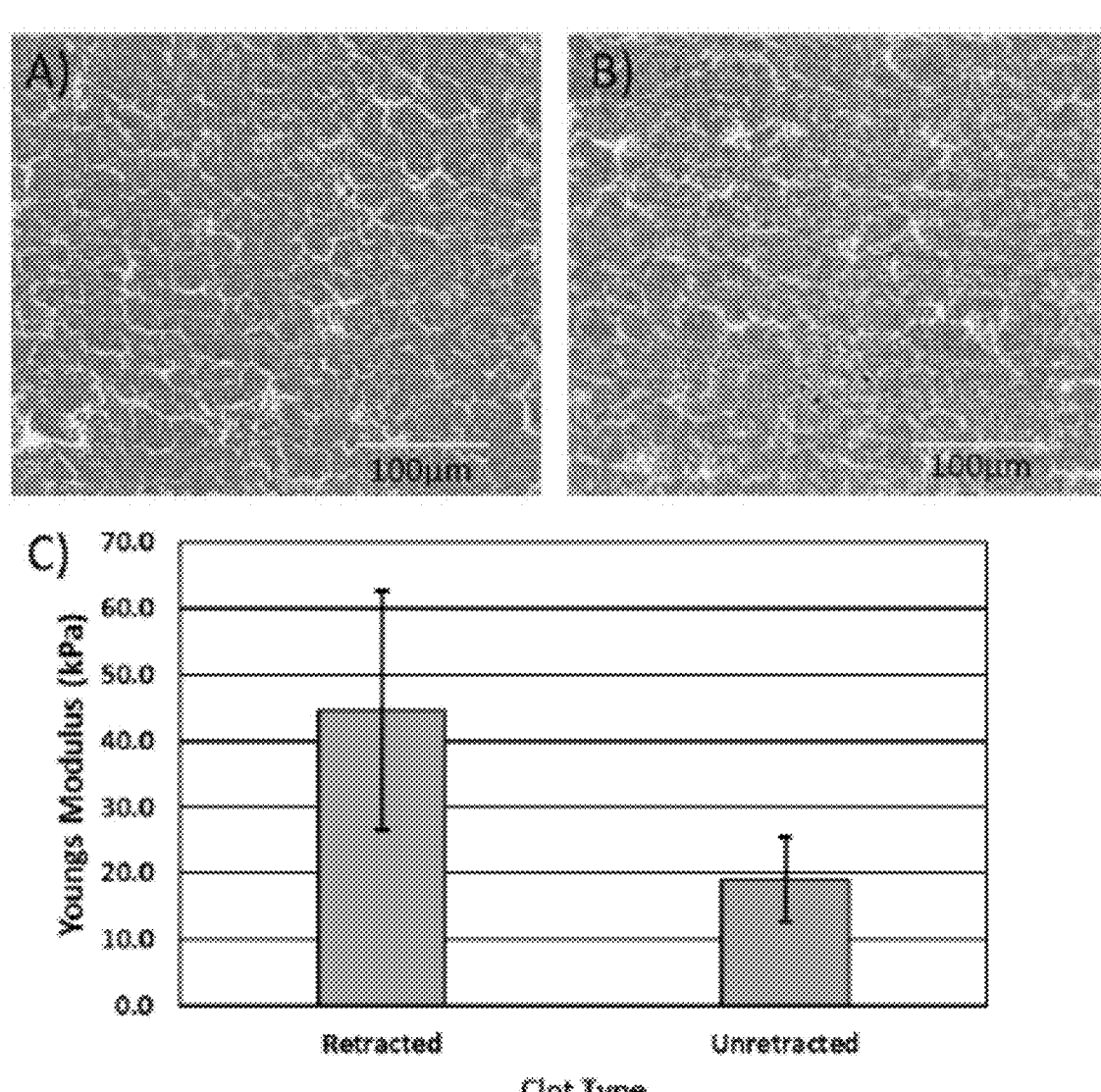
*FIG. S3C*

STACKING ACTIVE LAYERS

PZT-4 MULTILAYER

ATTACHMENT OF SI BASE

PIEZO STACK

SILICON BASE

SLICING FOR GAPE

DICING SAW

FILING IN PDMS

PDMS

CUTTING TO PIECES

PIEZO STACK

PDMS   SILICON BASE

INTEGRATION OF FOCAL LENSE

ALUMINUM LENS

MPPS

WIRING

PARYLENE-C     E-SOLDER

BOTTOM VIEW

APPLICATION OF BACKING LAYER

AIR STACKING

FIG. 18A

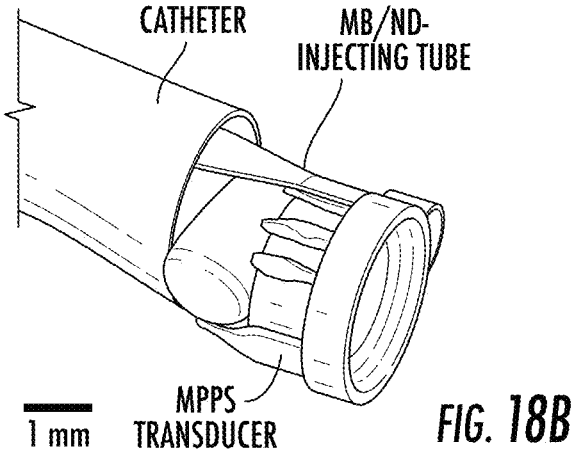

CATHETER    MB/ND-INJECTING TUBE 1 mm

MPPS TRANSDUCER

FIG. 18B

FIG. 25A
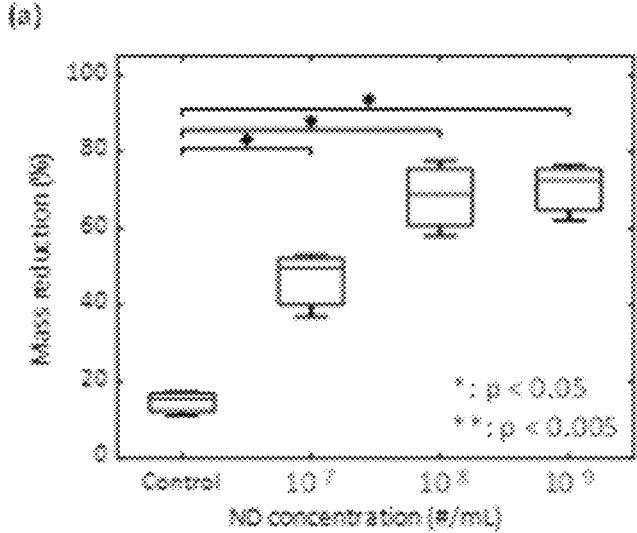
(a)
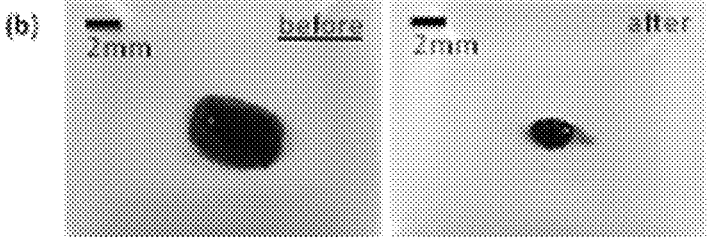
(b)
FIG. 25B       FIG. 25C

IVUS transducer attached at a micro catheter

1

2

Blood clot formation

Artery

Side view                    Rear view

Side view

Rear view

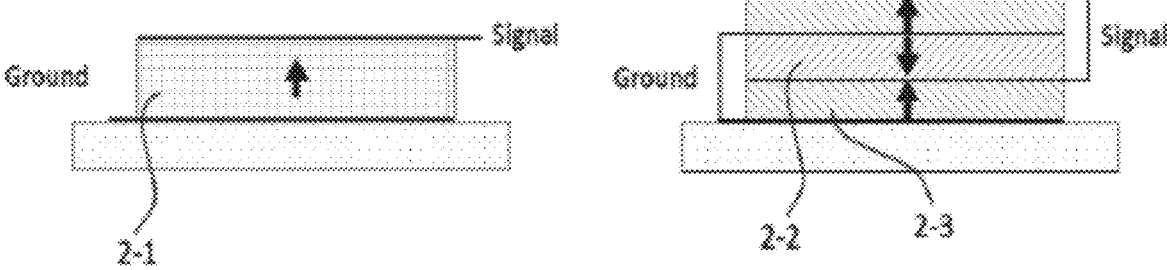
FIG. 33                    FIG. 34

AI₂O₃/EPOXY MATCHING LAYER

COPPER SHIM

100 μm

COUPLER

OPTICAL FIBER LGFU
TRANSDUCER

*FIG. 42A*
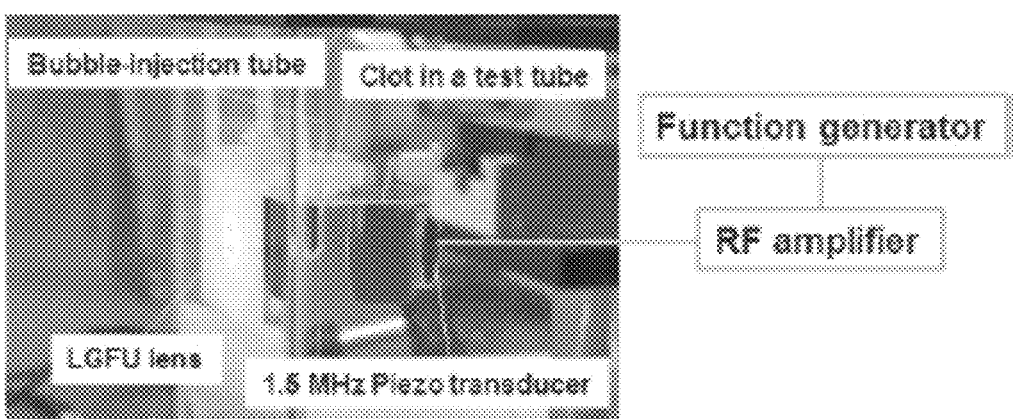
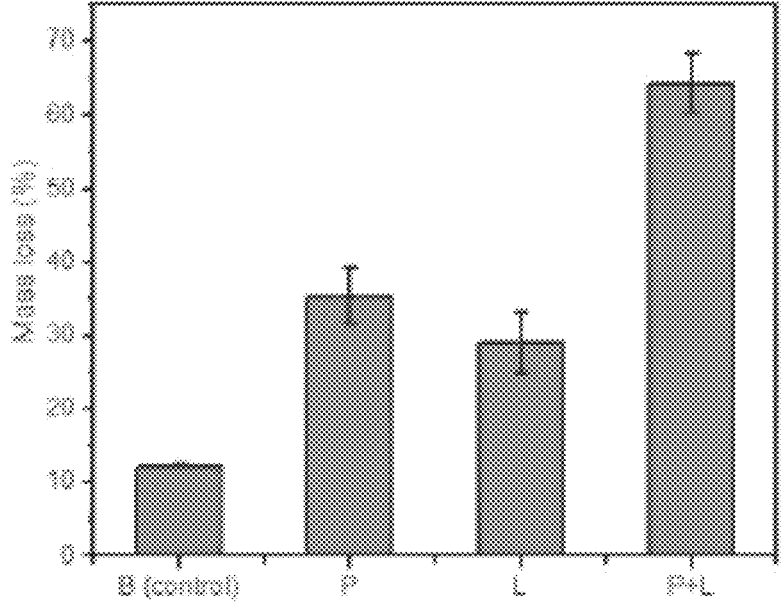
*FIG. 42B*

METHODS AND SYSTEMS FOR USING PHASE CHANGE NANODROPLETS TO ENHANCE SONOTHROMBOLYSIS

PRIORITY APPLICATIONS

This application is a continuation-in-part of U.S. patent application Ser. No. 16/317,983 filed Jan. 15, 2019, which is a national stage application under 35 U.S.C. § 371 of PCT Application Number PCT/US2017/042372, filed Jul. 17, 2017, which claims the benefit of U.S. Provisional Patent Application Ser. No. 62/362,687, filed Jul. 15, 2016. This application further claims the benefit of U.S. Provisional Patent Application Ser. No. 62/897,759, filed Sep. 9, 2019. The disclosures of each of the aforementioned applications is incorporated herein by reference it its entirety.

GOVERNMENT INTEREST

This invention was made with government support under Grant Numbers HL141967 and EB015508 awarded by the National Institutes of Health. The government has certain rights in the invention.

TECHNICAL FIELD

The subject matter described herein relates to disrupting blood clots using ultrasound energy. More particularly, the subject matter described herein relates to methods and systems for using phase change nanodroplets to enhance sonothrombolysis.

BACKGROUND

Sonothrombolysis refers to the process of using ultrasound energy to disrupt blood clots. While sonothrombolysis is noninvasive when compared to surgical methods for removing blood clots, it is desirable when using sonothrombolysis to treat clots with levels of ultrasound energy levels that are effective at disrupting clots but that do not damage surrounding tissue. In addition, it is sometimes desirable to perform sonothrombolysis transcutaneously to avoid the need for intravascular ultrasound probes. There is also a need for effective treatment of retracted blood clots.

In light of these and other goals, there exists a need for improved methods and systems for sonothrombolysis.

SUMMARY

A method for using metastable perfluorocarbon nanodroplets for ultrasonic lysis of blood clots includes administering metastable perfluorocarbon nanodroplets into a blood vessel that includes or that leads to a blood vessel that includes a blood clot, the metastable perfluorocarbon nanodroplets each have a liquid core comprising a perfluorocarbon material that has a boiling point below 25° C. at atmospheric pressure and that remains stable in liquid form at 25° C. at atmospheric pressure. The method further includes applying ultrasound energy to the perfluorocarbon nanodroplets within or surrounding the blood clot, causing the perfluorocarbon nanodroplets to vaporize and convert to bubbles, which cavitate and lyse the blood clot.

A system for using metastable perfluorocarbon nanodroplets for ultrasonic lysis of blood clots includes means for administering metastable perfluorocarbon nanodroplets into a blood vessel that includes or that leads to a blood vessel that includes a blood clot, the metastable perfluorocarbon nanodroplets each have a liquid core comprising a perfluorocarbon material that has a boiling point below 25° C. at atmospheric pressure and that remains stable in liquid form at 25° C. at atmospheric pressure. The system further includes an ultrasound transducer for applying ultrasound energy to the perfluorocarbon nanodroplets within or surrounding the blood clot, causing the perfluorocarbon nanodroplets to vaporize and convert to bubbles, which cavitate and lyse the blood clot.

The subject matter described herein may be implemented in hardware, software, firmware, or any combination thereof. As such, the terms "function" "node" or "module" as used herein refer to hardware, which may also include software and/or firmware components, for implementing the feature being described. In one exemplary implementation, the subject matter described herein may be implemented using a computer readable medium having stored thereon computer executable instructions that when executed by the processor of a computer control the computer to perform steps. Exemplary computer readable media suitable for implementing the subject matter described herein include non-transitory computer-readable media, such as disk memory devices, chip memory devices, programmable logic devices, and application specific integrated circuits. In addition, a computer readable medium that implements the subject matter described herein may be located on a single device or computing platform or may be distributed across multiple devices or computing platforms.

BRIEF DESCRIPTION OF THE DRAWINGS

FIG. 2 is a flow chart of an exemplary process for using metastable phase change nanodroplets to enhance sonothrombolysis;

FIGS. 3A-3D illustrate an experimental setup for in vitro sonothrombolysis tests. FIG. 3A is a front view of a flow model that simulates partial occlusion of a deep vein. FIG. 3B illustrates a blood clot sample fixed by a nylon mesh. A yellow arrow denotes flow direction (scale bar=10 mm).

FIG. 3C is a side view of the setup; the clot fragmentation was monitored and captured by a camera with a zoom lens (×50). A 5 MHz piston transducer was used as a passive cavitation detector. FIG. 3D illustrates a representative photo of an unretracted aged clot sample (288 mg);

FIGS. 4A-4C illustrate graphs of thrombolytic efficacy (in terms of percent clot mass reduction during 10 min-treatment, n=5) and passive cavitation detection results (N=30) of each treatment group. In FIG. 4A, the control group was treated with neither ultrasound nor agent infusion. The stable and inertial cavitation doses were determined from the area under curves (AUCs) of measured cavitation spectra (supplementary material). In FIG. 4B, the AUCs in the range of 1.5-2.5 MHz determine the stable cavitation dose, In FIG. 4C, the AUCs in the range of 2.2-6.8 MHz except superharmonic contents ($3f_0$, $4f_0$, $5f_0$, $6f_0$, and $7f_0$ in the ±0.2 MHz frequency range) determine the inertial cavitation dose, where $f_0$ is the fundamental frequency (1 MHz). The asterisk (*) indicates a significant difference ($p<0.05$).

Figure 5A:
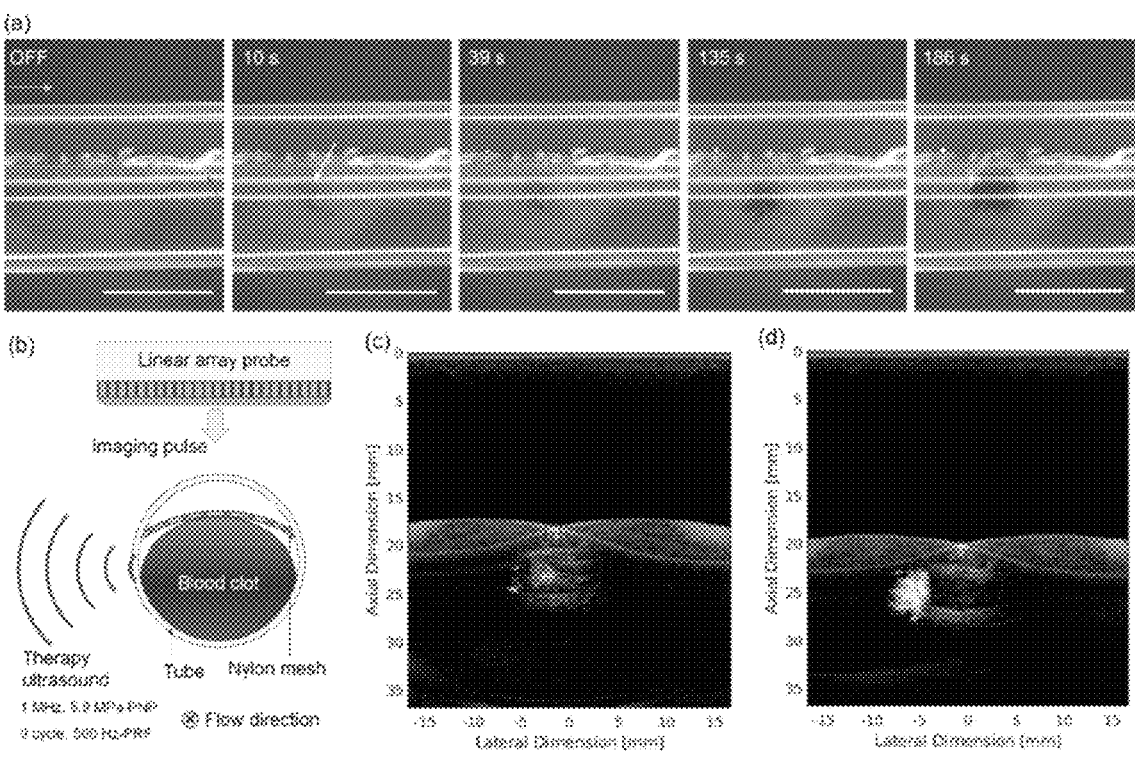

The p values comparing the treatment groups are tabulated in the supplementary material;

FIGS. 5A-5C illustrate ultrasonic cavitation inside aged clots by nanodroplet-mediated short-pulse ultrasound (group 3). FIG. 5A illustrates representative captured images of a cavitating nanodroplet-induced internal erosion. The therapy wave propagates out of the image plane (scale bar=5 mm).

Figure 6A:
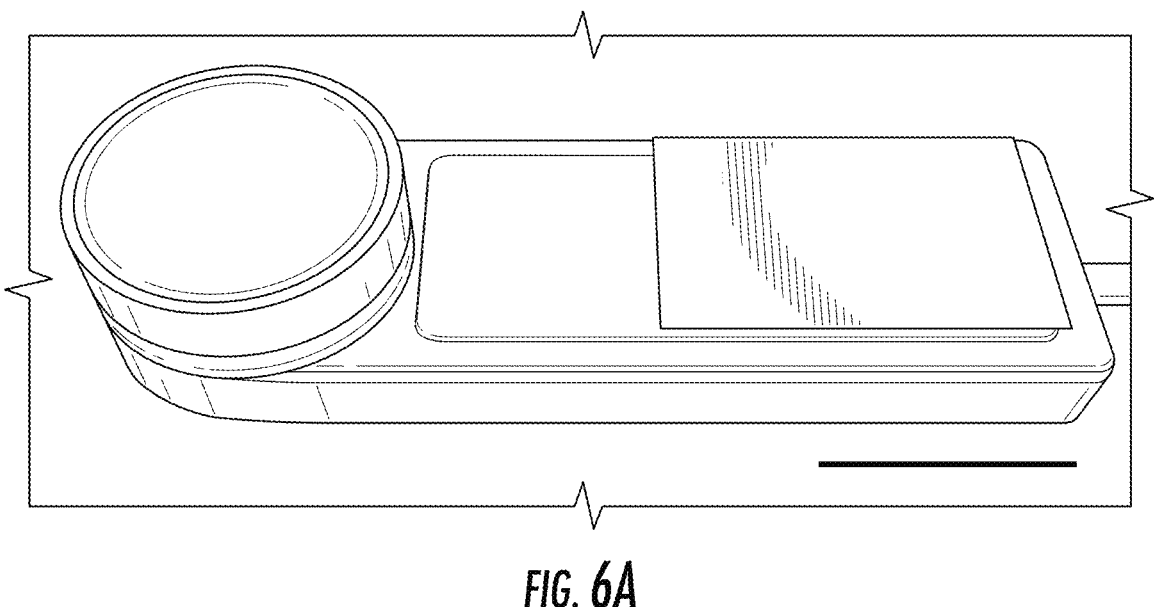
Figure 6B:
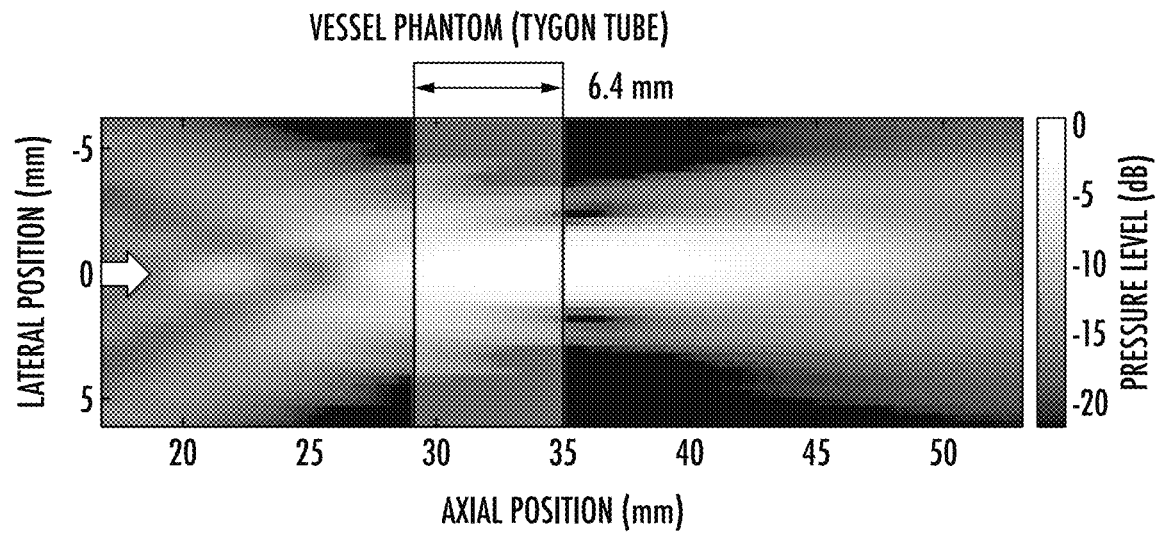
Figure 7B:
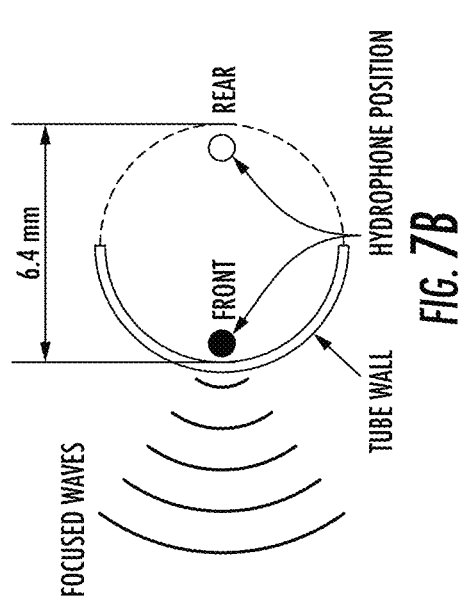
Figure 7D:
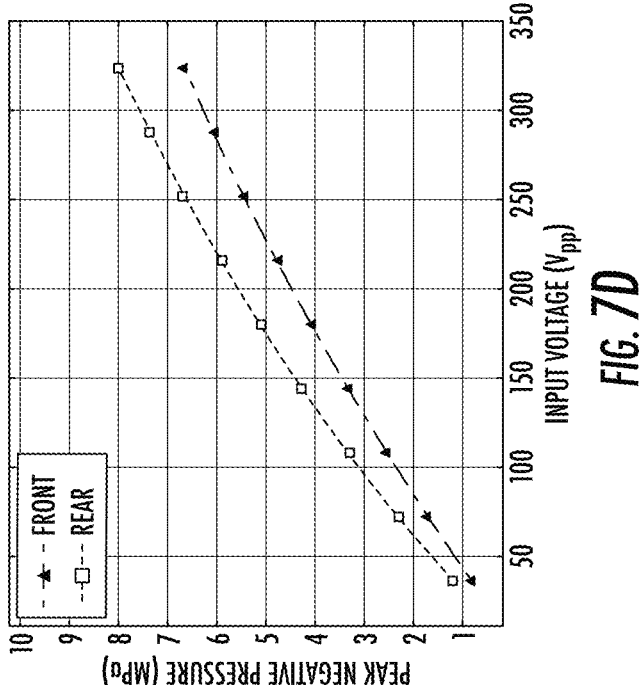
Figure 7A:
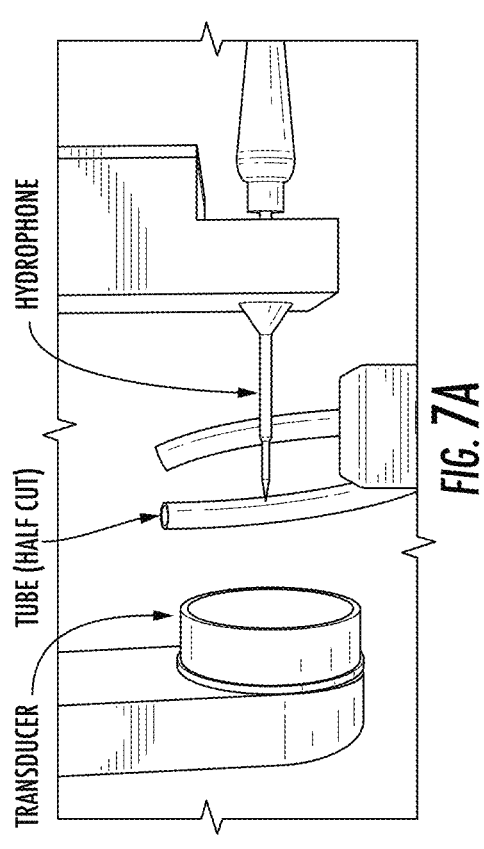
Figure 7C:
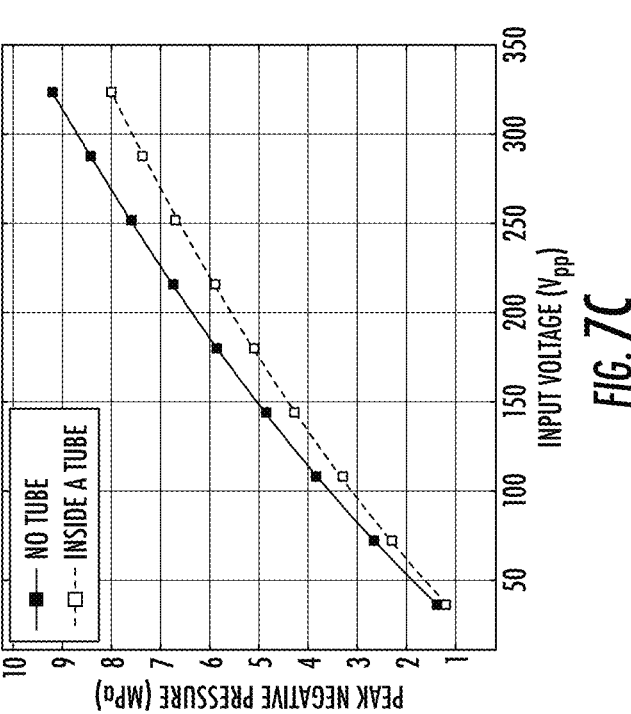
Figures 8A, 8B, 8C, 8D:
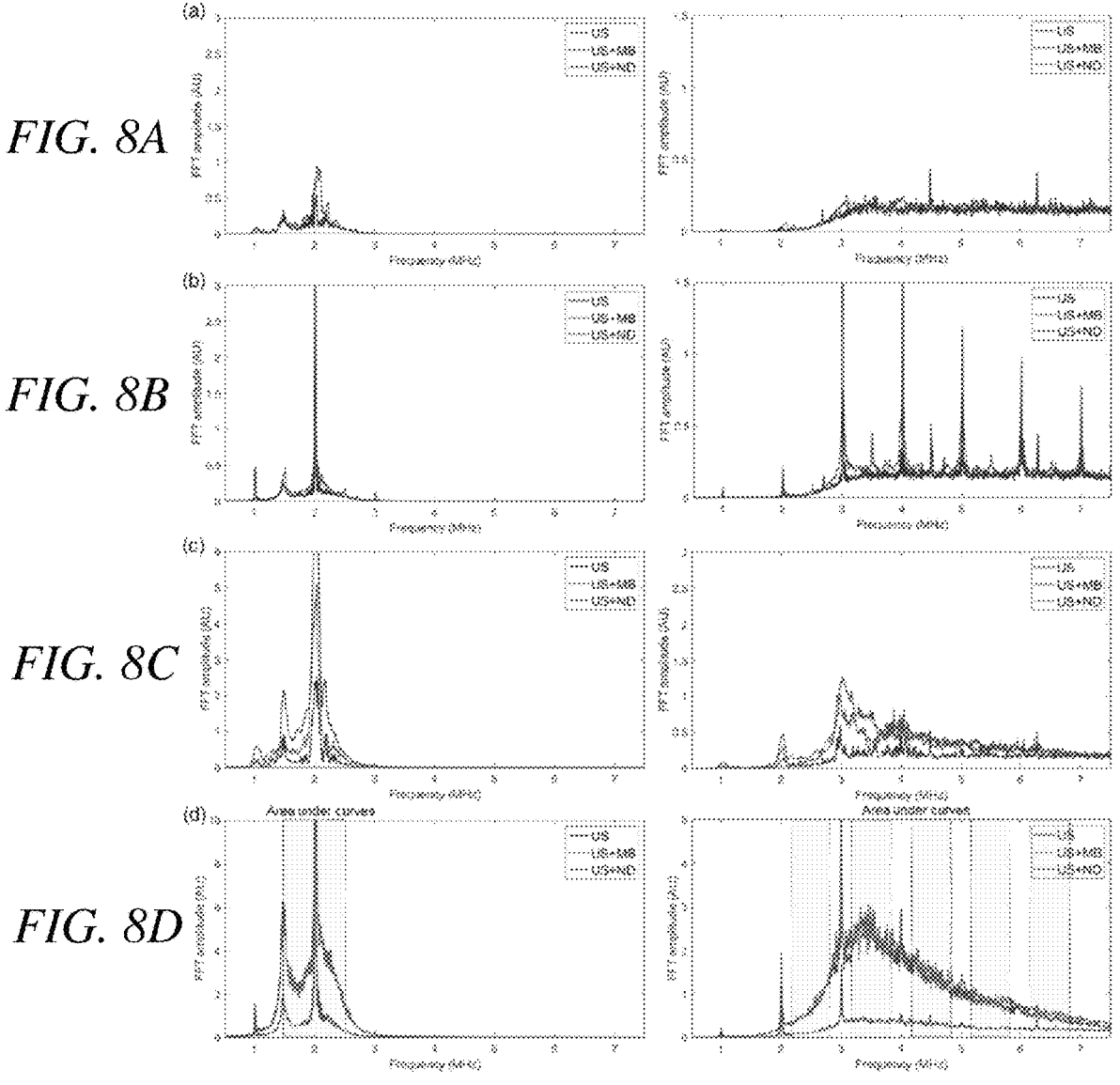
Figure 9:
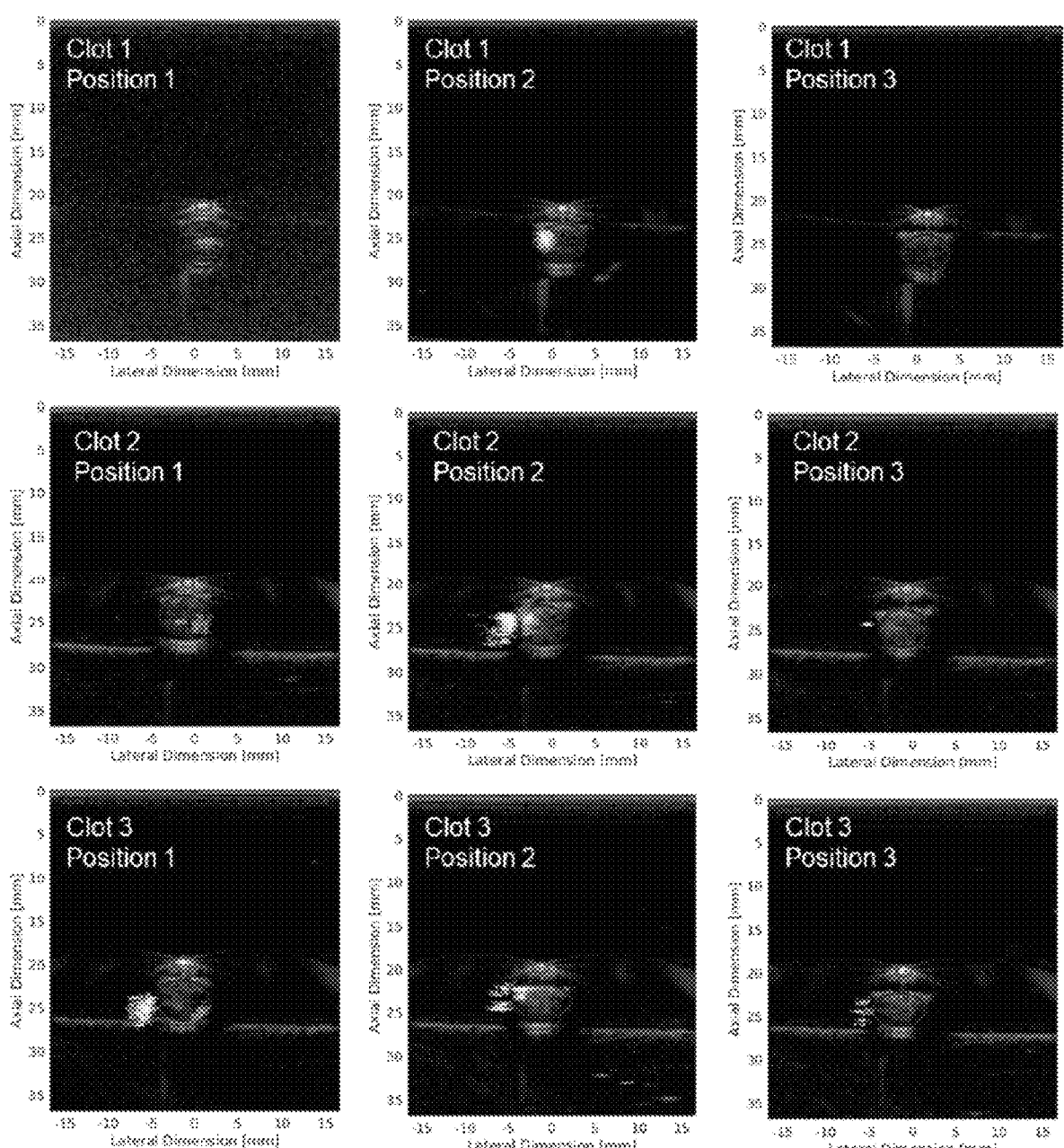

A yellow arrow indicates a flow direction. Within 10 s of the treatment, micro-sized cavities were observed (a solid white arrow). The solid green lines indicate the reflected LED lamp light from the tube outer surface. FIG. 5B is a schematic of ultrasound imaging of cavitation clouds during the clot erosion. The grayscale image (called a B-mode image) shows the clot in a tube, and the overlaid colored data indicates the presence of cavitation. FIG. 5C depicts the US+ND cavitation zone (yellow-green cloud) which is located inside the clot cross-section, In FIG. 5D, the US+MB case shows cavitation clouds outside of the clot. The blue-dotted circles indicate approximated inner tube diameter, and the blue arrows indicate a nylon mesh (FIGS. 5C and 5D);

FIGS. 6A and 6B illustrate a therapy transducer; FIG. 6A is a photo of the 1 MHz focused ultrasound transducer (scale bar=30 mm), FIG. 6B is a beam profile of the focused ultrasound transducer. A red arrow shows the wave propagation direction. A Tygon tube was positioned to align the maximum pressure at the back wall;

FIGS. 7A-7D illustrate a characterization of the pressure field inside a vessel phantom. FIG. 7A is a photo of the measurement setup. A half-cut Tygon tube was positioned in front of a needle hydrophone to measure the attenuated in a tube. FIG. 7B is a schematic of the pressure measurement. FIG. 7C is a graph of a measured peak-negative pressure (PNP, with a tube vs. without a tube) as a function of the input voltage. FIG. 7D is a graph of PNP at the front-end and the rear-end of a vessel phantom (Tygon tube with a 6.4 mm inner diameter);

FIGS. 8A-8D illustrate passive cavitation detection results of each treatment group (N=30): FIG. 8A group 1, FIG. 8B group 2, FIG. 8C group 3, and FIG. 8D group 4. The frequency spectra were transformed from the bandpass-filtered cavitation signals with the passband of 1.5-2.5 MHz for stable cavitation (second harmonic content) (d, left), and the passband of 3-7 MHz for inertial cavitation (broadband noise) (d, right). The stable and inertial cavitation doses were determined from the area under curves (AUCs, gray areas with a dashed outline). The AUCs in the range of 1.5-2.5 MHz determine the stable cavitation dose, and the AUCs in the range of 2.2-6.8 MHz except for superharmonic contents ($3f_0$, $4f_0$, $5f_0$, $6f_0$, and $7f_0$ in the $\pm0.2$ MHz frequency range) determine the inertial cavitation dose, where $f_0$ is the fundamental frequency (1 MHz);

FIG. 9 illustrates cavitation cloud images of the US+ND case with the group 3 treatment (5.9 MPa-PNP, 0.45%-duty cycle). The cross-sectional area of a clot sample (blue circle) is the region of interest (ROI). The metric for the in-clot-cavitation is a ratio of the cavitation cloud image intensity in ROI to the total sum of the cavitation cloud image intensity. The image artifacts (red circles) were excluded from the total intensity sum.

Figure 10:
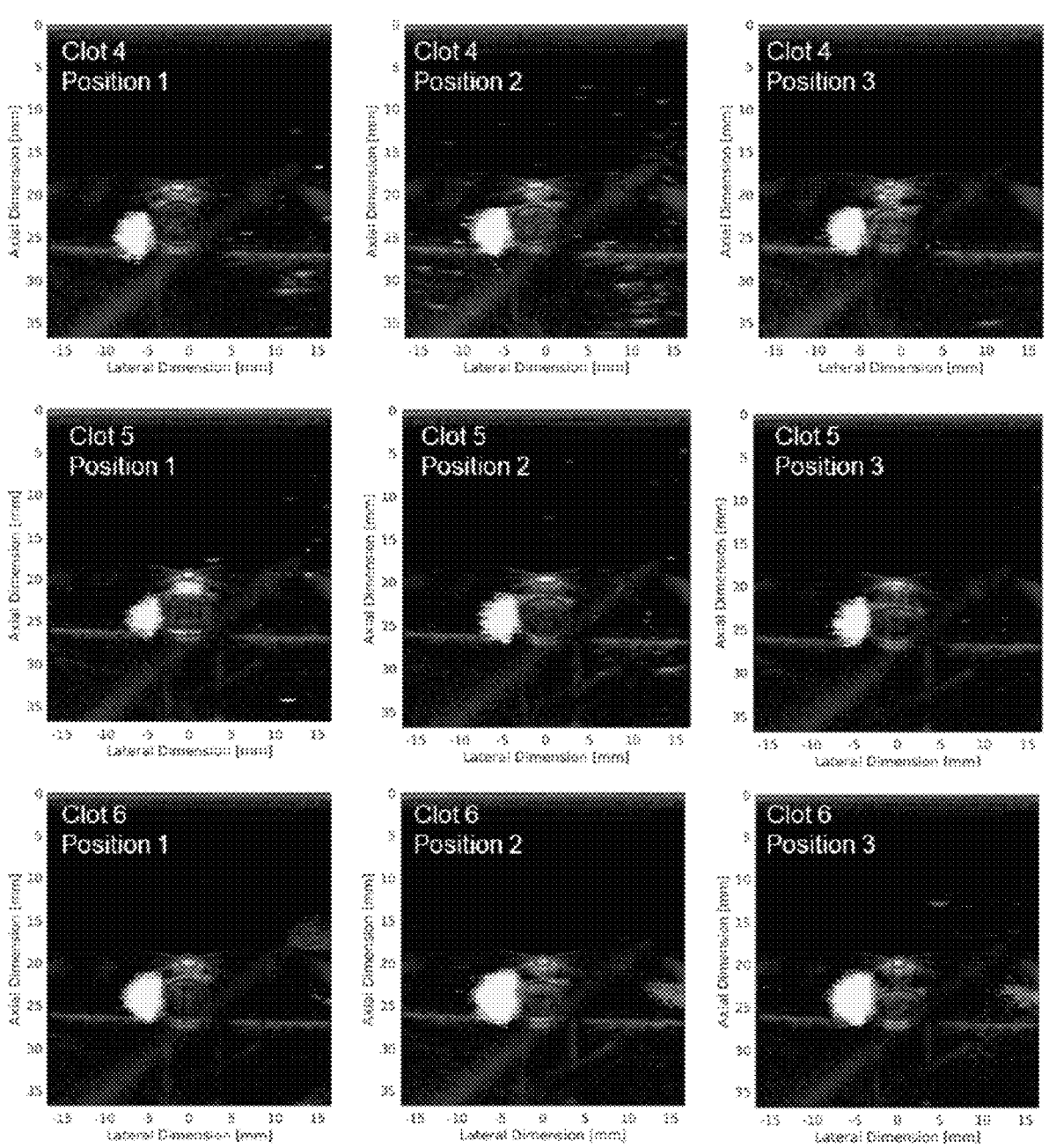
Figure 11:
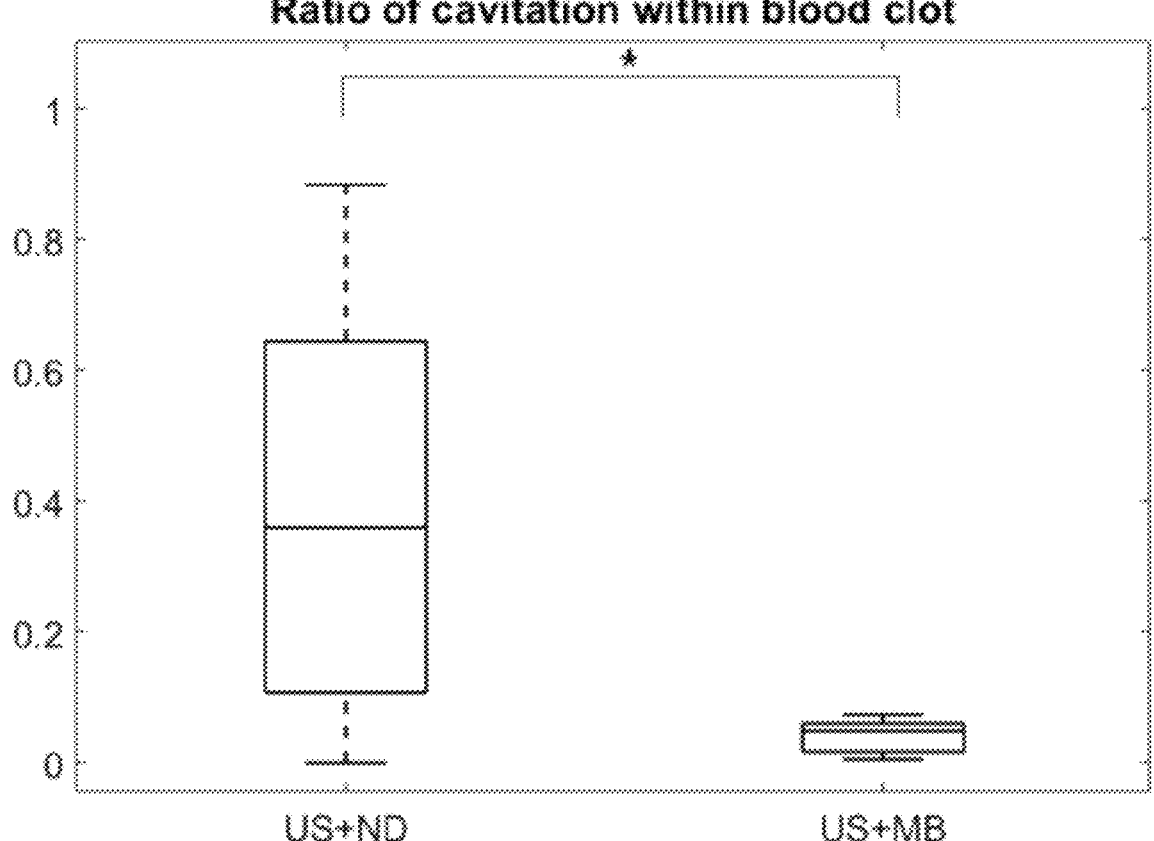
Figures 12A, 12B:
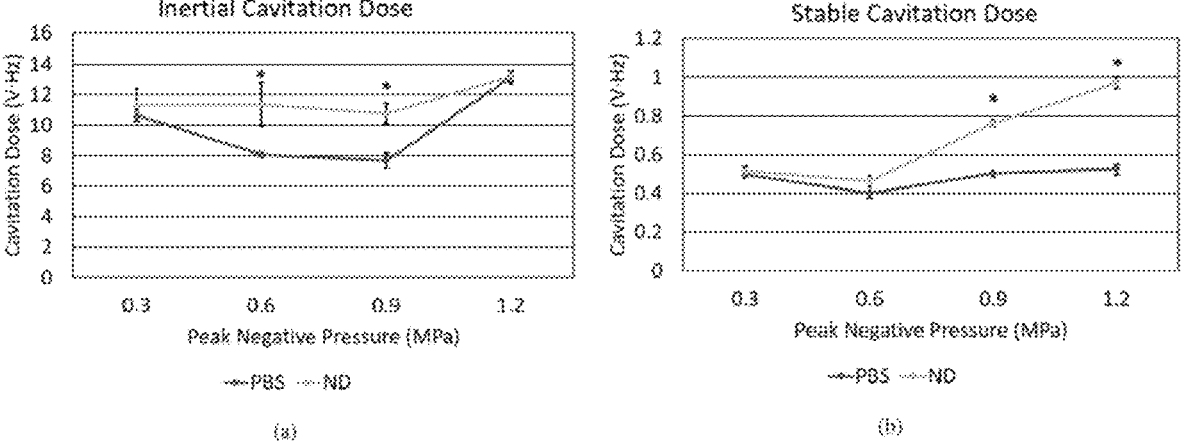
Figure 13:
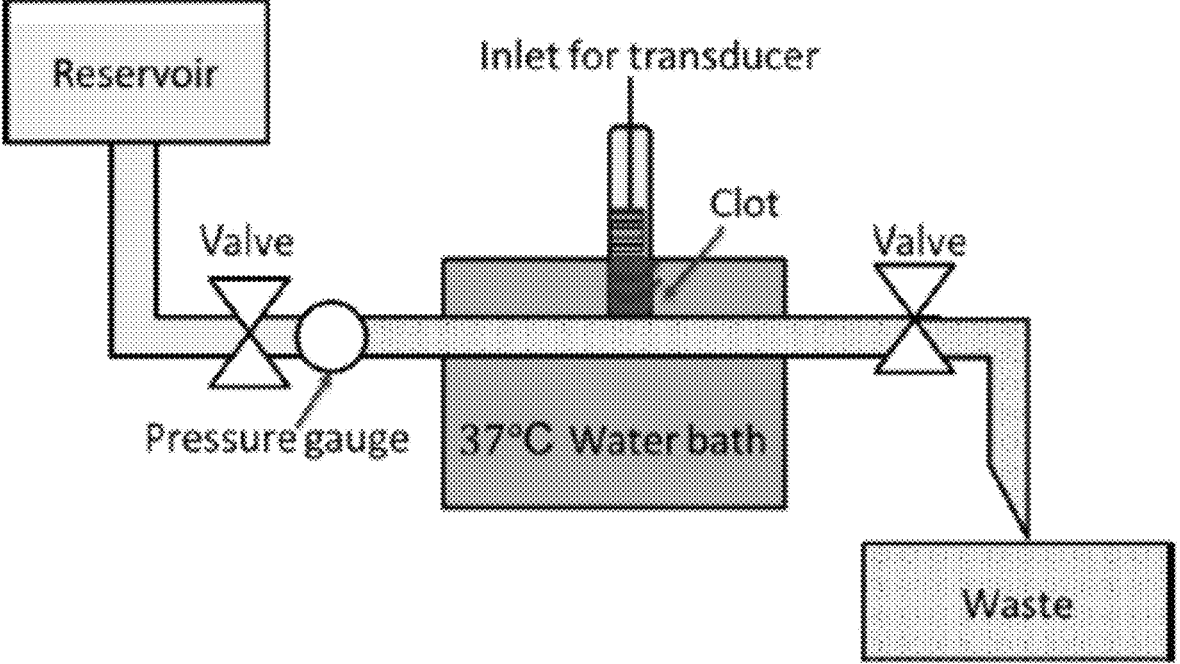
Figure 14A:
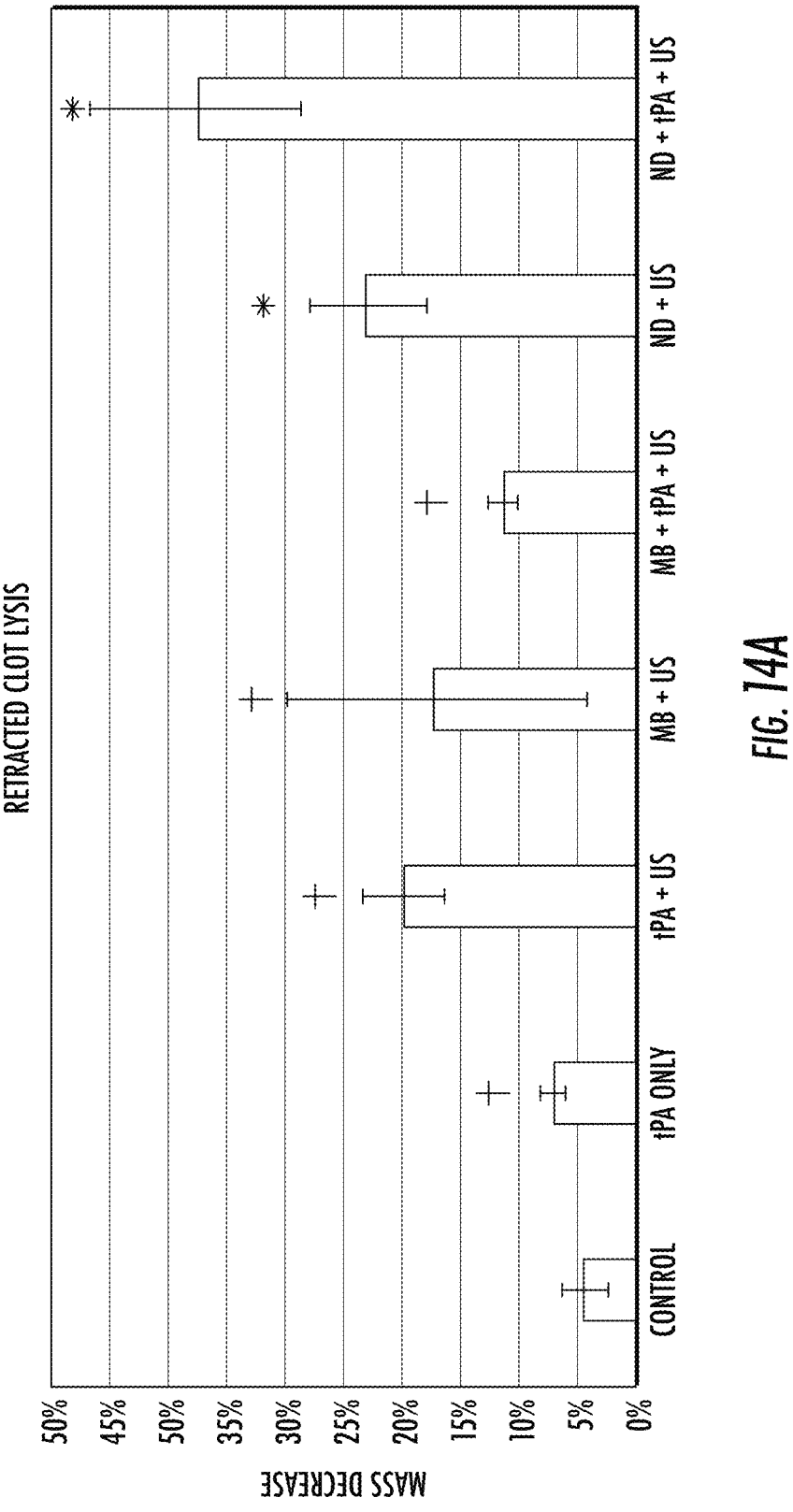
Figure 14D:
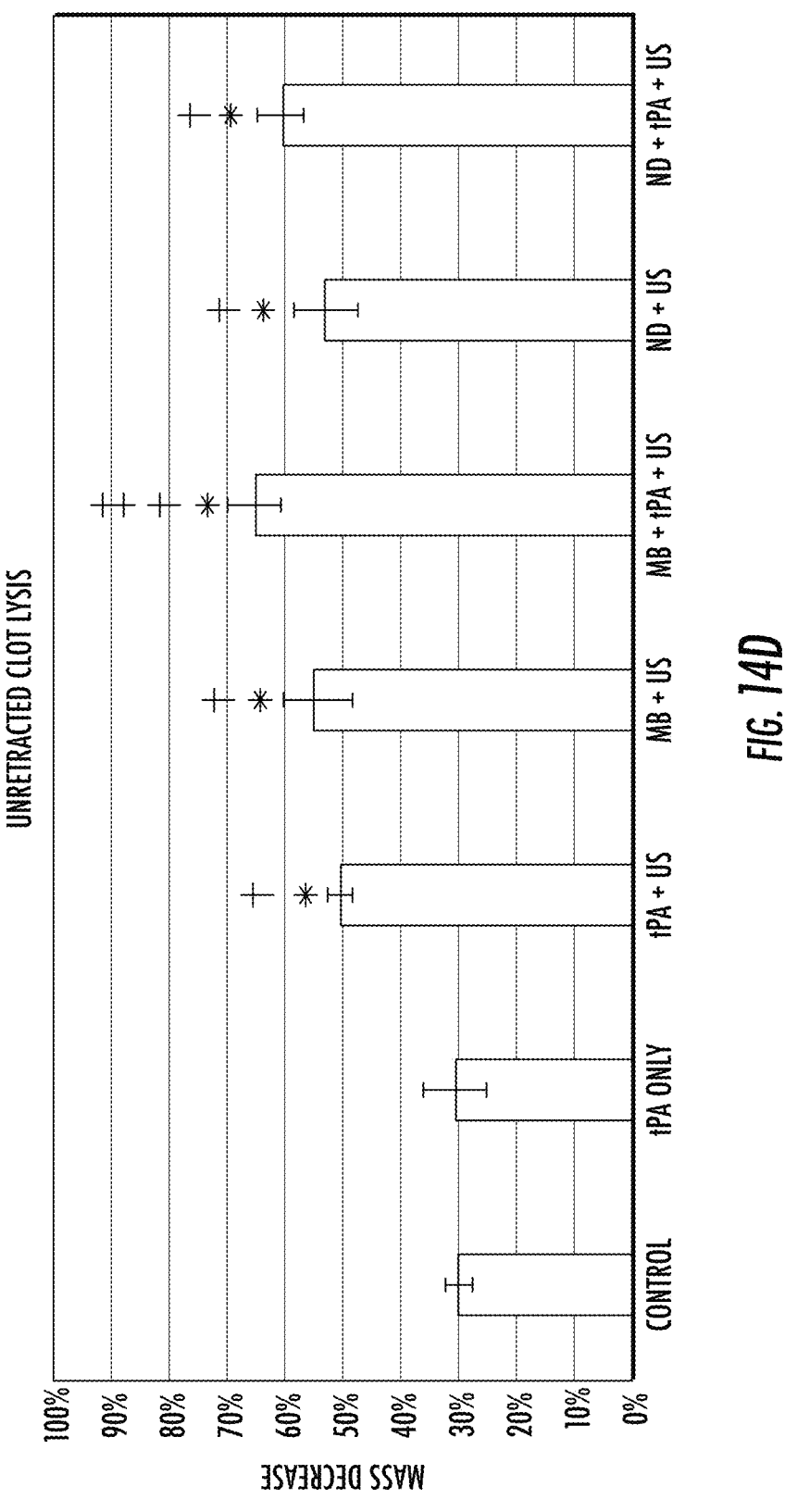
Figure 14E:
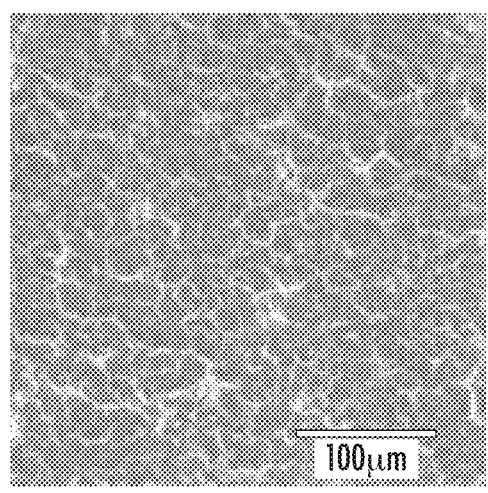
Figure 14F:
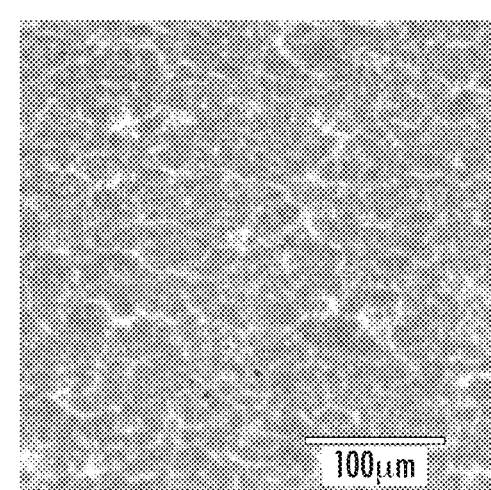
Figure 14G:
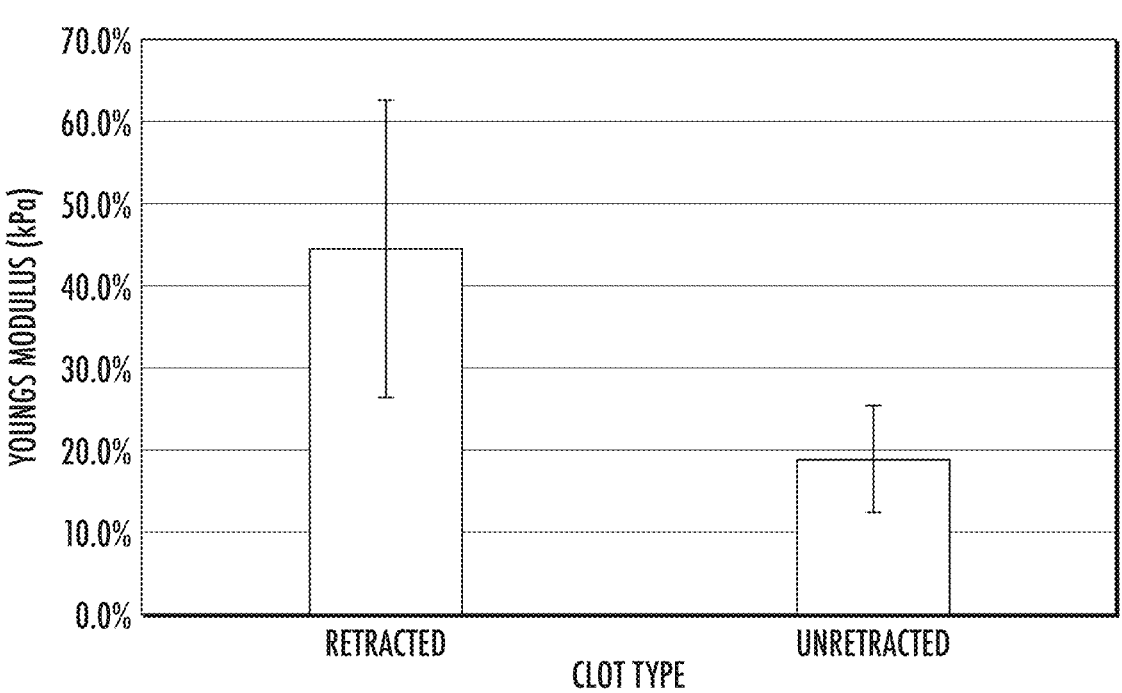

FIG. 10 illustrates cavitation cloud images of the US+MB case with the group 3 treatment (5.9 MPa-PNP, 0.45%-duty cycle). The cross-sectional area of a clot sample (blue circle) is the region of interest (ROI). The metric for the in-clot-cavitation is a ratio of the cavitation cloud image intensity in ROI to the total sum of the cavitation cloud image intensity. The image artifacts (red circles) were excluded from the total intensity sum;

FIG. 11 illustrates a comparison of the in-clot-cavitation metric (the ratio of the cavitation cloud image intensity in ROI to the total sum of the cavitation cloud image intensity) between the US+ND case and the US+MB case (n=9). The lower values of the MB case indicated cavitation occurred almost entirely outside the clot, whereas NDs often generated cavitation internal to the clot (although variance of cavitation location was substantial). The asterisk (*) indicates a significant difference ($p<0.05$);

FIGS. 12A and 12B are illustrate graphs of (FIG. 12A) inertial and (FIG. 12B) stable cavitation doses for nanodroplet mediated sonothrombolysis with different pressures. The ultrasound excitation parameters were 700 kHz, 10 ms pulse length and 20 cycles. * indicates the control group;

FIG. 13 is a diagram of an exemplary experimental setup for testing nanodroplet mediated sonothrombolysis;

FIG. 14 illustrates graph of retracted clot lysis results for different treatment conditions with a peak negative pressure of 0.9 MPa. * indicates $p<0.05$ compared to the control and t indicates $p<0.05$ when compared to ND=tPA+US;

Figure S1A illustrates percent mass decrease of unre-tracted clots and Figure S1B illustrates percent mass decrease of retracted clots for nanodroplet mediated sono-thrombolysis at different peak negative pressures. * indi-cates $p<0.05$ compared to the control group in each case.

Figure 15:
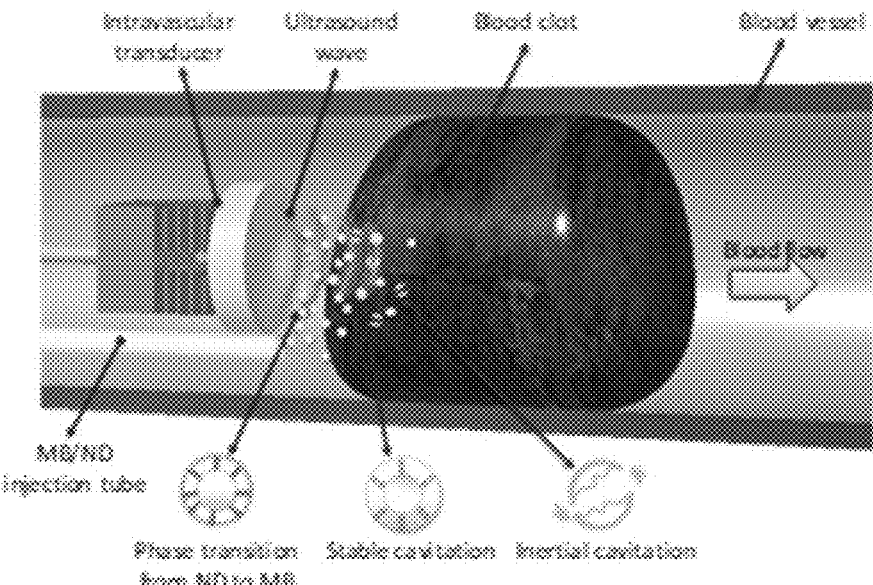
Figure 16:
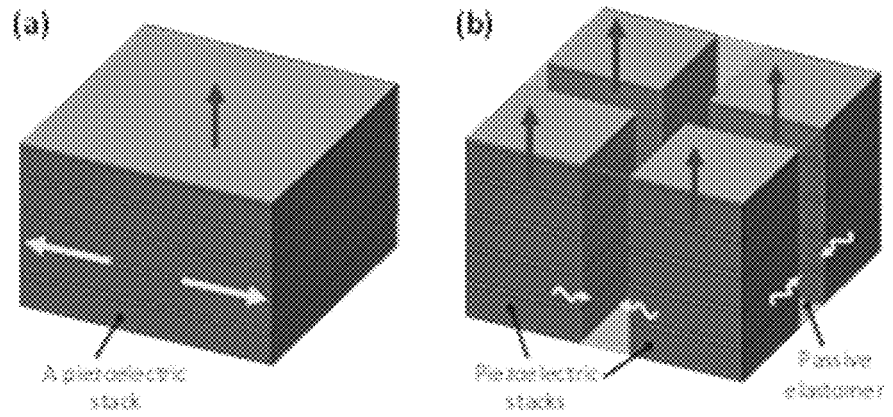
Figure 17:
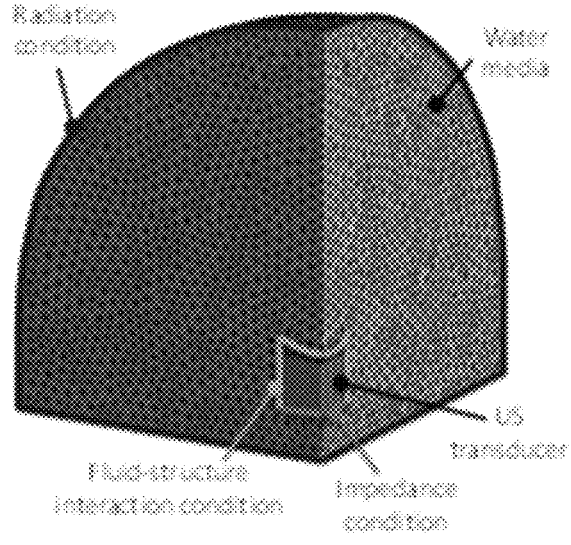
Figure 19:
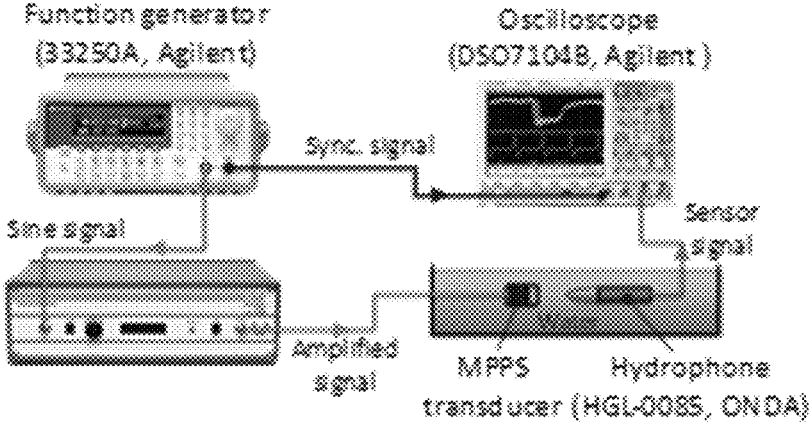
Figure 20:
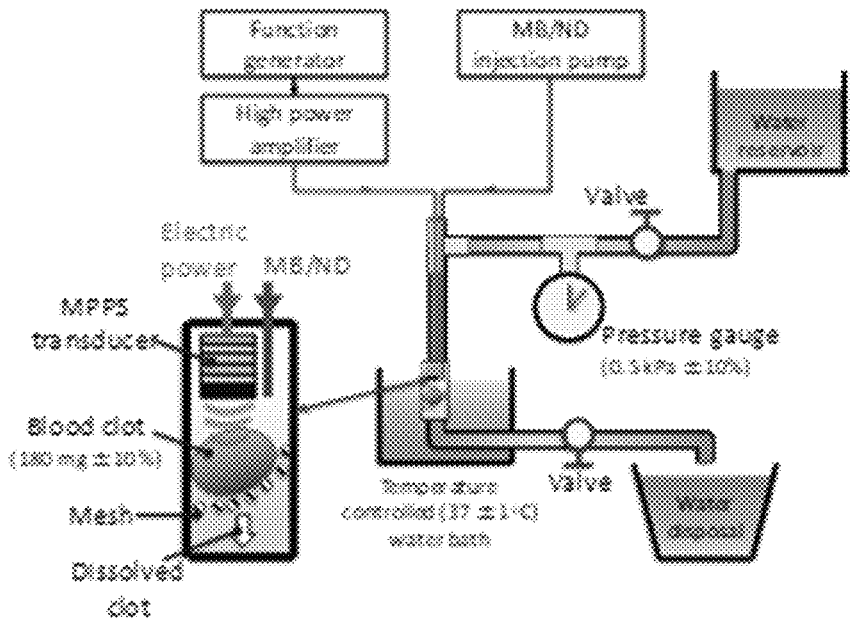
Figure 21A:
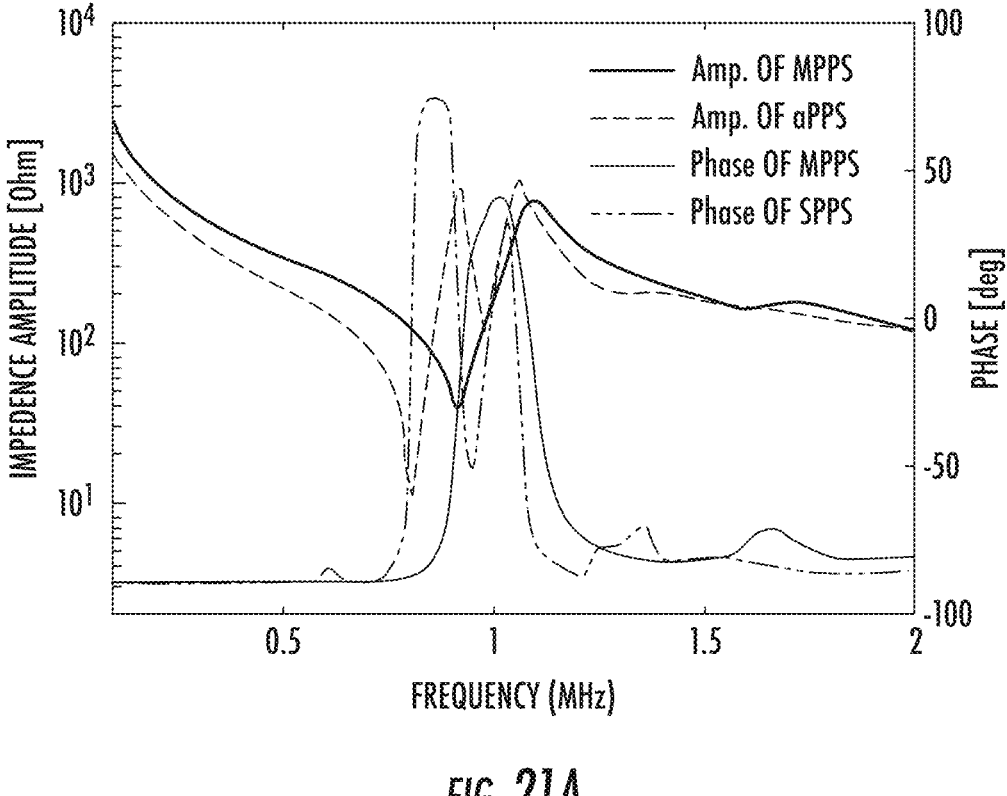
Figure 21B:
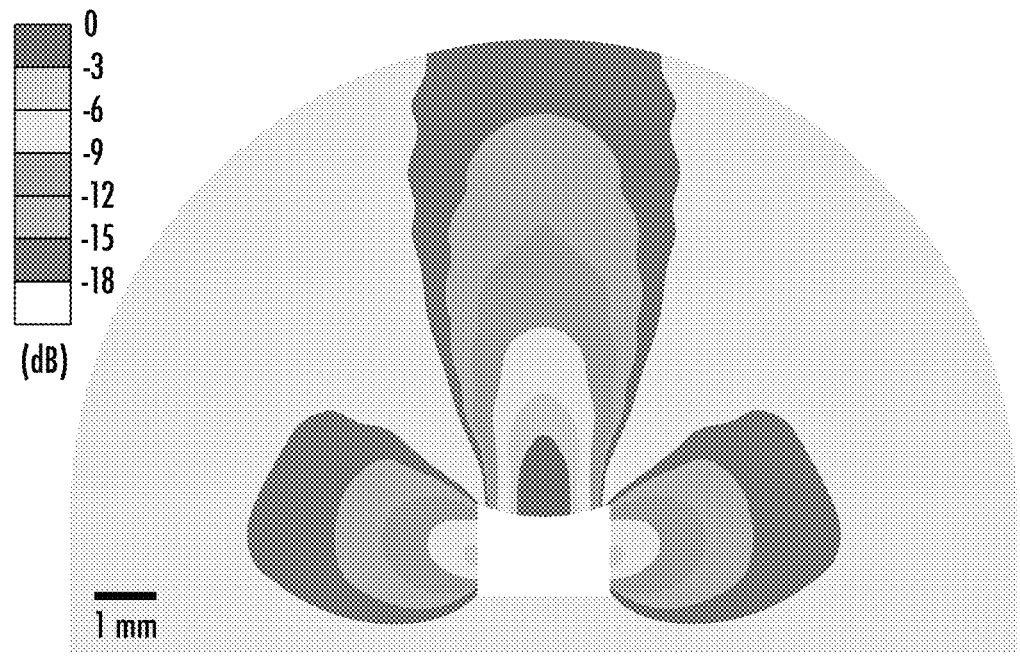
Figure 21C:
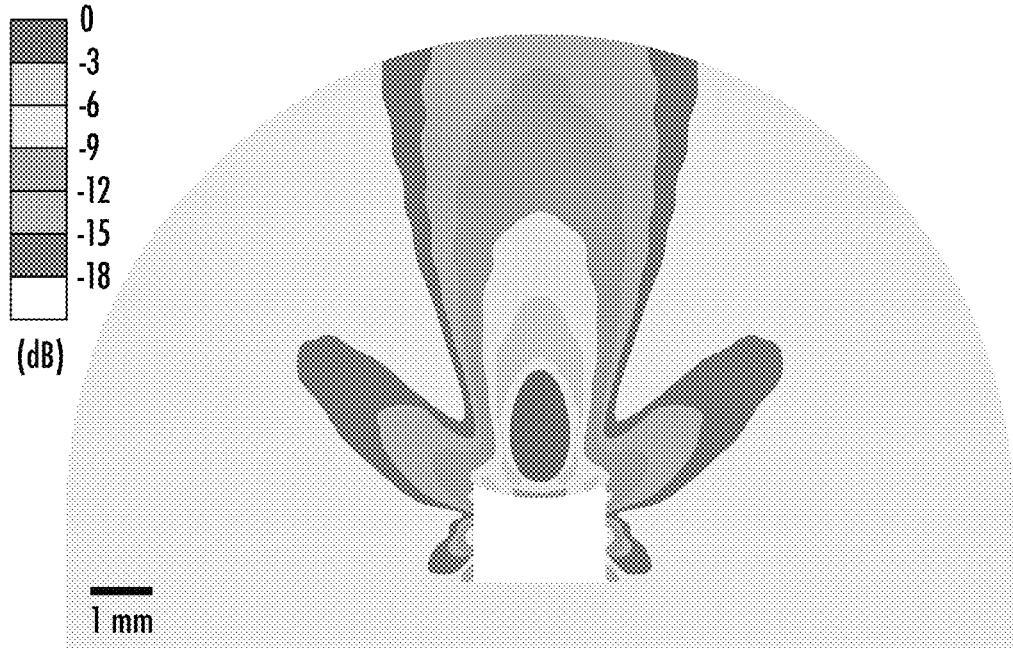
Figure 22A:
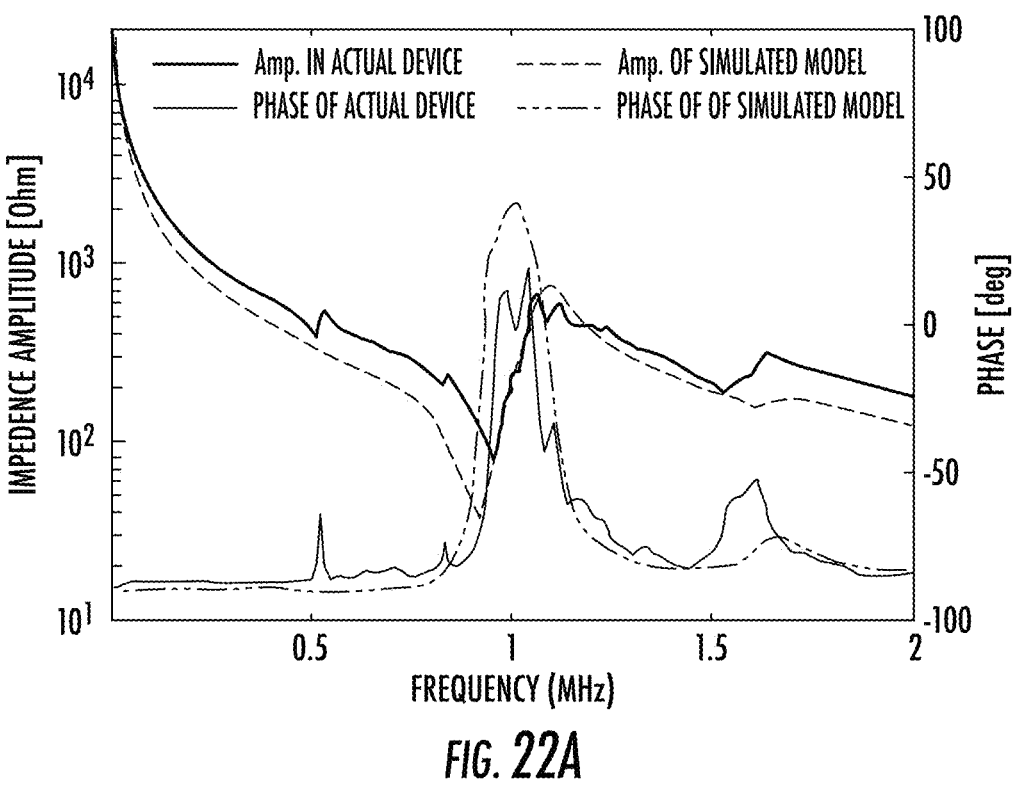
Figure 22B:
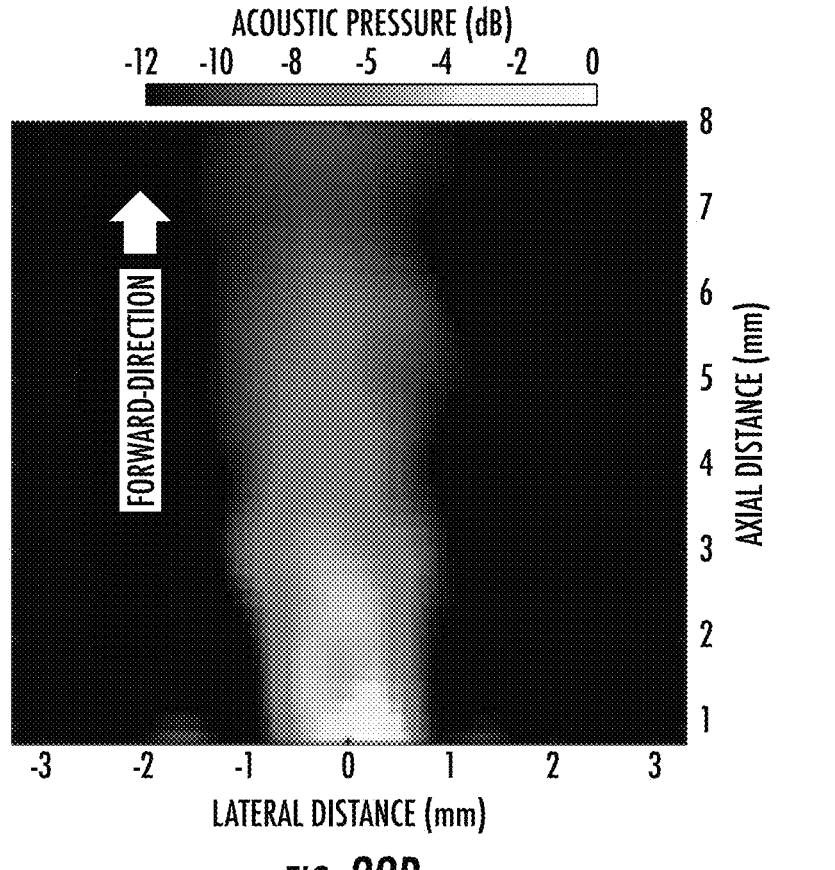
Figure 22C:
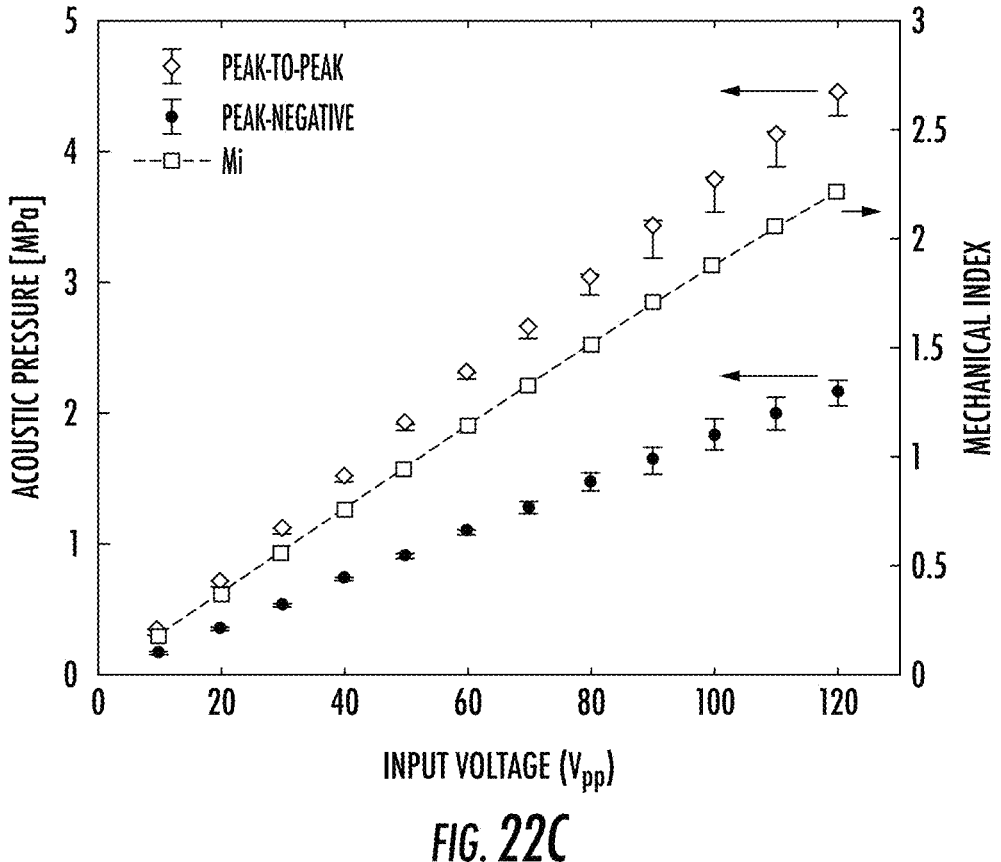
Figure 23:
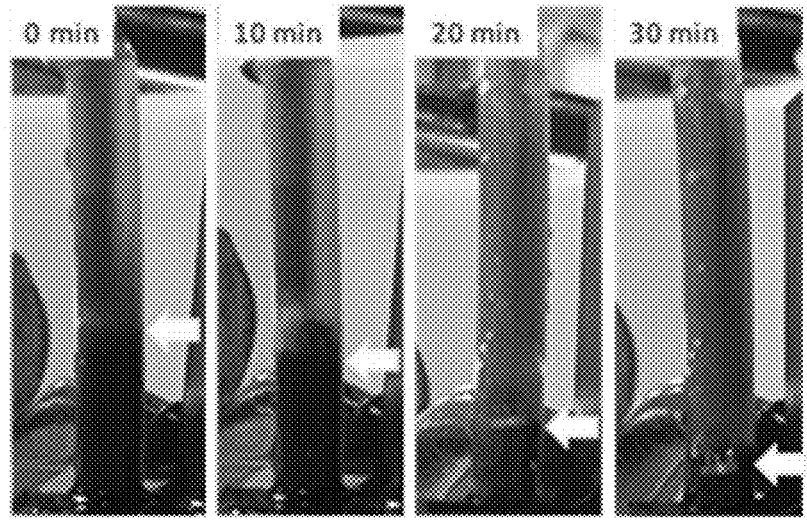
Figure 24:
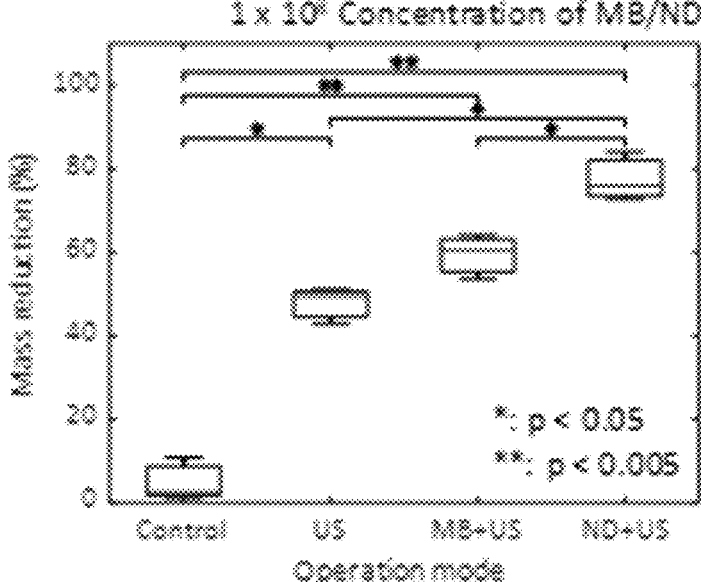
Figures 26A, 26B, 26C, 26D:
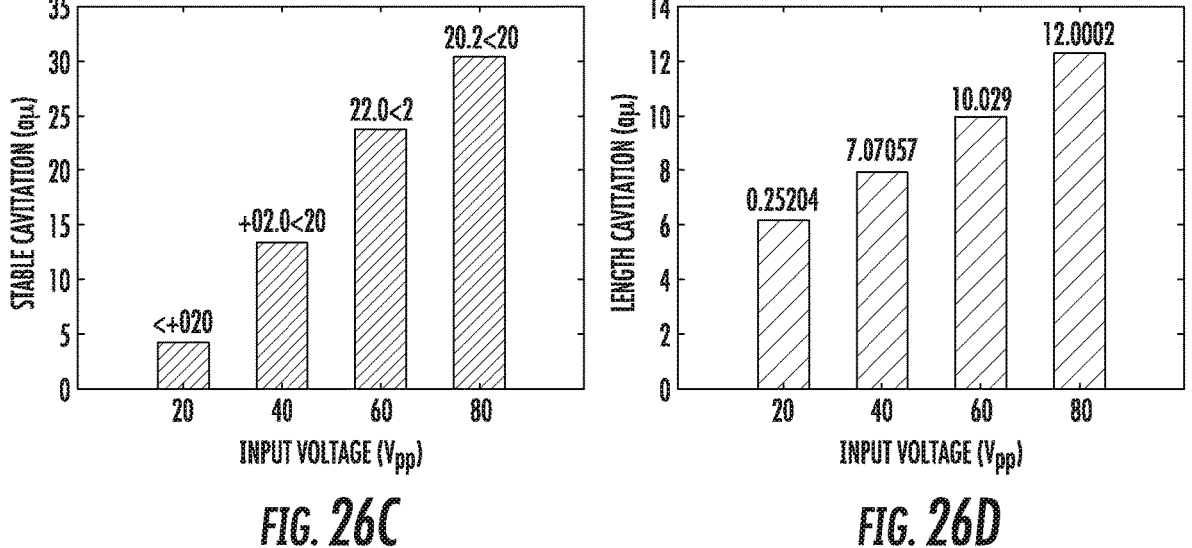
Figures 27A, 27B, 27C:
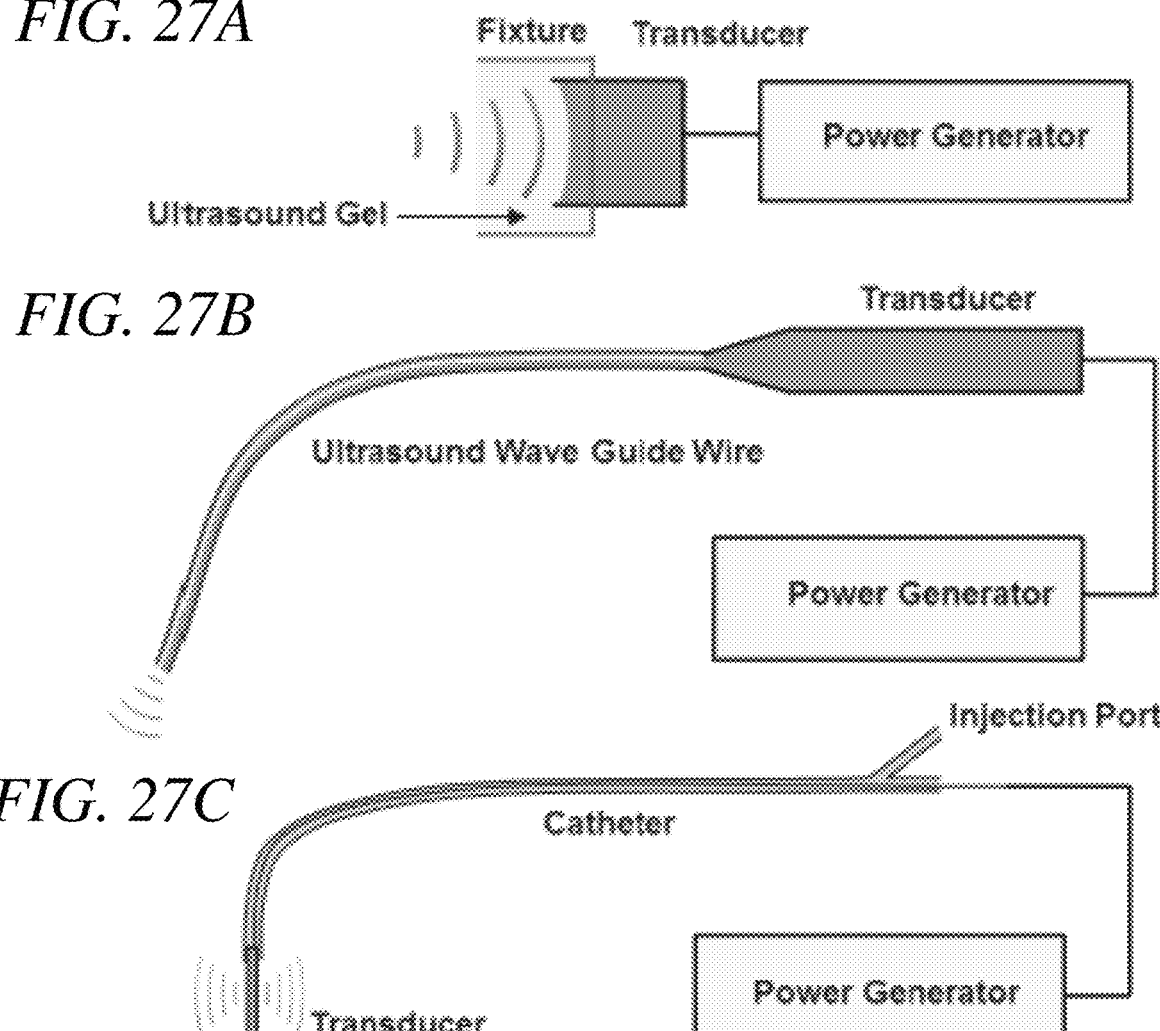
Figure 28:
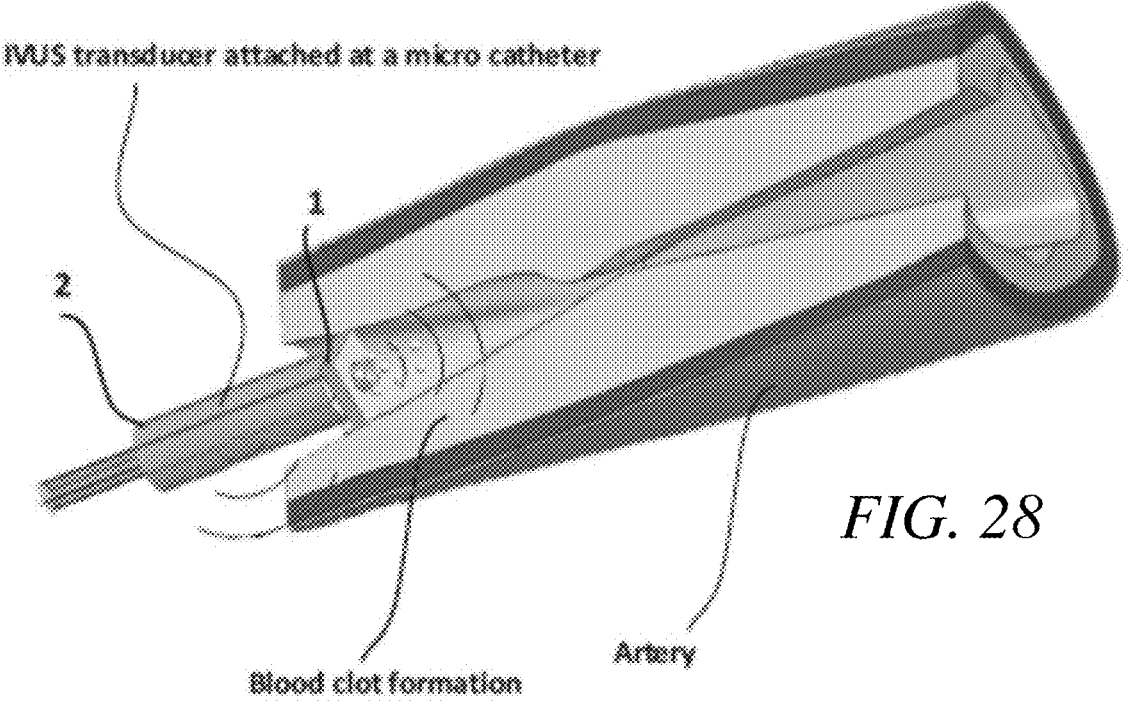
Figure 29:
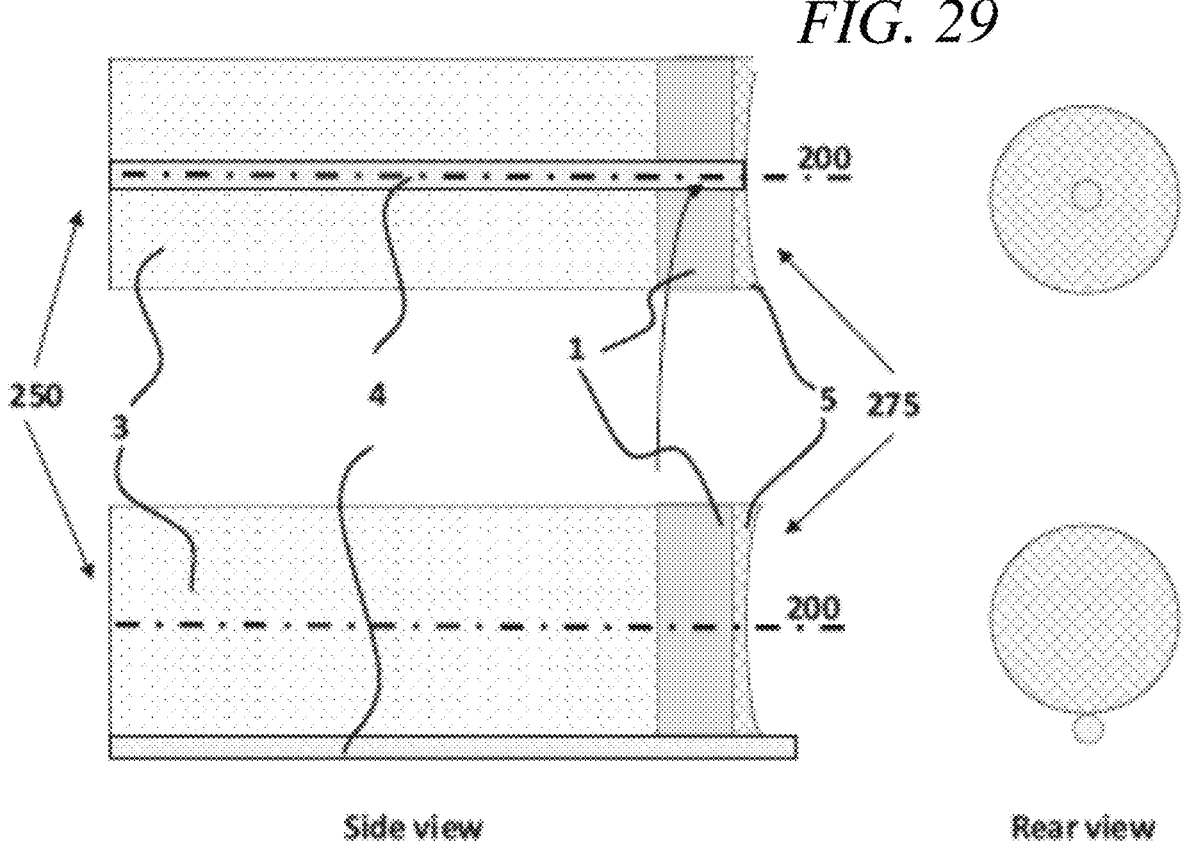
Figure 30:
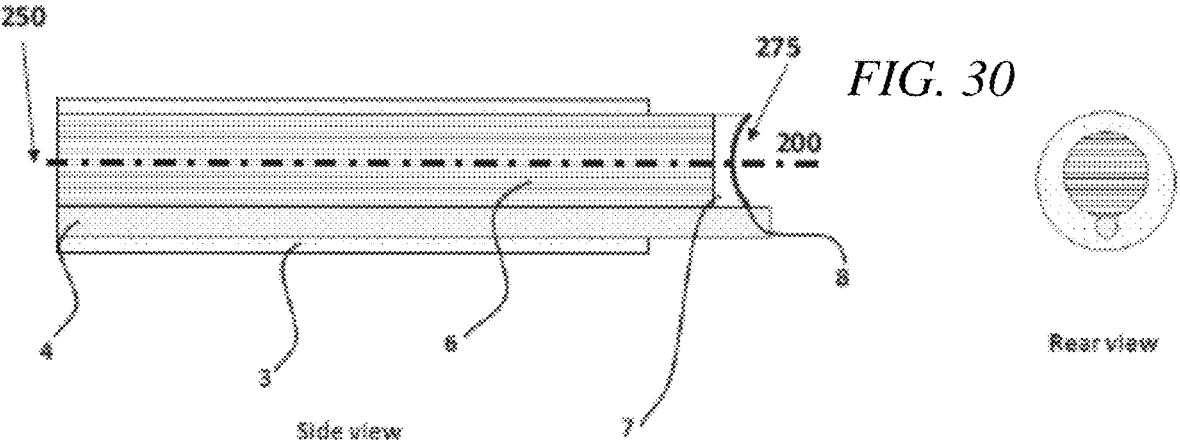
Figures 31, 32:
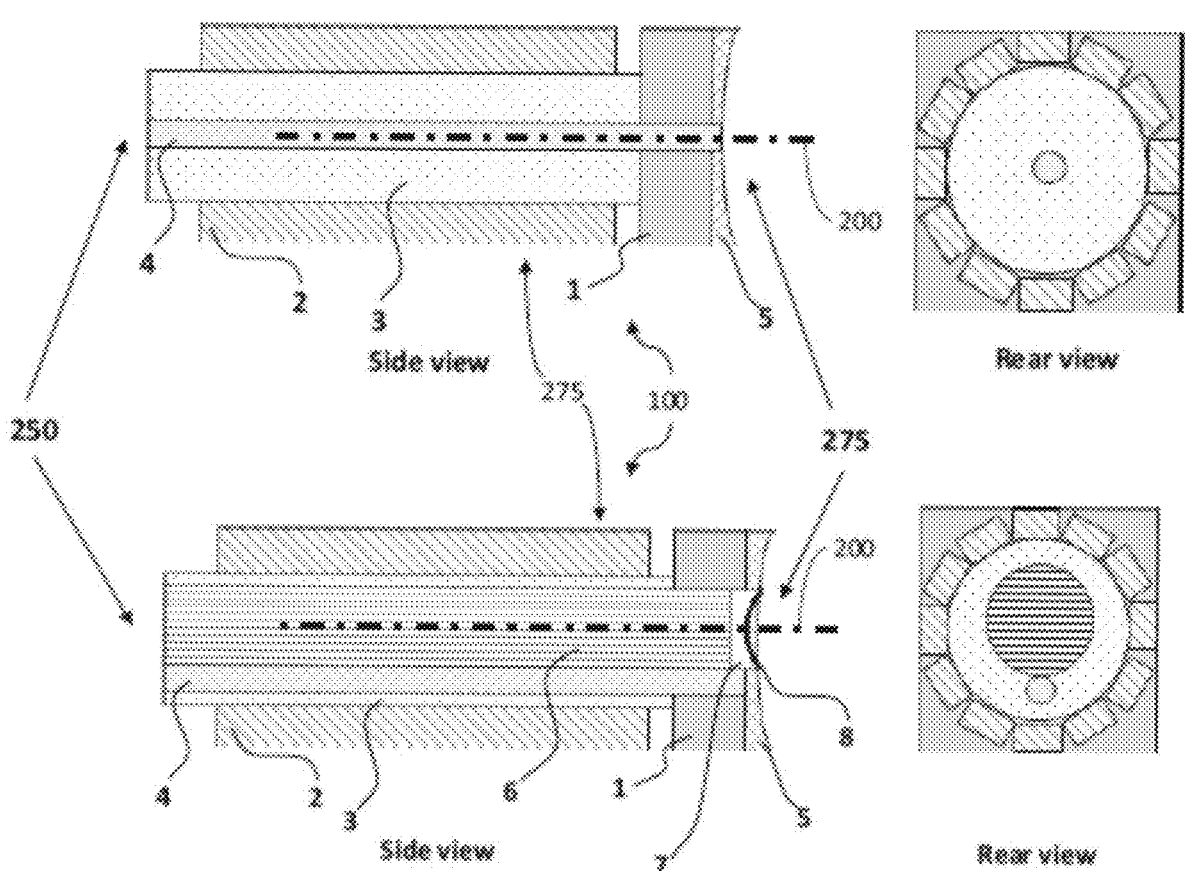
Figure 35:
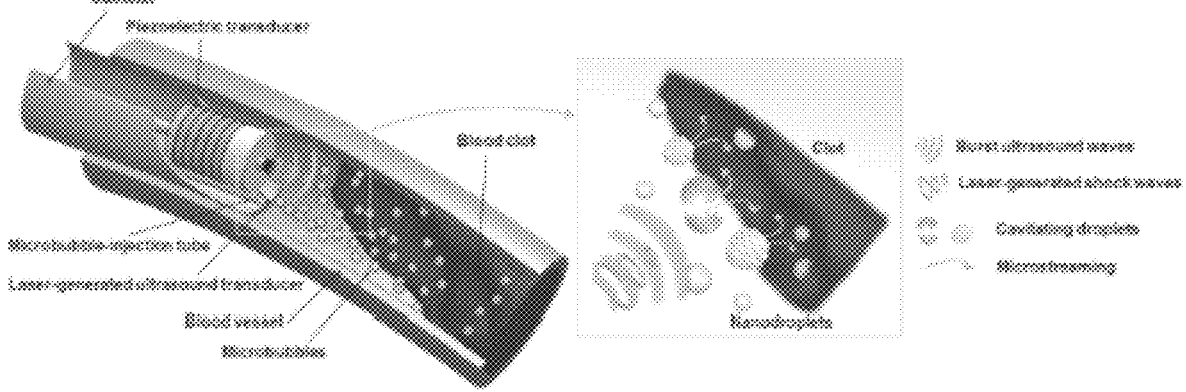
Figure 36A:
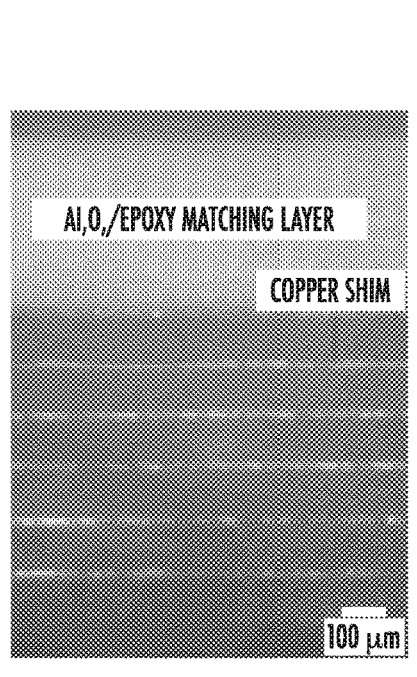
Figure 36B:
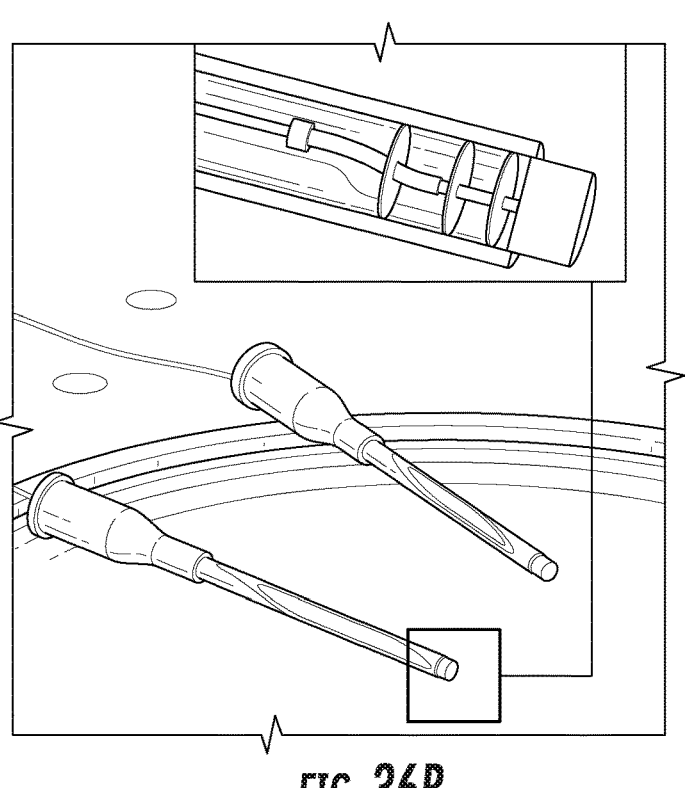
Figure 36C:
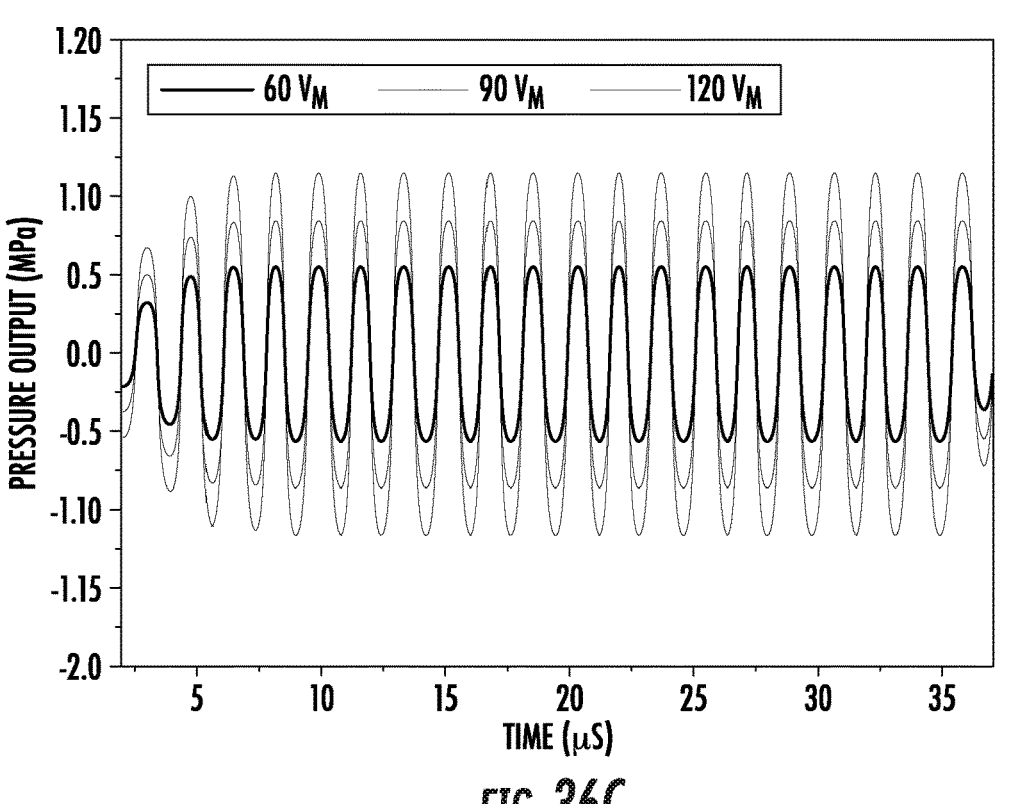
Figure 37A:
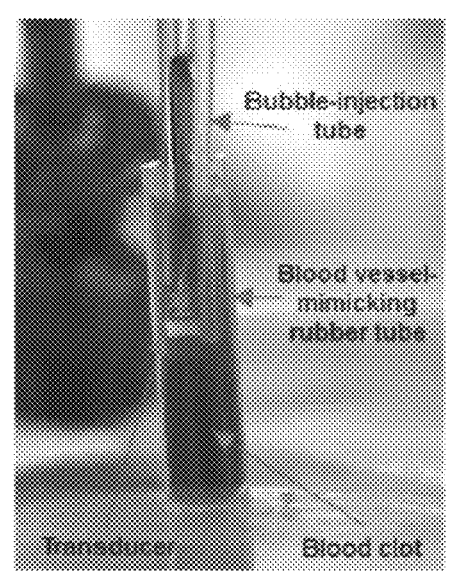
Figure 37B:
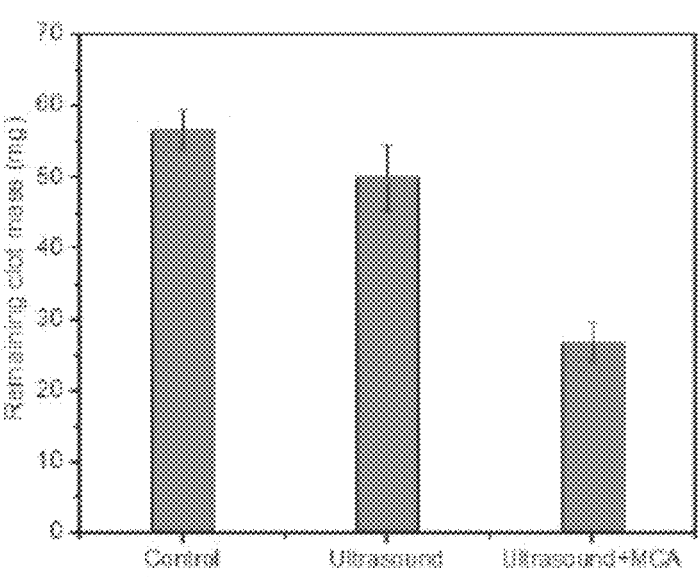
Figure 38:
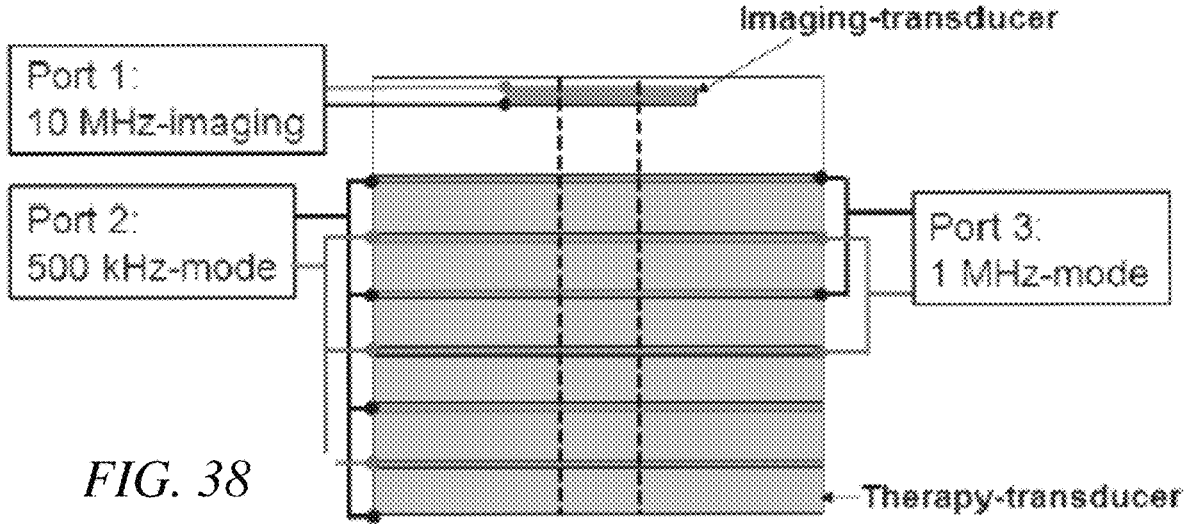
Figure 39:
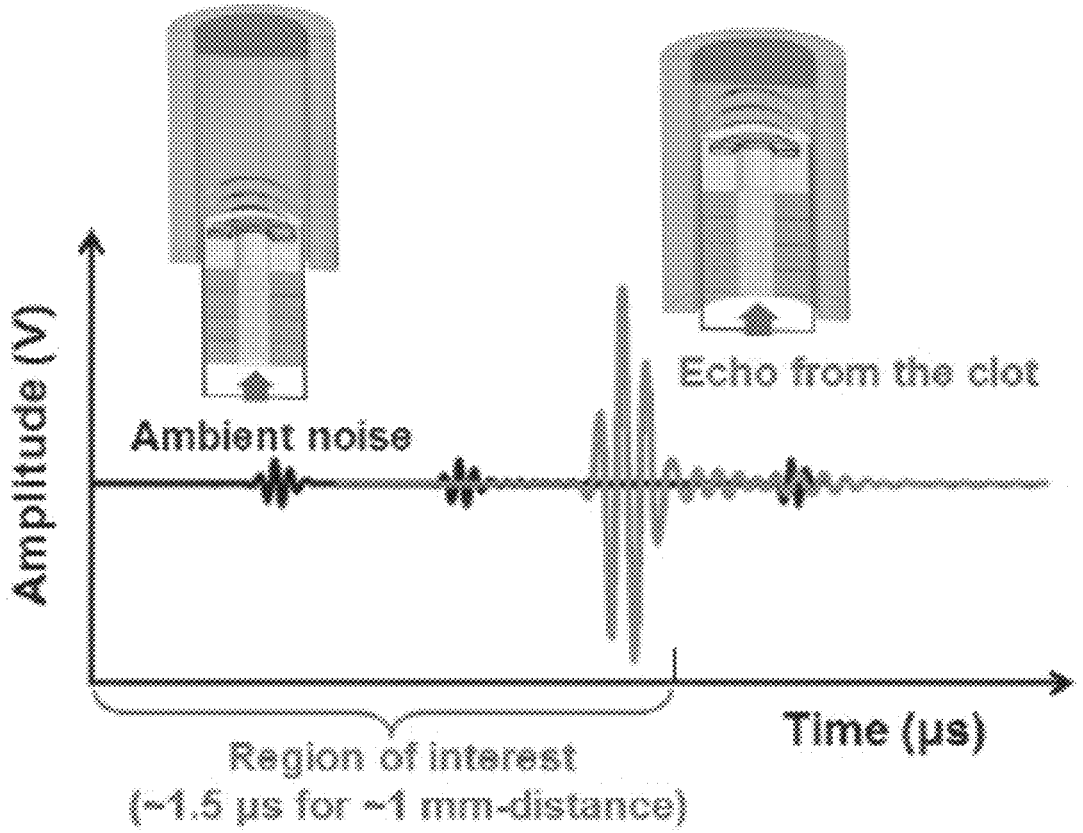
Figure 40A:
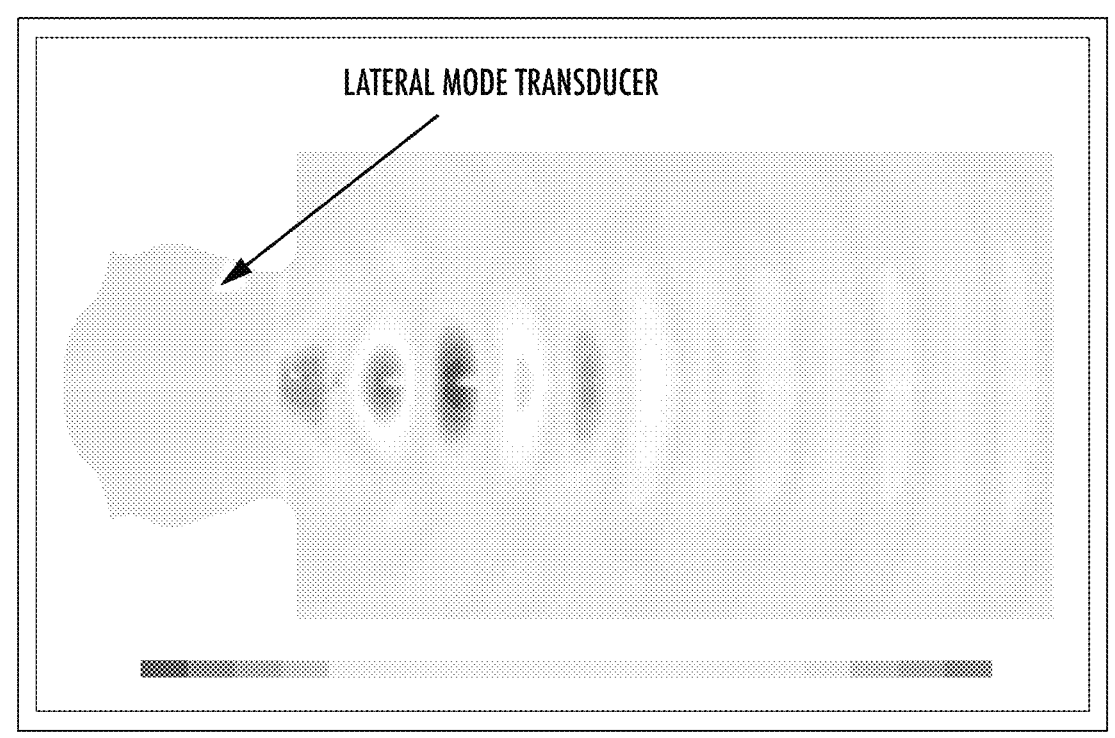
Figure 40B:
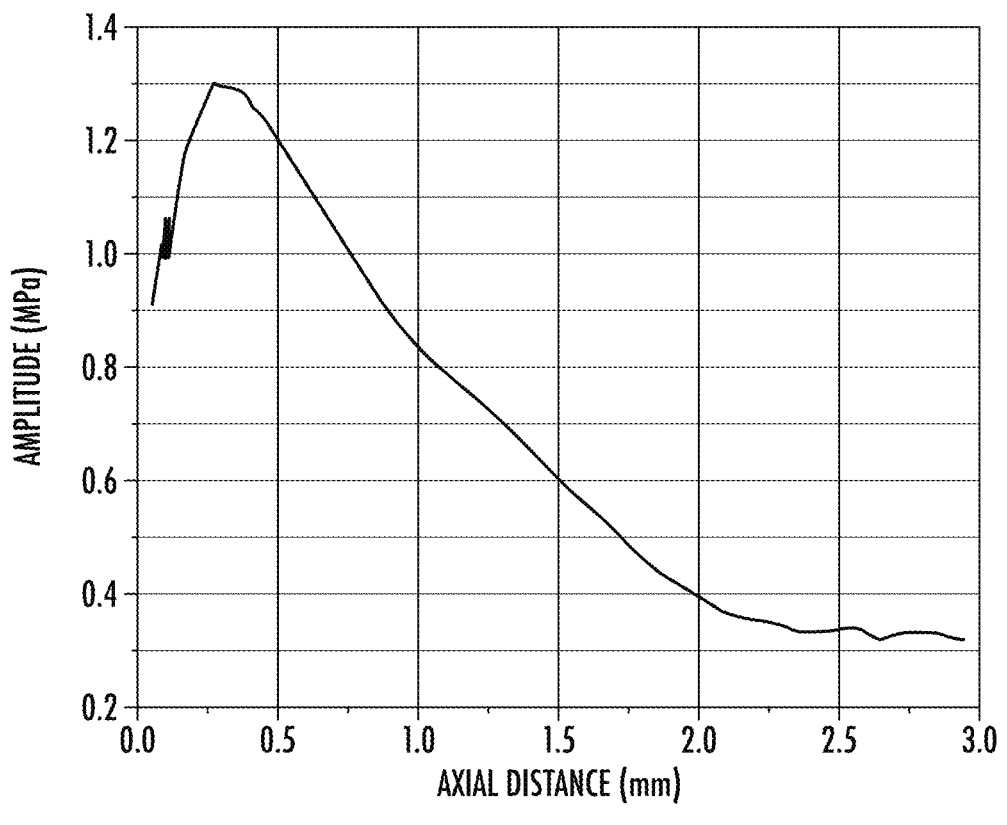
Figure 41A:
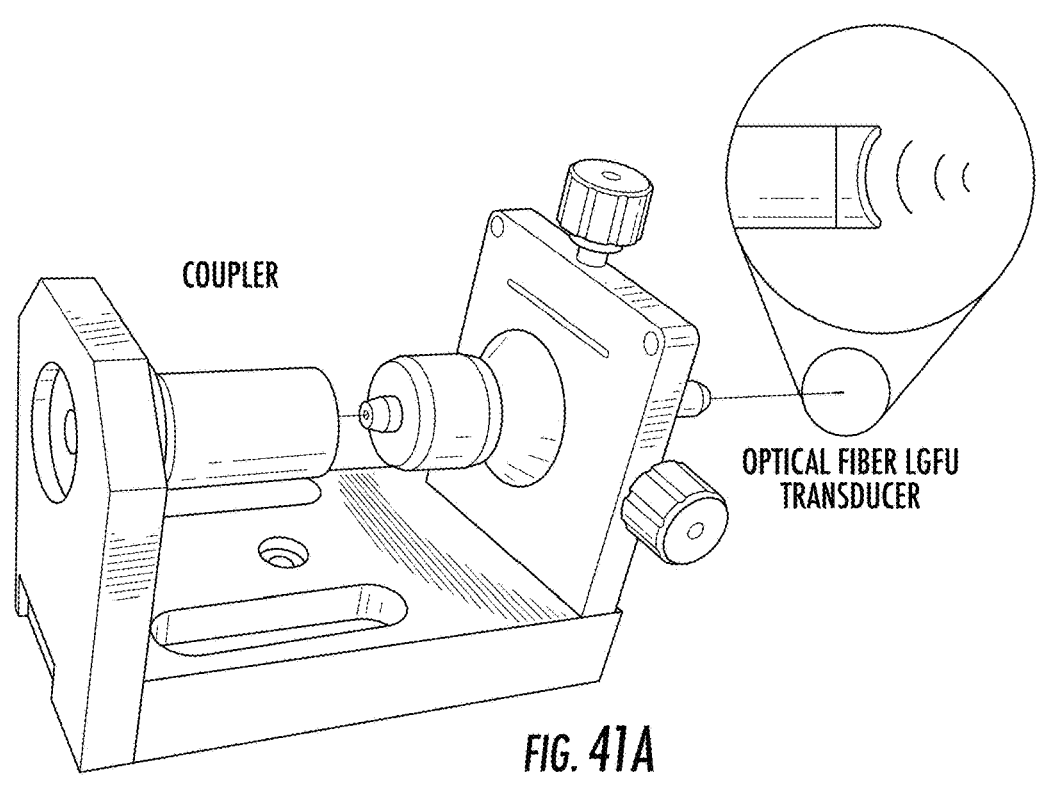
Figure 41B:
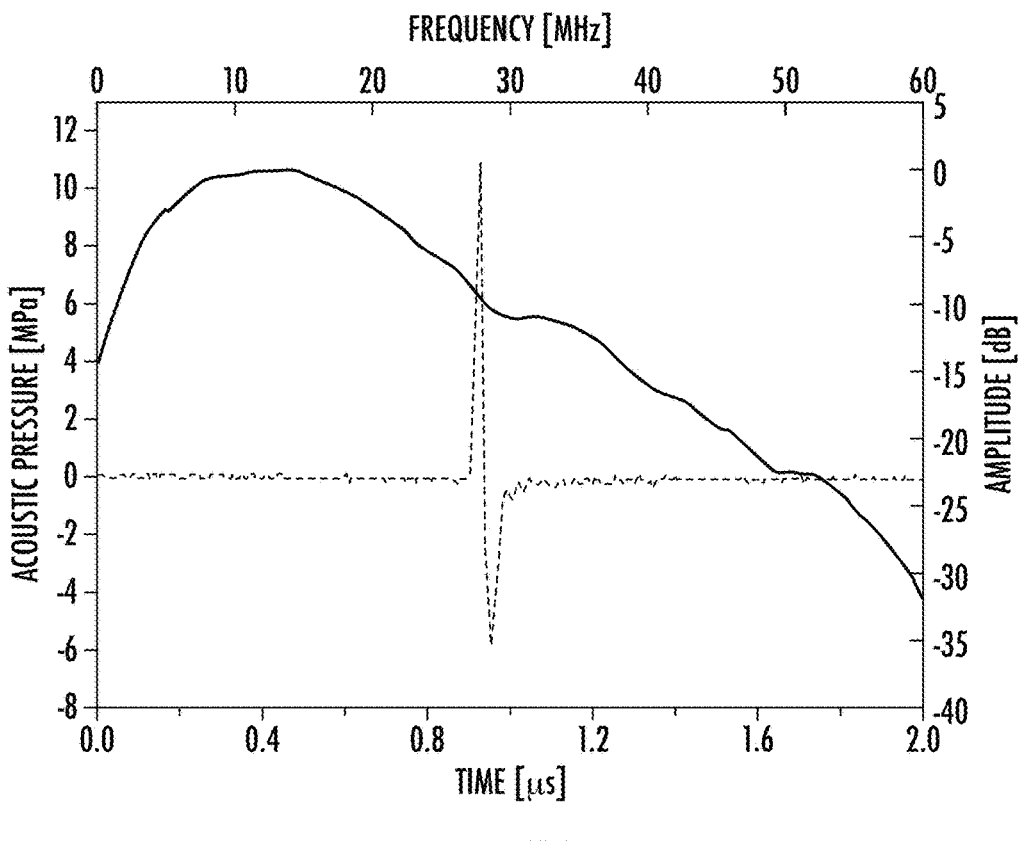
Figure 43:
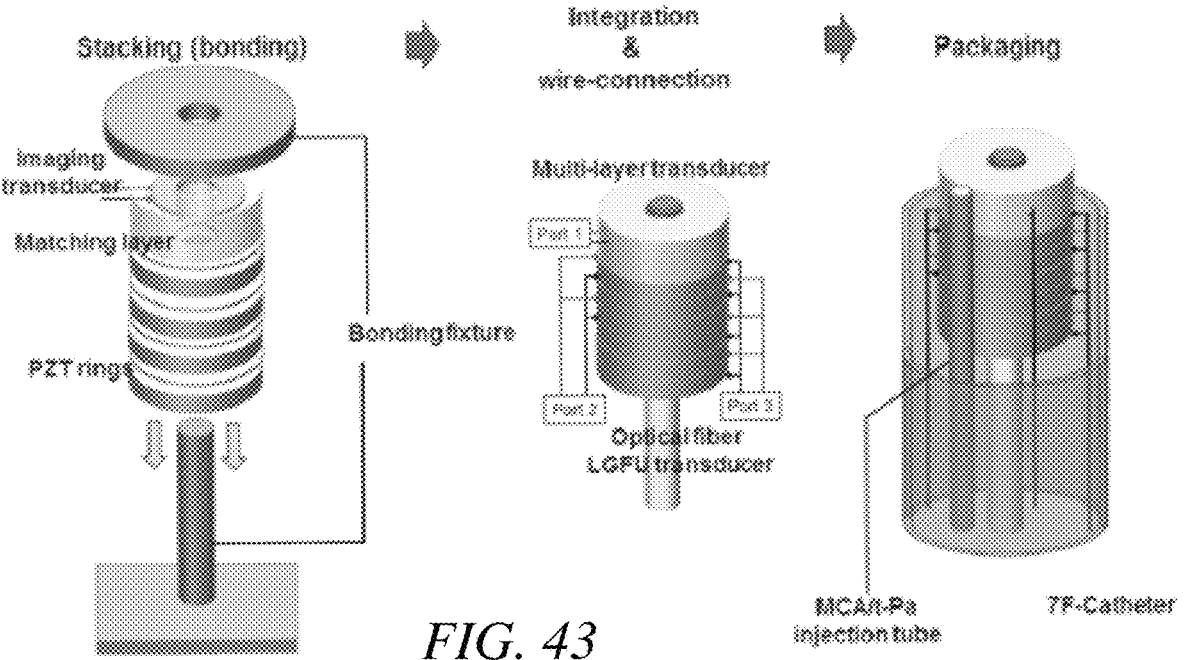
Figure 44:
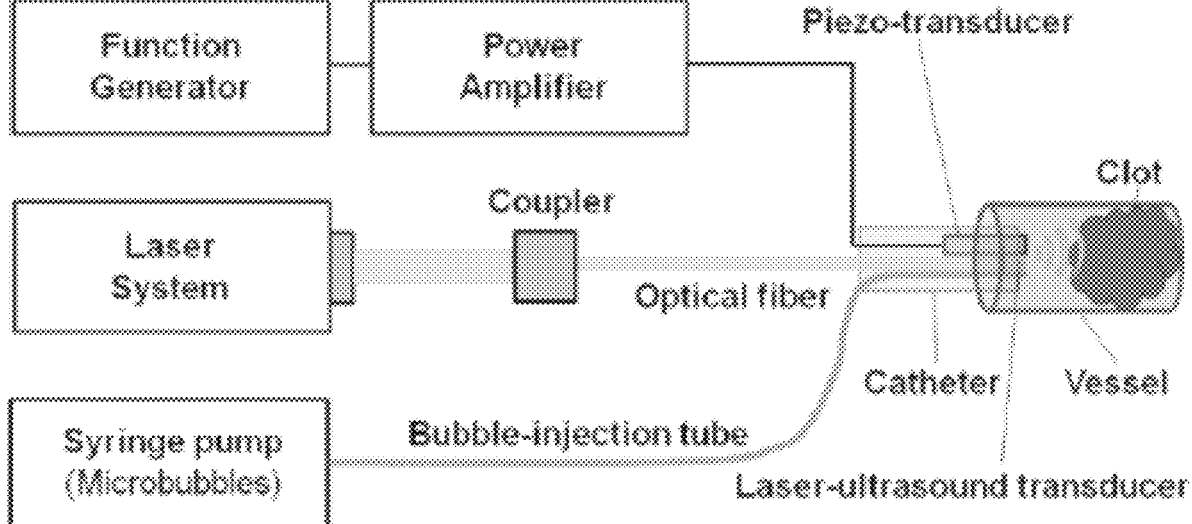

Figure S2 is a graph illustrating unretracted clot lysis results for different treatment conditions with a peak nega-tive pressure of 0.9 MPa. * indicates $p<0.05$ compared to control, t indicates $p<0.05$ compared to tPA only, and t indicates $p<0.05$ compared to tPA+US;

Figure S3A is an image of a histology slide of a retracted clot; Figure S3B is an image of a histology slide of an unretracted clot; Figure S3C is a graph of the calculated Young's modulus of clots;

FIG. 15 is a schematic diagram of nanodroplet mediated ultrasound thrombolysis inside of a blood vessel;

FIG. 16 is a schematic diagram illustrating mechanical structures of SPPS (a) and MPPS (b), where the red arrows indicate thickness vibration mode and the yellows indicate lateral mode;

FIG. 17 illustrates the finite element (FE) model and boundary conditions for a simulation;

FIG. 18A illustrates an exemplary fabrication procedure for the MPPS transducer and FIG. 18B is a photo of the fabricated transducer;

FIG. 19 is a schematic diagram of a test setup for testing the MPPS transducer;

FIG. 20 illustrates an in vitro test setup involving the intravascular US dynamic flow model for the demonstration of thrombolysis;

FIGS. 21-21C illustrate simulation results of the SPPS and MPPS transducers; FIG. 21A illustrates electric imped-ance responses; acoustic pressure fields by the SPPS (FIG. 21B) and by the MPPS transducer (FIG. 21C);

FIGS. 22A-22C illustrates experimental results of the fabricated MPPS transducer; (FIG. 22A) electric impedance responses, (FIG. 22B) acoustic pressure fields and (FIG. 22C) the sensitivity of the pressure output at the focal spot and the mechanical index;

FIG. 23 illustrates representative images of the demon-stration of nanodroplet-mediated thrombolysis for 30 min-utes of sonication, where the white arrow in each image indicates the vertical position of the transuscer;

FIG. 24 is a graph illustrating a comparison of throm-bolytic rate under four treatment groups (without flow): 1) control, 2) ultrasound only, 3) ultrasound with MB, and 4) ultrasound with ND (n=3);

FIGS. 25A-25C illustrate the influence of ND concentra-tions from 0 to $10^9$ ND/mL (FIG. 25A) and the blood clot prior to (FIG. 25B) and after (FIG. 25C) the treatment at $10^9$ ND/mL, where the number of tests is three for each test group;

FIGS. 26A-26D illustrate results of a study of the ND cavitation effect using the MPPS transducer; (FIG. 26A) acoustic pressure output in time domain under 80 Vpp, (FIG. 26B) frequency spectrum with respect to input voltage level, and quantifications of (FIG. 26C) stable and (FIG. 26D) inertial cavitation, where the inset (blue rectangular box) figure in FIG. 26A represents the nonlinearity of the wave signal and the green circles in FIG. 26B indicate super-harmonic terms of the wave signal;

FIGS. 27A-27C schematically illustrate various ultra-sound-induced thrombolysis techniques, including (FIG. 27A) transcutaneous-delivered external ultrasound (TDEU); (FIG. 27B) catheter-delivered external transducer ultrasound (CETU); and (FIG. 27C) catheter-delivered transducer-tipped ultrasound (CTTU);

FIG. 28 schematically illustrates a catheter-mounted, small aperture, hybrid, IVUS thrombolysis transducer device, according to one aspect of the present disclosure;

FIG. 29 schematically illustrates a front-firing, piezoelectric stacked-type, flat or focused element, according to one aspect of the present disclosure;

FIG. 30 schematically illustrates a front-firing, LGFU transducer element, according to one aspect of the present disclosure;

FIG. 31 schematically illustrates a dual excitation, catheter-delivered, laser ultrasound thrombolysis (DECLUT) system, according to one aspect of the present disclosure, having a side viewing piezoelectric cylindrical array transducer and a piezoelectric forward viewing flat or focused transducer;

FIG. 32 schematically illustrates a dual excitation, catheter-delivered, laser ultrasound thrombolysis (DECLUT) system, according to one aspect of the present disclosure, having a side viewing piezoelectric cylindrical array transducer and a hybrid forward viewing flat or focused transducer;

FIGS. 33 and 34 schematically illustrate a structure of a piezoelectric (e.g., capable of operation in lateral mode or thickness mode or longitudinal mode) element, according to aspects of the present disclosure, with FIG. 32 illustrating a single layer piezoelectric element and FIG. 33 illustrating a multi-layer stacked structure;

FIG. 35 schematically illustrates intravascular sono-thrombolysis using a DECLUT catheter, low-frequency (<1 MHz) burst waves and laser-generated shock waves to generate microstreaming caused by cavitation of injected 5 droplets/microbubbles;

FIGS. 36A-36C schematically illustrate a piezoelectric multi-layer transducer having (FIG. 36A) 6 layers of 255 ☐m thick PZT-5A ceramics and 22 μm-thick copper shims as intermediate electrode layers; (FIG. 36B) transducers on a 16 gauge needle tip; and (FIG. 36C) a measured pressure output with the 20 cycle of sinusoidal voltage input of 60, 90, 120 Vpp at 550 kHz;

FIGS. 37A and 37B schematically illustrate a test arrangement and result for a piezoelectric multi-layer transducer involving (FIG. 37A) an in vitro test arrangement using a bovine blood clot stored in a PVC test tube filled with saline water; and (FIG. 37B) in vitro test results of a 30 minute treatment with microbubble injection for a clot mass reduction of 50% in 15;

FIG. 38 schematically illustrates a multi-frequency piezoelectric transducer arrangement combining a 10 MHz imaging transducer with 500 kHz and 1 MHz therapy transducers;

FIG. 39 schematically illustrates self-A-mode imaging by DECLUT transducer arrangement;

FIGS. 40A and 40B schematically illustrate an analysis of a lateral-mode transducer including (FIG. 40A) an ANSYS simulation on wave propagation of a 1.2×1.2×0.3 mm3 PZT-5H lateral mode transducer at its resonance frequency; and (FIG. 40B) a calculated axial pressure output profile;

FIGS. 41A and 41B schematically illustrate an optical fiber LGFU transducer (FIG. 41A) fixed at a coupler; and (FIG. 41B) a measured waveform and frequency spectrum of the optical fiber LGFU transducer with 1.5 mJ laser input;

FIGS. 42A and 42B schematically illustrate in vitro thrombolysis tests for a dual excitation of LGFU and piezo-ultrasound arrangement, including (FIG. 42A) an experimental arrangement for a dual-excitation test; and (FIG. 42B) mass loss for each treatment case (P, L, and P+L denote treatment of piezo-ultrasound, LGFU, and dual-excitation of piezo-ultrasound and LGFU, respectively);

FIG. 43 schematically illustrates an integration procedure of an optical fiber LGFU transducer and a multi-layer transducer; and FIG. 44 schematically illustrates an experimental DECLUT system, according to one aspect of the present disclosure.

DETAILED DESCRIPTION

The subject matter described herein involves the user of metastable phase change nanodroplets to enhance sono-thrombolysis. In one example the metastable phase change nanodroplets are perfluorocarbon nanodroplets having a liquid quid core comprising a perfluorocarbon material that has a boiling point below 25° C. at atmospheric pressure and that remains stable in liquid form at 25° C. at atmospheric pressure. Examples of metastable phase change nanodroplets and methods for making such nanodroplets are described in U.S. Pat. No. 9,427,410, the disclosure of which is incorporated herein by reference int its entirety. Examples of perfluorocarbon materials that can be used for the metastable phase change nanodroplets include decafluorobutane and perfluoropropane.

The cores of at least some of the metastable phase change nanodroplets may be encapsulated within a shell. In some examples, the shell may be made of a lipid, a polymer, or a protein that surrounds the core. A therapeutic agent, such as a blood clot lysing agent, may be located within (i.e., between the inner and outer diameters of the shell material, on (located on the shell surface outside of the outer diameter of the shell), or inside of the inner diameter of the shell to deliver the therapeutic agent to the subject. A therapeutic agent may also be co-administered with the metastable phase change nanodroplets. In one example, the therapeutic agent may be a lysing agent or an anticoagulant.

In one example, the cores of at least some of the perfluorocarbon nanodroplets may include only materials that have boiling points below 25° C. at atmospheric pressure and that remain stable in liquid form at 25° C. at atmospheric pressure. In other examples, the cores of at least some of the perfluorocarbon nanodroplets may include mixtures of 1) materials that have boiling points below 25° C. at atmospheric pressure and that remain stable in liquid form at 25° C. at atmospheric pressure and 2) materials that have boiling points above 25° C. at atmospheric pressure and that remain stable in liquid form at 25° C. at atmospheric pressure.

The methods and systems described herein include administering metastable phase change nanodroplets into a blood vessel of a subject where at least some of the nanodroplets surround and/or penetrate a blood clot. Ultrasound energy is then applied to the blood clot, including the metastable phase change nanodroplets within and/or surrounding the clot, causing the metastable phase change nanodroplets to oscillate in diameter, cavitate, vaporize, and lyse the clot from within and/or surrounding the clot. By "surrounding the blood clot", it is meant that the metastable phase change nanodroplets are positioned within the blood vessel outside of the blood clot on at least one side of the blood clot. The ultrasound energy may be applied transcutaneously using an ultrasound transducer external to the subject or intravascularly, using an intravascular ultrasound transducer capable of applying ultrasound energy to the clot from within the vasculature of the subject. As will be described in more detail below, the use of metastable perfluorocarbon nanodroplets to enhance sonothrombolysis allows blood clots to be lysed at lower energy levels than without using metastable nanodroplets.

Figure 1:
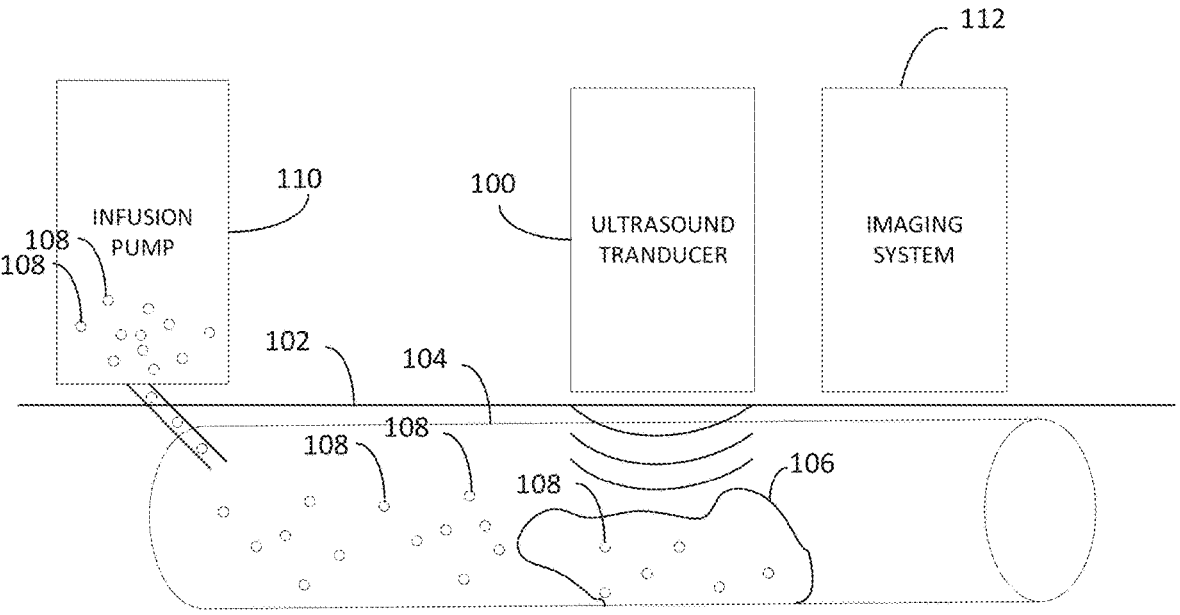
FIG. 1 is a block diagram of a system for using metastable phase change nanodroplets to enhance sonothrombolysis.

FIG. 1 is a block diagram illustrating an exemplary system for using metastable phase change nanodroplets for enhanced sonothrombolysis. Referring to FIG. 1, an ultrasound transducer 100, which in the illustrated example is external to the subject, delivers ultrasound energy transcutaneously through the skin 102 and a blood vessel 104 to a blood clot 106. Phase change nanodroplets 108 are administered into blood vessel 104 using an infusion pump 110. At least some of phase change nanodroplets 108 penetrate blood clot 106. When ultrasound transducer 100 applies ultrasound energy to blood clot 106, the phase change nanodroplets 108 that have penetrated blood clot 106 oscillate in diameter, cavitate, and eventually burst, which facilitates lysis of clot 106 from within. The application of the ultrasound energy causes the liquid cores of nanodroplets 108 to change from a liquid to a gaseous state, converting the nanodroplets to bubbles. Once in a gaseous state, the core expands until the shell containing the core bursts. The bursting of the shell and the expansion in diameter of the shell facilitate lysis of blood clot 106.

In some examples, the lysis of a blood clot, such as blood clot 106 using metastable nanodroplets 108 occurs at a rate that is at least double the rate of lysis using the same level of ultrasound energy and other acoustic parameters (such as frequency and duration of energy application) without using metastable nanodroplets 108.

In some examples, metastable nanodroplets 108 have diameters ranging from 10 nm to 300 nm. In other examples, metastable perfluorocarbon nanodroplets 108 have diameters ranging from 10 nm to 750 nm.

In one example, applying ultrasound energy may include applying ultrasound energy with a peak negative pressure that is less than 3 megapascals. In another example, applying the ultrasound energy includes applying the ultrasound energy with a peak negative pressure that is less than 5.9 megapascals. In still another example, applying the ultrasound energy includes applying the ultrasound energy with a peak negative pressure that is less than 12 megapascals. In still another example, applying the ultrasound energy includes applying the ultrasound energy at a frequency selected from the range of 300 kHz and 2 MHz. In still another example, applying the ultrasound energy includes applying the ultrasound energy at a frequency selected from the range of 2 MHz and 10 MHz. In still another example, applying the ultrasound energy includes applying the ultrasound energy with a peak negative pressure of no more than 5.9 megapascals at 1 MHz. In one particular example, at least some of metastable nanodroplets 108 can be vaporized using a peak negative pressure that is less than 4.5 MPa with 15 cycles at 1 MHz and 25° C.

In some examples, applying the ultrasound energy to blood clot 106 includes configuring ultrasound transducer 100 to generate ultrasound pulses having a duty cycle of no more than 45%. In some examples, the ultrasound energy applied by ultrasound transducer 100 may have an acoustic intensity of no more than 34.8 Watts per square centimeter, in other examples, no more than 15 Watts per square centimeter, and in other examples, no more than 5.2 Watts per square centimeter.

As indicated above, one problem with some blood clot treatment methods is the inability to effectively lyse retracted clots. Using phase change nanodroplets that are activated to lyse the clot from within, even retracted clots can be lysed effectively.

In addition to enhancing lysis of blood clot 106, metastable phase change nanodroplets 108 may also be used to detect the location and/or presence of a blood clot, such as blood clot 106 with the vasculature of a subject. To locate a blood clot within the vasculature of a subject, the blood vessel where a clot is suspected to be located can be infused with metastable phase change nanodroplets 108. While infusing the blood vessel with metastable phase change nanodroplets 108, transducer 100 may apply ultrasound energy to the blood vessel. The same ultrasound transducer or a separate ultrasound transducer may monitor acoustic signals emanating from the blood vessel resulting from oscillations in diameter and/or bursting of metastable phase change nanodroplets caused by the application of ultrasound energy. The location of the from which the acoustic signals emanate may be used to locate a blood clot. For example, a higher relative concentration of acoustic signals caused by nanodroplet oscillations and bursting may indicate the presence of phase change nanodroplets that are stationary and embedded within a blood clot.

In some examples, acoustic signals from the cavitation of microbubbles produced from metastable phase change nanodroplets 108 are detected by a transducer, which may be the same or a different transducer from transmitting transducer 100, and the acoustic energy detected by the detecting transducer from the $2^{nd}$ harmonic and higher frequencies of the detected energy caused by the cavitating microbubbles is used to indicate the presence and/or location of the cavitation occurring at the clot.

In some examples, ultrasound is utilized to form an image of the clot and acoustic signals of cavitation are overlaid on the image of the clot. For example, the detected ultrasound energy from the clot itself may be used to form an image of the clot. The detected ultrasound energy from the cavitation of the microbubbles formed from metastable phase change nanodroplets 108 may be overlaid on top of the image of the clot. In FIG. 5C described above, the gray portion of the image within the blue circle shows a blood clot inside of a tube. The yellow and green portion of the image depicts cavitation activity caused by the nanodroplets inside the clot in FIG. 5C and caused by microbubbles outside of the clot in FIG. 5D.

As indicated above, metastable phase change nanodroplets 108 may be used to deliver therapeutic agents, such as blood clot lysing agents, to a subject. In general, a material for enhancing breakdown of the blood clot can be delivered in conjunction with (i.e., using the nanodroplets as the delivery mechanism or administered separately from but at or near the same time as the nanodroplets) the nanodroplets and ultrasound energy. The material may be delivered using metastable phase change nanodroplets as the delivery vehicles or separately from the metastable phase change nanodroplets. In one example, the material for enhancing breakdown of the blood clot comprises a tissue plasminogen activator. In another example, the therapeutic agent delivered in conjunction with the nanodroplets may be an anticoagulant.

According to another aspect of the subject matter described herein, ultrasound may be used to obtain an image of a clot within a blood vessel at one frequency. Metastable nanodroplets, such as perfluorocarbon nanodroplets may be administered into the blood vessel. Ultrasound energy may be applied to the metastable phase change nanodroplets within the clot at a second frequency that is different from the first frequency, causing the metastable phase change nanodroplets to vaporize and convert to bubbles, which cavitate within the blood clot and lyse the blood clot. In one example, the first frequency is at least double the second frequency. As with the examples described above, the metastable phase change nanodroplets are allowed to penetrate the blood clot prior to the causing of the perfluorocarbon nanodroplets to vaporize and convert to bubbles. As a result, the lysis of the blood clot occurs from within the clot.

The system illustrated in FIG. 1 may include means for administering a material for enhancing breakdown of the blood clot in conjunction with the nanodroplets and ultrasound energy and means for generating an image of the blood clot with acoustic signals from cavitation overlaid on the image of the blood clot. For example, infusion pump 110 separate from ultrasound transducer 100 is one example of means for administering the therapeutic agent. In another example, the means for administering the therapeutic agent may comprise a tube (and associated infusion pump) that is integrated with ultrasound transducer 100, in the case where ultrasound transducer 100 is an intravascular transducer.

An imaging system 112 is an example of the means for generating an image of the blood clot and the cavitation. In one example, imaging system 112 may use or include ultrasound probe 100 to generate the images of the clot and the cavitation. In another example, imaging system 112 may include a clip-on device associated with ultrasound probe 110 to generate and detect ultrasound energy used to generate an image of the blood clot and the cavitation. In one example, imaging system 112 may use ultrasound energy that is twice the frequency of the ultrasound energy used to generate cavitation. In yet another example, the frequency of the ultrasound energy used to generate the cavitation is at least twice the frequency of the ultrasound energy used by imaging system 112 to generate the images of the blood clot and the cavitation.

It is understood that imaging system 112 may include at least one processor and associated memory as well as computer-executable instructions for causing the processor to generate the images of the blood clot and the cavitation from the ultrasound energy. An example of images that may be generated by imaging system 112 are described below with respect to FIGS. 5B and 5C.

In one example, acoustic signals from the cavitation are detected by a transducer and utilized to indicate the presence or location of the cavitation occurring at near (i.e., within about 1 mm to no more than about 3 mm of the clot surface) or within the blood clot.

FIG. 2 is a flow chart illustrating an exemplary process for using phase change nanodroplets for enhances sonothrombolysis. Referring to FIG. 2, in step 200, the process includes using ultrasound to obtain an image of a blood clot within a blood vessel. For example, ultrasound transducer 100 may apply ultrasound energy transcutaneously to an area where a blood clot is suspected to be located, and the same or a separate ultrasound transducer may detect the ultrasound energy produced by the clot and produce an image of the clot from the produced ultrasound energy. In another example, an intravascular ultrasound probe may be used to obtain an image of a blood clot.

In step 202, the method includes administering metastable perfluorocarbon nanodroplets into a blood vessel that includes or that leads to a blood vessel that includes a blood clot, the metastable perfluorocarbon nanodroplets each have a liquid core comprising a perfluorocarbon material that has a boiling point below 25° C. at atmospheric pressure and that remains stable in liquid form at 25° C. at atmospheric pressure. For example, phase change nanodroplets 108 may be infused into the blood vessel of a subject by an infusion pump, such as infusion pump 110 illustrated in FIG. 1.

In step 204, the process includes applying ultrasound energy to the perfluorocarbon nanodroplets within and/or surrounding the blood clot, causing the perfluorocarbon nanodroplets to vaporize and convert to bubbles, which cavitate and lyse the blood clot. For example, ultrasound transducer 100 may apply ultrasound energy transcutaneously to the perfluorocarbon nanodroplets 108 that penetrate blood clot 106, causing the perfluorocarbon nanodroplets to convert to bubbles, which cavitate and eventually burst, causing lysis of blood clot 106 from within blood clot 106.

The following section describes a scientific study in which phase change nanodroplets are used to disrupt unretracted aged clots from cavitation internal to the clot.

Phase Change Nanodroplets Disrupt Unretracted Aged Clots Efficiently Through Cavitation Internal to Clot Surface The study demonstrates enhanced cavitation inside aged blood clots by using low-boiling point (−2° C.) perfluorocarbon phase-change nanodroplets and pulsed ultrasound. Aged (>3 day) clots have dense fibrin structure and less permeable compared to fresh clots. These aged clots are more resistant to current drug-based thrombolysis including sonothrombolysis, due to their dense fibrin structure. Microbubble-mediated, ultrasound-enhanced drug penetration techniques for aged clots have not been effective due to the limited permeation of microbubbles into clots with sub-microns pores. We hypothesized that perfluorocarbon phase-change nanodroplets could penetrate and then cavitate inside aged clots, and this internal ultrasonic cavitation would enhance the sonothrombolysis efficacy. Phase-change nanodroplets are hundred-nanometer size, liquid-filled nanoparticles which convert to a gaseous state upon excitation by acoustic energy. We investigated the thrombolytic effects of lipid shell-decafluorobutane nanodroplets compared to microbubbles with the identical formulation in a flow model that contains an aged bovine blood clot. Short burst ultrasound (1 MHz, 5.9 MPa-peak-negative pressure, 9 cycles, 2 ms-repetition) was applied in three different therapy scenarios: ultrasound only, ultrasound with microbubbles, and ultrasound with nanodroplets (n=5). Nanodroplet-mediated treatment realized an averaged thrombolysis rate of 3.8±0.27%/min, which shows a significant rate increase (p<0.05) compared to the microbubble-mediated case (2.7±0.34%/min). We observed distinctive internal erosion at the middle of bovine clot samples from nanodroplet-mediated ultrasound, whereas the microbubble-mediated case generated surface erosion. Ultrasound imaging during sonothrombolysis demonstrated that nanodroplets generated cavitation clouds inside an aged clot, whereas the microbubble-cavitation formed larger cavitation clouds only outside a clot sample.

Sonothrombolysis is a minimally invasive, ultrasound-based clot dissolution technique for the treatment of thrombo-occlusive vascular diseases, such as deep vein thrombosis, and pulmonary embolism.[1] One of the primary mechanisms of sonothrombolysis is cavitation[2]. Both stable and inertial cavitation apply shear stress on blood clots by microstreaming, microjetting, and shock waves.[3] To enhance this cavitational effect, microbubble contrast agents have been used as cavitation nuclei.[4,5] With lower peak-negative pressure (PNP) amplitude (0.5-2 MPa) than the free bubble nucleation threshold (PNP>13.5 MPa),[6] infused microbubbles oscillate and rupture near the clot resulting in clot dissolution.[7,8] Moreover, microbubbles might permeate into a clot by the acoustic radiation force.[9] Since the penetrating microbubbles disrupt the fibrin network and facilitate more fluid transport into clots, the penetration of cavitation nuclei directly affects thrombolytic efficacy.[10] However, this penetration of microbubbles is limited for aged clots (>3 days), also referred to as retracted clots.[11] During clot retraction, the fibrin network shrinks increasing its density and lowering porosity, which results in the reduced permeability of microbubbles or micro-drug particles.[12] Microbubble-mediated ultrasound (PNP of 0.5 MPa) has demonstrated only negligible improvement of drug permeation for retracted clots,[11] which is likely caused by the limited penetration of 1-10 micrometer size bubbles into the dense and stiff clot structure.[11,12] We hypothesized that submicron-size cavitation nuclei would facilitate the cavitation inside retracted clots, and thus improving thrombolysis efficacy. Ultrasound radiation force and microstreaming due to cavitation is hypothesized to enhance the penetration of nanodroplet particles into a clot even more efficiently than microbubbles. Phase-change nanodroplets are hundred-nanometer size, liquid-filled nanoparticles, which convert to a gaseous state upon excitation by acoustic energy.[13] Previous sonothrombolysis studies using nanodroplets demonstrated the cavitation-induced clot lysis with reduced acoustic power[14] and reduced clot debris size[15], but the improved permeation of nanodroplets into retracted clots compared to microbubbles and the consequent thrombolytic improvement has not been demonstrated yet. We hypothesize that nanodroplets change their phase (liquid to gas) inside the retracted clots, and this internal cavitation results in more efficient clot fractionation than microbubble-mediated sonothrombolysis. We test this hypothesis using low-boiling point (−2° C.) lipid-shell perfluorocarbon phase-change nanodroplets and compare with their precursor microbubbles through an experimental study in vitro. Low-boiling point nanodroplets, formulated with perfluorocarbons which are in a gas state at room temperature and pressure, provide an advantage of requiring less acoustic energy than those made with perfluorocarbons which are in a liquid state at room temperature and pressure.

Figures 3A, 3B, 3C, 3D:
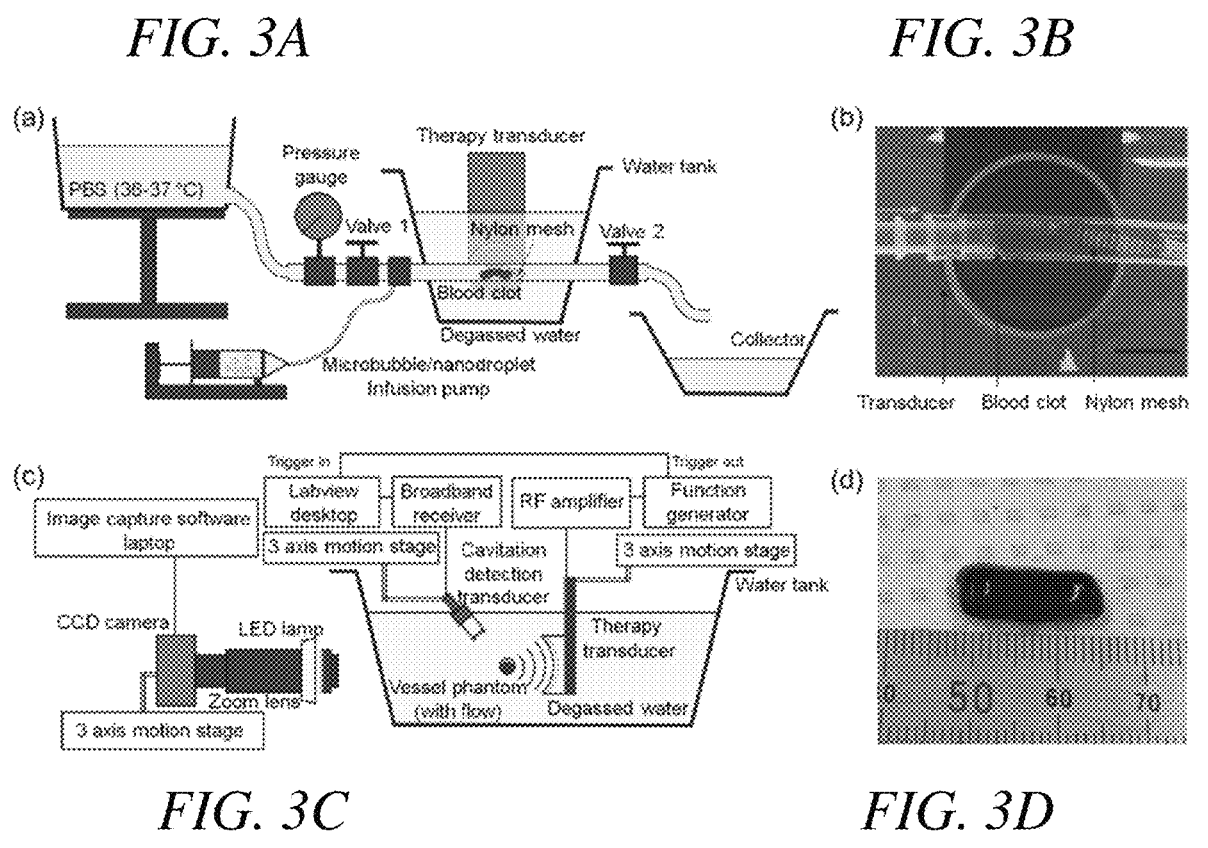

This reduced energy may help avoid undesired damage to surrounding healthy tissue. We utilized a vessel-flow model that is similar to the one developed in the previous study (FIG. 3A).[16] The method mimicked partial occlusion (70-75% occlusion) in a vein. As shown in FIG. 3B, a blood clot sample was fixed in a vessel phantom (0.8 mm in thickness, 6.4 mm in inner diameter, TYGON S3TM E-3603) by using a nylon mesh (1 mm grid size, 500 μm thick, WN1000, Industrial Netting, MN, USA). Due to the similar acoustic impedance of blood clot (1.67-1.7 MRayl) and nylon (2.9-3.1 MRayl), we assumed that the hard-boundary effect of the mesh is negligible. The reservoir height was controlled to apply constant pressure (0.1 psi) in a channel which is in the reported femoral vein pressure range,16 and the partially occluded flow rate (80±15 ml/min) was maintained. A 1 MHz focused transducer (33 mm-aperture diameter, 35 mm-focal distance, H-131, Sonic Concepts, Inc., WA, USA) was used as a therapy transducer positioned 29 mm away from a vessel phantom (FIG. 3C). The axial full-width-half-maximum (FWHM) of the transducer was measured[17]0.4±0.3 mm, and the lateral FWHM at 29 mm away is 3.0±0.3 mm. We measured cavitation signals using a 5 MHz piston transducer (V309, Panametrics, USA) which was positioned 50 mm away from the tube on a 45°-angled axis. The sonothrombolysis process was monitored by a USB camera (MLE-0030-U, Mightex).

Bovine unretracted aged clot samples were prepared following the method described in Ref. 11. Bovine blood (Densco Marketing, Inc., Woodstock, IL, USA) was mixed with 2.5-3.0% calcium chloride ($CaCl_2$)) solution (Fisher Scientific) with a volume ratio of 10:1 (100 ml blood and 10 ml CaCl2).[17,18] The mixture was transferred to 1.8 ml-transfer pipettes (Thermo Scientific™ 33620S, the outer diameter of 6.6 mm). After 3 hours in a 37° C. water bath, the blood clot-filled pipettes were stored at 4° C. for 4 days. A 302±22 mg clot sample (approximated dimension of 15 mm length and 5 mm diameter) was used for each thrombolysis test (FIG. 3D).

We used decafluorobutane (DFB, $C_4F_{10}$, boiling point of −2° C.) as a core of microbubbles and nanodroplets. DFB nanodroplets were prepared using the method described in Ref. 13. Precursor lipid-shell DFB microbubbles were synthesized in-house as previously described.[19] The agitation of a 3 ml vial (1.5 ml of lipid solution and a headspace pressurized with DFB) using a Vialmix (Lantheus Medical Imaging, N. Billerica, MA, USA) generates lipid-shelled microbubbles with a DFB gas core.[8] This procedure yielded the approximated bubble concentration of 1×1010/ml and the averaged diameter of 1.1±0.5 μm. The DFB microbubbles were condensed into liquid-core nanodroplets with a size of 100-200 nm.[19] The nanodroplets were diluted with phosphate-buffered saline (PBS) to make an averaged counts of 1×109/ml (1:10 volume ratio) for infusing into the flow model. During the 10 min thrombolysis treatment, we continuously infused nanodroplets using a syringe pump (PHD2000, Harvard Apparatus) with the infuse rate of 80 μl/min. Dilution and infusion of microbubbles followed the same procedure as for the nanodroplets.

Using the flow model, we tested thrombolytic efficacy of three different treatment cases: A) ultrasound only (US), B) microbubble-mediated ultrasound (US+MB), and C) nanodroplet-mediated ultrasound (US+ND). During the 10 min-treatment, the treatment zone moved along clot length direction with a 4 mm sub-step: 4 min at the center of a clot and 3 min at each ±4 mm position. The control group was treated with neither ultrasound nor agent infusion. We divided the ultrasound conditions into 4 different groups, as shown in the Table 1 to test thrombolytic efficacy caused by different cavitation doses and radiation forces. For example, due to the similar acoustic intensities, we expected that group 2 and group 3 might generate the similar acoustic radiation force-induced acoustic streaming on the target clot, but the difference of cavitation levels caused by the PNP difference (2.3 vs. 5.9 MPa) would result in differences in thrombolytic efficacy (measured via percent mass reduction). We tested five samples in each treatment case, and the statistical significance was determined by one-way unbalanced ANOVA and Tukey's honest significant difference test ($p < 0.05$). 20

TABLE 1

Acoustic condition groups; each condition was applied to three different treatment cases: 1) ultrasound only (US), 2) microbubble-mediated ultrasound (US + MB), and 3) nanodroplet-mediated ultrasound (US + ND). PNP, PRF, and $I_{SPTA}$ denote peak-negative pressure, pulse-repetition frequency, and spatial-peak temporal-average acoustic intensity, respectively. The PNP values are the maximums of pressure distribution in a vessel phantom. The ultrasound specification is described in the supplementary material.

| Insonation group | PNP (MPa) | Cycles | PRF (Hz) | Duty cycle (%) | $I_{SPTA}$, (W/cm$^2$) |
|---|---|---|---|---|---|
| 1 | 2.3 | 9 | 500 | 0.45 | 0.79 |
| 2 | 2.3 | 300 | 100 | 3 | 5.29 |
| 3 | 5.9 | 9 | 500 | 0.45 | 5.22 |
| 4 | 5.9 | 300 | 100 | 3 | 34.8 |

Passive cavitation detection signals were post-processed following the previously reported method to calculate stable and inertial cavitation doses.[21,22] The second harmonic ($2f_0$) component was used to calculate stable cavitation dose (SCD) by band-pass filtering the data (n=30) from 1.5 to 2.5 MHz (Butterworth, order 5), where $f_0$ is the operating frequency of therapy waves (1 MHz). Broadband (3-7 MHz) noise content was used to calculate inertial cavitation dose (ICD). Since superharmonic content ($3f_0$, $4f_0$, $5f_0$, $6f_0$, and $7f_0$) are also associated with nonlinear bubble oscillation (stable cavitation),[23] each superharmonic with ±0.2 MHz range was subtracted for the ICD calculation. The area under curves (AUCs) of filtered frequency spectra determine cavitation doses.

Figure 4A:
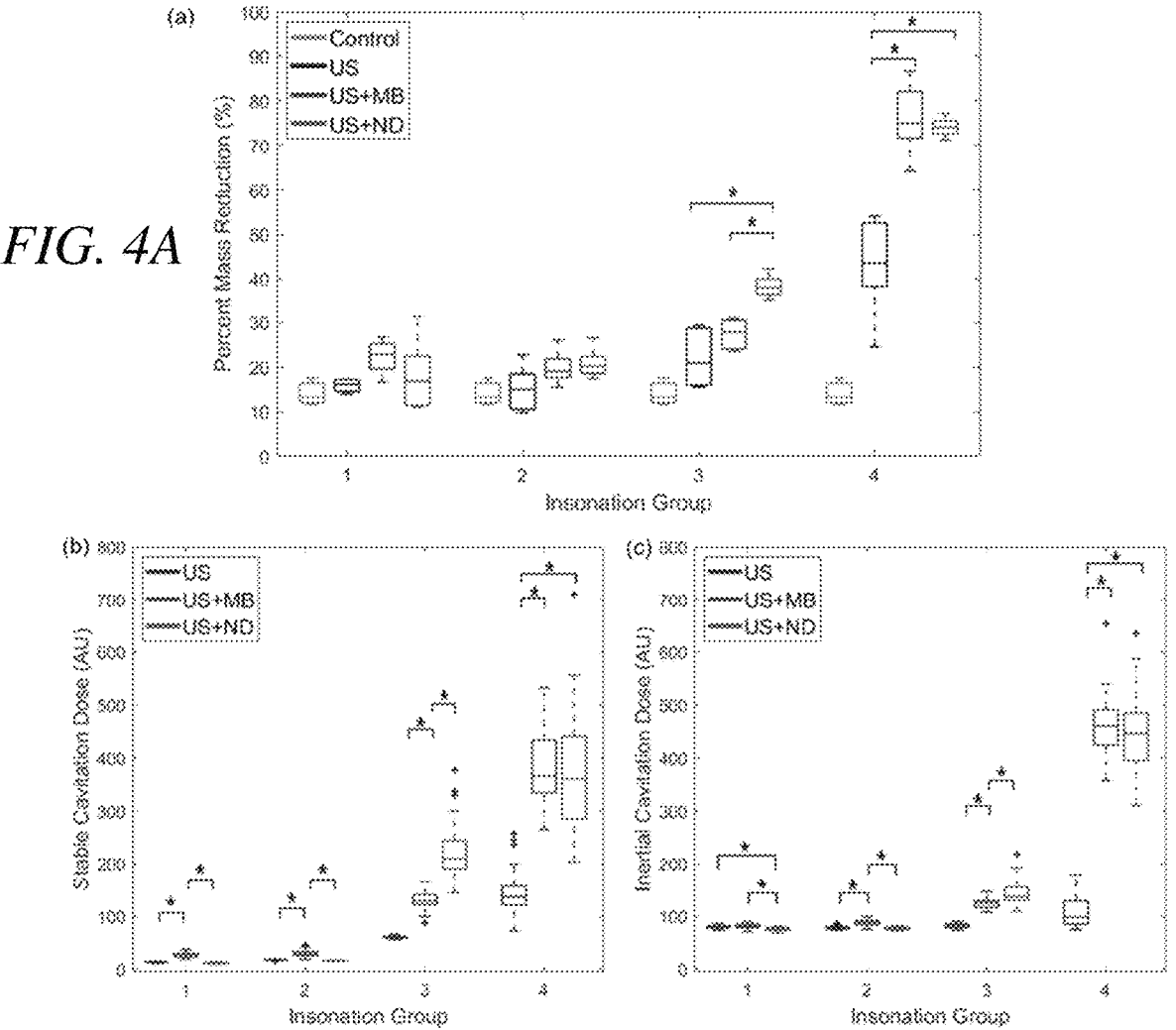

The percent mass loss of each treatment group is shown in FIG. 4A. All treatment groups with the infusion of microbubbles and nanodroplets exhibited a higher average mass reduction than the control group, but these differences were not significant for treatment with 2.3 MPa of PNP (groups 1 and 2). According to the previous studies, the mechanical index (MI) of 2.3 which is defined as PNP (in MPa) divided by square root of f0 (in MHz) is sufficiently high to induce inertial cavitation of both DFB microbubbles (destruction by MI>0.4)24 and nanodroplets (vaporization by MI>0.9). 25 However, the magnitude of cavitation at 2.3 MPa PNP is likely insufficient to cause noticeable clot fragmentation within 10 min. This result correlates with the passive cavitation detection data (FIGS. 4B and 4C). For both stable and inertial cavitation, the 2.3 MPa PNP groups showed significantly lower cavitation levels than the 5.9 MPa PNP groups. Note that for even the slightly higher cavitation doses (p<0.01) of the MB+US cases, the low-level cavitation (both SCD and ICD<100) by 2.3 MPa PNP had no significant effect on clot dissolution.

With 5.9 MPa of PNP (insonation group 3 and 4), most treatments exhibited significantly higher thrombolytic efficacies compared to the control group. The US+ND treatment in group 3 showed higher clot mass reduction than other cases with significant difference (p<0.01). We interpreted this result as a correlation with the higher SCD and ICD of the US+ND case than the US+MB case (FIGS. 4B and 4C). We presumed that the cavitation dose difference correlates with the cavitation location, where vaporizing the nanodroplets followed by cavitation occur inside a clot sample, whereas the microbubbles cavitate outside of a clot sample due to their larger size excluding them from penetrating the clot. We further clarified this hypothesis by analyzing digital camera images and additional ultrasound B-mode imaging, which is described later below with respect to FIGS. 5A-5D. Due to the much lower PNP (5.9 MPa) than the shock scattering threshold of bubble nucleation (>13.5 MPa),[6] the short pulse ultrasound without any cavitation nuclei showed inconsistent thrombolysis improvement than the control group (p=0.04). Note that despite the similar acoustic intensity of group 2 and 3, there was a noticeable difference on thrombolysis efficacy of the most treatment cases, which correlated with differences in cavitation (e.g., 16 vs. 225 SCD of US+ND case).

Group 4 resulted in significantly improved (up to 5-fold) thrombolytic efficacy than other insonation groups. Without infusing cavitation nuclei, the acoustic intensity of 34.8 W/cm$^2$ produced 43±12% clot mass reduction. At this power, the clot sample was visually observed to be agitated by radiation force-induced acoustic microstreaming, and this agitation produced partial clot dissolution. By adding microbubbles (US+MB) or nanodroplets (US+ND), high-level cavitation (both SCD and ICD>350) was further enhanced (FIGS. 4B and 4C), and consequently, mass reduction was increased to 76±8% over the same 10 min-treatment. At this highest power, there was no significant difference in clot lysis between US+MB and US+ND cases.

The clot samples in insonation group 3, exposed to nanodroplets, exhibited a unique clot fragmentation process compared to other treatment groups. Clot erosion was observed to start internally, at the center of the aged clot (FIG. 5A), rather than the periphery. After multiple micro cavities appeared within 10 s of the excitation, a distinctive inner erosion with a ~2 mm-diameter cavity emerged. During group 3 treatments, this internal erosion was recognizable as a signature of nanodroplet-mediated pulsed ultrasound treatment. Examination of the location of erosion cavities through visual observation of clots exposed to acoustic energy directed at the center of the clot samples (N=21) demonstrated erosion occurring in the clot center 0% (0/21) for ultrasound only, 14.3% (3/21) for US+MB, and 76.2% (16/21) for US+ND treatments. The primary factor causing the internal erosion was further elucidated by B-mode imaging of the clot (FIG. 5B) using an ATL L11-5 linear array controlled by a Vantage ultrasound system (Verasonics, Kirkland, WA, USA). Imaging results showed that the US+ND treatment generated a cavitation cloud inside the cross-section of a clot (in addition to some external cavitation) (FIG. 5C), whereas the US+MB case produced a large but external cavitation cloud near the surface of the clot, without the presence of internal cavitation (FIG. 5D). We quantified these observations by defining a metric of the US video intensity ratio of cavitation clouds that were located within in a cross-sectional area of a clot (supplementary material, S5). Analysis of nine images (3 treatment spots for 3 clot samples) resulted in a significantly different (p=0.004) ratio of cavitation internally to externally for the US+ND case (0.38±0.30) compared to the US+MB case (0.04±0.03). These results suggest that the nanodroplets vaporized and cavitated by pulsed ultrasound penetrate the aged clots, and the subsequent internal cavitation process, i.e., oscillation, microstreaming, and rupture of resultant bubbles, occurs within the internal fibrin structure.

In summary, we observed ultrasonic cavitation disrupting aged clots without cavitation nuclei as well as with microbubbles and with nanodroplets through an in vitro thrombolysis study. With moderate-amplitude (PNP of 5.9 MPa), short-pulse (duty cycle of 0.45%) ultrasound, nanodroplets produced the greatest clot dissolution (3.8±0.3%/min compared to microbubbles 2.7±0.3%/min). Furthermore, the mechanism of nanodroplet enhanced clot lysis was observed to be unique, involving cavitation internal to the clot mass, compared to cavitation on the clot surface for microbubbles. This short-pulse insonation which was most effective with nanodroplets was similar to the high-amplitude, short-pulse histotripsy, except utilizing a much lower PNP (5.9 MPa vs. >13.5 MPa).[16] Similarly, we expect the same benefits of histotripsy over long-pulsed (>10% duty cycle) high-intensity-focused ultrasound therapy, namely precise spatial control of the cavitation delivery and reduced heat deposition in surrounding tissue, yet with a lower pressure output requirement. This may present a novel means to achieve effective, rapid clot disruption with minimal damage to healthy tissue. Our future work will further investigate optimum ultrasound specification (PNP, cycle, and PRF) for nanodroplet-mediated sonothrombolysis with various perfluorocarbon nanodroplets.

REFERENCES

[1] J.-M. Escoffre and A. Bouakaz, Therapeutic Ultrasound (Springer, 2016).

[2] S. Datta, C.-C. Coussios, L. E. McAdory, J. Tan, T. Porter, G. De Courten-Myers, and C. K. Holland, Ultrasound Med. Biol. 32, 1257 (2006).

[3] S. Mitragotri, Nat. Rev. Drug Discov. 4, 255 (2005).

[4] S. Datta, C. C. Coussios, A. Y. Ammi, T. D. Mast, G. M. de Courten-Myers, and C. K. Holland, Ultrasound Med. Biol. 34, 1421 (2008).

[5] K. Tachibana and S. Tachibana, Circulation 92, 1148 (1995).

[6] D. Maxwell, T.-Y. Wang, C. a. Cain, J. B. Fowlkes, O. a. Sapozhnikov, M. R. Bailey, and Z. Xu, J. Acoust. Soc. Am. 130, 1888 (2011).

[7] A. F. Prokop, A. Soltani, and R. A. Roy, Ultrasound Med. Biol. 33, 924 (2007).

[8] J. Kim, B. D. Lindsey, W.-Y. Chang, X. Dai, J. M. Stavas, P. A. Dayton, and X. Jiang, Sci. Rep. 7, 3454 (2017).

[9] C. Acconcia, B. Y. C. Leung, A. Manjunath, and D. E. Goertz, Ultrasound Med. Biol. 40, 2134 (2014).

[10] C. Acconcia, B. Y. C. Leung, A. Manjunath, and D. E. Goertz, Ultrasound Med. Biol. 41, 2774 (2015).

[11] J. T. Sutton, N. M. Ivancevich, S. R. Perrin, D. C. Vela, and C. K. Holland, Ultrasound Med. Biol. 39, 813 (2013).

[12] X. Zhang, G. E. Owens, C. A. Cain, H. S. Gurm, J. Macoskey, and Z. Xu, Ultrasound Med. Biol. 42, 1903 (2016).

[13] P. S. Sheeran, S. Luois, P. A. Dayton, and T. O. Matsunaga, Langmuir 27, 10412 (2011).

[14] D. Pajek, A. Burgess, Y. Huang, and K. Hynynen, Ultrasound Med. Biol. 40, 2151 (2014).

[15] S. Guo, X. Guo, X. Wang, D. Zhou, X. Du, M. Han, Y. Zong, and M. Wan, Ultrason. Sonochem. 54, 183 (2019).

[16] X. Zhang, G. E. Owens, H. S. Gurm, Y. Ding, C. A. Cain, and Z. Xu, IEEE Trans. Ultrason. Ferroelectr. Freq. Control 62, 1342 (2015).

[17] D. Suo, Z. Jin, X. Jiang, P. A. Dayton, and Y. Jing, Appl. Phys. Lett. 110, 023703 (2017).

[18] J. Kim, W. Chang, B. D. Lindsey, P. A. Dayton, J. M. Stavas, X. Dai, and X. Jiang, in IEEE Int. Ultrason. Symp. IUS (2016), pp. 8-11.

[19] J. D. Rojas and P. A. Dayton, Ultrasound Med. Biol. 45, 192 (2019).

[20] K. B. Bader, K. J. Haworth, H. Shekhar, A. D. Maxwell, T. Peng, D. D. McPherson, and C. K. Holland, Phys. Med. Biol. 61, 5253 (2016).

[21] M. Wan, Y. Feng, and G. R. ter Haar, Cavitation in Biomedicine (Springer Netherlands, Dordrecht, 2015).

[22] S. M. Fix, A. Novell, Y. Yun, P. A. Dayton, and C. B. Arena, J. Ther. Ultrasound 5, 1 (2017).

[23] J. Kim, S. Li, S. Kasoji, P. A. Dayton, and X. Jiang, Ultrasonics 63, 7 (2015).

[24] B. D. Lindsey, J. D. Rojas, and P. A. Dayton, Ultrasound Med. Biol. 41, 1711 (2015).

[25] S. Y. Wu, S. M. Fix, C. B. Arena, C. C. Chen, W. Zheng, O. O. Olumolade, V. Papadopoulou, A. Novell, P. A. Dayton, and E. E. Konofagou, Phys. Med. Biol. 63, (2018).

Supplementary Materials

S1. Therapy Transducer

In this in vitro sonothrombolysis study, a focused ultrasound transducer (33 mm-aperture diameter, 35 mm focal distance, H-131, Sonic Concepts, Inc., WA, USA) was used to apply peak-negative pressure (PNP) up to 5.9 MPa to blood clot samples. The transducer was integrated with an impedance tuning circuit (FIG. 6A) for 50-ohm impedance at its operating frequency (1 MHz). The beam profile of the transducer was characterized with a raster scanned hydrophone (FIG. 6B), showing that the probe exhibited an axial full-width-half-maximum (FWHM) of 17.4±0.3 mm and a lateral FWHM of 2.4±0.3 at the focus (~34 mm from the aperture). At the front end of the therapy zone in the tube (~29 mm in axial position), the lateral FWHM was 3.0±0.3 mm.

S2. Pressure Amplitude in a Vessel Mimicking Tube

We characterized the transmitting sensitivity of the focused transducer. The transducer was connected to an arbitrary function generator signal (AFG3021C, Tektronix, Inc., Beaverton, OR, USA) and a 60 dB radio-frequency amplifier (Model A500, Electronic Navigation Industries Inc., Rochester, NY). The pressure output of the transducer at 1 MHz pulsed excitation (9 cycles, 100 ms pulse repetition) was measured by using a needle hydrophone (HNA-0400, Onda Corp., Sunnyvale, CA, USA). To measure the pressure inside a vessel phantom (Tygon tube, 0.8 mm in thickness, 6.4 mm in inner diameter, TYGON S3TM E-3603), a half-cut tube was positioned in front of a needle hydrophone (FIG. 7A), and the attenuated peak-negative pressure (PNP) through a tube wall was characterized. The measured PNP at the front wall inside the tube was compared with the PNP at a rear wall of the tube (FIG. 7B) to check the difference of applied pressure on ~5 mm-diameter (302±22 mg) clot samples.

The attenuation through the tube wall (0.8 mm) at 1 MHz was measured 1.15 dB (FIG. 7C). Thus, 88% of the pressure was delivered to the blood clots in the tube. The pressure difference between the front and rear of the tube lumen was measured 2.15 dB (FIG. 7D). The applied pressure at the rear of a blood clot is 128% higher than the pressure at the front. We listed the rear lumen pressure values in TABLE 1. The front lumen PNP values of insonation group 1 and group 3 were 1.7 MPa and 4.7 MPa, respectively.

S3. Passive Cavitation Detection

We calculated the stable cavitation dose (SCD) and inertial cavitation dose (ICD) through the post-signal processing described as follow. First, we applied the band-pass filters to the acquired time-domain cavitation signals (n=30) using the MATLAB Statistical Toolbox (Mathworks, Natick, MA, USA). The Butterworth filter (order 5) with the pass-band of 1.5-2.5 MHz was used for calculating SCD since stable cavitation involves dominant second harmonic ($2f_0$, where $f_0$ is the therapy frequency, 1 MHz) and ultra-harmonic ($1.5f_0$ and $2.5f_0$) content. The same filter was used with the pass-band of 3-7 MHz for calculating ICD because internal cavitation (bubble collapse) emits broadband noise signals. Second, the filtered signals were transformed to the frequency-domain spectra by Fast-Fourier Transform, and the 30 spectra were averaged. The averaged spectra are shown in FIGS. 8A-8D. The area under curves (AUCs) at the frequency range of 1.5-2.5 MHz determined the SCD (FIG. 8D, left). For calculating ICD, AUCs at the frequency range of 3-7 MHz were used. Since this frequency range includes higher harmonics (e.g., $3f_0$, $4f_0$, $5f_0$, and $6f_0$) that associate with stable cavitation, we excluded the areas at the frequency ranges of 1.8-2.2 MHz, 2.8-3.2 MHz, 3.8-4.2 MHz, 4.8-5.2 MHz, 5.8-6.2 MHz, and 6.8-7.2 MHz as shown in FIG. 8D, right).

S4. Statistical Analysis

We conducted statistical analysis using MATLAB Statistical Toolbox (The Mathworks, Natick, MA, USA). We tested five samples in each treatment case (n=5), and the statistical significance was determined by one-way unbalanced ANOVA with an a level of 0.05. Tukey's honest significant difference test was performed to confirm the significant differences between the means of treatment groups (adjusted p<0.05). All the adjusted p values of Tukey's honest significance test of thrombolysis efficacy test (FIG. 4A) and cavitation detection tests (FIGS. 4B and 4C) with 30 data lines (N=30) are tabulated in TABLE S1 and TABLE S2, respectively.

TABLE S1

The p values of Tukey's honest significance tests (n = 5) comparing the thrombolytic efficacy of each treatment group as shown in FIG. 4A. The bold values indicate a significant difference between the treatment groups (p < 0.05).

|  |  | US | US + MB | US + ND |
|---|---|---|---|---|
| Group 1 | Control | 0.94 | 0.07 | 0.58 |
|  | US | — | 0.18 | 0.88 |
|  | US + MB | 0.18 | — | 0.52 |
| Group 2 | Control | 0.98 | 0.14 | 0.07 |
|  | US | — | 0.25 | 0.13 |
|  | US + MB | 0.25 | — | 0.98 |
| Group 3 | Control | 0.04 | <0.01 | <0.01 |
|  | US | — | 0.22 | <0.01 |
|  | US + MB | 0.22 | — | 0.04 |
| Group 4 | Control | <0.01 | <0.01 | <0.01 |
|  | US | — | <0.01 | <0.01 |
|  | US + MB | <0.01 | — | 0.97 |

TABLE S2

The p values of Tukey's honest significance tests (N = 30) comparing the cavitation dose of each treatment group, as shown in FiGS. 4B and 4C. The values are tabulated with the form of 'stable cavitation dose (inertial cavitation dose).' The bold values indicate a significant difference between the treatment groups (p < 0.05).

|  |  | US + MB | US + ND |
|---|---|---|---|
| Group 1 | US | <0.01 (0.30) | 0.04 (<0.01) |
|  | US + MB | — | <0.01 (<0.01) |
| Group 2 | US | <0.01 (<0.01) | 0.44 (0.44) |
|  | US + MB | — | <0.01 (<0.01) |
| Group 3 | US | <0.01 (<0.01) | <0.01 (<0.01) |
|  | US + MB | — | <0.01 (<0.01) |
| Group 4 | US | <0.01 (<0.01) | <0.01 (<0.01) |
|  | US + MB | — | 0.93 (0.41) |

S5. Ultrasound Imaging of Cavitation Clouds During the Short-Pulse Treatment

Cavitation detection imaging was conducted using a Vantage 256 scanner (Verasonics, Kirkland, WA, US). An ATL L11-5 linear array was used to image the transverse cross-sections of the blood clots during thrombolysis treatment, using 0.10 MI, 7.813 MHz plane-wave transmissions at 20 fps. Cavitation was detected by subtracting adjacent frames. Maximum intensity projections (MIPs) of the differences between 300 consecutive frames were used to visualize the locations of cavitation during treatment. These MIPs were thresholded to remove differences attributable to noise variance and then overlaid upon a pre-treatment b-mode image acquired using a focused imaging scheme.

To compare cavitation locations between the nanodroplet (ND) and microbubble (MB) cases, a metric conveying the ratio of cavitation within the blood clot versus the total cavitation was devised. The MIPs were first binarized to represent cavitation detection. Then, an elliptical region of interest (ROI) was selected to represent the blood clot (blue ellipses in the cavitation cloud images shown in FIGS. 9 and 10. Any pixels where cavitation was detected within this ROI were counted to represent the cavitation within the clot. It then follows that any pixels with cavitation outside of this ROI were summed to represent the cavitation outside of the clot. The number of cavitation pixels within the clot over the summation of both interior and exterior cavitation pixels was calculated and recorded for our metric. For the cavitation outside of the clot, there was an artifact attributed to the scattering from the tube. For each MIP, a second ROI was drawn around this artifact and excluded from the analysis (red ellipses). Mean and standard deviation statistics were calculated for both the US+ND and US+MB cases (n=9). As shown in FIG. 11, the metric exhibits a significantly different (p=0.005) ratio of the US+ND case (0.38±0.3) compared to the US+MB case (0.04±0.03).

The following section describes another scientific study in which phase change nanodroplets are used in combination with a tissue plasiminogen activator (tPA) to enhance sonothrombolysis of retracted blood clots.

Nanodroplet Mediated Intravascular Sonothrombolysis of Retracted Blood Clots Current tissue plasminogen activator (tPA) and microbubble (MB) mediated sonothrombolysis techniques have been challenged to efficiently disrupt retracted clots due to the high density and low porosity of the clots. Nanodroplets have the potential to enhance clot lysis due to their small size and ability to penetrate into retracted clots to enhance drug delivery. For the first time, we demonstrate that a forward-viewing intravascular (FVI) transducer can be used for nanodroplet (ND) mediated sonothrombolysis. In retracted blood clots, combined ND and tPA mediated sonothrombolysis was able to significantly enhance retracted clot lysis compared to traditional microbubble and tPA mediated sonothrombolysis techniques.

Deep vein thromboses (DVT) affect 300,000-600,000 patients in the United States every year[1,2]. Despite the common occurrence, DVT are difficult to treat with conventional methods used for other blood clot types such as middle cerebral artery (MCA) occlusions. DVT blood clots tend to be older, denser, stiffer, and retracted as compared to unretracted clots typically encountered in middle cerebral artery occlusions. Thrombolytic agent treatment, such as systemic tissue plasminogen activator (tPA) administration for DVT can take over 24 hours to be effective[3-5]. However, such long treatment durations and high doses of tPA (1000 mg/ml) can greatly increase the risk of internal hemorrhage due to off target effects, most notably intracranial hemorrhage can lead to stroke or death[4]. Other more targeted treatments include mechanical removal via mechanical thrombectomy. While effective at removing the clot, this technique has a risk for causing endothelial damage or producing large clot debris that lead to a pulmonary embolism[6-8]. As such, there is a need to develop site specific DVT treatments which minimize the tPA dose and treatment time necessary for effective clot treatment.

Sonothrombolysis is a method that uses ultrasound to facilitate the removal of blood clots. Sonothrombolysis has been particularly effective at treating unretracted blood clots and improving tPA treatment by incorporating ultrasound contrast agents such as microbubbles (MB)[9]. MBs act as cavitation nuclei which can result in stable cavitation (bubble oscillation) and inertial cavitation (bubble collapse), which are the primary mechanisms for MB mediated sonothrombolysis[9]. However, when it comes to applications of treating retracted clots, even MB mediated sonothrombolysis is challenged to disrupt clots efficiently[10]. Histotripsy and high intensity focused ultrasound (HIFU) have also been used in preclinical studies to treat retracted clots, however, these methods use high peak negative pressures of up to 15 MPa, which requires a large external ultrasound transducer, thus these techniques cannot be used to treat vessel locations with ultrasound blockage, e.g., pulmonary embolism with vessels blocked by the lung or ribs[11-16].

Nanodroplets (NDs) are an ultrasound contrast agent which has recently been applied not only for enhanced ultrasound imaging, but for enhanced drug delivery and more recently, sonothrombolysis of retracted clots[17-25]. Given the small size of NDs (100-300 nm) compared to MBs (1-10 mm), NDs have the potential to penetrate into retracted clots with low porosity, allowing for greater diffusion of tPA and cavitation effects inside the clots[19,26]. For ND mediated sonothrombolysis, typical studies use an external HIFU device for these excitations[23-25]. While initial studies are promising, it requires the peak negative pressures of 3-5 MPa to activate the ND, which exceeds the safety limit for ultrasound imaging and causes concerns for clinical translation. Low boiling point phase change NDs may overcome the limitations of current ND techniques by reducing the pressure necessary for ND activation and by extension clot lysis[23,26,27].

Our group has developed a forward viewing intravascular (FVI) sub-megahertz transducer for sonothrombolysis which is effective for tPA and MB mediated sonothrombolysis in unretracted clot models28-30. An intravascular system does not have the treatment location limitation of using an external transducer. Compared to a clinical standard side viewing intravascular transducer that can only treat partially blocked vessels, this FVI system enables treatment of both partially and completely blocked vessels[31].

Given the potential for ND mediated sonothrombolysis for site specific treatment of retracted clots, in this study we investigated the feasibility of using our FVI transducer combined with ND and tPA for sonothrombolysis in retracted clots. First, we evaluated the ability of the FVI transducer to activate low-boiling point phase change nanodroplets and generate cavitation via passive cavitation detection. We then demonstrated that ND mediated sonothrombolysis, in combination with tPA can treat retracted clots.

Passive cavitation detection (PCD) was performed similarly to our previous study[30]. The peak negative pressure (PNP) of the FVI transducer was varied from 0.3 MPa to 1.2 MPa. Nanodroplets were injected into a venous flow model at a rate of 0.1 ml/min and phosphate buffered saline (PBS) served as the control. The transducer excitation parameters were a center frequency of 700 kHz, 10 ms pulse length, and 20 cycles. Cavitation signals were detected using a hydrophone (HGL-0085, ONDA Corp., Sunnyvale, CA, USA). 3 radio frequency (RF) signals were collected for each condition. Inertial and stable cavitation doses were calculated using MATLAB (MATLAB R2018b, Mathworks, Natick, MA, USA). The stable cavitation dose was calculated based on the area under the curve of the second harmonic ($2f_0 \pm 0{:}5 f_0$) of the frequency spectrum of the radiofrequency (RF) data. The inertial cavitation dose was calculated based on the area under the curve of the broadband noise of the 3rd-6th harmonics (FIGS. 12A and 12B). From here it was determined that an peak negative pressure of 0.9 MPa was sufficient for ND activation.

Upon demonstrating the feasibility of ND mediated sonothrombolysis in retracted and unretracted clots (S1), we sought to further enhance retracted clot lysis with NDs and to compare ND mediated sonothrombolysis to existing sonothrombolysis techniques. In order to enhance retracted clot lysis, we combined NDs with a low dose of tPA. Given the success of MB mediated sonothrombolysis with a low dose tPA in unretracted clots, we chose to combine ND-mediated sonothrombolysis with a low dose tPA. We compared ND+tPA mediated sonothrombolysis to a negative control of PBS alone, tPA treatment alone, ND-mediated thrombolysis, MB mediated sonothrombolysis, and MB+tPA mediated sonothrombolysis.

Bovine blood was used to prepare clots as done previously[15,28-30,32-36]. Acid citrate dextrose (ACD) anticoagulated blood was mixed with 2.75% Calcium Chloride in a 10:1 ratio (50 mL blood/5 mL $CaCl_2$)). Unretracted clots were prepared by adding the blood mixture to plastic centrifuge tubes. Retracted clots were prepared by adding the blood mixture to borosilicate glass pipettes as described by Sutton et al.[10,15] Clots were then incubated in a 37° C. water bath for 3 hours. The clots were then stored in a refrigerator at 4° C. for 3-14 days. Clot characterization results can be found in the supplementary results (S3).

Experiments were performed in a venous flow model. The flow model consisted of a reservoir of degassed water, 37° C. water bath, and waste container (FIG. 13). The pressure was maintained at $3{:}5 \pm 0{:}5$ mmHg. The retracted and unretracted clots were prepared to a final mass of $150 \pm 20$ mg. Each treatment conditional was applied to both retracted and unretracted clots and repeated 3 times each, for 66 total clots (33 unretracted, 33 retracted).

The FVI transducer was installed into an integrated catheter system (Sonovascular, Inc.) with a lumen for the treatment injection. The total catheter diameter is 3 mm. Each treatment was injected into the flow system via a syringe pump at a rate of 0.1 ml/min for 30 minutes. The center frequency of the transducer was 700 kHz with a duty cycle of 5.7% (200 cycles, 5 ms pulse length). As implemented in our previous studies, in order to ensure penetration of ultrasound contrast agents into the clot, the ultrasound output was manually switched "on" for 2 minutes (5.7% duty cycle) and "off" for 30 seconds throughout the 30-minute treatment period to allow for penetration of the treatment solutions into the clot[28,30].

The thrombolysis experiments compared various sonothrombolysis techniques to nanodroplet mediated sonothrombolysis techniques. tPA was prepared as described previously[30]. The treatment conditions were PBS alone (control), tPA alone (1.0 mg/ml), US alone, tPA+US, MB+US (108 MB/ml), MB+tPA+US (108 MB/ml, 1.0 mg/ml), ND+US (108 ND/ml, 1.0 mg/ml), and ND+tPA+ US. The peak negative pressure used for these experiments was 0.9 MPa. A description of the ultrasound contrast agent and tPA preparation can be found in the supplemental data (S4).

In retracted clots, ND+tPA mediated sonothrombolysis significantly outperformed tPA alone, MB mediated sonothrombolysis, and MB+tPA mediated sonothrombolysis (FIG. 14). Additionally, ND and ND+tPA mediated sonothrombolysis were the only conditions which statistically improved retracted clot lysis compared to the negative control group. A similar comparison study was conducted in unretracted clots, where it was shown that ND mediated sonothrombolysis performs as well as tPA mediated thrombolysis and MB mediated sonothrombolysis (S2). One-way ANOVA and Tukey's honest squared difference was used to assess significance between treatment groups for the thrombolysis experiments. The significance level was set to $p < 0.05$.

We demonstrated the first use of ND+tPA mediated sonothrombolysis with a forward viewing intravascular transducer for effective lysis of retracted clots. This technique achieved effective treatment of retracted clots without the need for high amplitude ultrasound treatment such as with high intensity focused ultrasound or histotripsy. In unretracted clots, this technique is as effective as tPA mediated sonothrombolysis and MB mediated sonothrombolysis. Our results indicate that these low boiling point NDs may be an alternative to traditional thrombolytic approaches to help decrease the negative side-effects of thrombolytic treatments. We also demonstrated that these NDs, when combined with tPA, can significantly enhance retracted clot lysis compared to MB and MB+tPA mediated approaches. Our results correspond well with a study by Sutton et al. comparing MB and tPA mediated sonothrombolysis in unretracted and retracted clots, wherein MB mediated sonothrombolysis did not improve retracted clot lysis. Here we demonstrate that NDs can be used to enhance tPA mediated sonothrombolysis in retracted clots. In addition, this was achieved using a relatively low peak negative pressure of 0.9 MPa (within the FDA safety limit mechanical index=1.9) compared to higher PNPs of up to 15 MPa as used in other external sonothrombolysis techniques for retracted clots.

While exciting, future work should involve assessing the safety of ND mediated sonothrombolysis. Metrics such as clot debris size and vessel damage should be assessed in order to understand the safety of ND mediated sonothrombolysis with the FVI transducer compared to HIFU techniques for retracted clots. The parameters used in this study were based on our previous MB mediated results. Future parameter optimization, such as duty cycle, treatment duration, and pulse width, is also warranted to increase the treatment efficacy for nanodroplet mediated sonothrombolysis. Cavitation was detected and assumed to be the mechanism of ND mediated sonothrombolysis. In addition to cavitation, we hypothesize that the small size of the nanodroplets allows them to penetrate into the dense fibrin clot before activation, thus forming larger channels for the tPA to diffuse into the clot and improve efficacy. Further mechanistic studies are warranted for improvement of ND mediated sonothrombolysis.

We demonstrated the use of low-boiling point phase change nanodroplets for intravascular sonothrombolysis. Additionally, we showed that combining ND+tPA+US can significantly improve retracted clot lysis, which may improve current approaches for treating retracted clots. Our forward viewing intravascular transducer can be used for nanodroplet mediated sonothrombolysis to treat both retracted and unretracted clots using a low peak negative pressure compared to other high intensity sonothrombolysis techniques.

Supplementary Material

See supplementary material for the clot lysis results from peak negative pressure analysis, unretracted clot lysis results for treatment condition comparison, retracted and unretracted clot characterization methods and results, and ultrasound contrast agent and tissue plasminogen activator preparation methods.

REFERENCES

[1] M. G. Beckman, W. C. Hooper, S. E. Critchley, and T. L. Ortel, "Venous Thromboembolism A Public Health Concern," American Journal of Preventative Medicine 38, S495-S501 (2010).

[2] J. Heit, "Epidemiology of venous thromboembolism," Nature Reviews Cardiology 12, 464-474 (2015).

[3] M. DiNisio, N. Es, and H. Buller, "Deep vein thrombosis and pulmonary embolism," Lancet 388, 3060-3073 (2016).

[4] L. Watson, C. Broderick, and A. M. P., "Thrombolysis for acute deep vein thrombosis," Cochrane Database of Systematic Reviews, 3060 3073 (2016).

[5] 5M. B. Streiff, G. C. J. M. Agnelli, M. Crowther, S. Eichinger, R. M. R. D. lopes, S. Moll, and J. Ansell, "Guidance for the treatment of deep vein thrombosis and pulmonary embolism," Journal of Thrombosis and Thrombolysis 41, 32-67 (2016).

[6] Karthikesalingam, E. L. Young, R. J. Hinchliffe, I. M. Loftus, M. M. Thompson, and P. J. E. Holt, "REVIEW A Systematic Review of Percutaneous Mechanical Thrombectomy in the Treatment of Deep Venous Thrombosis," European Journal of Vascular & Endovascular Surgery 41, 554-565(2011).

[7] W. T. Kuo, M. K. Gould, J. D. Louie, J. K. Rosenberg, D. Y. Sze, andL. V. Hofmann, "Catheter-directed Therapy for the Treatment of Massive Pulmonary Embolism: Systematic Review and Meta-analysis of Modern Techniques," Journal of Vascular Interventional Radiology 20, 1431-1440 (2009).

[8] T. P. P. S. T. Investigators, "Safety and Effectiveness of a New Generation of Mechanical Devices for Clot Removal in Intracranial Large Vessel Occlusive Disease," Stroke 40, 2761-2768 (2009).

[9] L. Goel and X. Jiang, "Advances in Sonothrombolysis Techniques Using Piezoelectric Transducers," Sensors 20, 1288 (2020). J. T. Sutton, N. M. Ivancevich, S. R. Perrin, D. C. Vela, and C. K. Holland, "Clot Retraction Affects the Extent of Ultrasound-Enhanced Thrombolysis in an Ex Vivo Porcine Thrombosis Model," Ultrasound in Medicine and Biology 39, 813-824 (2013), arXiv:NIHMS150003.

[10] T. Holscher, D. Fisher, and R. Raman, "Noninvasive Transcranial Clot Lysis Using High Intensity Focused Ultrasound," Journal of Neurology & Neurophysiology 01 (2011), 10.4172/2155-9562. S1-002.

[11] T. Holscher, R. Raman, D. J. Fisher, G. Ahadi, E. Zadicario, and A. Voie, "Effects of varying duty cycle and pulse width on high-intensity focused ultrasound (HIFU)-induced transcranial thrombolysis," Journal of Therapeutic Ultrasound, 1-18 (2013).

[13] A. Burgess, Y. Huang, A. C. Waspe, M. Ganguly, D. E. Goertz, and K. Hynynen, "High-intensity focused ultrasound (HIFU) for dissolution of clots in a rabbit model of embolic stroke," PLoS ONE 7, 1-7 (2012).

[14] S. Xu, Y. Zong, Y. Feng, R. Liu, X. Liu, Y. Hu, S. Han, and M. Wan, "Dependence of pulsed focused ultrasound induced thrombolysis on duty cycle and cavitation bubble size distribution," Ultrasonics Sonochemistry 22, 160-166 (2015).

[15] X. Zhang, G. E. Owens, C. A. Cain, H. S. Gurm, J. Macoskey, and Z. Xu, "Histotripsy Thrombolysis on Retracted Clots," Ultrasound in Medicine and Biology 42, 1903-1918 (2016).

16. X. Zhang, J. J. Macoskey, K. Ives, G. E. Owens, H. S. Gurm, J. Shi, M. Pizzuto, C. A. Cain, and Z. Xu, "Non-Invasive Thrombolysis Using Microtripsy in a Porcine Deep Vein Thrombosis Model," Ultrasound in Medicine and Biology 43, 1378-1390 (2017).

[17] G. P. Luke, A. S. Hannah, and S. Y. Emelianov, "Super-Resolution Ultrasound Imaging in Vivo with Transient Laser-Activated Nanodroplets," Nano Letters 16, 2556-2559 (2016).

[18] J. O. Szablowski, A. Bar-Zion, and M. G. Shapiro, "Achieving Spatial and Molecular Specificity with Ultrasound-Targeted Biomolecular Nanotherapeutics," Accounts of Chemical Research 52, 2427-2434 (2019).

[19] L. Ma, Y. Wang, S. Zhang, X. Qian, N. Xue, Z. Jiang, 0. U. Akakuru, J. Li, Y. Xu, and A. Wu, "Deep Penetration of Targeted Nanobubbles Enhanced Cavitation Effect on Thrombolytic Capacity," Bioconjugate Chem. 31, 369-374 (2020).

[20] Y. Zhong, Y. Zhang, J. Xu, J. Zhou, J. Liu, M. Ye, L. Zhang, B. Qiao, Z.-g. Wang, H.-t. Ran, and D. Guo, "Low-Intensity Focused Ultrasound-Responsive Phase-Transitional Nanoparticles for Thrombolysis without Vascular Damage: A Synergistic Nonpharmaceutical Strategy," ACS Nano 13, 3387-3403 (2019).

[21] D. S. Li, S. Schneewind, M. Bruce, Z. Khaing, M. O'Donnell, and L. Pozzo, "Spontaneous Nucleation of Stable Perfluorocarbon Emulsions for Ultrasound Contrast Agents," Nano Letters 19, 173-181 (2019).

[22] X. Song, L. Feng, C. Liang, K. Yang, and Z. Liu, "Ultrasound Triggered Tumor Oxygenation with Oxygen-Shuttle Nanoperfluorocarbon to Overcome Hypoxia-Associated Resistance in Cancer Therapies," Nano Letters 16, 6145-6153 (2016).

[23] D. Pajek, A. Burgess, Y. Huang, and K. Hynynen, "High-Intensity Focused Ultrasound Sonothrombolysis: The Use of Perfluorocarbon Droplets to Achieve Clot Lysis at Reduced Acoustic Power," Ultrasound in Medicine and Biology 40, 2151-2161 (2014), arXiv: NIHMS150003.

[24] J. Brüßer, B. Strehlow, A. Becker, R. Schubert, J. Schümmelfeder, C. Nimsky, and U. Bakowsky, "Nanoscaled ultrasound contrast agents for enhanced sonothrombolysis," Colloids and Surfaces B: Biointerfaces 172, 728-733 (2018).

[25] S. Guo, X. Guo, X. Wang, D. Zhou, X. Du, M. Han, Y. Zong, and M. Wan, "Reduced clot debris size in sonothrombolysis assisted with phase-change nanodroplets," Ultrasonics—Sonochemistry 54, 183-191 (2019).

[26] J. Kim, R. DeRuiter, L. Goel, Z. Xu, X. Jiang, and P. Dayton, "A Comparison of Sonothrombolysis in Aged Clots Between Low Boiling Point Phase Change Nanodroplets and Microbubbles of the Same Composition," Ultrasound in Medicine and Biology, In Review (2020).

[27] P. S. Sheeran, S. H. Luois, L. B. Mullin, T. O. Matsunaga, and P. A. Dayton, "Design of ultrasonically-activatable nanoparticles using low boiling point perfluorocarbons," Biomaterials 33, 3236-3269 (2012).

[28] J. Kim, B. D. Lindsey, W. Y. Chang, X. Dai, J. M. Stavas, P. A. Dayton, and X. Jiang, "Intravascular forward-looking ultrasound transducers microbubble-mediated sonothrombolysis," Scientific Reports 7, 1-10 (2017).

[29] B. Zhang, H. Kim, H. Wu, Y. Gao, and X. Jiang, "Sonothrombolysis with magnetic microbubbles under a rotational magnetic field," Ultrasonics 98, 62-71 (2019).

[30] L. Goel, H. Wu, H. Kim, B. Zhang, J. Kim, P. Dayton, Z. Xu, and X. Jiang, "Examining the influence of low dose Tissue Plasminogen Activator on Microbubble Mediated Forward-Viewing Intravascular Sonothrombolysis," Ultrasound in Medicine and Biology, In Press (2020).

[31] R. P. Engelberger, V. Schroeder, M. Nagler, R. Prince, D. Periard, D. Hayoz, and N. Kucher, "Enhanced Thrombolysis by Ultrasound-Assisted Catheter-Directed Thrombolysis and Microbubbles in an In Vitro Model of Iliofemoral Deep Vein Thrombosis," Thrombosis and Haemostasis 119, 1094-1101 (2019).

[32] D. Suo, S. Guo, W. Lin, X. Jiang, and Y. Jing, "Thrombolysis using multifrequency high intensity focused ultrasound at MHz range: An in vitro study," Physics in Medicine and Biology 60, 7403-7418 (2015).

[33] D. Suo, Z. Jin, X. Jiang, P. A. Dayton, and Y. Jing, "Microbubble mediated dual-frequency high intensity focused ultrasound thrombolysis: An in vitro study," Applied Physics Letters 110, 1-5 (2017).

[34] D. Suo, B. Govind, J. Gu, P. A. Dayton, and Y. Jing, "Dynamic assessment of dual-frequency microbubble-mediated sonothrombolysis in vitro," Journal of Applied Physics 125, 084702 (2019).

[35] X. Zhang, L. Jin, E. Vlaisavljevich, G. E. Owens, H. S. Gurm, A. Charles, Z. Xu, A. Arbor, C. Diseases, A. Arbor, and A. Arbor, "Non-invasive Thrombolysis using Microtripsy: A Parameter Study," IEEE Transactions on Ultrasonics Ferroelectrics and Frequency Control 62, 2092-2105 (2015).

[36] A. Shi, J. Lundt, Z. Deng, J. Macoskey, H. Gurm, G. Owens, X. Zhang, T. L. Hall, and Z. Xu, "Integrated Histotripsy and Bubble Coalescence Transducer for Thrombolysis," Ultrasound in Medicine and Biology 44, 2697-2709 (2018).

Supplementary Material

Figures S1A-S3B described above in the Brief Description of the drawings illustrate results of treating unretracted and retracted clots with a combination of ultrasound and phase change nanodroplets.

S1

Figures S1A and S1B present percent mass decrease of unretracted and unretracted clots for nanodroplet mediated sonothrombolysis at different peak negative pressures.

S2

Figure S2 presents unretracted clot lysis results for different treatment conditions with a peak negative pressure of 0.9 MPa.

S3

Figures S3A-S3C present results of verification of unretracted and retracted clots. The degree of clot retraction was verified using histology and stiffness measurements. Hemoxatocin and Eosin (H\&E) staining was conducted on the retracted and unretracted clot samples. Samples were prepared to 5 µm thickness and imaged using an EVOS compound light microscope (EVOS FL Auto Imaging System, Life Technologies Corporation, Carlsbad, CA, USA). The porosity of the clots was calculated via the percent of white pixels in the images using a custom image processing algorithm (MATLAB R2018b, Mathworks, Natick, MA, USA). Clot stiffness was characterized via uniaxial testing. Clots were mounted to a BioTester mechanical testing system (BioTester, Cell Scale, Waterloo, ON, Canada). The specimens were then subject to cyclical loading under 3 strain conditions. Young's modulus was calculated from the resulting force-displacement curves, providing comparative stiffness values for retracted and unretracted clots. S4: Description of ultrasound contrast agent and tissue plasminogen activator preparation.

Lipid-shelled, decafluorobutane (DFB) gas core nanodroplets were prepared as previously described (Sheeran, P. S.; Luois, S. H.; Mullin, L. B.; Matsunaga, T. O.; Dayton, P. A. Design of ultrasonically activatable nanoparticles using low boiling point perfluorocarbons. Biomaterials 2012, 33, 3236-3269).

Briefly, lipid-shelled DFB microbubbles (MB) were synthesized and condensed into liquid-core nanodroplets with an average size of 100-200 nm and concentration of $10^{10}$ND/ml. Nanodroplets were then diluted with phosphate buffered saline (PBS) to a final concentration of $10^8$ ND/ml for all treatment conditions. The microbubbles themselves have a mean microbubble diameter of 1.1 µm, with an initial concentration of $10^{10}$ MB/ml. In the MB treatment conditions, the final concentration was $10^8$ MB/ml.

Tissue plasminogen activator (Cathflo Activase, Genentech USA, Inc) was prepared via the manufacturer's instructions to a concentration of (1000 µg/ml), aliquoted, and stored at −20° C. until use. For experiments, tPA was then diluted to the working concentration of (1.0 µg/ml) using phosphate buffered saline. In the combined ND+tPA and MB+tPA conditions, tPA was added to the diluted ND and MB solutions to a final concentration of (1.0 µg/ml).

The following section describes a single pillar and a multi-pillar piezoelectric stack transducer and associated methods for performing nanodroplet mediated intravascular sonothrombolysis.

Multi-Pillar Piezoelectric Stack Transducer for Nanodroplet Mediated Intravascular Sonothrombolysis We aim to develop a nanodroplet (ND)-mediated intravascular ultrasound (US) transducer for deep vein thrombosis treatments. The US device, having an efficient forward directivity of the acoustic beam, is capable of expediting the clot dissolution rate by activating cavitation of NDs injected onto a thrombus. Methods: We designed and prototyped a multi-pillar piezoelectric stack (MPPS) transducer composed of four piezoelectric stacks. Each stack was made of five layers of PZT-4 plates having a dimension of 0.85× 0.85×0.2 mm³. The transducer was characterized by measuring the electric impedance and acoustic pressure, compared to simulation results. Next, in-vitro tests were conducted in a blood flow mimicking system using the transducer equipped with an ND injecting tube. Results: The miniaturized transducer, having an aperture size of 2.8 mm, provided a high mechanical index of 1.52 and a relatively wide focal zone of 3.4 mm at 80 $V_{pp}$, 0.96 MHz electric input. The mass-reduction rate of the proposed method (NDs+US) was assessed to be 2.3 and 2.5%/min with and without the flow model, respectively. The rate was higher than that (0.7-1.5%/min) of other intravascular ultrasound modalities using micron-sized bubble agents. Conclusion: The ND-mediated intravascular sonothrombolysis using MPPS transducers was demonstrated with an unprecedented lysis rate, which may offer a new clinical option for DVT treatments. Significance: The MPPS transducer generated a high acoustic pressure (~3.1 MPa) at a distance of approximately 2.2 wavelengths from the small aperture, providing synergistic efficacy with nanodroplets for thrombolysis without thrombolytic agents.

Introduction

Deep vein thrombosis (DVT), the formation of a thrombus in the deep venous system, may be induced by certain factors such as immobility (e.g., prolonged bed rest, obesity, and surgery) and hypercoagulation caused by smoking, injury to veins, cancer, genetic issue, and leg fracture [1]. Common symptoms of DVT include leg pain, swelling, and skin discoloration [2]. Furthermore, thrombus in legs can result in serious conditions when a piece of the blood clot travels through the circulation system and lodges in one of the pulmonary arteries, resulting in pulmonary embolism [3]. Reduced amount of blood flow into the lung, due to the blockage, may also decrease the amount of oxygen absorbed by the lung, causing a life-threatening condition with a high sudden death rate (>25%) [4]. It is, therefore, crucial to treat DVT appropriately and promptly to minimize potential complications.

DVT is mostly treated through medications, such as anticoagulants, that make it hard for blood to clot [5]. Anticoagulants prevent blood clots from getting bigger and traveling through the bloodstream. However, some patients cannot take anticoagulants because of bleeding risk [6]. In addition, the treatment requires a relatively long time (e.g., at least three months) for blood clots to be dissolved naturally [7]. Meanwhile, mechanical treatment can be considered for patients who cannot have medication treatments. For instance, vena cava filters, placed via minor surgery, prevent thrombus from moving to the heart and lung [5], [8], although such mechanical filters still have potential complications, such as perforation with retroperitoneal bleeds, embolization, and filter fracture [9]. Thrombolysis using the focused US has been recently introduced by some researchers [10]-[12]. The focused US is capable of dissolving thrombus noninvasively without surgery [13], whereas the US must be precisely directed to the target region so as not to damage unwanted surrounding tissues [14]. These current techniques still do not provide an optimal clinical solution for DVT treatments.

Interstitial therapeutic US devices have recently shown clinical potential considering overall clinical aspects, such as safety, cost, treatment time burden, and effectiveness-to-risk ratio. In contrast to typical noninvasive focused US methods, intravascular transducers, due to their relatively small geometric dimension, allow the localized sonification of a target region while suppressing excessive exposure of surrounding tissue and organs [15]-[18]. Direct interaction with the target enables the intravascular device to achieve the clinical goal with a relatively low electric power (<20 W) [15]-[18]. Furthermore, the interstitial transducer can precisely deliver a sufficiently high acoustic pressure over a target region without damaging unwanted tissues [15], [18], [19]. Meanwhile, some researchers investigated intravascular US transducers, capable of performing in a small vascular (2-5 mm), for a variety of therapeutic purposes, such as tissue ablation [19], [20], drug delivery [21], [22], and thrombolysis [23], [24]. In 2014, the FDA approved a side-looking, minimally invasive endovascular therapeutic device (EkoSonic™ Endovascular System, Boston Scientific, Marlborough, MA) for use in treating pulmonary embolism [25]. The therapeutic efficacy of thrombolysis has been demonstrated using the device, along with microbubble injection [26]. This FDA-approved technique has demonstrated safe and improved permeation of recombinant tissue plasminogen activator (rt-PA) by low-power ultrasound. However, some randomized clinical trials show that this low-power ultrasound effect is not significant, even showing no difference between localized rt-PA delivery alone and ultrasound-assisted delivery [27]. Higher power output may solve this problem but its side-viewing design that directly aims vessel lumen hinders applying this easy solution. J. Kim et al. [23] suggested a microbubble (MB)-mediated intravascular sonothrombolysis technique, using a miniaturized forward-viewing US transducer that has a relatively high yet spatially confined acoustic pressure output (~2 MPa in the peak-to-peak level) with the aid of a multilayered piezoelectric stack and a concave lens. The therapeutic efficiency of the forward-viewing device, combined with medication (i.e., rt-PA), was further demonstrated in [28]. B. Zhang et al. [29] utilized the cavitation of magnetic MBs concentrated around the target clot by using a forward-viewing transducer. However, existing intravascular US transducers have a relatively short focal distance (<1-1.5 mm) due to their small aperture size and relatively low operation frequency (<0.7 MHz). The short spatial coverage in an axial direction is disadvantageous to cause cavitation effects of MBs in a sufficient target volume, thus limiting treatment efficiency (<30-50% mass reduction for 30 min in-vitro).

Microbubbles (i.e., micron-sized, lipid-shelled gas bubbles) are known to increase the rate of thrombolysis, in combination with sonication, over a certain mechanical index (MI) level (i.e., MI>0.3 for inertial cavitation) [30]. However, MBs have a relatively short lifetime in-vivo, which restricts effective therapeutic time during US treatments [31]. Moreover, due to their relatively large size (approximately 2 μm on average), MBs may remain confined on tissue surface and not penetrate the target region. In contrast, nanodroplets (ND), composed of liquid (condensed) perfluorocarbons with a smaller diameter (<300 nm on average), exhibit effective permeability to a target tissue [32]. Furthermore, NDs remain viable for a relatively longer time than MB agents in blood circulation [33]. Despite the potential advantage of NDs, applications incorporated with intravascular US transducers are hardly found in the literature due to the insufficient acoustic pressure and the limited focal range of existing intravascular devices [27]-[29].

The goals of this study are to (1) develop a customized intravascular US transducer that overcomes the limitation of current intravascular transducers by transmitting sufficient acoustic pressure over a long distance (>2 wavelengths) under a sub-megahertz operation condition, and (2) to evaluate the therapeutic efficacy of ND-mediated thrombolysis combined with the new device under static and dynamic flow models, respectively. It was hypothesized that (1) nano-sized droplets can more effectively permeate a deep region of a target clot than other micron-size bubbles, and (2) the acoustic droplet vaporization and cavitation of NDs with more proximity to the target center can be activated by delivering sufficiently high acoustic energy generated by the developed transducer. FIG. 15 presents a schematic view of the ND-mediated intravascular US thrombolysis.

Materials and Methods

Transducer Design

The intravascular US transducer needs to transmit a high acoustic pressure output, causing a sufficient MI (>0.3) for agent-assisted inertial cavitation [30], onto a relatively far distance (>3 mm) from the small aperture to generate effective cavitation of ND. MI level induced by US wave is defined as follows [34]:

$$MI = \overline{P} \Big/ \sqrt{f} \qquad (1)$$

where $\overline{P}$ is the negative pressure level in MPa, and f is the frequency in MHz. (1) indicates that a relatively low frequency (e.g., <1 MHz) is advantageous to achieve a high MI. However, it is relatively difficult for sub-megahertz transducers to achieve a long focal distance since the Fresnel zone depends on wavelength as follows [35]:

$$\text{Fresnal zone} = r^2 \Big/ \lambda \qquad (2)$$

where r is the radius of aperture, and A is the wavelength. For example, the far-field of a 1 MHz transducer having a diameter of 2 mm would begin from the distance of the half wavelength. As such, novel design approaches are needed for sub-megahertz transducers to extend the forward directivity of the acoustic beam to a relatively far distance (>2λ).

Sub-megahertz transducers require a relatively thick (>1 mm) dimension of the active material. The electrical impedance of the thick piezoelectric plate becomes relatively high due to the low capacitance, requiring a high input voltage to drive the transducer. A multilayered design for the piezoelectric stack was thus adopted for the US transducer to reduce the impedance level at the driving frequency. For the active layer, PZT-4 material was used because of its high mechanical quality factor and electric robustness [36]. Five active layers (200 μm-thick each) were stacked together to decrease electric impedance and intensify acoustic power with the extensional mode. The overall thickness of active layers (i.e., 1 mm) was smaller than the lateral dimension of the transducer (2 mm); hence, the lateral vibration mode can be more predominant at the first resonance frequency. For the suppression of the lateral vibration mode, the concept of a 1-3 composite structure (1-D connection of piezoelectric element and 3-D connection of polymer matrix) was adopted for the transducer design. Notably, our multi-pillar piezoelectric stack (MPPS) design is different from simply stacking up conventional 1-3 composite layers [37], [38]; 1) MPPS design comprises relatively large-cross-sectional-area pillar (>λ) compared to conventional 1-3 composite designs (<0.2λ). This makes MPPS oscillation separated from polymer matrix oscillation, whereas a fine periodic dimension is crucial for the homogenized, in-phase oscillation of conventional 1-3 composites. 2) a fine-periodic structure of 1-3 composite is considered as an effective single-phase medium typically with 50-70% stiffness of piezoelectric ceramics. The lowered stiffness makes the stacked-layer vulnerable to damped oscillation effect caused by intermediate bonding layers compared to the same structure of PZT ceramic stacks as shown in MPPS design (FIG.

16). We designed four pillars that separated by polydimethylsiloxane (PDMS) to realize pure extensional vibration suppressing both mode coupling and bonding layers effects. Next, a concave metallic lens with a radius curvature of 2 mm was integrated on top of the MPPS to focus the acoustic pressure output. Lastly, air-backing was applied at the rear side of the MPPS for the effective transmission of the acoustic wave to the forward direction.

Numerical Simulation

Numerical simulations were conducted using ANSYS (Rel. 17.1, ANSYS, Inc., Canonsburg, PA), a commercial finite element (FE) analysis software, to predict the performance of the designed transducer. Table I lists the material properties of individual parts in the transducer. FIG. 17 presents the boundary conditions of the FE model. Fluid-structure interaction (FSI) condition was applied to the interface between the transducer model and the water media, which transforms the mechanical vibration of the transducer into acoustic pressure in water. Meanwhile, acoustic radiation condition was used at the outer surfaces of the water media to restrict reflections at the boundaries. The acoustic impedance of 500 Rayls was applied at the rear surface of the transducer to simulate air-backing [40]. The FE analysis was performed for a single-pillar piezoelectric stack (SPPS) transducer (FIG. 16A) to confirm the effectiveness of the MPPS design (FIG. 16B).

Jose, CA). The gap was filled with PDMS (Sylgard™ 184, Dow Corning, Midland, MI), and the stack was diced to achieve a sectional dimension of 2×2 mm$^2$, making it a 1-3 composite structure. After integrating a metallic concave lens on top of the MPPS, the silicon substrate was removed from the sample. The electrodes of the MPPS were connected with a coaxial cable (5381-006, AWG 38, Hitachi Cable America Inc., Manchester, NH) after isolating unneeded electrodes, using Parylene-C sheets. Meanwhile, air-backing was fabricated by making a composite of air microbubbles (Blatek Inc., State College, PA) and epoxy (Epotek® 301, Epoxy Tech. Inc., San Jose, CA) with a volume ratio of 3:1. The mixture was applied at the rear side of the MPPS, with a thickness of about 1 mm. Finally, a parylene-C layer was deposited on the transducer surface to make it waterproof by using a Parylene coater (SCS Labcoter®, PDS 2010, SCS, Indianapolis, IN).

The prototyped transducer was characterized based on electric impedance response and acoustic pressure output. Electric impedance response was measured in the frequency range from 5 kHz to 2 MHz using an impedance analyzer (4294A, Agilent Tech. Inc., Santa Clara, CA). The impedance curve was compared with the simulation result to confirm the integrity of the fabricated transducer and determine approximate operation frequency condition. The required electric power was estimated using the following formula [19]:

TABLE I

MATERIAL PROPERTIES OF THE MPPS TRANSDUCER [19], [39].

| | Properties | Value | | Properties | Value |
|---|---|---|---|---|---|
| PZT-4 | $\rho$ (kg/m$^3$) | 7,500 | Aluminum | $\rho$ (kg/m$^3$) | 2,700 |
| | $s_{11}^E$ (×10$^{-12}$ Pa$^{-1}$) | 12.3 | | Y (GPa) | 70.0 |
| | $s_{33}^E$ (×10$^{-12}$ Pa$^{-1}$) | 15.5 | | v | 0.33 |
| | $s_{31}^E$ (×10$^{-12}$ Pa$^{-1}$) | −5.31 | E-solder | $\rho$ (kg/m$^3$) | 2600 |
| | $s_{15}^E$ (×10$^{-12}$ Pa$^{-1}$) | 39.0 | | Y (GPa) | 5.8 |
| | $e_{31}$ (C/m$^2$) | −5.2 | | v | 0.38 |
| | $e_{33}$ (C/m$^2$) | 15.1 | PDMS | $\rho$ (kg/m$^3$) | 1,030 |
| | $\varepsilon_{11}^S/\varepsilon_0$ | 762 | | Y (GPa) | 1.32 × 10-4 |
| | $\varepsilon_{33}^S/\varepsilon_0$ | 663 | | v | 0.49 |

$s_{xx}^E$: compliance under free electric field,
$e_{xx}$: piezoelectric coefficient,
$\varepsilon_{xx}^S$, $\varepsilon_0$: dielectric constant under free strain,
Y: Young's modulus, p: density, and v: Poisson's ratio.

Transducer Fabrication and Characterization

FIGS. 18A and 18B illustrate the fabrication procedure of the MPPS transducer. Each active layer (i.e., PZT-4) was lapped into the thickness of 200 μm, followed by the deposition of the electrodes with Au/Cr (200/10 nm). Each active layer was stacked together, using conductive silver epoxy (E-Solder 3022, Von Roll Inc., Cleveland, OH) as an intermediate bonding layer (approximately 20 μm). The piezoelectric stack was attached to a silicon wafer, using a wax-resin to hold the specimen for the following dicing process. The stack was partially sliced with a kerf width of 300 μm (DISCO 322, DISCO Hi-Tec America, Inc., San $$P_{avg} = \eta \frac{1}{1-\zeta} \frac{V_{eff}^2}{Z} \qquad (3)$$

where $\zeta$ denotes the reflection coefficient due to the electric mismatch, $\eta$ is the duty cycle (%), Z indicates the electrical impedance at operating frequency of the transducer, and $V_{eff}$ is the effective input voltage. Next, acoustic pressure output induced by the transducer was measured using a hydrophone (HGL-0085, ONDA Corp., Sunnyvale, CA). FIG. 19 shows a schematic of the test setup. The function generator (33250A, Agilent Tech. Inc., Santa Clara, CA) transmitted a sinusoidal pulse of 15 cycles per 10 ms to the power amplifier (75A250A, AR, Souderton, PA). The amplified signal was fed into the MPPS transducer.

Microbubbles and Nanodroplets Preparation

MBs and NDs were formed by mechanical agitation in accordance with previous research in [32], [41]. The lipid-shelled MBs and NDs were composed of decafluorobutane cores. The concentration of each solution was estimated to be approximately $1\times10^{10}$/mL. Each solution was diluted by $10^{-2}$ their original concentration in sterile saline to evaluate the performance of each agent in thrombolysis. Furthermore, the ND solution was diluted by $10^{-3}$, $10^{-2}$, and $10^{-1}$ in saline water, respectively, to investigate the influence of ND concentration. The mean diameters of MBs and NDs particles were $1.1\pm0.5$ μm and approximately 300 nm, respectively [42].

Blood Clot Incubation

Blood clots for in vitro tests were prepared following our previous works in [23], [28]. Fresh bovine blood (Densco Marketing Inc., Woodstock, IL) was mixed with 2.75% (w/v) $CaCl_2$) solution (Fisher Scientific, Fair Lawn, NJ) in a volume ratio of 10:1 (i.e., 5 mL $CaCl_2$) solution for 50 mL bovine blood). The mixture was loaded in Tygon tubes having an inner diameter of 6.35 mm. Next, the Tygon tubes with the blood-$CaCl_2$) solution were placed inside a 37° C. water bath for three hours to coagulate the blood. The coagulated blood was stored at 4° C. for a week. Finally, the clot samples in the Tygon tubes were sliced into a cylindrical shape to weigh 180 mg±10% in mass.

Blood Clot Incubation

FIG. 20 illustrates a blood flow mimicking system for the demonstration of the thrombolytic efficacy of the developed transducer. A clot sample was placed in the transparent plastic vessel, where a mesh-shape fabric was inserted in the artificial vessel to prevent the blood clot from flowing away while retaining a certain hydraulic pressure level (i.e., 0.5 kPa) [40]. The hydraulic pressure level was controlled in accordance with the height of a water reservoir. The pressure level in the flow system was monitored using a pressure gauge. The US transducer was operated under 80 $V_{pp}$ electric input and a duty cycle of 8.3% (i.e., 400 pulses for a period, 5 ms). During the 30 min treatment, the clot was continuously insonified for 2 min to activate cavitation of either NDs or MBs and rested for 30 sec to sufficiently disseminate the cavitation agent to the clot.

The test was conducted in both static and dynamic flow models, respectively. For the static flow test, the lysis rate of the ND-mediated sonification (i.e., NDs+US) was compared with other reference cases: MBs+US, US only, and controlled (i.e., without US). Based on the test result in the static flow model, the influence of ND concentration was investigated in the dynamic flow model, varying the ND concentration from 0 to $10^9$ numbers/mL. Each test was repeated three times (n=3).

Results and Discussion

Transducer Characterization

FIG. 21A compares electric impedance responses of the MPPS and the SPPS transducers estimated by the numerical simulation. For the SPPS model, the lateral and the extensional vibration modes are found at 0.80 and 0.98 MHz, respectively. Both modes are slightly coupled together according to the phase diagram. In contrast, in the MPPS model, the lateral vibration mode was almost suppressed owing to the 1-3 composite structure. Meanwhile, the predominant extensional mode was observed at around 0.93 MHz. The MPPS transducer exhibited a relatively broad frequency bandwidth ($f_r$=0.93 MHz and $f_a$=1.10 MHz), where $f_r$ and $f_a$ denote the resonance and the anti-resonance frequency, respectively. Furthermore, the impedance amplitude at the resonance (38.9 Ohm) was expected to have a low loss in electric power due to the close electric matching with the electric wire (i.e., 50 Ohm). FIGS. 21B and 21C represent acoustic pressure fields produced by the extensional vibration mode of the SPPS and the MPPS transducer, respectively. While the −6 dB focal zone of the SPPS was from 0 to 1.7 mm from the aperture, that of the MPPS was estimated to be from 0.1 to 3.0 mm. The acoustic beam in the SPPS transducer spreads along the side direction (FIG. 21B), whereas the beam pattern in the MPPS predominantly directs along the forward direction, suppressing acoustic radiation to the side direction (FIG. 21C). For instance, the −12 dB acoustic beam along the side direction reached about 1.33 mm in the SPPS transducer, whereas it was only around 0.56 mm in the MPPS.

Based on the simulation results, the MPPS transducer was fabricated and characterized as regards electric impedance and acoustic pressure output. FIG. 22A represents the electric impedance of the actual device. The impedance level was about 74.3 Ohms at 0.96 MHz, showing a reliable agreement (~3.3% discrepancy in the resonance frequency) with the simulation result in FIG. 21A. FIG. 22B is the acoustic pressure field represented in the dB scale. The ~6 dB focal zone reached up to 3.4 mm, and the beam width was estimated to be about 1.7 mm. The sensitivity of the transducer was estimated to be about 0.018 MPa/$V_{pp}$ (FIG. 22C). The corresponding MI was about 1.97 under 120 $V_{pp}$ input. Since MI level over 1.5 is enough to stimulate both stable and inertial cavitation effects [43], [44], and in vivo application of contrast agents over the level of 1.9 is restricted [45], 80 $V_{pp}$ was chosen to operate the MPPS transducer in the following in vitro test. MB-mediated cavitation effect induced by an intravascular transducer has been presented and discussed in our previous research in [23]. Cavitation effect of NDs using the intravascular transducer is investigated in Appendix A. Table II summarizes the specifications of the MPPS transducer.

TABLE II

SPECIFICATIONS OF THE DEVELOPED MPPS TRANSDUCER.

| Operating frequency | 0.96 MHz | Impedance | 74.3 Ω |
|---|---|---|---|
| 6 dB– focal zone | ~3.4 mm | Beam width | 1.7 mm |
| Peak-to-peak pressure | 3.05 MPa | Peak negative pressure | 1.49 MPa |
| Mechanical index | 1.52 | Electric power[1] | 1.1 W |

[1] under 8.3% duty cycle of 80 $V_{pp}$ sine actuation

In Vitro Test Results

The therapeutic effect of ND-mediated intravascular sonication was initially demonstrated using the MPPS transducer without water flow in the test system. FIG. 23 visualizes the dissolution of a blood clot over time (i.e., 30 min). A red-colored cloud was observed right after operating the transducer due to the cavitation effect in the clot, and the cloud became denser as the clot dissolved further. FIG. 24 compares the lysis rate under different test conditions: NDs+US, MBs+US, US only, and control groups. The ND-mediated ultrasound achieved an average mass reduction of 76.0% and a maximum of 84.1%. The mean lysis rate was estimated at approximately 4.6 mg/min (=2.53%/min).

Conversely, percentile mass reductions in the cases of MBs+ US and US only were around 60.4% and 49.5%, respectively. The thrombolysis rate obtained by NDs+US is a statistically meaningful improvement compared to other conditions (p<0.05) [46].

Following the confirmation of the efficacy of ND-mediated sonication, further thrombolysis tests were consequently demonstrated in a flow model (FIG. 20). FIG. 25A presents the thrombolysis rate with respect to ND concentration. While the thrombolysis rate increases in the ND concentration of $10^8$ ND/mL compared with the control and the $10^7$ ND/mL group, there was no significant increase after $10^9$ ND/mL. Notably, the thrombolysis rate in the flow model was slightly decreased by about 9.3% compared to the results without flow. FIG. 25B presents the bovine blood clot pre- and post-treatment. ND-mediated sonication can successfully dissolve the coagulated blood clot over 76% within 30 min.

Discussion

An intravascular US transducer was designed to deliver a high acoustic pressure output (>3 MPa in the peak-to-peak level) to a relatively far distance (>3 mm) than the previous forward-viewing intravascular ultrasound designs [23], [28], [29]. The MPPS design demonstrated that the passive material disconnected the lateral connectivity of the active layers, by which the wave transmission along the side direction was effectively suppressed. The simulation results in FIG. 21B affirmed that a typical piezoelectric stack (SPPS) cannot suppress the acoustic pressure output to the side direction due to the predominant lateral vibration mode at 0.8 MHz. In contrast, FIG. 21C exhibited that the predominant extensional vibration mode at about 0.93 MHz is advantageous to deliver the acoustic pressure output along the forward direction (FIG. 22B). For these reasons, the MPPS transducer can be expected to have fewer concerns and clinical complications, such as potential vessel damages caused by unnecessary exposure to the side direction ultrasound beam.

The developed transducer provided a relatively long axial focal zone (>3 mm) (FIG. 22B) compared with existing intravascular devices owing to the MPPS design [23], [28]. The extended focal zone of the MPPS transducer covered the most of an entire clot volume which helped to induce the phase transition (i.e., ND to MB) of NDs and the cavitation within blood clots. The hundreds-nano-sized particles possibly penetrate a blood clot, whereas the typical transducer having either a short focal distance (<1.5 mm) or a low acoustic pressure output (<2 MPa) is not suitable to create sufficient cavitation of ND within the clot. FIG. 24 shows that ND-mediated sonication outperforms other modalities (i.e., US only and US+MBs). The efficient penetration of NDs and the cavitation within the clot can help to disrupt the biostructure more effectively as we anticipated.

The influence of ND concentration was investigated as shown in FIG. 24. The dose over $10^8$ ND/mL did not further increase the mass reduction rate. The distribution of cavitating nanodroplets affects cavitation-induced sonothrombolysis. Although a larger number of cavitating NDs generates more shear-stress in a clot, too many cavitating NDs (i.e., $10^9$ ND/mL) in an ultrasound beam path largely scatters the US energy that hinders the sufficient US delivery for ND cavitation in a further target zone [47]. Meanwhile, compared to the lysis rate without the flow model (FIG. 24), the dissolution rate was reduced by 9.3%. The decrease of the lysis rate in the flow model could be caused as a portion of the injected NDs flows away and does not remain in a static location.

The lysis rate of the proposed method (2.1-2.8%/min) was relatively high in comparison with that of other existing modalities (0.7-1.5%/min), using micron-sized bubble agents combined with intravascular transducers [23], [29], [48]. Such direct comparison would not straightforwardly support the superiority of the proposed method since each study considered the different test parameters in terms of clot size, clot type (e.g., porcine, bovine, and human), and US condition (e.g., duty cycle, voltage level, and frequency). Nonetheless, such a high lysis rate in the ND-mediated intravascular sonication was meaningful as showing the potential of the practical applications. Meanwhile, this study did not consider the influence of chemical agents, such as rt-PA [49]; hence, the application of rt-PA to the ND-mediated sonication can further improve treatment efficacy. Accordingly, the dose of the medications can be minimized by adopting the intravascular thrombolysis technique, thus reducing the possibility of complications, such as bleeding.

The specific aim of this study is a new device development with a preliminary feasibility demonstration. Thus, there is room for further studies as the clinical research on the topic is still in its infantile stages. ND-mediated thrombolysis has to be further validated through either ex vivo or in vivo tests, following in vitro validation using human blood clots as demonstrated in [48]. Histological studies should be also conducted to evaluate the safety of the proposed modality. Parametric studies on the long-term usage of the device should also be encouraged. Moreover, optimal driving conditions (e.g., pulse repetition frequency, duty cycle, driving voltage, and operation frequency) of the device should be further investigated through extensive combinations of the parameters. Nevertheless, the research results presented in this paper demonstrate the clinical potential of the ND-mediated intravascular sonication for DVT treatment.

CONCLUSION

This section illustrates a miniaturized, forward-looking, intravascular, US transducer for the treatment of DVT. The transducer used multi-pillar active elements (similar to 1-3 composite structure) for piezoelectric stacks and a passive elastomer. Owing to the efficient extensional vibration mode of the transducer, the MPPS transducer can deliver a sufficiently high rarefactional pressure output (~1.5 MPa) to a far distance (>2λ) from the aperture. The acoustic beam produced by the device also exhibited effective directivity along the forward direction, which aided to expedite the ND-mediated thrombolysis. Moreover, compared to common piezoelectric multilayer designs, suppressing the acoustic beam to the side direction potentially would be expected to reduce clinical complications, such as damage in the vessel wall. Meanwhile, the introduction of a flow model degraded treatment efficacy as the NDs could not stay in a static position due to the flow; nonetheless, the percentile mass reduction was still over 68%. Finally, this research result was meaningful in that the relatively high lysis rate (2.1-2.8%/min) was achieved without the aid of thrombolytics. To conclude, the ND-mediated intravascular sonothrombolysis using MPPS transducers will provide an expedited clinical option for DVT treatments.

Appendix A—Cavitation Effect of Nanodroplet

The objective of this section is to confirm the cavitation effect of ND induced by the developed MPPS transducer. The experiment followed our previous setup in [23]. A hydrophone (HGL-0085, ONDA Corp., Sunnyvale, CA) measured the acoustic pressure output of the artificial vessel upon the sonication of 30 cycles of a sine wave for 0.5 ms over ND. The measured signal over time was transformed into the frequency domain by using MATLAB (rel. 2019a, MathWorks, Natick, MA). To quantify the stable cavitation effect of ND, the frequency signal was filtered in the range of the operation frequency ±10% to obtain the second harmonic of the signal, followed by the summation of the spectrum magnitude. The quantification of the inertial cavitation was obtained by applying the band-stop (i.e., notch) filter to the primary and the super-harmonic frequency bands (marked in the green circle in FIG. 26B) and by summing up the filtered frequency signal. For both the bandpass and the notch digital filtering, the 6th order of Butterworth filter was used.

FIGS. 26A-26D illustrate measurements of the pressure signal measured by the hydrophone. The acoustic pressure output induced by a sinusoidal input (in the inset of FIG. 26A) was significantly distorted due to the shock wave produced by the inertial cavitation and the super-harmonic terms resulting from the stable cavitation of ND. FIG. 26B represents the frequency spectrum of the acoustic pressure signal with respect to the input voltage level of the device. Transmitting a higher acoustic pressure output (i.e., applying a high electric power to the transducer) tends to increase the magnitude of super-harmonics and the broadband noise. FIG. 26C and FIG. 26D quantified the intensity of the stable and the inertial cavitation, respectively. The test results show that the MPPS transducer can generate ND cavitation and increase cavitation effects by amplifying the electric power to the MPPS transducer.

REFERENCES

[1] E. Previtali, P. Bucciarelli, S. M. Passamonti, and I. Martinelli, "Risk factors for venous and arterial thrombosis," Blood Transfusion, vol. 9, no. 2, pp. 120-138, 2011.
[2] S. R. Kahn, "The clinical diagnosis of deep venous thrombosis: integrating incidence, risk factors, and symptoms and signs," Archives of Internal Medicine, vol. 158, no. 21, pp. 2315-2323, 1998.
[3] F. A. Anderson, H. B. Wheeler, R. J. Goldberg, D. W. Hosmer, N. A. Patwardhan, B. Jovanovic, A. Forcier, and J. E. Dalen, "A population-based perspective of the hospital incidence and case-fatality rates of deep vein thrombosis and pulmonary embolism: the Worcester DVT Study," Archives of Internal Medicine, vol. 151, no. 5, pp. 933-938, 1991.
[4] M. G. Beckman, W. C. Hooper, S. E. Critchley, and T. L. Ortel, "Venous thromboembolism: a public health concern," American Journal of Preventive Medicine, vol. 38, no. 4, pp. S495-S501, 2010.
[5] J. P. Galanaud, J. P. Laroche, and M. Righini, "The history and historical treatments of deep vein thrombosis," Journal of Thrombosis and Haemostasis, vol. 11, no. 3, pp. 402-411, 2013.
[6] H. Robert-Ebadi, G. Le Gal, and M. Righini, "Use of anticoagulants in elderly patients: practical recommendations," Clinical Interventions in Aging, vol. 4, pp. 165-177, 2009.
[7] L. Mazzolai, V. Aboyans, W. Ageno, G. Agnelli, A. Alatri, R. Bauersachs, M. P. A. Brekelmans, H. R. Buller, A. Elias, D. Farge, S. Konstantinides, G. Palareti, P. Prandoni, M. Righini, A. Torbicki, C. Vlachopoulos, M. Brodmann, "Diagnosis and management of acute deep vein thrombosis: a joint consensus document from the European Society of Cardiology working groups of aorta and peripheral vascular diseases and pulmonary circulation and right ventricular function," European Heart Journal, vol. 39, no. 47, pp. 4208-4218, 2018.
[8] L. J. Greenfield and M. C. Proctor, "Recurrent thromboembolism in patients with vena cava filters," Journal of Vascular Surgery, vol. 33, no. 3, pp. 510-514, 2001.
[9] T. G. Van Ha, "Complications of inferior vena caval filters," Seminars in Interventional Radiology, vol. 23, no. 2, pp. 150-155, 2006.
[10] G. Goudot, T. Mirault, B. Arnal, C. Boisson-Vidal, B. Le Bonniec, P. Gaussem, A. Galloula, M Tanter, E. Messas, and M. Pernot, "Pulsed cavitational therapy using high-frequency ultrasound for the treatment of deep vein thrombosis in an in vitro model of human blood clot," Physics in Medicine & Biology, vol. 62, no. 24, pp. 9282-9294, 2017.
[11] W. Yang and Y. Zhou, "Effect of pulse repetition frequency of high-intensity focused ultrasound on in vitro thrombolysis," Ultrasonics Sonochemistry, vol. 35, pp. 152-160, 2017.
[12] R. J. Siegel and H. Luo, "Ultrasound thrombolysis," Ultrasonics, vol. 48, no. 4, pp. 312-320, 2008.
[13] C. Wright, K. Hynynen, and D. Goertz, "In vitro and in vivo high intensity focused ultrasound thrombolysis," Investigative Radiology, vol. 47, no. 4, pp. 217, 2012, 2012.
[14] C. J. Shaw, G. R. ter Haar, I. H. Rivens, D. A. Giussani, and C. C. Lees, "Pathophysiological mechanisms of high-intensity focused ultrasound-mediated vascular occlusion and relevance to non-invasive fetal surgery," Journal of The Royal Society Interface, vol. 11, no. 95, 20140029, 2014.
[15] R. Chopra, N. Baker, V. Choy, A. Boyes, K. Tang, D. Bradwell, and M. J. Bronskill, "MRI compatible transurethral ultrasound system for the treatment of localized prostate cancer using rotational control," Medical Physics, vol. 35, no. 4, pp. 1346-1357, 2008.
[16] G. Sommer, K. B. Pauly, A. Holbrook, J. Plata, B. Daniel, D. Bouley, H. Gill, P. Prakash, V. Salgaonkar, P. Jones, and C. Diederich, "Applicators for MR-guided ultrasonic ablation of BPH," Investigative Radiology, vol. 48, no. 6, pp. 387-394, 2013.
[17] D. Melodelima, C. Lafon, F. Prat, Y. Theillère, A. Arefiev, and D. Cathignol, "Transoesophageal ultrasound applicator for sector-based thermal ablation: first in vivo experiments," Ultrasound in Medicine and Biology, vol. 29, no. 2, pp. 285-291, 2003.
[18] T. D. Mast, P. G. Barthe, I. R. S. Makin, M. H. Slayton, C. P. Karunakaran, M. T. Burgess, and S. M. Rudich, "Treatment of rabbit liver cancer in vivo using miniaturized image-ablate ultrasound arrays," Ultrasound in Medicine and Biology, vol. 37, no. 10, pp. 1609-1621, 2011.
[19] H. Kim, H. Wu, N. Cho, P. Zhong, K. Mahmood, H. Lyerly, and X. Jiang, "Miniaturized intracavitary forward-looking ultrasound transducer for tissue ablation," IEEE Transactions on Biomedical Engineering, to be published, 2019.
[20] X. Liu, N. Ellens, E. Williams, E. C. Burdette, P. Karmarkar, C. R. Weiss, D. Kraitchman, and P. A. Bottomley, "High-resolution intravascular MRI-guided perivascular ultrasound ablation," Magnetic Resonance in Medicine, vol. 83, no. 1, pp. 240-253, 2020.

[21] A. J. Dixon, J. P. Kilroy, A. H. Dhanaliwala, J. L. Chen, L. C. Phillips, M. Ragosta, A. L. Klibanov, and B. R. Wamhoff, and J. A. Hossack, "Microbubble-mediated intravascular ultrasound imaging and drug delivery," *IEEE Transactions on Ultrasonics, Ferro-electrics, and Frequency Control,"* vol. 62, no. 9, pp. 1674-1685, 2015.

[22] A. J. Dixon, A. H. Dhanaliwala, J. L. Chen, and J. A. Hossack, "Enhanced intracellular delivery of a model drug using microbubbles produced by a microfluidic device," *Ultrasound in Medicine & Biology*, vol. 39, no. 7, pp. 1267-1276, 2013.

[23] J. Kim, B. D. Lindsey, W. Y. Chang, X. Dai, J. M. Stavas, P. A. Dayton, and X. Jiang, "Intravascular forward-looking ultrasound transducers for microbubble-mediated sonothrombolysis," *Scientific Reports*, vol. 7, no. 3454, 2017.

[24] U. K. Ballehaninna, A. Hingorani, E. Ascher, A. Shiferson, N. Marks, E. Aboian, R. Jimenez, T. Jacob, and T. McIntyre, "Acute superior mesenteric artery embolism: reperfusion with AngioJet hydrodynamic suction thrombectomy and pharmacologic thromboly-sis with the EKOS catheter," *Vascular*, vol. 20, no. 3, pp. 166-169, 2012.

[25] FDA News, [Online] https://www.fdanews.com/ar-ticles/164759-fda-clears-ekos-ekosonic-endovascular-system, Accessed on May 2020.

[26] C. A. Owens, "Ultrasound-enhanced thrombolysis: EKOS EndoWave infusion catheter system," *Seminars in Interventional Radiology*, vol. 25, no. 1, pp. 037-041, 2008.

[27] R. P. Engelberger, D. Spirk, T. Willenberg, A. Alatri, D. D, Do, I. Baumgartner, and N. Kucher, "Ultrasound-assisted versus conventional catheter-directed throm-bolysis for acute iliofemoral deep vein thrombosis," *Circulation: Cardiovascular Interventions*, vol. 8, no. 1, e002027, 2015.

[28] L. Goel, H. Wu, H. Kim, B. Zhang, J. Kim, P. A. Dayton, Z. Xu, and X. Jiang, "Examining the influence of low-dose tissue plasminogen activator on microbubble-mediated forward-viewing intravascular sonothrombolysis," *Ultrasound in Medicine & Biology*, to be published, 2020.

[29] B. Zhang, H. Kim, H. Wu, Y. Gao, and X. Jiang, "Sonothrombolysis with magnetic microbubbles under a rotational magnetic field," *Ultrasonics*, vol. 98, pp. 62-71, 2019.

[30] L. Galiuto, L. Badano, K. Fox, R. Sicari, and J. L. Zamorano, *The EAE textbook of echocardiography*, Ch. 7, Oxford University Press, 2011.

[31] L. Mullin, R. Gessner, J. Kwan, M. Kaya, M. A. Borden, and P. A. Dayton, "Effect of anesthesia carrier gas on in vivo circulation times of ultrasound microbubble contrast agents in rats," *Contrast Media & Molecular Imaging*, vol. 6, no. 3, pp. 126-131, 2011.

[32] L. C. Moyer, K. F. Timbie, P. S. Sheeran, R. J. Price, G. W. Miller, and P. A. Dayton, "High-intensity focused ultrasound ablation enhancement in vivo via phase-shift nanodroplets compared to microbubbles," *Journal of Therapeutic Ultrasound*, vol. 3, no. 7, 2015.

[33] N. Rapoport, K. H. Nam, R. Gupta, Z. Gao, P. Mohan, A. Payne, N. Todd, X. Liu, T. Kim, J. Shea, C. Scaife, D. L. Parker, E. K. Jeong, and A. M. Kennedy, "Ultrasound-mediated tumor imaging and nanotherapy using drug loaded, block copolymer stabilized perfluo-rocarbon nanoemulsions," *Journal of Controlled Release*, vol. 153, no. 1, pp. 4-15, 2011.

[34] P. C. Chu, W. Y. Chai, C. H. Tsai, S. T. Kang, C. K. Yeh, and H. L. Liu, "Focused ultrasound-induced blood-brain barrier opening: association with mechani-cal index and cavitation index analyzed by dynamic contrast-enhanced magnetic-resonance imaging," *Sci-entific Reports*, vol. 6, no. 33264, 2016.

[35] T. S. Curry, J. E. Dowdey, and R. C. Murry, *Chris-tensen's Physics of Diagnostic Radiology*, 4th ed., Lippincott Williams & Wilkins, 1990.

[36] J. Fan, W. A. Stoll, and C. S. Lynch, "Nonlinear constitutive behavior of soft and hard PZT: Experi-ments and Modeling," *Acta Materialia*, vol. 47, no. 17, pp. 4415-4425, 1999.

[37] D. M. Mills and S. W. Smith, "Multi-layered PZT/polymer composites to increase signal-to-noise ratio and resolution for medical ultrasound transducers," *IEEE Transactions on Ultrasonics, Ferroelectrics, and Frequency Control*, vol. 46, no. 4, pp. 961-971, 1999.

[38] J. Kim and Y. Roh, "Homogenization of PMN-PT/epoxy 1-3 piezocomposites by resonator measurements and finite element analysis," *Sensors and Actuators A: Physical*, vol. 206, pp. 97-106, 2014.

[39] I. D. Johnston, D. K. McCluskey, C. K. L. Tan, and M. C. Tracey, "Mechanical characterization of bulk Sylgard 184 for microfluidics and microengineering," *Journal of Micromechanics and Microengineering*, vol. 24, no. 3, 035017, 2014.

[40] J. Ma, S. Guo, D. Wu, X. Geng, and X. Jiang, "Design, fabrication, and characterization of a single-aperture 1.5-MHz/3-MHz dual-frequency HIFU trans-ducer," *IEEE Transactions on Ultrasonics, Ferroelec-trics, and Frequency Control*, vol. 60, no. 7, pp. 1519-1529, 2013.

[41] P. S. Sheeran, S. H. Luois, L. B. Mullin, T. O. Matsunaga, and P. A. Dayton, "Design of ultrasoni-cally-activatable nanoparticles using low boiling point perfluorocarbons," *Biomaterials*, vol. 33, no. 11, pp. 3262-3269, 2012.

[42] J. Kim, R. M. DeRuiter, L. Goel, Z. Xu, X. Jiang, and P. A. Dayton, "A comparison of sonothrombolysis in aged clots between low boiling point phase change nanodroplets and microbubbles of the same composi-tion," *Ultrasound in Medicine and Biology*, submitted for publication.

[43] X. Zhang, G. E. Owens, H. S. Gurm, Y. Ding, C. A. Cain, and Z. Xu, "Noninvasive thrombolysis using histotripsy beyond the intrinsic threshold (mi-crotripsy)," *IEEE Transactions on Ultrasonics, Ferro-electrics, and Frequency Control*, vol. 62, no. 7, pp. 1342-1355, 2015.

[44] J. Šponer, "Theoretical estimation of the cavitation threshold for very short pulses of ultrasound," *Ultra-sonics*, vol. 29, no. 5, pp. 376-380, 1991.

[45] T. Şen, 0. Tüfekçioğlu, and Y. Koza, "Mechanical index," *Anatolian Journal of Cardiology*, vol. 15, no. 4, pp. 334-346, 2015.

[46] S. N. Goodman, "Toward evidence-based medical statistics. 1: The P value fallacy," *Annals of Internal Medicine*, vol. 130, no. 12, pp. 995-1004, 1999.

[47] C. Vanhille and K. Hynynen, "Numerical simulations of the nonlinear interaction of a bubble cloud and a high intensity focused ultrasound field," *Acoustics*, vol. 1, no. 4, pp. 825-836, 2019.

[48] R. P. Engelberger, V. Schroeder, M. Nagler, R. Prince, D. Periard, D. Hayoz, and N. Kucher, "Enhanced thrombolysis by ultrasound-assisted cath-eter-directed thrombolysis and microbubbles in an in vitro model of iliofemoral deep vein thrombosis," *Thrombosis and Haemostasis*, vol. 119, no. 7, pp. 1094-1101, 2019.

[49] M. J. Stone, V. Frenkel, S. Dromi, P. Thomas, R. P. Lewis, K. C. P. Li, M. Horne III, and B. J. Wood, "Pulsed-high intensity focused ultrasound enhanced tPA mediated thrombolysis in a novel in vivo clot model, a pilot study," *Thrombosis Research*, vol. 121, no. 2, pp. 193-202, 2007.

The following section describes another example of an ultrasound transducer array and associated methods for intravascular nanodroplet-mediated thrombolysis.

Deep vein thrombosis or deep venous thrombosis (DVT) is the formation of blood clots within the deep leg veins. The most serious complication of DVT is pulmonary embolism (PE) which is a blockage of a pulmonary artery by a blood clot that detaches from vein walls and travels through the heart to the lungs. Pulmonary embolism (PE) is fatal in more than 100,000 cases annually in the U.S. alone, presents as sudden death in 20-25% of cases, and causes considerable morbidity and health care costs among survivors. Therefore, an effective acute treatment for PE is critically important.

Current PE treatment techniques, such as pharmacological dissolution or fibrinolysis, mechanical fragmentation, and pharmacomechanical thrombolysis, may be hindered by low thrombolysis efficiency, bleeding complications, a relatively high failure rate, vein injury associated severe regional dysfunction, recurrence, and the risk of distal embolism due to the relatively large size of clot debris. Recent technologies, such as catheter-based side-looking intravascular ultrasound thrombolysis (e.g., EKOS) have somewhat improved performance, but still may suffer from relatively long treatment times (i.e., >10 hours) and concerns about tissue damage from overexposure to acoustic energy. Furthermore, relatively long fluoroscopy times for catheter guidance present some risk to patient and caregiver.

The recombinant tissue-type plasminogen activator (t-PA) has been used for fibrinolysis, but the limitations thereof may include frequent bleeding complications, prolonged infusion time required for the thrombolysis procedure (average 48-53 hours), and high failure rate (about 20%) of fibrinolysis despite the early (within <6 hours) treatment. The mechanical retrieval has been accomplished by using various types of thrombectomy catheters, such as a rotablator, a corkscrew-shaped tip (MERCI), aspiration, rotational, oscillating (Trellis), and rheolytic (Angiojet) thrombectomy. Pharmacomechanical thrombolysis (PMT) has been implemented to use the thrombolytic agent as well as combination of thrombus fragmentation by mechanical devices. Commonly used PMT catheters for relatively large thrombus burden are Angiojet and Trellis. Although these techniques are used to reduce the treatment time with a relatively high success rate, several limitations have been noted, including associated vein injury which leads to severe regional dysfunction, and occurrence of distal embolism due to relatively large size of clot debris.

Ultrasound-based approaches have been developed to overcome these limitations and promote efficiency of thrombolysis, without increasing the risk of systemic bleeding complications. The 'sonothrombolysis' approach has exhibited a high benefit-to-risk ratio due to its ability to provide a controlled region of clot dissolution and to resolve clots quickly with limited mechanical contact with either the thrombus or the surrounding vein wall. There are two main mechanisms of the ultrasound-induced techniques: 1) microstreaming, involving jets arising from cavitation adjacent to the clot surface which mechanically cleaves clot fragments; and 2) enhanced penetration of a chemical thrombolytic agent due to the microstreaming.

Ultrasound-delivery methods for thrombolysis (ultrasound-induced thrombolysis) are generally categorized into three techniques: 1) transcutaneous-delivered external ultrasound (TDEU), 2) catheter-delivered external transducer ultrasound (CETU), and 3) catheter-delivered transducer-tipped ultrasound (CTTU) (see, e.g., FIGS. 1A-1C). The TDEU technique is usually accompanied with high-intensity-focused ultrasound (HIFU) for dissolving the clots by cavitation-induced microstreaming. Although this approach is relatively fast, t-PA-free, and noninvasive, there is, for example, potential for damaging the vessel and surround tissue by ultrasound-induced heating due to the large focal spot (i.e., >5 mm) of relatively low-frequency (i.e., <1 MHz) ultrasound energy.

The CETU technique uses low-frequency (i.e., 20-50 kHz) ultrasound waves transmitted through a catheter guidewire acting as a wave guide. Limitations of this technique include, for example, a narrow bandwidth of usable frequencies, dissipation of ultrasound energy in the wave guide, and increased risk associated with direct contact on the clot. In comparison with other methods, the CTTU technique has exhibited several advantages including, for example, efficient delivery of acoustic energy, flexible frequency control, and negligible ultrasound-induced heating on surrounding tissue. It has been generally accepted that CTTU only facilitates clot dissolution by utilizing low intensity ultrasound to enhance clot permeability to t-PA, which reflects that thrombolysis efficiency of CTTU relies 5 on some amount of t-PA, while the administered t-PA dose must be limited due to potential bleeding complications and strict contraindication criteria.

Currently, a commonly used CTTU technique is the EKOS system (EKOSONIC Endovascular System from EKOS Corporation of Bothell, WA), which does not fracture or break the thrombus, but uses ultrasound to help loosen the fibrin strands within the clot, allowing deeper penetration of lytic agent and reducing the risk of distal embolism. Although this treatment is characterized by reduced dose of t-PA and treatment time (usually 24-48 hours), in comparison with a conventional catheter-directed thrombolysis (CDT) which usually takes three to five days, it may be desirable to further reduce the t-PA dose and extensive treatment time in order to reduce the risk of hemorrhage and to reduce costs. For higher lytic rate with decreased dose of t-PA, the current limitation of a CTTU technique is the lack of miniaturized (i.e., capable of fitting in a 7-French or smaller catheter), low-frequency ultrasound transducers to generate microstreaming arising from cavitation. Therefore, there exists a need for catheter based therapy for PE or DVT, for a device which is compact in size and provides sufficient acoustic output for cavitation-induced microstreaming, with a compact focal spot and precise spatiotemporal delivery of a minimal dose of a lytic agent.

Cavitation enhancement involves enhancing the mechanical effect of cavitation induced microstreaming, through the application of microbubbles. The presence of microbubbles at the clot surface, typically in the form of ultrasound contrast agents, causes a substantially improved lytic rate than without microbubbles. In vivo and in vitro studies with microbubbles for TDEU application have shown more than 100% improved lytic rate than the case without microbubbles. However, it may be desirable to improve (reduce) variation of microbubbles for lytic enhancement under reduced acoustic pressure. Perfluorocarbon nanodroplets are compositionally similar to bubbles, except for involving a perfluorocarbon core in a liquid state. These droplets can be produced at a fraction of the size of microbubbles (i.e., 100-200 nm), and demonstrate improved stability and circulation time. Upon exposure to a sufficient acoustic threshold, these 'phase change agents' vaporize, converting to microbubbles. Intravascular administration of perfluorocarbon droplets has been demonstrated to reduce the sonication power required to achieve recanalization to 24±5% of the necessary power without droplets. The benefit of these nanodroplets over microbubbles is twofold: 1) nanodroplets can penetrate into the clot matrix more efficiently than microbubbles, and 2) increased stability of nanodroplets allows them to be delivered via a catheter. In contrast, microbubbles may be challenging to deliver via a catheter due to their pressure sensitivity, and thus microbubbles are typically administered systemically.

A nanodroplet formulation, substantially similar in composition to lipid encapsulated microbubbles, has been utilized as a contrast agent. This procedure starts with a microbubble preparation, and compresses the microbubbles into droplets. The droplets stay in this form, until exposed to a sufficient acoustic threshold, due to surface tension and bulk nucleation properties of the liquid core. One benefit of this formulation compared to other phase change agents, such as those made with perfluoropentane, is that a low-boiling point gas core, such as perfluoropropane or decafluorobutane, is utilized, and thus can be readily converted to microbubbles at low mechanical indices. Sub-micron agents of perfluoropentane or higher boiling point perfluorocarbons, on the other hand, require substantially more acoustic power, thereby increasing the potential for bioeffects.

Shock wave enhanced lysis is another way to increase the lytic rate of the TDEU technique, namely by using a pulsed laser for laser-enhanced acoustic cavitation. In this regard, the combined excitation of the target clot by HIFU and a 730 nm laser with higher than 27 mJ/cm2 input, may result in about 50% higher lytic efficiency. However, the use of laser energy of 27 mJ/cm2 for direct exposure of the clot is over the safety limit (26.4 mJ/cm2 for 730 nm laser) recommended by the American National Standards Institute (ANSI) for concerns regarding light energy-induced heating or chemical breakdown.

In light of the state of the art, there exists a need for improved technologies for providing safe and effective thrombus treatment.

The above and other needs are met by aspects of the present disclosure which, in one aspect, provides a catheter-implemented transducer device for intravascular thrombolysis. Such a transducer device comprises a catheter defining a longitudinal axis and having opposed proximal and distal ends. A first ultrasonic transducer arrangement (piezoelectric) is disposed about the distal end and oriented perpendicularly to the longitudinal axis. A second ultrasonic transducer arrangement (piezoelectric) is disposed about the distal end of the catheter and oriented parallel to the longitudinal axis. A third ultrasonic transducer arrangement (laser) is disposed about the distal end of the catheter and oriented perpendicularly to the longitudinal axis, and/or a supply conduit is arranged along the catheter and is configured to supply microbubbles, droplets, or t-PA outwardly of the first ultrasonic transducer arrangement from the distal end of the catheter. An associated method is also provided.

Alternatively or additionally, the first ultrasonic transducer arrangement includes an array of ultrasonic transducer elements. The array has a lateral dimension and defining an aperture less than a lateral dimension of the catheter. Optionally, each of the plurality of ultrasonic transducer elements is comprised of a piezoelectric ceramic or a piezoelectric relaxor single crystal.

Alternatively or additionally, the first ultrasonic transducer arrangement is configured as a stacked structure of ultrasonic transducer elements operable in a longitudinal mode to emit forward viewing low-frequency ultrasonic energy and to generate pressure.

Alternatively or additionally, the first ultrasonic transducer arrangement is configured operate in a lateral mode to emit forward viewing low-frequency ultrasonic energy within a frequency range of between less than 1 MHz and about 3 MHz.

Alternatively or additionally, the second ultrasonic transducer arrangement includes a plurality of ultrasonic transducer elements arranged about a circumference of the distal end of the catheter. Each of the plurality of ultrasonic transducer elements is oriented parallel to the longitudinal axis. Optionally, each of the plurality of ultrasonic transducer elements is comprised of a piezoelectric ceramic or a piezoelectric relaxor single crystal.

Alternatively or additionally, the second ultrasonic transducer arrangement is configured to operate in a lateral resonance mode emitting side viewing acoustic waves.

Alternatively or additionally, the first and second ultrasonic transducer arrangements are each configured as a stacked structure of transducer elements operable in a lateral mode to cooperate to generate forward viewing and side viewing waves with pressure capable of inducing cavitation about the distal end of the catheter.

Alternatively or additionally, the third ultrasonic transducer arrangement further includes a laser-generated focused ultrasound (LGFU) lens disposed about the distal end of the catheter and oriented perpendicularly to the longitudinal axis with acoustic waves propagating parallel to the longitudinal axis. Optionally, the LGFU lens is configured as a plano or a concave optical lens a laser ultrasound transduction layer. Optionally, the LGFU lens is arranged to share a focal point with the first ultrasonic transducer arrangement.

Alternatively or additionally, the transducer device further includes a micro-optical fiber or fiber bundle that extends along the longitudinal axis of the catheter and into operable engagement with the LGFU lens. The micro-optical fiber or fiber bundle is configured to direct laser light to and through the LGFU lens. The laser light directed through the LGFU lens interacts with the laser ultrasound transduction layer thereof to photo acoustically convert the laser light to ultrasonic energy, and the converted ultrasonic energy cooperates with ultrasonic energy emitted by an ultrasonic transducer arrangement to induce cavitation about the distal end of the catheter.

Alternatively or additionally, the transducer device further includes a supply conduit arranged along the catheter. The supply conduit is configured to supply at least one of droplets, microbubbles, or a pharmaceutical compound outwardly of the at least one ultrasonic transducer arrangement from the distal end of the catheter.

In another aspect, a catheter-implemented transducer device for intravascular thrombolysis is provided. Such a transducer device includes a catheter defining a longitudinal axis and having opposed proximal and distal ends. At least one ultrasonic transducer arrangement is disposed about the distal end. Additionally, the at least one ultrasonic transducer arrangement is configured as a multi-layer stacked structure of ultrasonic transducer elements.

Alternatively or additionally, the at least one ultrasonic transducer arrangement emits low-frequency ultrasonic energy within a frequency range of between less than 1 MHz and about 3 MHz.

Alternatively or additionally, the at least one ultrasonic transducer arrangement emits ultrasonic waves that propagate parallel or perpendicular to the longitudinal axis.

Alternatively or additionally, the at least one ultrasonic transducer arrangement is configured to operate in a lateral or longitudinal mode.

Alternatively or additionally, the at least one ultrasonic transducer arrangement includes a plurality of ultrasonic transducer elements arranged about a circumference of the distal end of the catheter. Each of the plurality of ultrasonic transducer elements is oriented parallel to the longitudinal axis.

Alternatively or additionally, the transducer device further includes at least two ultrasonic transducer arrangements disposed about the distal end of the catheter. The at least two ultrasonic transducer arrangements operate in a lateral or longitudinal mode to cooperate to generate pressure capable of inducing cavitation about the distal end of the catheter.

Alternatively or additionally, the transducer device further includes an acoustic lens arranged adjacent to and outwardly of the at least one ultrasonic transducer arrangement. The acoustic lens is configured to obtain a focused acoustic field generated by the at least one ultrasonic transducer arrangement.

Alternatively or additionally, the transducer device further includes a laser-generated focused ultrasound (LGFU) lens disposed about the distal end of the catheter and oriented perpendicularly to the longitudinal axis. The LGFU lens is arranged to share a focal point with the at least one ultrasonic transducer arrangement.

Alternatively or additionally, the transducer device further includes a supply conduit arranged along the catheter. The supply conduit is configured to supply at least one of droplets, microbubbles, or a pharmaceutical compound outwardly of the at least one ultrasonic transducer arrangement from the distal end of the catheter.

In yet another aspect, a catheter-implemented transducer device for intravascular thrombolysis is provided. Such a transducer device includes a catheter defining a longitudinal axis and having opposed proximal and distal ends. At least one laser ultrasonic transducer arrangement is disposed about the distal end.

Alternatively or additionally, the at least one laser ultrasonic transducer arrangement includes a laser-generated focused ultrasound (LGFU) lens disposed about the distal end and oriented perpendicularly to the longitudinal axis with acoustic waves propagating parallel to the longitudinal axis.

Alternatively or additionally, the LGFU lens is arranged to share a focal point with the at least one laser ultrasonic transducer arrangement.

Alternatively or additionally, the LGFU lens is configured as a plano or a concave optical lens a laser ultrasound transduction layer.

Alternatively or additionally, the transducer device further includes a micro-optical fiber or fiber bundle that extends along the longitudinal axis of the catheter and into operable engagement with the LGFU lens. The micro-optical fiber or fiber bundle is configured to direct laser light to and through the LGFU lens. The laser light directed through the LGFU lens interacts with the laser ultrasound transduction layer thereof to photo acoustically convert the laser light to ultrasonic energy, and the converted ultrasonic energy cooperates with ultrasonic energy emitted by an ultrasonic transducer arrangement to induce cavitation about the distal end of the catheter.

Alternatively or additionally, the transducer device further includes a supply conduit arranged along the catheter. The supply conduit is configured to supply at least one of droplets, microbubbles, or a pharmaceutical compound outwardly of the at least one laser ultrasonic transducer arrangement from the distal end of the catheter.

In yet another aspect, a catheter-implemented transducer device for intravascular thrombolysis is provided. Such a transducer device includes a catheter defining a longitudinal axis and having opposed proximal and distal ends. A first ultrasonic transducer arrangement is disposed about the distal end and oriented perpendicularly to the longitudinal axis. A second ultrasonic transducer arrangement is disposed about the distal end of the catheter and oriented parallel to the longitudinal axis. A supply conduit is arranged along the catheter and is configured to supply microbubbles, droplets, or a pharmaceutical compound outwardly of the first ultrasonic transducer arrangement from the distal end of the catheter.

Alternatively or additionally, the first ultrasonic transducer arrangement includes an array of ultrasonic transducer elements. The array has a lateral dimension and defining an aperture less than a lateral dimension of the catheter. Optionally, each of the plurality of ultrasonic transducer elements is comprised of a piezoelectric ceramic or a piezoelectric relaxor single crystal.

Alternatively or additionally, the first ultrasonic transducer arrangement is configured as a stacked structure of ultrasonic transducer elements operable in a longitudinal mode to emit forward viewing low-frequency ultrasonic energy and to generate pressure.

Alternatively or additionally, the first ultrasonic transducer arrangement is configured operate in a lateral mode to emit forward viewing low-frequency ultrasonic energy within a frequency range of between less than 1 MHz and about 3 MHz.

Alternatively or additionally, the second ultrasonic transducer arrangement includes a plurality of ultrasonic transducer elements arranged about a circumference of the distal end of the catheter. Each of the plurality of ultrasonic transducer elements is oriented parallel to the longitudinal axis. Optionally, each of the plurality of ultrasonic transducer elements is comprised of a piezoelectric ceramic or a piezoelectric relaxor single crystal.

Alternatively or additionally, the second ultrasonic transducer arrangement is configured to operate in a lateral resonance mode emitting side viewing acoustic waves.

Alternatively or additionally, the first and second ultrasonic transducer arrangements are each configured as a stacked structure of transducer elements operable in a lateral mode to cooperate to generate forward viewing and side viewing waves with pressure capable of inducing cavitation about the distal end of the catheter.

Alternatively or additionally, the transducer device further includes a laser ultrasonic transducer arrangement disposed about the distal end and oriented perpendicularly to the longitudinal axis. The laser ultrasonic transducer arrangement further includes a laser-generated focused ultrasound (LGFU) lens disposed about the distal end of the catheter and oriented perpendicularly to the longitudinal axis with acoustic waves propagating parallel to the longitudinal axis. Optionally, the LGFU lens is configured as a plano or a concave optical lens a laser ultrasound transduction layer.

Optionally, the LGFU lens is arranged to share a focal point with the first ultrasonic transducer arrangement.

Alternatively or additionally, the transducer device further includes a micro-optical fiber or fiber bundle that extends along the longitudinal axis of the catheter and into operable engagement with the LGFU lens. The micro-optical fiber or fiber bundle is configured to direct laser light to and through the LGFU lens. The laser light directed through the LGFU lens interacts with the laser ultrasound transduction layer thereof to photoacoustically convert the laser light to ultrasonic energy, and the converted ultrasonic energy cooperates with ultrasonic energy emitted by an ultrasonic transducer arrangement to induce cavitation about the distal end of the catheter.

In another aspect, a catheter-implemented transducer device for intravascular thrombolysis is provided. Such a transducer device includes a catheter defining a longitudinal axis and having opposed proximal and distal ends. At least one ultrasonic transducer arrangement is disposed about the distal end. Additionally, the at least one ultrasonic transducer arrangement is configured to operate in a lateral mode.

Alternatively or additionally, the at least one ultrasonic transducer arrangement emits low-frequency ultrasonic energy within a frequency range of between less than 1 MHz and about 3 MHz.

Alternatively or additionally, the at least one ultrasonic transducer arrangement emits ultrasonic waves that propagate parallel or perpendicular to the longitudinal axis.

Alternatively or additionally, the at least one ultrasonic transducer arrangement includes a plurality of ultrasonic transducer elements arranged about a circumference of the distal end of the catheter. Each of the plurality of ultrasonic transducer elements is oriented parallel to the longitudinal axis.

Alternatively or additionally, the transducer device further includes at least two ultrasonic transducer arrangements disposed about the distal end of the catheter. The at least two ultrasonic transducer arrangements operate in a lateral or longitudinal mode to cooperate to generate pressure capable of inducing cavitation about the distal end of the catheter.

Alternatively or additionally, the transducer device further includes an acoustic lens arranged adjacent to and outwardly of the at least one ultrasonic transducer arrangement. The acoustic lens is configured to obtain a focused acoustic field generated by the at least one ultrasonic transducer arrangement.

Alternatively or additionally, the transducer device further includes a laser-generated focused ultrasound (LGFU) lens disposed about the distal end of the catheter and oriented perpendicularly to the longitudinal axis. The LGFU lens is arranged to share a focal point with the at least one ultrasonic transducer arrangement.

Alternatively or additionally, the transducer device further includes a supply conduit arranged along the catheter. The supply conduit is configured to supply at least one of droplets, microbubbles, or a pharmaceutical compound outwardly of the at least one ultrasonic transducer arrangement from the distal end of the catheter.

The aspects, functions and advantages discussed herein may be achieved independently in various example implementations/aspects or may be combined in yet other example implementations/aspects, further details of which may be seen with reference to the following description and drawings.

The present disclosure now will be described more fully hereinafter with reference to the accompanying drawings, in which some, but not all aspects of the disclosure are shown.

Indeed, the disclosure may be embodied in many different forms and should not be construed as limited to the aspects set forth herein; rather, these aspects are provided so that this disclosure will be thorough and complete, will fully convey the scope of the disclosure to those skilled in the art, and will satisfy applicable legal requirements. Like numbers refer to like elements throughout. As used in this specification and the claims, the singular forms "a," "an," and "the" include plural referents unless the context clearly dictates otherwise.

Aspects of the present disclosure are directed to a dual excitation, catheter-delivered, laser ultrasound thrombolysis (DECLUT) system (see, e.g., FIGS. 28 and 35) for improving an intravascular sonothrombolysis procedure. Such a system 100 may, for example, include several devices individually implemented in different approaches to addressing the thrombolysis issue, each of the devices/approaches having demonstrated thrombolysis efficacy in preliminary testing, as well as through other empirical data. Aspects of the present disclosure thus combine certain of these individual devices/approaches in order to, for example, improve lytic rate and reduce treatment time, improve clot lysis performance, and improve safety.

Referring now to FIGS. 29-32, example catheter-implemented transducer devices are described. More particularly, in one aspect, the present disclosure (see, e.g., FIGS. 31 and 32) provides a catheter-implemented transducer device 100 for intravascular thrombolysis. Such a device 100 comprises a catheter 3 defining a longitudinal axis 200 and having opposed proximal and distal ends 250, 275. A first ultrasonic transducer arrangement 1 is disposed about the distal end 275 and is oriented with acoustic waves propagating parallel to the longitudinal axis 200. A second ultrasonic transducer arrangement 2 is disposed about the distal end 275 and is oriented with acoustic waves propagating perpendicular to the longitudinal axis 200. A third ultrasonic transducer arrangement 7 and 8 is disposed about the distal end 275 and is oriented with acoustic waves propagating parallel to the longitudinal axis 200. As described herein, the third ultrasonic transducer arrangement is a laser ultrasonic transducer arrangement, which includes a laser-generated focused ultrasound (LGFU) lens and a coating layer such as a laser ultrasound transduction layer (e.g., light absorption and thermal expansion layers) as described below. As described above, the first, second, and/or third ultrasonic transducer arrangements are arranged about the distal end 275. For example, the first, second, and/or third ultrasonic transducer arrangements can be arranged in proximity to the distal end 275 as shown in the figures. The location of the first, second, and/or third ultrasonic transducer arrangements in the figures are provided only as examples. This disclosure contemplates that the first, second, and/or third ultrasonic transducer arrangements can be arranged near, adjacent to, above, below, to the side, spaced from, etc. relative to the distal end 275. A supply conduit 4 is arranged along the catheter 3 and is configured to supply nanodroplets, microbubbles, t-PA, and/or other blood thinner drug (e.g., pharmaceutical compound) outwardly of the first ultrasonic transducer arrangement 1 from the distal end 275 of the catheter 3. As shown in FIG. 31, the supply conduit 4 is arranged centrally with respect to the catheter 3 (e.g., along the longitudinal axis 200). As shown in FIG. 32, the supply conduit 4 is arranged off-center with respect to the catheter 3 and parallel to the longitudinal axis 200. The arrangements of the supply conduit with respect to the catheter 3 in FIGS. 5 and 6 are provided only as examples. This disclosure contemplates that the supply conduit 4 can be arranged in other locations with respect to the catheter 3.

The first ultrasonic transducer arrangement 1 may comprise an array of ultrasonic transducer elements, the array having a lateral dimension and defining an aperture less than a lateral dimension of the catheter 3. The first ultrasonic transducer arrangement 1 is oriented perpendicular to the longitudinal axis 200 as shown in FIGS. 31 and 32. In some aspects, the first ultrasonic transducer arrangement 1 is configured as a stacked structure of ultrasonic transducer elements (e.g., a multi-layer stacked structure with a plurality of ultrasonic transducer elements) operable in a longitudinal mode to emit low-frequency ultrasonic energy and to generate acoustic pressure. In some aspects, an acoustic lens is arranged adjacent to and outwardly of the transducer 1 to obtain a focused acoustic field generated by the transducer 1 as shown in FIGS. 31 and 32. In some instances, the first ultrasonic transducer arrangement 1 is configured to operate in a lateral mode or in a longitudinal mode to emit low-frequency ultrasonic energy within a frequency range of between about <1 MHz and about 3 MHz.

The second ultrasonic transducer arrangement 2 includes a plurality of ultrasonic transducer elements arranged about a circumference of the distal end 275 of the catheter 3, wherein each of the plurality of ultrasonic transducer elements is oriented parallel to the longitudinal axis 200. Accordingly, the ultrasonic energy emitted by the second ultrasonic transducer arrangement 2 is directed radially outward from the catheter 3. In some aspects, each of the plurality of ultrasonic transducer elements of the first and/or second ultrasonic transducer arrangement 1, 2, is comprised of a PZT ceramic or other piezoelectric materials including, for example, relaxor-PT single crystals and non-lead piezoelectrics. In other aspects, the first and/or second ultrasonic transducer arrangement 1, 2 may be configured to be operable in a lateral resonance mode. In still other aspects, the first and/or second ultrasonic transducer arrangement 1, 2 is/are each configured as a stacked structure of ultrasonic transducer elements operable in a lateral mode or longitudinal mode to cooperate to generate pressure capable of inducing cavitation about the distal end 275 of the catheter 3.

In particular aspects, the device 100 may further include a laser-generated focused ultrasound (LGFU) lens 7 disposed about the distal end 275 of the catheter 3 and oriented perpendicularly to the longitudinal axis 200 as shown in FIG. 32. An LGFU transducer for precise ultrasound therapy may be effective. The LGFU transducer, comprised of a LGFU lens and laser ultrasound transduction layer (e.g., a light absorption layer and a thermal expansion layer) may be capable of generating shock waves with high negative pressure (>10 MPa) at a tight focal spot (<1 mm), which can allow precise control of cavitation, and thus may be effective in intravascular thrombolysis. For example, the LGFU lens 7 is configured as a plano or a concave optical lens coated with a laser ultrasound transduction layer 8. The laser ultrasound transduction layer 8 can include a light absorption layer (e.g., carbon black, carbon nano-fiber film, carbon nanotubes, carbon nano-particles, metal nano-particles) and a thermal expansion layer (e.g., polydimethylsiloxane (PDMS) or other polymers or plastics or other thermoelastic material). In some aspects, the LGFU lens 7 is arranged and configured to share a focal point with the acoustic lens of the first ultrasonic transducer arrangement 1. A micro 20 optical fiber (or fiber bundle) 6 may also extend along the longitudinal axis 200 of the catheter 3 and into operable engagement with the LGFU lens 7. The micro-optical fiber 6 may be configured to direct laser light to and through the LGFU lens 7, wherein the laser light directed through the LGFU lens 7 is absorbed by the laser ultrasound transduction layer 8 and photoacoustically converted to ultrasonic energy, which cooperates with ultrasonic energy emitted by the first ultrasonic transducer arrangement 1 to induce cavitation about the distal end 275 of the catheter 3.

In another aspect, the present disclosure (see, e.g., FIG. 29) provides a front-firing, piezoelectric stacked-type, flat or focused element for intravascular thrombolysis. Such a device comprises a catheter 3 defining a longitudinal axis 200 and having opposed proximal and distal 30 ends 250, 275. A first ultrasonic transducer arrangement 1 is disposed about the distal end 275 and is oriented with acoustic waves propagating parallel to the longitudinal axis 200. Additionally, an acoustic lens is arranged adjacent to and outwardly of the transducer 1 to obtain a focused acoustic field generated by the transducer 1. Additionally, a supply conduit 4 is arranged along the catheter 3 and is configured to supply nanodroplets, microbubbles, t-PA, and/or other blood thinner drug (e.g., pharmaceutical compound) outwardly of the first ultrasonic transducer arrangement 1 from the distal end 275 of the catheter 3. The catheter 3, first ultrasonic transducer arrangement 1, acoustic lens, and supply conduit 4 are described in detail above and therefore not described in further detail with respect to FIG. 29.

In another aspect, the present disclosure (see, e.g., FIG. 30) provides a front-firing, LGFU transducer element for intravascular thrombolysis. Such a device comprises a catheter 3 defining a longitudinal axis 200 and having opposed proximal and distal ends 250, 275. The device includes a laser ultrasonic transducer arrangement disposed about the distal end 275 and oriented with acoustic waves propagating parallel to the longitudinal axis 200. As described herein, the laser ultrasonic transducer arrangement includes a LGFU 7 lens and a laser ultrasound transduction layer 8. The device also includes a micro-optical fiber (or fiber bundle) 6 extending along the longitudinal axis 200 of the catheter 3 and into operable engagement with the LGFU lens 7. Additionally, a supply conduit 4 is arranged along the catheter 3 and is configured to supply nanodroplets, microbubbles, t-PA, and/or other blood thinner drug (e.g., pharmaceutical compound) outwardly of the laser ultrasonic transducer arrangement from the distal end 275 of the catheter 3. The catheter 3, micro-optical fiber 6, LGFU lens 7, laser ultrasound transduction layer 8, and supply conduit 4 are described in detail above and therefore not described in further detail with respect to FIG. 30.

More particularly, a catheter-mounted small aperture hybrid ultrasound transducer array is configured and arranged for ultrasound thrombolysis, in an approach with minimal use of a pharmacological agent. This device is capable of generating ultrasound or ultrasonic energy in axial and radial directions of the catheter when the transducer is close to a blood clot (see, e.g., FIG. 28 having first and second ultrasonic transducers 1 and 2, respectively). In some aspects, the catheter diameter is 2 mm and an external diameter of the transducer assembly is about 2 mm. In some instances, the catheter diameter is 2 mm or even larger. It should be understood that the dimensions for the catheter and/or transducer are provided only as examples and can have other values. Various combinations of forward-viewing piezo-transducer, side-viewing piezo-transducer, and forward-viewing LGFU-transducer are available. Six example configurations of IVUS transducers are: 1) a front-firing, piezoelectric stacked-type, flat or focused element (see, e.g., FIG. 29); 2) a front-firing, LGFU transducer element (see, e.g., FIG. 30); 3) combined front and side-firing piezoelectric transducer (see, e.g., FIG. 31); 4) a front firing piezoelectric ultrasound transmitter combined with a laser-generated focused ultrasound (LGFU) transducer (see, e.g., FIG. 32 excluding transducer 2); 5) front-firing LGFU combined with the side-firing piezoelectric elements (see, e.g., FIG. 32 excluding transducer 1); and 6) combined front-firing piezoelectric transducer, front firing LGFU element and side-firing piezo-elements (see, e.g., FIG. 32).

For both a piezoelectric and a hybrid laser-piezoelectric IVUS transducer, the front firing element may have a multi-layer stacked structure (see, e.g., FIG. 34) for higher acoustic power, and smaller capacitance which leads to good electrical impedance matching with relatively low electrical impedance at the resonance of the transducer device. The total thickness of front firing transducer element is about 0.5 mm-<5 mm for the frequency range of <1 to 3 MHz, which is advantageous for efficient thrombolysis and microbubble excitation. The side firing array transducer elements may have a single layer structure and operate in lateral mode. In one instance, due to the limited diameter of arteries (~2 mm), the low-frequency thickness mode of side-firing elements (>1 mm thickness for <1 to 3 MHz) is difficult to achieve. Thus, as an example, ultrasound generation with a lateral mode (e.g., 1.9 MHz at 500 μm width) is practical for this application. Among many piezoelectric ceramics, crystals, and composites, PZT-2, PZT-5A, PZT-5H ceramics and single crystals including, for example, PMN-PT, PZN-PT and PIN PMN-PT, generally show high ultrasound wave radiation along the thickness direction in the lateral mode. It should be understood that PZT-2, PZT-5A, and PZT-5H ceramic and/or PMNPT, PZN-PT, or PIN-PMN-PT crystal are provided only as examples. This disclosure contemplates using other ceramics, crystals, and/or composites with the devices described herein.

The front-firing element of a hybrid IVUS transducer may be combined with a multilayer stack piezoelectric transducer element and an LGFU lens. The LGFU lens may be comprised of a plano or a concave optical lens coated with carbon black and polydimethylsiloxane (PDMS), or carbon nano-fiber film and PDMS, or other light absorption materials and PDMS or other thermoelastic materials. In one example, a 532 nm laser light can be delivered through an optical fiber to the lens and the carbon-based material layer (e.g., carbon black, carbon nanotubes, carbon nano-fiber film, or carbon nano-particles) on the lens absorbs the light. The rapidly increased temperature due to the absorbed laser energy induces a rapid thermal expansion of the PDMS layer, and then a shock wave is generated outwardly of the front side of the lens. High amplitude shock waves can be achieved with high laser energy, and single-pulsed cavitation is also induced when the focal points of LGFU lens and the piezoelectric element are coincident. For both IVUS transducer arrangements, a micro-tube (e.g., supply conduit 4 in FIGS. 29-32) may be disposed inside the catheter to inject nanodroplet, microbubble, and t-PA agents (or other pharmaceutical compound) outwardly of the front firing transducer element to the treatment location.

Characteristics of the catheter-mounted, small aperture, hybrid ultrasound transducers and arrays for intravascular thrombolysis can include one or more of the following: 1) a small aperture transducer fabricated small enough to fit within some space-limited application environments (i.e., within the catheter); 2) a transducer that can transmit ultrasound in a low frequency range (<1-3 MHz), which may be advantageous for thrombolysis efficiency and microbubble excitation by using multi-layer stacked thickness mode and lateral mode operation; 3) injection of nanodroplets/microbubbles (e.g., via supply conduit 4 in FIGS. 29-31) to the treatment position through a micro tube (e.g., supply conduit) inside and extending along the catheter, to relieve cavitation threshold PNP; 4) high pressure generation through both front and side firing transducer elements to induce the cavitation by using multi-layer stacked thickness mode and lateral mode operations; 5) a front-firing piezoelectric transducer element (e.g., component 1 in FIGS. 29, 31, and 32 and components 2-2 and 2-3 in FIG. 34), wherein the multilayer stacked structure device is configured to achieve low-frequency operation and high pressure generation; 6) a front-firing LGFU lens (e.g., components 7 and 8 in FIGS. 30 and 32) having a carbon black, carbon nano-fiber film, or carbon nano-particles, combined with PDMS, to generate shock waves outwardly of the front side of the catheter, wherein the focal point shared with the piezoelectric element can efficiently induce the cavitation; 7) a micro-optical fiber (e.g., component 6 in FIGS. 30 and 32) implemented to deliver laser light to the LGFU lens; and/or 8) side-firing piezoelectric array elements (e.g., component 2 in FIGS. 31 and 32 and 20 component 2-1 in FIG. 33), wherein PZT ceramics and/or piezoelectric single crystals are used as an element of a cylindrical array which is operable in a lateral resonance mode.

In one particular approach, ultrasound and laser ultrasound implemented in relation to thrombolysis, tissue ablation, and drug delivery, for example, have demonstrated cavitation enhancement and enhanced thrombolysis through a multi-frequency strategy. The multi frequency strategy provides enhanced cavitation by using multi-frequency excitation, either through multiple piezoelectric transducers at frequencies <3 MHz or a laser-excited acousto-optic transducer. In this regard, a forward-looking multi-frequency catheter transducer for sonothrombolysis may be an advantageous configuration. The forward-looking transducer arrangement may, for example, facilitate ultrasound image guidance, reduce the amount of fluoroscopy required, limit the likelihood of catheter-clot contact, and direct acoustic energy forward towards the clot rather than directly towards the vessel wall. A combination of photoacoustic and piezo transducers may provide both shock wave high frequency excitation and low frequency excitation, which may facilitate exciting of cavitation in microbubble agents. Certain data also suggests multi-frequency sonothrombolysis provides better clot dissolution performance over single frequency thrombolysis.

In addition, the catheter (e.g., component 3 in FIGS. 29-32) may also be configured to facilitate local administration, for example, of low-boiling point phase-change perfluorocarbon nanodroplets. Data suggests that sub-micron agents intercalate into clot matrices, and convert to cavitating microbubbles in response to acoustic energy, providing enhanced clot disruption over traditional microbubbles. Thus, aspects of the disclosure involve the development, optimization, and integration of several technologies for sonothrombolysis. Aspects of the DECLUT system can, for example, 1) improve lysis rate and significantly reduce treatment time, 2) reduce required pharmacologic lytic administration dose, thereby reducing off-target bioeffects, 3) reduce lysis fragment size, thereby reducing likelihood of downstream embolism, 4) reduce thermal and mechanical damage to off-target tissue, and/or 5) reduce fluoroscopy exposure to patient and caregiver.

Aspects of the present disclosure may thus implement low-frequency (<1 MHz-3 MHz) piezoelectric transducers for catheter-based sonothrombolysis by implementing small-aperture, low-frequency piezoelectric ultrasound transducers, with sufficient acoustic output for enhanced cavitation, into a 7-French or smaller catheter. In addition, nanodroplet formulation and size are optimized for clot-busting propensities, in conjunction with the ultrasonic energy.

In addition, an optical fiber laser generated focused ultrasound (LGFU) transducer may be integrated into the catheter. When combined with the low frequency piezoelectric transducer, high-efficiency multi-frequency treatment may result. More particularly, combined excitation by low frequency continuous waves and LGFU shock waves, in addition to spatiotemporal delivery of t-PA and microbubbles/droplets, can provide quick and safe thrombolysis. For example, a miniaturized piezoelectric multifrequency ultrasound transducer (<1.5 mm in diameter) may be integrated in a catheter to generate cavitation-induced microstreaming, while an enhanced cavitation effect may be realized by using LGFU shock waves to cause inertial cavitation.

Furthermore, forward-looking ultrasound waves provide ultrasound image guidance for clot detection without damaging intimal layers of vein walls. That is, a high-frequency (~10 MHz) imaging piezoelectric transducer stacked in front of the low frequency therapy-transducer may provide image guidance, while minimal t-PA delivery combined with microbubbles/droplets reduce sizes of clot debris after the treatment to minimize the risk of recurrent and distal embolism. Finally, a 200 nanometer-diameter or smaller phase-change droplet agent formulation, converting to ~1 micron microbubbles with reduced acoustic energy, will better penetrate clot matrices than standard microbubble formulations and cause optimally efficient thrombolysis. An exemplary specification for a DECLUT system as disclosed herein, is shown below in Table 1:

| External size | <7 French |
| Frequency | ~0.5 MHz-3 MHz for burst ultrasound (front firing and side firing) |
| | ~10 MHz for LGFU |
| | ~10 MHz single-pulse for A-mode imaging (forward looking) |
| Ultrasound output | MI of up to 1.9 for <1-3 MHz burst ultrasound |
| | MI of up to 1.9 for ~10 MHz LGFU |
| Focal length | <1.5 mm |
| −6 dB focal spot size | <3 mm in axial direction |
| | <1.5 mm in lateral direction |
| t-PA dose | <100 µg |
| Lytic rate | >3% mass loss/min |

Aspects of a DECLUT system, as disclosed herein, may thus advantageously realize, for example, 90% dissolution in 30 minutes (3% mass loss/min) with the use of t-PA of <100 µg, as compared to existing sonothrombolysis techniques (e.g. EKOS) which needs >15 hours for complete lysis (approximately 0.11% mass loss/min) with the use of t-PA of 10-20 mg. Accordingly, faster (i.e., >10 times) clot dissolution is achieved compared to current sonothrombolysis approaches (e.g. EKOS) through the combined mechanism of ultrasound mediated fibrinolysis and micro-fragmentation arising from cavitation-induced microstreaming at a reduced cavitation threshold, which is attributed to the MCA/droplet and dual-ultrasound excitation. Moreover, safer clot-dissolution may be realized over current catheter-based thrombolysis techniques (e.g. Angiojet, Trellis, and EKOS) due to, for instance, the minimal use and precise delivery of lytic agent, and reduced physical contact to the target clot and the acoustic exposure of the surrounding vessel wall. In instances where implemented, forward looking ultrasound image guidance will to help reduce fluoroscopy exposure to patient and caregiver.

In some aspects, the ultrasonic transducer(s) is/are used to excite the injected microbubble contrast agents (MCA) or nanodroplets to cause enhanced cavitation-induced microstreaming. These low-frequency (<1 MHz-3 MHz) miniaturized (<1.5 mm) piezoelectric transducers or arrays thereof may be configured as multi-layer structures and/or to be operable in a lateral mode. Moreover, the tightly focused high-pressure shock wave excitation provided by the LGFU transducer is utilized for intravascular thrombolysis. For the higher lytic rate, these two different forward looking transducers may share the same focal spot, enhancing cavitation effects due to the reduced cavitation pressure threshold by dual-sonication. Although sufficient lytic rate can be expected without t-PA injection for this DECLUT system, reducing the risk of bleeding complications, minimal t-PA dose can eliminate the risk of potential recurrent or distal embolism which could occur due to clot debris, as with current systems. The integrated device will be located approximately >1 mm away from the target clot, and hence there is no direct contact between the device and the clot, which may enhance the safety of the device/procedure and still allow precise spatiotemporal delivery of t-PA and microbubbles/droplets.

For low-frequency ultrasound excitation with sufficient conditions for cavitation, the piezoelectric transducer(s) can be configured to account for spatial limitations (e.g., an aperture of <1.5×1.5 mm2). Thus, a multi-layer stacked longitudinal-mode resonator (electrical field and wave propagation are both along the catheter axial direction) and/or a lateral-mode resonator (electrical field is perpendicular to the catheter axial direction, while the acoustic wave propagates along the axial direction) may be implemented. The total thickness of a longitudinal mode transducer may be greater than about 1.5 mm such that the transducer has a resonance frequency lower than 1 MHz. However, the achievable acoustic output of a monolithic piezoelectric bulk element is limited, due to low capacitance, low strain and the driving voltage limitation. The multi-layer stacked configuration has electrically-parallel and mechanically serial connection of stacked elements, which provides a more efficient ultrasonic transducer transmitter with lower electrical impedance, higher strain and the capability of multi-frequency modes. For the lateral-mode transducer, the lateral-resonance frequency is dependent on the lateral dimension (perpendicular to the electrical field), and is independent of the thickness (parallel to the electrical field). Thus, the thickness of the lateral mode transducer can be configured with lower electrical impedance. Both the multi-layer stacked and lateral mode transducers exhibit a low operating frequency (<1 MHz) and multi-frequency ultrasound within a <7-french catheter as well as acceptable electrical impedance (<500 ohm) at the resonance frequency for forward looking and side looking high intensity ultrasound-induced cavitation. Moreover, the high frequency (10 MHz) forward looking ultrasound image can be used to guide the positioning of the catheter, while reducing the fluoroscopy exposure for the practitioner.

The high-pressure output at the tight focal spot of the LGFU arrangement may also be utilized for intravascular thrombolysis. A miniaturized carbon nanoparticle (CNP)/PDMS LGFU transducer implements an optical fiber for exciting microbubbles with high-pressure (>10 MPa) shock waves, which is difficult to achieve with miniaturized piezoelectric ultrasound transducers. The pressure output of the LGFU arrangement at the focal spot is sufficient to drive substantial microbubble cavitation and microstreaming in as focused manner in proximity to the target clot, while minimizing the potential risk of vessel injury due to the tight focal spot size (<2 mm in axial direction and <1 mm in lateral direction) of a fiber LGFU transducer/arrangement.

Enhanced cavitation by dual-acoustic excitation may be useful for therapeutic ultrasound applications as well as thrombolysis. Combining the high frequency shock waves generated by the LGFU transducer/arrangement and low-frequency burst waves generated from the piezoelectric ultrasound transducers are applied for thrombolysis with higher efficiency, wherein the dual-acoustic excitation can result in a higher lytic rate than conventional ultrasound-mediated fibrinolysis, such as EKOS (i.e., treatment time>15 hours in average). Low-boiling point phase change contrast agents may comprise, for example, liquid perfluorobutane nanodroplets which vaporize into microbubbles upon interaction with acoustic energy. Such low boiling point perfluorocarbon can be vaporized at even low acoustic pressures (less than a MI of 1.9), whereas traditional perfluoropentane or perfluorohexane nanodroplets require substantially higher energy levels to phase convert, due to Laplace pressure and homogeneous nucleation. These liquid perfluorobutane nanodroplets are very stable in liquid precursor form and are thus relatively robust and able to withstand high hydrostatic pressure and shear that occurs when pumping bubbles rapidly down a long small-bore of a catheter to the treatment site. Furthermore, these droplets can be readily configured in the <100-300 nanometer size range, for improved clot penetration compared to <1-3 micron bubbles while achieving smaller debris fragment size. Upon activation by ultrasonic energy, the resulting microbubbles behave similarly or identically to traditional microbubbles, but may result in improved clot lysis due to clot intercalation.

In some aspects, a small-aperture, low-frequency piezoelectric ultrasound transducer may be formed and configured with sufficient acoustic output (MI~0.3-1.9) for enhanced cavitation in a 7F catheter. A multi-layer stacked design may improve power transfer efficiency of the transducer in transmit mode. Multi-layer transducers are also able to increase element capacitance by a factor of N2 since they are stacked mechanically in series and electrically in parallel, where N is the total number of layers, which has significant effects on the transducer transmitting sensitivity. That is, the power output $P_{out}=V_{out}^2/R_m$ is maximized when the mechanical resistance $R_m$ is minimized, given the equation of $R_m$, $$R_m = \frac{\pi}{4k_{eff}f^2 w C_0} Z_a$$

where $k_{eff}$ is the electromechanical coupling of the piezo-
electric, $C_0$ is the static element capacitance, and $Z_a$ is
the ratio of front acoustic loads to that of the piezo-
electric element. Thus, in a multilayer transducer, the
$R_m$ is decreased by a factor of $N^2$, resulting in an equal
increase in power output. Therefore, multi-layering can
significantly reduce the transmit voltage of the trans-
ducer for the same output pressure. A comparison
between a single layer and a 5-layer PZT 2D array
found that a ~5.6 dB transmitting efficiency gain could
be obtained with the 5-layer design. In one instance, a
miniaturized, low-frequency, high-power transducer
was implemented for MCA-involved sonothromboly-
sis, the transducer array comprising PZT-5A 6-layer
transducers with an aperture of 1.2×1.2 mm2 and the
total thickness of 1.7 mm, and exhibited a longitudinalextensional-mode resonance frequency of 550 kHz (see, e.g., FIGS. 36A-36C). The achieved peak-to-peak pressure output was about 2.2 MPa at the driving voltage of 120 $V_{pp}$ (FIG. 36C). The PNP was about 1 MPa and the corresponding MI was 1.4, which is sufficient for cavitation-induced microstreaming.

The exemplary transducer was then implemented in in vitro thrombolysis tests (FIG. 37A). A microbubble-injection tube was integrated with the transducer, and the transducer-tipped needle was positioned 1 mm away from the target blood clot stored in the saline water-filled vessel-mimicking tube (inner diameter of 3 mm). The blood clot was exposed to the low-frequency (550 kHz) ultrasound with a duty cycle of 7% (300 cycle burst with 5 ms of pulse duration). The treatment time was 30 min, and the lytic rate of treatment cases with and without MCA were compared. For the bubble injection case, microbubbles were injected at a concentration of 1×108/mL and at a flow rate of 0.1 ml/min. As shown in FIG. 37B, ultrasound treatment with MCA shows the clot mass reduction of 50%, whereas ultrasound excitation alone without MCA showed less than 10% clot mass loss. Thus, these results suggest that the low frequency multi-layer transducer with a small aperture (1.2× 1.2 mm2) can be used to generate sufficient acoustic output for effective MCA-mediated thrombolysis. The achieved lytic rate with MCA was 1.67%/min, though a higher lytic rate may be achieved with the use of t-PA, because other studies indicate that MCA-involved sonothrombolysis with the use of 0.32 μg/mL t-PA improves the lytic rate ~5× more than the same treatment without t-PA.

Another advantage of a multi-layer stacked design is that multi-frequency operation can be realized. More particularly, in one instance, a single-aperture, dual-layer HIFU transducer (diameter of 25 mm) was implemented to operate at 1.5 MHz and 3 MHz, simultaneously. The transducer has half-wavelength and quarter-wavelength resonance modes at frequencies of 1.5 MHz and 3.1 MHz, respectively. Efficacy of dual-frequency excitation showed a 5% higher cavitation-induced temperature increment for tissue ablation, wherein the mechanism of the improvement is the reduced threshold pressure for cavitation with dual frequency excitation. In another instance, dual-frequency excitation for TDEU thrombolysis was implemented to reduce the required acoustic power for sonothrombolysis. The 1.5 MHz HIFU transducer was used, and the multi-frequency excitation case (e.g. 1.4 MHz+1.5 MHz) was compared with the single-frequency excitation (1.5 MHz) case. The dual-frequency ultrasound was able to accelerate the lytic rate by a factor of 2-4 compared to the single frequency case. No significant differences were found between dual-frequencies with different frequency differences (0.025, 0.05, and 0.1 MHz), or between dual-frequency and triple-frequency.

In dual-frequency therapy transducer design, half-wavelength resonance frequency is determined by the total thickness of the stacked-layers. Once the total-thickness frequency is selected, the quarter-wavelength resonance frequency is determined as twice of the half wavelength case (FIG. 38). Although the frequency components are determined by the 1-dimensional analysis for the wave propagation along the thickness direction, the proper number of layers, the achievable pressure output, the corresponding MI, and the beam profile at each frequency with a given electrical input, must all be analyzed and optimized, for example, by finite element analysis (FEA), and the optimal dimension determined based on the FEA results. For example, ANSYS FEA software (ANSYS Mechanical APDL, ANSYS Academic Research, Release 15.0.7, ANSYS, Inc., Canonsburg, Pennsylvania USA) can accurately simulate acoustic performance of the stacked-type multilayer transducers, and can be used to optimize design factors such as total thickness, number of layers, and aperture size for the aimed beam diameter (<1 mm) and MI (>1.0) at the target distance (>1 mm). Generally, lower-frequency ultrasound excitation realizes a higher lytic rate. However, the lower frequency ultrasound beam has a larger beam width, though focal spot size and beam profile are important design factors for forward-looking intravascular therapeutic-ultrasound transducers, since the redundant ultrasound beam may cause ultrasound-associated vascular injury. As such, the beam width of burst-waves in a DECLUT catheter can be optimized by using a customized concave lens. Generally, a –6 dB beam width can be approximately estimated by the equation, $$BD_{-6\,Db} \approx 1.41(R/D)(c/f),$$

where R, D, c, and f denote a radius of the curvature of a concave lens, the diameter of the lens, the wave velocity of the medium, and the operating frequency, respectively. With the aperture of 1.2×1.2 mm² at the operating frequency of 500 kHz and 1 MHz for the 1 mm focal distance, the –6 dB beam diameter for each frequency can be approximately calculated as 3 mm and 1 mm, respectively. Based on the target size, proper lens material and radius of curvature can be optimized, and the corresponding focal gain, –6 dB beam width, and focal spot size can be determined. The specifications of a dual-frequency, multi-layer transducer is shown, for example, in Table 2:

| | |
|---|---|
| Aperture | 1.2 × 1.2 mm² |
| # of layer | ~6 layers |
| Impedance at resonance | <100 Ω at both resonance frequencies |
| Frequency | A-mode imaging: >10 MHz |
| | Sonothrombolysis: <1-3 MHz |
| Ultrasound output | MI of -up to 1.9 (FDA diagnostic ultrasound limit is 1.9) |
| Focal length | >1 mm |
| –6 dB focal spot size | ~2 mm in axial direction < vessel diameter |

For the high-frequency (>10 MHz) imaging transducer, pulse-echo response can be estimated by KLM modeling, and it is expected that A-mode imaging is available by way of the imaging transducer disposed in front of the low-frequency therapy transducer (FIG. 39). It has been shown that a high-frequency (>12 MHz) transducer in a stacked-type multi-frequency transducer did not affect the transmitting performance of the low-frequency (2 MHz) transducer.

For a multi-layer stacked configuration transducer, piezo plates (e.g. PZT-2 having an area of 5×5 mm² and thickness of 250~350 μm) can be stacked with a 20 μm-thick copper shim between adjacent piezo plates. The quarter-wavelength matching layer can be made of alumina powder/epoxy bond mixture with an acoustic impedance of ~7-8 MRayl is attached at the front side. After bonding of the layers, the assembly is diced to obtain an aperture of 1.2×1.2 mm². The transducer(s) are wire-connected and mounted in a 7F catheter as a forward-looking transducer arrangement. The resulting multi-layer transducers exhibit multi-frequency modes, reasonably high sensitivity and bandwidth at high frequency for imaging guidance, and sufficient MI for enhanced cavitation. The multi-layered transducer configuration with the small aperture for mounting in a 7F catheter generally requires a small bonding area to maintain sufficient bonding condition.

The low-frequency transducer for a DECLUT system may also be configured as a lateral-mode transducer where the resonance frequency is determined by the lateral dimension and is the operating frequency. Once the lateral dimension is determined (i.e., 1.2 mm), the usual piezoelectric lateral mode frequency is in the range of 1-2 MHz, which is independent of the thickness as long as the lateral dimension is at least 3 times larger than the thickness. In one example, a relatively small size (1.2×1.2×0.3 mm³) PZT-5H lateral mode transducer can generate about 1 MPa PNP output with 100 $V_{pp}$ sinusoidal excitation at 1.5 MHz lateral mode frequency (see, e.g., FIGS. 40A and 40B).

Optical fiber LGFU transducers are fabricated from CNP/PDMS composite film and such miniaturized LGFU transducers are integrated into a 7 French catheter for thrombolysis. A laser ultrasound transducer comprised of a CNP/PDMS composite film can be prepared using a candle soot process. In comparison with other carbon-based composite films (e.g., carbon-black, carbon-nanotube, carbon-nanofiber with PDMS layer), the CNP/PDMS film exhibits a higher light-to-acoustic energy conversion ratio due to a higher light absorption coefficient and a faster heat transfer characteristic due to a low interfacial thermal resistance. Moreover, the CNP/PDMS film can be formed through a relatively easy and cost-efficient candle soot fabrication process. The miniaturized LGFU transducers for catheter thrombolysis (CTTU) can comprise an optical fiber LGFU transducer prepared using a CNP/PDMS film (FIG. 41A). In one example, an optical fiber (0.6 mm in diameter) CNP/PDMS LGFU with a lens (1 mm in diameter) can generate a high-pressure shock wave (peak to peak pressure of 16 MPa with 11 MHz center frequency) at 1 mm away from the transducer (FIG. 41B). The implemented laser input was only 1.5 mJ of a 532 nm pulsed laser, and thus higher pressure output can correspond to higher laser input.

An initial in vitro test was used to evaluate the lytic efficiency of the dual-excitation of LGFU and low-frequency burst ultrasound. In the initial test, a LGFU transducer (diameter of 12 mm and radius-of-curvature of 12.4 mm) and a piezoelectric transducer (1.5 MHz, diameter of 30 mm and focal length of 30 mm) were used to evaluate the feasibility of dual excitation for thrombolysis regardless of size and catheter design. The LGFU transducer was comprised of carbon-black and PDMS, and the peak frequency was 11 MHz. The experimental arrangement is as shown in FIG. 42A. Three different treatment cases were compared: the treatments with 1) piezo transducer only, 2) LGFU only, and 3) dual-excitation of piezo transducer and LGFU. Each treatment time was 15 minutes. The test result is shown in FIG. 42B. The case of dual excitation exhibited higher mass loss than the other two cases: 85% higher than piezo transducer treatment only and 100% higher than LGFU treatment only. These results demonstrate that the dual-excitation of LGFU and low-frequency burst waves is beneficial to MCA-involved sonothrombolysis due to the enhanced cavitation effect, and therefore the overall lytic rate can be significantly improved with the use of small dose of t-PA (<0.3 μg/mL).

A PDMS concave lens can be fabricated by using the capillary effect of uncured PDMS at the top of a plastic tube having an inner diameter of 0.8 mm. After curing the PDMS lens, a CNP layer can be deposited on the concave surface by a candle-soot process. A PDMS thermal expansion layer can be coated on the CNP layer by dip-coating. The fabricated LGFU lens has a diameter of 0.5 mm and a radius-of-curvature of about 1 mm. A 0.3 mm-diameter optical fiber is attached to the LGFU lens by using optical glue. The integration of the LGFU transducer with the multi-layer transducer can be processed as shown in FIG. 43. A micro-tube (ID: 0.3 mm, OD: 1 mm) for injecting the microbubble and t-PA can be attached at the side of the integrated transducer, and the integrated assembly mounted on the tip of a 7F catheter. The optical fiber LGFU transducer is mounted on a fiber-coupler (FIG. 43), because the initial beam diameter of a 532 nm Nd:YAG pulsed laser (Minilite I, Continuum Inc., Santa Clara, CA) is about 10 mm. FIG. 44 shows the integrated DECLUT system.

Aspects of the present disclosure thus combine and cooperate to provide a device having a low-frequency (<1 MHz), miniaturized (<1.5 mm in diameter), high acoustic output (MIof 0.3-1.9) multi-frequency intravascular piezoelectric ultrasound transducer for forward looking image guided intravascular thrombolysis. Optical fiber CNP/PDMS LGFU transducers generate high-pressure (<5 MPa-20 MPa) shock wave to enhance cavitation-induced microstreaming near the clot. Combined t-PA and MCA/nanodroplets reduce required acoustic energy and improve lytic rate. Dual-excitation of the blood clot by LGFU shock waves and burst waves by the piezoelectric ultrasound transducer leads to enhanced cavitation at a tight focal spot (a fraction of a vessel diameter) while reducing potential risk of injury to the vessel wall. Low-boiling point phase change agents further serve as a microbubble thrombolysis source, but provide improved stability for inter-catheter delivery and improved clot penetration and subsequent lysis.

Any of the ultrasound transducers or methods described herein can be used in combination with metastable phase change nanodroplets to enhance lysis of blood clots.

The disclosure of each of the references listed herein is hereby incorporated herein by reference in its entirety.

Many modifications and other aspects of the disclosures set forth herein will come to mind to one skilled in the art to which these disclosures pertain having the benefit of the teachings presented in the foregoing descriptions and the associated drawings. Therefore, it is to be understood that the disclosures are not to be limited to the specific aspects disclosed and that equivalents, modifications, and other aspects are intended to be included within the scope of the appended claims. Although specific terms are employed herein, they are used in a generic and descriptive sense only and not for purposes of limitation.

What is claimed is:

1. A method for generation of cavitation internal to a blood clot mass greater than would be achievable with microbubble cavitation agents for a given level of applied ultrasound energy, the method comprising:

administering metastable liquid perfluorocarbon nano-droplets into a blood vessel that includes or leads to a blood vessel that includes a blood clot, where the metastable liquid perfluorocarbon nanodroplets each have a liquid core comprising a perfluorocarbon material that has a boiling point below 25° C. at atmospheric pressure and the liquid core is encapsulated within a shell, where the metastable liquid perfluorocarbon nanodroplets are in a metastable state and remain stable in liquid form at 25° C. at atmospheric pressure, and where the metastable liquid perfluorocarbon nanodroplets have diameters sufficiently small to penetrate into the blood clot mass, wherein the diameters range from 10 nanometers to 750 nanometers;

allowing for at least some of the metastable liquid perfluorocarbon nanodroplets to penetrate the blood clot; and applying ultrasound energy to the blood clot mass, causing the metastable liquid perfluorocarbon nanodroplets within the blood clot, causing the liquid cores of the metastable liquid perfluorocarbon nanodroplets that penetrated the blood clot, to convert from a liquid state to a gaseous state due to the application of the ultrasound energy, resulting in cavitation occurring within the blood clot, wherein a metric of cavitation occurring within the blood clot due to the cavitation from the metastable liquid perfluorocarbon nanodroplets that penetrated the blood clot and converted to the gaseous state exceeds the metric of cavitation that would occur within the blood clot due to microbubbles administered externally to the blood clot and to which the ultrasound energy is applied, wherein applying the ultrasound energy includes applying the ultrasound energy intravascularly using an ultrasound transducer, wherein the nanodroplets that penetrate the blood clot spatially control cavitation delivery to reduce heating of tissue surrounding the blood clot, and wherein the cavitation occurring within the blood clot causes lysis of the blood clot.

2. The method of claim 1 wherein the metastable liquid perfluorocarbon nanodroplets are allowed to penetrate the blood clot prior to applying the ultrasound energy that causes the liquid cores of the nanodroplets to convert from the liquid state to the gaseous state.

3. The method of claim 1 wherein the applying of the ultrasound energy causes the liquid cores of the metastable liquid perfluorocarbon nanodroplets to convert from the liquid state to the gaseous state at or adjacent to a surface of the blood clot, cavitate, and mediate lysis of the blood clot.

4. The method of claim 1 wherein the lysis of the blood clot with the metastable liquid perfluorocarbon nanodroplets occurs at a rate which is at least double than a rate of lysis of the blood clot without the presence of the metastable liquid perfluorocarbon nanodroplets at the same acoustic parameters.

5. The method of claim 1 wherein the metastable liquid perfluorocarbon nanodroplets have diameters ranging from 10 nm to 300 nm.

6. The method of claim 1 wherein applying the ultrasound energy includes applying the ultrasound energy with a peak negative pressure that is less than 3 megapascals.

7. The method of claim 1 wherein applying the ultrasound energy includes applying the ultrasound energy with a peak negative pressure that is less than 5.9 megapascals.

8. The method of claim 1 wherein applying the ultrasound energy includes applying the ultrasound energy with a peak negative pressure that is less than 12 megapascals.

9. The method of claim 1 wherein the frequency used to apply the ultrasound energy is selected from a range of 300 KHz to 2 MHz.

10. The method of claim 1 wherein the frequency used to apply the ultrasound energy is selected from a range of 2 MHz to 10 MHZ.

11. The method of claim 1 wherein a plurality of the metastable liquid perfluorocarbon nanodroplets can be vaporized at less than 4.5 MPa with 15 cycles at 1 MHz and 25° C.

12. The method of claim 1 wherein applying the ultrasound energy includes using ultrasound pulses having a duty cycle of no more than 45%.

13. The method of claim 1 wherein applying the ultrasound energy includes applying the ultrasound energy with an acoustic intensity of no more than 34.8 Watts per square centimeter.

14. The method of claim 1 wherein applying the ultrasound energy includes applying the ultrasound energy with an acoustic intensity of no more than 15 Watts per square centimeter.

15. The method of claim 14 wherein ultrasound is utilized to form an image of the blood clot and acoustic signals of cavitation are overlaid on the image of the clot.

16. The method of claim 1 wherein applying the ultrasound energy includes applying the ultrasound energy with an acoustic intensity of no more than 5.2 Watts per square centimeter.

17. The method of claim 1 wherein the blood clot comprises a retracted blood clot.

18. The method of claim 1 wherein the metastable liquid perfluorocarbon nanodroplets comprise at least decafluorobutane or perfluoropropane.

19. The method of claim 1 wherein the shell of each of the metastable liquid perfluorocarbon nanodroplets comprises a lipid, a polymer, or a protein material surrounding the perfluorocarbon core.

20. The method of claim 1 wherein acoustic signals from the cavitation are detected by a transducer and utilized to indicate the presence or location of the cavitation occurring at near or within the blood clot.

21. The method of claim 1 where acoustic signals from the cavitation are detected by a transducer, and energy from a $2^{nd}$ harmonic and higher from the shells increasing in diameter and bursting is used to indicate the presence and/or location of the cavitation occurring near or within the blood clot.

22. The method of claim 1 comprising administering a material for enhancing breakdown of the blood clot in conjunction with the metastable liquid perfluorocarbon nanodroplets and ultrasound energy.

23. The method of claim 22 wherein the material comprises an anti-coagulant.

24. The method of claim 22 wherein the material for enhancing breakdown of the blood clot comprises a tissue plasminogen activator.

25. The method of claim 1 comprising using ultrasound to obtain an image of the blood clot at a first frequency and wherein applying the ultrasound energy causing the cavitation comprises applying the ultrasound energy at a second frequency that is at least double the first frequency.

26. The method of claim 1 comprising using ultrasound to obtain an image of a blood clot within a blood vessel at a first frequency which is at least double a frequency of the ultrasound energy causing the cavitation.

27. The method of claim 1 wherein the metric of cavitation occurring within the blood clot comprises a ratio of cavitation within the blood clot to a total cavitation occurring within and outside of the blood clot.

28. The method of claim 1 wherein the metastable liquid perfluorocarbon nanodroplets comprise metastable liquid perfluorobutane nanodroplets.

29. A system for generation of cavitation internal to a blood clot mass greater than would be achievable with microbubble cavitation agents for a given level of applied ultrasound energy, the system comprising:

means for administering metastable liquid perfluorocarbon nanodroplets into a blood vessel that includes or that leads to a blood vessel that includes a blood clot and for allowing at least some of the metastable liquid perfluorocarbon nanodroplets to penetrate the blood clot, where the metastable liquid perfluorocarbon nanodroplets each have a liquid core comprising a perfluorocarbon material that has a boiling point below 25° C. at atmospheric pressure and the liquid core is encapsulated within a shell, where the metastable liquid perfluorocarbon nanodroplets are in a metastable state and would remain stable in liquid form at 25° C. at atmospheric pressure, and where the metastable liquid perfluorocarbon nanodroplets have diameters sufficiently small to penetrate into the blood clot mass, wherein the diameters range from 10 nanometers to 750 nanometers; and an ultrasound transducer for applying ultrasound energy intravascularly to the blood clot mass, causing the liquid cores of the metastable liquid perfluorocarbon nanodroplets within and surrounding the blood clot to convert from a liquid state to a gaseous state due to the application of the ultrasound energy, resulting in cavitation occurring within the clot, wherein a metric of cavitation occurring within the blood clot due to the cavitation from the metastable liquid nanodroplets that penetrated the blood clot and converted to the gaseous state exceeds the metric of cavitation that would occur within the blood clot due to microbubbles administered externally to the blood clot and to which the ultrasound energy is applied, and wherein the nanodroplets that penetrate the blood clot spatially control cavitation delivery to reduce heating of tissue surrounding the blood clot and the cavitation occurring within the blood clot causes lysis of the blood clot.

30. The system of claim 29 wherein the means for administering comprises an infusion pump.

31. The system of claim 29 wherein applying the ultrasound energy includes applying the ultrasound energy with a peak negative pressure that is less than 3 megapascals.

32. The system of claim 29 wherein applying the ultrasound energy includes applying the ultrasound energy with a peak negative pressure that is less than 5.9 megapascals.

33. The system of claim 29 wherein applying the ultrasound energy includes applying the ultrasound energy with a peak negative pressure that is less than 12 megapascals.

34. The system of claim 29 wherein the frequency used to apply the ultrasound energy is selected from a range of 300 KHz to 2 MHz.

35. The system of claim 29 wherein the frequency used to apply the ultrasound energy is selected from a range of 2 MHz to 10 MHz.

36. The system of claim 29 comprising means for administering a material for enhancing breakdown of the blood clot in conjunction with the metastable liquid perfluorocarbon nanodroplets and ultrasound energy.

37. The system of claim 29 comprising means for generating an image of the blood clot with acoustic signals from cavitation overlaid on the image of the blood clot.

38. The system of claim 29 wherein the metric of cavitation occurring within the blood clot comprises a ratio of cavitation within the blood clot to a total cavitation occurring within and outside of the blood clot.

39. The system of claim 29 wherein the metastable liquid perfluorocarbon nanodroplets comprise metastable liquid perfluorobutane nanodroplets.

* * * * *